United States Patent
Cheung et al.

(10) Patent No.: US 7,238,813 B2
(45) Date of Patent: Jul. 3, 2007

(54) CHEMICAL COMPOUNDS

(75) Inventors: Mui Cheung, Durham, NC (US); Philip Anthony Harris, Durham, NC (US); Masaichi Hasegawa, Tsukuba (JP); Satoru Ida, Keita (JP); Kazuya Kano, Tsukuba (JP); Naohiko Nishigaki, Tsukuba (JP); Hideyuki Sato, Tsukuba (JP); James Marvin Veal, Apex, NC (US); Yoshiaki Washio, Tsukuba (JP); Rob I. West, Stevenage (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 295 days.

(21) Appl. No.: 10/433,128

(22) PCT Filed: Nov. 28, 2001

(86) PCT No.: PCT/US01/44553

§ 371 (c)(1),
(2), (4) Date: Nov. 12, 2003

(87) PCT Pub. No.: WO02/44156

PCT Pub. Date: Jun. 6, 2002

(65) Prior Publication Data

US 2004/0082583 A1    Apr. 29, 2004

Related U.S. Application Data

(60) Provisional application No. 60/310,939, filed on Aug. 8, 2001, provisional application No. 60/253,868, filed on Nov. 29, 2000.

(51) Int. Cl.
*A61K 31/4184*    (2006.01)
*C07D 235/30*    (2006.01)

(52) U.S. Cl. ............................ 548/307.4; 514/388

(58) Field of Classification Search ............ 548/307.4
See application file for complete search history.

(56) References Cited

U.S. PATENT DOCUMENTS 5,447,860 A    9/1995    Ziegler
5,624,947 A    4/1997    Keown et al.
5,877,020 A    3/1999    Alitalo
6,030,831 A    2/2000    Godowski et al.

FOREIGN PATENT DOCUMENTS

| WO | 98/52558 | 11/1998 |
|----|----------|---------|
| WO | 98/52559 | 11/1998 |
| WO | 99/24035 | 5/1999 |
| WO | 99/32106 | 7/1999 |
| WO | 99/32110 | 7/1999 |
| WO | 99/32111 | 7/1999 |
| WO | 99/32436 | 7/1999 |
| WO | 99/32455 | 7/1999 |
| WO | 99/32463 | 7/1999 |
| WO | 00/41669 | 7/2000 |

OTHER PUBLICATIONS

Isner, J.M. et al., "Therapeutic Angiogenesis," *Fontiers in Bioscience*, 3, pp. 49-69, May 5, 1998.
Martiny-Baron, G., German DFG Priority Grant "Angiogenesis" SPP 1069, year not available.
Tyurina, L.A.. et al., "Relations between the structure and embryotoxic action of nitrogen-and sulfur-containing organic compounds," *Khimiko-Farmatsevticheskii Zhurnal* (1998), 32(2), pp. 21-27.
Siemeister, G. et al., "Two Independent Mechanisms Essential for Tumor Angiogenesis: Inhibition of Human Melanoma Xenograft Growth by Interfering with either the Vascular Endothelial Growth Factor Receptor Pathway or the Tie-2 Pathway," *Cancer Research*, 59, pp. 3185-3191, Jul. 1, 1999.
Schnurch, H. et al., Expression of tie-2, a member of a novel family of receptor tyrosine kinases, in the endothelial cell lineage, *Development*, 119, pp. 957-968 (1993).
Yancopoulos, G.D. et al., "Vasculogenesis, Angiogenesis, and Growth Factors: Ephrins Enter the Fray at the Border," *Cell*, vol. 93, pp. 661-664, May 29, 1998.
Peters, Kevin G., "Vascular Endothelial Growth Factor and the Angiopoietins Working Together to Build a Better Blood Vessel," *American Heart Association, Inc.*, 83, pp. 342-343 (1998).
Tyrina, L.A., et al., "Investigation of the Relationship Between the Structure of Nitrogen-and Sulphur-Containing Organic Compounds and Their Embryotoxic Action," *Konnekthnb astopos* (1998), pp. 21-27.

*Primary Examiner*—Laura L. Stockton
(74) *Attorney, Agent, or Firm*—John L. Lemanowicz; Jennifer L. Fox

(57) ABSTRACT

Benzimidazole derivatives, which are useful as TIE-2 and/or VEGFR2 inhibitors are described herein. The described invention also includes methods of making such benzimidazole derivatives as well as methods of using the same in the treatment of hyperproliferative diseases.

18 Claims, No Drawings

# CHEMICAL COMPOUNDS

This application is filed pursuant to 35 U.S.C. § 371 as a United States National Phase Application of International Application No. PCT/US01/44553 filed Nov. 28, 2001, which claims priority from Ser. No. 60/253,868 filed Nov. 29, 2000 and 60/310,939 filed Aug. 8, 2001.

BACKGROUND OF THE INVENTION

The present invention relates to benzimidazole derivatives, compositions and medicaments containing the same, as well as processes for the preparation and use of such compounds, compositions and medicaments. Such benzimidazole derivatives are useful in the treatment of diseases associated with inappropriate or pathological angiogenesis.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels. Normal angiogenesis is activated during tissue growth, from embryonic development through maturity, and then enters a period of relative quiescence during adulthood. Normal angiogensesis is also activated during wound healing, and at certain stages of the female reproductive cycle. Inappropriate or pathological angiogenesis has been associated with several disease states including various retinopathies; ischemic disease; atherosclerosis; chronic inflammatory disorders; and cancer. The role of angiogenesis in disease states is discussed, for instance, in Fan et al, Trends in Pharmacol Sci. 16:5–66; Shawver et al, DDT Vol. 2, No. 2 February 1997; Folkmann, 1995, Nature Medicine 1:27–31.

In cancer the growth of solid tumors has been shown to be angiogenesis dependent. (See Folkmann, J., J. Nat'l. Cancer Inst., 1990, 82, 4–6.) Consequently, the targeting of pro-angiogenic pathways is a strategy being widely pursued in order to provide new therapeutics in these areas of great, unmet medical need. The role of tyrosine kinases involved in angiogenesis and in the vascularization of solid tumors has drawn interest. Until recently most interest in this area has focused on growth factors such as vascular endothelial growth factor (VEGF) and its receptors termed vascular endothelial growth factor receptor(s) (VEGFR). VEGF, a polypeptide, is mitogenic for endothelial cells in vitro and stimulates angiogenic responses in vivo. VEGF has also been linked to inappropriate or pathological angiogenesis (Pinedo, H. M. et al. The Oncologist, Vol. 5, No. 90001, 1–2, April 2000). VEGFR(s) are protein tyrosine kinases (PTKs). PTKs catalyze the phosphorylation of specific tyrosyl residues in proteins involved in the regulation of cell growth and differentiation. (A. F. Wilks, Progress in Growth Factor Research, 1990, 2, 97–111; S. A. Courtneidge, Dev. Supp.l, 1, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401).

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. et al J. Cell Biol. 1995:129:895–898). Of particular interest is VEGFR-2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3–10, April 2000).

Angiopoieten 1 (Ang1), a ligand for the endothelium-specific receptor tyrosine kinase TIE-2 is a novel angiogenic factor (Davis et al, Cell, 1996, 87:1161–1169; Partanen et al, Mol. Cell Biol, 12:1698–1707 (1992); U.S. Pat. Nos. 5,521,073; 5,879,672; 5,877,020; and 6,030,831). The acronym TIE represents "tyrosine kinase containing Ig and EGF homology domains". TIE is used to identify a class of receptor tyrosine kinases, which are exclusively expressed in vascular endothelial cells and early hemopoietic cells. Typically, TIE receptor kinases are characterized by the presence of an EGF-like domain and an immunoglobulin (IG) like domain, which consists of extracellular folding units, stabilized by intra-chain disulfide bonds (Partanen et al Curr. Topics Microbiol. Immunol., 1999, 237:159–172). Unlike VEGF, which functions during the early stages of vascular development, Angi and its receptor TIE-2 function in the later stages of vascular development, i.e., during vascular remodeling (remodeling refers to formation of a vascular lumen) and maturation (Yancopoulos et al, Cell, 1998, 93:661–664; Peters, K. G., Circ. Res., 1998, 83(3): 342–3; Suri et al, Cell 87, 1171–1180 (1996)).

Consequently, inhibition of TIE-2 would be expected to serve to disrupt remodeling and maturation of new vasculature initiated by angiogenesis thereby disrupting the angiogenic process. Furthermore, inhibition at the kinase domain binding site of VEGFR-2 would block phosphorylation of tyrosine residues and serve to disrupt initiation of angiogenesis. Presumably then, inhibition of TIE-2 and/or VEGFR-2 should prevent tumor angiogenesis and serve to retard or eradicate tumor growth. Accordingly, a treatment for cancer or other disorder associated with inappropriate angiogenesis could be provided.

The present inventors have discovered novel benzimidazole compounds, which are inhibitors of TIE-2 and/or VEGFR-2 kinase activity. Such benzimidazole derivatives are useful in the treatment of disorders, including cancer, associated with inappropriate angiogenesis.

BRIEF SUMMARY OF THE INVENTION

In one aspect of the present invention, there is provided a compound of Formula (I):

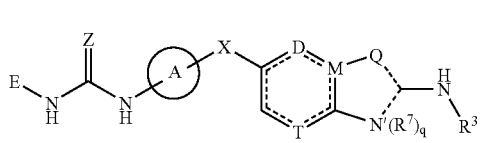

(I)

or a salt, solvate, or physiologically functional derivative thereof:

wherein:
E is aryl substituted by $R^1$ and $R^2$, or
  unsubstituted heteroaryl, or
  heteroaryl substituted with $R^1$, or
  heteroaryl substituted by $R^1$ and $R^2$, or
  $R^1$ and $R^2$ together with the atoms of E to which they are attached form a cyloalkyl,
  aryl, or heterocyclic ring fused to E;
A is aryl, heteroaryl, or heterocyclic;
X is S, O, S(O)$_2$, S(O), C(H)$_2$, C(H)(OH), or C(O);
Z is O or S;
p is 0 or 1;
q is 0 or 1;
the dotted line bonds "- - -" attached to Q and N' represent a single bond or a double bond wherein when q is 0 the dotted line bond "- - -" attached to Q is a single bond and the dotted line bond attached to N' is a double bond, and when q is 1 the dotted line bond "- - -" attached to Q is a double bond and the dotted line bond attached to N' is a single bond; and
the dotted line within the 6 membered ring containing D, M, and T represents appropriate aromatic bonds;
D is CH, T is $CR^8$, M is C and Q is $N(R^7)_p$, wherein p is 0 and q is 1; or
D is CH, T is $CR^8$, M is C and Q is $N(R^7)_p$, wherein p is 1 and q is 0; or
D is CH, T is $CR^8$, M is C and Q is S or O; wherein q is 0;
D is N, T is $CR^8$, M is C and Q is $N(R^7)_p$, wherein either p or q is 0 and the other is 1; or
D is CH, T is N, M is C and Q is $N(R^7)_p$, wherein either p or q is 0 and the other is 1; or
D is CH, T is $CR^8$, M is N and Q is CH, wherein q is 0;
$R^1$ is $C_1$–$C_6$ alkyl, $C_1$–$C_6$ haloalkyl, aryl, heteroaryl, heterocyclic, halogen, $C_1$–$C_6$ alkoxy, $C_1$–$C_6$ haloalkoxy, aralkyl, aralkoxy, aryloxy, $C_1$–$C_6$ alkylsulfanyl, $C_1$–$C_6$ haloalkylsulfanyl, $C_1$–$C_6$alkylsulfenyl, $C_1$–$C_6$ alkylsulfonyl, —NO$_2$, —NR$^4$R$^5$, —C(O)OR$^6$, —CN, —C(O)NR$^4$R$^5$, —S(O)$_2$NR$^4$R$^5$, cyanoalkyl;
$R^2$ is hydrogen, $C_1$–$C_6$ alkyl, $C_1$–$C_6$ haloalkyl, aryl, heteroaryl, heterocyclic, aralkyl, aralkoxy, aryloxy, halogen, $C_1$–$C_6$ alkoxy, $C_1$–$C_6$ haloalkoxy, $C_1$–$C_6$ alkylsulfanyl, $C_1$–$C_6$ haloalkylsulfanyl, $C_1$–$C_6$ alkylsulfenyl, $C_1$–$C_6$ alkylsulfonyl, oxo, hydroxy, —NO$_2$, —NR$^4$R$^5$, —C(O)OR$^6$, —CN, —C(O)NR$^4$R$^5$, —S(O)$_2$NR$^4$R$^5$, or cyanoalkyl;
$R^3$ is hydrogen, $C_1$–$C_6$ alkyl, aryl, aralkyl, aralkoxy, heteroaryl, heterocyclic, —RR$^6$, —RNR$^4$R$^5$, —C(O) R$^6$, —C(O)NR$^4$R$^5$, —C(O)OR$^6$, —C(O)RO R$^6$, —C(O)RC(O)OR$^6$, —C(O)R R$^6$, —C(O)RR' R$^6$, —C(O)ROR'OR"O R$^6$, —C(O)ROR'O R$^6$, —C(O)RNR$^4$R$^5$, —C(O)RNR$^4$C(O) R$^6$, —C(O)RNR$^4$C(O)OR$^6$, —C(O)ORNR$^4$R$^5$, —S(O)$_2$ R$^6$, or —S(O)$_2$NR$^4$R$^5$; or
$R^3$ is $C_1$–$C_6$ alkylene or $C_1$–$C_6$ alkylene substituted with oxo, and is linked together with the nitrogen to which it is attached and to one of the benzimidazole nitrogens to form a heterocylic compound fused to the benzimidazole;
R, R', and R", are each independently selected from $C_1$–$C_6$ alkylene, arylene, heteroarylene, $C_3$–$C_7$ cycloalkylene, or heterocyclylene;
R''' is $C_1$–$C_6$ alkyl, aryl, heteroaryl, aralkyl, $C_3$–$C_7$cycloalkyl, or heterocyclic;
$R^4$ and $R^5$ are each independently selected from hydrogen, $C_1$–$C_6$ alkyl, $C_1$–$C_6$ haloalkyl, $C_1$–$C_6$alkylsulfanyl, $C_1$–$C_6$alkylsulfenyl, $C_1$–$C_6$alkylsulfonyl, aryl, heteroaryl, aralkyl, heterocyclic, $C_3$–$C_7$cycloalkyl, —C(O)OR$^6$, —C(O)NR'''R''', —C(O)NR'''H, —C(O)NH$_2$, or —S(O)$_2$NR'''R''';
$R^6$is hydrogen, $C_1$–$C_6$ alkyl, $C_1$–$C_6$haloalkyl, aryl, heteroaryl, aralkyl, heterocyclic, or $C_3$–$C_7$ cycloalkyl;
$R^7$ is hydrogen, $C_1$–$C_6$ alkyl, —S(O)$_2$ R$^6$, —RNR$^4$R$^5$, —RR$^6$
$R^8$ is hydrogen or halogen; and when $R^1$ is Cl, $R^2$ is hydrogen or Cl, $R^3$ is —C(O)OCH$_3$, E and A are phenyl, D is CH, T is CH, M is C, Q is $N(R^7)_p$, where $R^7$ is H, wherein either p or q is 0 and the other is 1, and Z is O, then X is O, S(O), S(O)$_2$, CH2, CH(OH), or C(O).

In a second aspect of the present invention, there is provided a compound of Formula (I):

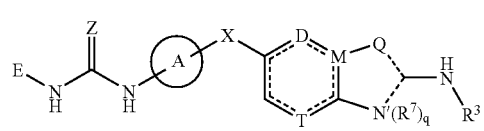

(I)

or a salt, solvate, or physiologically functional derivative thereof:

wherein:
E is unsubstituted heteroaryl, or
  heteroaryl substituted with $R^1$, or
  heteroaryl substituted by $R^1$ and $R^2$;
A is aryl, heteroaryl, or heterocyclic;
X is S, O, S(O)$_2$, S(O), CH$_2$, CH(OH), or C(O);
Z is O or S;
p is 0 or 1;
q is 0 or 1;
the dotted line bonds "- - -" attached to Q and N' represent a single bond or a double bond wherein when q is 0 the dotted line bond "- - -" attached to Q is a single bond and the dotted line bond attached to N' is a double bond, and when q is 1 the dotted line bond "- - -" attached to Q is a double bond and the dotted line bond attached to N' is a single bond; and
the dotted line within the 6 membered ring containing D, M, and T represents appropriate aromatic bonds;
D is CH, T is $CR^8$, M is C and Q is $N(R^7)_p$, wherein p is 0 and q is 1; or
D is CH, T is $CR^8$, M is C and Q is $N(R^7)_p$, wherein p is 1 and q is 0; or
D is CH, T is $CR^8$, M is C and Q is S or O; wherein q is 0;
D is N, T is $CR^8$, M is C and Q is $N(R^7)_p$, wherein either p or q is 0 and the other is 1; or
D is CH, T is N, M is C and Q is $N(R^7)_p$, wherein either p or q is 0 and the other is 1; or
D is CH, T is $CR^8$, M is N and Q is CH, wherein q is 0;
$R^1$ is $C_1$–$C_6$ alkyl, $C_1$–$C_6$ haloalkyl, aryl, heteroaryl, heterocyclic, halogen, $C_1$–$C_6$ alkoxy, $C_1$–$C_6$ haloalkoxy, aralkyl, aralkoxy, aryloxy, $C_1$–$C_6$ alkylsulfanyl, $C_1$–$C_6$ haloalkylsulfanyl, $C_1$–$C_6$ alkylsulfenyl, $C_1$–$C_6$ alkylsulfonyl, —$NO_2$, —$NR^4R^5$, —C(O)$OR^6$, —CN, —C(O)$NR^4R^5$, $S(O)_2NR^4R^5$, or cyanoalkyl;

$R^2$ is hydrogen, $C_1$–$C_6$ alkyl, $C_1$–$C_6$ haloalkyl, aryl, heteroaryl, heterocyclic, aralkyl, aralkoxy, aryloxy, halogen, $C_1$–$C_6$ alkoxy, $C_1$–$C_6$ haloalkoxy, $C_1$–$C_6$ alkylsulfanyl, $C_1$–$C_6$ haloalkylsulfanyl, $C_1$–$C_6$ alkylsulfenyl, $C_1$–$C_6$ alkylsulfonyl, oxo, hydroxy, —$NO_2$, —$NR^4R^5$, —C(O)$OR^6$, —CN, —C(O)$NR^4R^5$, —$S(O)_2NR^4R^5$, or cyanoalkyl;

$R^3$ is hydrogen, $C_1$–$C_6$ alkyl, aryl, aralkyl, aralkoxy, heteroaryl, heterocyclic, —$RR_6$, —$RNR^4R^5$, —C(O) $R^6$, —C(O)$NR^4R^5$, —C(O)$OR^6$, —C(O)RO $R^6$, —C(O)RC(O)$OR^6$, —C(O)R $R^6$, —C(O)RR'$R^6$, —C(O)ROR'OR"O $R^6$, —C(O)ROR'O $R^6$, —C(O)$RNR^4R^5$, —C(O)$RNR^4$C(O) $R^6$, —C(O)$RNR^4$C(O)$OR^6$, —C(O)$ORNR^4R^5$, —$S(O)_2 R^6$, or —$S(O)_2NR^4R^5$; or $R^3$ is $C_1$–$C_6$ alkylene or $C_1$–$C_6$ alkylene substituted with oxo, and is linked together with the nitrogen to which it is attached and to one of the benzimidazole nitrogens to form a heterocylic compound fused to the benzimidazole;

R, R', and R", are each independently selected from $C_1$–$C_6$ alkylene, arylene, heteroarylene, $C_3$–$C_7$cycloalkylene, or heterocyclylene;

R''' is $C_1$–$C_6$ alkyl, aryl, heteroaryl, aralkyl, $C_3$–$C_7$cycloalkyl, or heterocyclic;

$R^4$ and $R^5$ are each independently selected from hydrogen, $C_1$–$C_6$ alkyl, $C_1$–$C_6$ haloalkyl, $C_1$–$C_6$alkylsulfanyl, $C_1$–$C_6$alkylsulfenyl, $C_1$–$C_6$alkylsulfonyl, aryl, heteroaryl, aralkyl, heterocyclic, $C_3$–$C_7$ cycloalkyl, —C(O)$OR^6$, —C(O)NR'''R''', —C(O)NR'''H, —C(O)$NH_2$, or —$S(O)_2NR'''R'''$;

$R^6$ is hydrogen, $C_1$–$C_6$ alkyl, $C_1$–$C_6$ haloalkyl, aryl, heteroaryl, aralkyl, heterocyclic, or $C_3$–$C_7$ cycloalkyl;

$R^7$ is hydrogen, $C_1$–$C_6$ alkyl, —$S(O)_2 R^6$, —$RNR^4R^5$, —$RR^6$; and $R^8$ is hydrogen or halogen.

In a third aspect of the present invention, there is provided a compound of Formula (II):

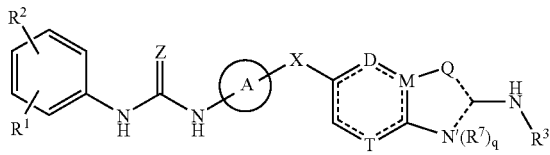

(II)

or a salt, solvate, or physiologically functional derivative thereof:

wherein:
A is aryl, heteroaryl, or heterocyclic;
X is S, O, $S(O)_2$, S(O), $CH_2$, CH(OH), or C(O);
Z is O or S;
p is 0 or 1;
q is 0 or 1;
the dotted line bonds "- - -" attached to Q and N' represent a single line bond or a double bond wherein when q is 0 the dotted line bond "- - -" attached to Q is a single bond and the dotted line bond attached to N' is a double bond, and when q is 1 the dotted line bond "- - -" attached to Q is a double bond and the dotted line bond attached to N' is a single bond; and the dotted line within the 6 membered ring containing D, M, and T represents appropriate aromatic bonds;

D is CH, T is CR⁸, M is C and Q is $N(R^7)_p$, wherein p is 0 and q is 1; or

D is CH, T is $CR^8$, M is C and Q is $N(R^7)_p$, wherein p is 1 and q is 0; or

D is CH, T is $CR^8$, M is C and Q is S or O; wherein q is 0;

D is N, T is $CR^8$, M is C and Q is $N(R^7)_p$, wherein either p or q is 0 and the other is 1; or D is CH, T is N, M is C and Q is $N(R^7)_p$, wherein either p or q is 0 and the other is 1; or D is CH, T is $CR^8$, M is N and Q is CH, wherein q is 0;

$R^1$ is $C_1$–$C_6$ alkyl, $C_1$–$C_6$ haloalkyl, aryl, heteroaryl, heterocyclic, halogen, $C_1$–$C_6$ alkoxy, $C_1$–$C_6$ haloalkoxy, aralkyl, aralkoxy, aryloxy, $C_1$–$C_6$ alkylsulfanyl, $C_1$–$C_6$ haloalkylsulfanyl, $C_1$–$C_6$ alkylsulfenyl, $C_1$–$C_6$ alkylsulfonyl, —$NO_2$, —$NR^4R^5$, —C(O)$OR^6$, —CN, —C(O)$NR^4R^5$, —$S(O)_2NR^4R^5$, or cyanoalkyl;

$R^2$ is hydrogen, $C_1$–$C_6$ alkyl, $C_1$–$C_6$ haloalkyl, aryl, heteroaryl, heterocyclic, aralkyl, aralkoxy, aryloxy, halogen, $C_1$–$C_6$ alkoxy, $C_1$–$C_6$ haloalkoxy, $C_1$–$C_6$ alkylsulfanyl, $C_1$–$C_6$ haloalkylsulfanyl, $C_1$–$C_6$ alkylsulfenyl, $C_1$–$C_6$ alkylsulfonyl, oxo, hydroxy, —$NO_2$, —$NR^4R^5$, —C(O)$OR^6$, —CN, —C(O)$NR^4R^5$, —$S(O)_2NR^4R^5$, or cyanoalkyl; or $R^1$ and $R^2$ together with the phenyl ring atoms to which they are attached form a cyloalkyl or aryl ring fused to the phenyl ring;

$R^3$ is hydrogen, $C_1$–$C_6$ alkyl, aryl, aralkyl, aralkoxy, heteroaryl, heterocyclic, —$RR^6_1$, —$RNR^4R^5$, —C(O) $R^6$, —C(O)$NR^4R^5$, —C(O)$OR^6$, —C(O)RO $R^6$, —C(O)RC(O)$OR^6$, —C(O)R $R^6$, —C(O)RR'$R^6$, —C(O)ROR'OR"O $R^6$, —C(O)ROR'O $R^6$, —C(O)$RNR^4R^5$, —C(O)$RNR^4$C(O) $R^6$, —C(O)$RNR^4$C(O)$OR^6$, —C(O)$ORNR^4R^5$, —$S(O)_2 R^6$, or —$S(O)_2NR^4R^5$; or $R^3$ is $C_1$–$C_6$ alkylene or $C_1$–$C_6$ alkylene substituted with oxo, and is linked together with the nitrogen to which it is attached and to one of the benzimidazole nitrogens to form a heterocylic compound fused to the benzimidazole;

R, R', and R", are each independently selected from $C_1$–$C_6$ alkylene, arylene, heteroarylene, $C_3$–$C_7$cycloalkylene, or heterocyclylene;

R''', is $C_1$–$C_6$ alkyl, aryl, heteroaryl, aralkyl, $C_3$–$C_7$cycloalkyl, or heterocyclic;

$R^4$ and $R^5$ are each independently selected from hydrogen, $C_1$–$C_6$ alkyl, $C_1$–$C_6$haloalkyl, $C_1$–$C_6$alkylsulfanyl, $C_1$–$C_6$alkylsulfenyl, $C_1$–$C_6$alkylsulfonyl, aryl, heteroaryl, aralkyl, heterocyclic, $C_3$–$C_7$ cycloalkyl, —C(O)$OR^6$, —C(O)NR'''R''', —C(O)NR'''H, —C(O)$NH_2$, or —$S(O)_2NR'''R'''$;

$R^6$ is hydrogen, $C_1$–$C_6$ alkyl, $C_1$–$C_6$ haloalkyl, aryl, heteroaryl, aralkyl, heterocyclic, or $C_3$–$C_7$ cycloalkyl;

$R^7$ is hydrogen, $C_1$–$C_6$ alkyl, —$S(O)_2 R^6$, —$RNR^4R^5$, —$RR^6$ $R^8$ is hydrogen or halogen; and when $R^1$ is Cl, $R^2$ is H or Cl, $R^3$ is —C(O)$OCH_3$, A is phenyl, D is CH, T is CH, M is C and Q is $N(R_7)_p$, where $R^7$ is H, wherein either p or q is 0 and the other is 1 and Z is O, then X is O, S(O), =$S(O)_2$, $CH_2$, CH(OH) or C(O).

In a fourth aspect of the present invention, there is provided a compound of Formula (III):

(III)

or a salt, solvate, or physiologically functional derivative thereof:

wherein:
A is aryl, heteroaryl, or heterocyclic;
X is S, O, S(O)$_2$, S(O), CH$_2$, CH(OH), or C(O);
Z is O or S;
p is 0 or 1;
q is 0 or 1, wherein either p or q is 0, and the other is 1;
the dotted line bonds "- - -" attached to N' and N" represent a single bond or a double bond wherein when q is 0 the dotted line bond "- - -" attached to N' is a single bond and the dotted line bond attached to N" is a double bond, and when q is 1 the dotted line bond "- - -" attached to N' is a double bond and the dotted line bond attached to N" is a single bond;
R$^1$ is C$_1$–C$_6$ alkyl, C$_1$–C$_6$ haloalkyl, aryl, heteroaryl, heterocyclic, halogen, C$_1$–C$_6$ alkoxy, C$_1$–C$_6$ haloalkoxy, aralkyl, aralkoxy, aryloxy, C$_1$–C$_6$ alkylsulfanyl, C$_1$–C$_6$ haloalkylsulfanyl, C$_1$–C$_6$ alkylsulfenyl, C$_1$–C$_6$ alkylsulfonyl, —NO$_2$, —NR$^4$R$^5$, —C(O)OR$^6$, —CN, —C(O)NR$^4$R$^5$, —S(O)$_2$NR$^4$R$^5$, or cyanoalkyl;
R$^2$ is hydrogen, C$_1$–C$_6$ alkyl, C$_1$–C$_6$ haloalkyl, aryl, heteroaryl, heterocyclic, aralkyl, aralkoxy, aryloxy, halogen, C$_1$–C$_6$ alkoxy, C$_1$–C$_6$ haloalkoxy, C$_1$–C$_6$ alkylsulfanyl, C$_1$–C$_6$ haloalkylsulfanyl, C$_1$–C$_6$ alkylsulfenyl, C$_1$–C$_6$ alkylsulfonyl, oxo, hydroxy, —NO$_2$, —NR$^4$R$^5$, —C(O)OR$^6$, —CN, —C(O)NR$^4$R$^5$, —S(O)$_2$NR$^4$R$^5$, or cyanoalkyl; or
R$^1$ and R$^2$ together with the phenyl ring atoms to which they are attached form a cyloalkyl or aryl ring fused to the phenyl ring;
R$^3$ is hydrogen, C$_1$–C$_6$ alkyl, aryl, aralkyl, aralkoxy, heteroaryl, heterocyclic, —RR$^6$, —RNR$^4$R$^5$, —C(O) R$^6$, —C(O)NR$^4$R$^5$, —C(O)OR$^6$, —C(O)RO R$^6$, —C(O)RC(O)OR$^6$, —C(O)R R$^6$, —C(O)RR'R$^6$, —C(O)ROR'OR"O R$^6$, —C(O)ROR'O R$^6$, —C(O)RNR$^4$R$^5$, —C(O)RNR$^4$C(O) R$^6$, —C(O)RNR$^4$C(O)OR$^6$, —C(O)ORNR$^4$R$^5$, —S(O)$_2$ R$^6$, or —S(O)$_2$NR$^4$R$^5$; or
R$^3$ is C$_1$–C$_6$ alkylene or C$_1$–C$_6$ alkylene substituted with oxo, and is linked together with the nitrogen to which it is attached and to one of the benzimidazole nitrogens to form a heterocylic compound fused to the benzimidazole;
R, R', and R", are each independently selected from C$_1$–C$_6$ alkylene, arylene, heteroarylene, C$_3$–C$_7$cycloalkylene, or heterocyclylene;
R'" is C$_1$–C$_6$ alkyl, aryl, heteroaryl, aralkyl, C$_3$–C$_7$ cycloalkyl, or heterocyclic;
R$^4$ and R$^5$ are each independently selected from hydrogen, C$_1$–C$_6$ alkyl, C$_1$–C$_6$haloalkyl, C$_1$–C$_6$alkylsulfanyl, C$_1$–C$_6$alkylsulfenyl, C$_1$–C$_6$alkylsulfonyl, aryl, heteroaryl, aralkyl, heterocyclic, C$_3$–C$_7$ cycloalkyl, —C(O)OR$^6$, —C(O)NR'"R'"; —C(O)NR'"H, —C(O)NH$_2$, or —S(O)$_2$NR'"R'";
R$^6$ is hydrogen, C$_1$–C$_6$ alkyl, C$_1$–C$_6$haloalkyl, aryl, heteroaryl, aralkyl, heterocyclic, or C$_3$–C$_7$ cycloalkyl;

R$^7$ is hydrogen, C$_1$–C$_6$ alkyl, —S(O)$_2$ R$^6$, —RNR$^4$R$^5$, —RR$^6$
R$^8$ is hydrogen or halogen; and
when R$^1$ is Cl, R$^2$ is H or Cl, R$^3$ is —C(O)OCH$_3$, A is phenyl, and Z is O, then X is O, S(O), S(O)$_2$, CH$_2$, CH(OH), or C(O).

In a fifth aspect of the present invention, there is provided a compound of formula (IV)

(IV)

or a salt, solvate, or physiologically functional derivative thereof:

wherein:
E is unsubstituted heteroaryl, or
  heteroaryl substituted with R$^1$, or
  heteroaryl substituted by R$^1$ and R$^2$;
A is aryl, heteroaryl, or heterocyclic;
X is S, O, S(O)$_2$, S(O), CH$_2$, CH(OH), or C(O);
Z is O or S;
p is 0 or 1;
q is 0 or 1;
the dotted line bonds "- - -" attached to N' and N" represent a single bond or a double bond wherein when q is 0 the dotted line bond "- - -" attached to N' is a single bond and the dotted line bond attached to N" is a double bond, and when q is 1 the dotted line bond "- - -" attached to N' is a double bond and the dotted line bond attached to N" is a single bond;
R$^1$ is C$_1$–C$_6$ alkyl, C$_1$–C$_6$ haloalkyl, aryl, heteroaryl, heterocyclic, halogen, C$_1$–C$_6$ alkoxy, C$_1$–C$_6$ haloalkoxy, aralkyl, aralkoxy, aryloxy, C$_1$–C$_6$ alkylsulfanyl, C$_1$–C$_6$ haloalkylsulfanyl, C$_1$–C$_6$ alkylsulfenyl, C$_1$–C$_6$ alkylsulfonyl, —NO$_2$, —NR$^4$R$^5$, —C(O)OR$^6$, —CN, —C(O)NR$^4$R$^5$, —S(O)$_2$NR$^4$R$^5$, or cyanoalkyl;
R$^2$ is hydrogen, C$_1$–C$_6$ alkyl, C$_1$–C$_6$ haloalkyl, aryl, heteroaryl, heterocyclic, aralkyl, aralkoxy, aryloxy, halogen, C$_1$–C$_6$ alkoxy, C$_1$–C$_6$ haloalkoxy, C$_1$–C$_6$ alkylsulfanyl, C$_1$–C$_6$ haloalkylsulfanyl, C$_1$–C$_6$ alkylsulfenyl, C$_1$–C$_6$ alkylsulfonyl, oxo, hydroxy, —NO$_2$, —NR$^4$R$^5$, —C(O)OR$^6$, —CN, —C(O)NR$^4$R$^5$, —S(O)$_2$NR$^4$R$^5$, or cyanoalkyl;
R$^3$ is hydrogen, C$_1$–C$_6$ alkyl, aryl, aralkyl, aralkoxy, heteroaryl, heterocyclic, —RR$^6$, —RNR$^4$R$^5$, —C(O) R$^6$, —C(O)NR$^4$R$^5$, —C(O)OR$^6$, —C(O)RO R$^6$, —C(O)RC(O)OR$^6$, —C(O)R R$^6$, —C(O)RR'R$^6$, —C(O)ROR'R"O R$^6$, —C(O)ROR"O R$^6$, —C(O)RNR$^4$R$^5$, —C(O)RNR$^4$C(O) R$^6$, —C(O)RNR$^4$C(O)OR$^6$, —C(O)ORNR$^4$R$^5$, —S(O)$_2$ R$^6$, or —S(O)$_2$NR$^4$R$^5$; or
R$^3$ is C$_1$–C$_6$ alkylene or C$_1$–C$_6$ alkylene substituted with oxo, and is linked together with the nitrogen to which it is attached and to one of the benzimidazole nitrogens to form a heterocylic compound fused to the benzimidazole;
R, R', and R", are each independently selected from C$_1$–C$_6$ alkylene, arylene, heteroarylene, C$_3$–C$_7$cycloalkylene, or heterocyclylene;
R'" is C$_1$–C$_6$ alkyl, aryl, heteroaryl, aralkyl, C$_3$–C$_7$ cycloalkyl, or heterocyclic;

$R^4$ and $R^5$ are each independently selected from hydrogen, $C_1$–$C_6$ alkyl, $C_1$–$C_6$ haloalkyl, $C_1$–$C_6$alkylsulfanyl, $C_1$–$C_6$alkylsulfenyl, $C_1$–$C_6$alkylsulfonyl, aryl, heteroaryl, aralkyl, heterocyclic, $C_3$–$C_7$ cycloalkyl, —C(O)O$R^6$, —C(O)NR'''R''', —C(O)NR'''H, —C(O)NH$_2$, or —S(O)$_2$NR'''R''';

$R^6$ is hydrogen, $C_1$–$C_6$ alkyl, $C_1$–$C_6$ haloalkyl, aryl, heteroaryl, aralkyl, heterocyclic, or $C_3$–$C_7$ cycloalkyl;

$R^7$ is hydrogen, $C_1$–$C_6$ alkyl, —S(O)$_2$ $R^6$, —RNR$^4$R$^5$, —RR$^6$; and $R^8$ is hydrogen or halogen.

In a sixth aspect of the present invention, there is provided a pharmaceutical composition including a therapeutically effective amount of a compound of formula (I), or a salt, solvate, or a physiologically functional derivative thereof and one or more of pharmaceutically acceptable carriers, diluents and excipients.

In a seventh aspect of the present invention, there is provided a method of treating a disorder in a mammal, said disorder being mediated by inappropriate TIE-2 activity, including: administering to said mammal a therapeutically effective amount of a compound of formula (I) or a salt, solvate or a physiologically functional derivative thereof.

In an eighth aspect of the present invention, there is provided a compound of formula (I), or a salt, solvate, or a physiologically functional derivative thereof for use in therapy.

In a ninth aspect of the present invention, there is provided the use of a compound of formula (I), or a salt, solvate, or a physiologically functional derivative thereof in the preparation of a medicament for use in the treatment of a disorder mediated by inappropriate TIE-2 activity.

In a tenth aspect of the present invention, there is provided a method of treating a disorder in a mammal, said disorder being mediated by inappropriate TIE-2 activity, including: administering to said mammal therapeutically effective amounts of (i) a compound of formula (I), or a salt, solvate or physiologically functional derivative thereof and (ii) an agent to inhibit growth factor receptor function.

In an eleventh aspect of the present invention, there is provided a method of treating a disorder in a mammal, said disorder being characterized by inappropriate angiogenesis, including: administering to said mammal a therapeutically effective amount of a compound of formula (I), or a salt, solvate or physiologically functional derivative thereof.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbon having from one to twelve carbon atoms, optionally substituted with substituents selected from the group consisting of $C_1$–$C_6$ alkyl, $C_1$–$C_6$ alkoxy, $C_1$–$C_6$ alkylsulfanyl, $C_1$–$C_6$ alkylsulfenyl, $C_1$–$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$–$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$–$C_6$ alkyl" refers to an alkyl group as defined above containing at least 1, and at most 6, carbon atoms. Examples of branched or straight chained "$C_1$–$C_6$ alkyl" groups useful in the present invention include, but are not limited to, methyl, ethyl, n-propyl, isopropyl, isobutyl, n-butyl, t-butyl, n-pentyl, and isopentyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

As used herein, the term "$C_1$–$C_6$ alkylene" refers to an alkylene group, as defined above, which contains at least 1, and at most 6, carbon atoms respectively. Examples of "$C_1$–$C_6$ alkylene" groups useful in the present invention include, but are not limited to, methylene, ethylene, and n-propylene.

As used herein, the term "halogen" refers to fluorine (F), chlorine (Cl), bromine (Br), or iodine (I).

As used herein, the term "$C_1$–$C_6$ haloalkyl" refers to an alkyl group as defined above containing at least 1, and at most 6, carbon atoms substituted with at least one halogen, halogen being as defined herein. Examples of branched or straight chained "$C_1$–$C_6$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "$C_3$–$C_7$ cycloalkyl" refers to a non-aromatic cyclic hydrocarbon ring having from three to seven carbon atoms and which optionally includes a $C_1$–$C_6$ alkyl linker through which it may be attached. The $C_1$–$C_6$ alkyl group is as defined above. Exemplary "$C_3$–$C_7$ cycloalkyl" groups include, but are not limited to, cyclopropyl, cyclobutyl, cyclopentyl, cyclohexyl and cycloheptyl.

As used herein, the term "$C_3$–$C_7$ cycloalkylene" refers to a non-aromatic alicyclic divalent hydrocarbon radical having from three to seven carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring having one or more degrees of unsaturation containing one or more heteroatomic substitutions selected from S, SO, SO$_2$, O, or N, optionally substituted with substituents selected from the group consisting of C$_1$–C$_6$ alkyl, C$_1$–C$_6$ haloalkyl, C$_1$–C$_6$ alkoxy, C$_1$–C$_6$ alkylsulfanyl, C$_1$–C$_6$ haloalkylsulfanyl, C$_1$–C$_6$ alkylsulfenyl, C$_1$–C$_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or C$_1$–C$_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, SO$_2$, O, or N, optionally substituted with substituents selected from the group which includes lower alkyl lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include C$_1$–C$_6$ alkyl C$_1$–C$_6$ alkoxy, C$_1$–C$_6$ alkylsulfanyl, C$_1$–C$_6$ alkylsulfenyl, C$_1$–C$_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, C$_1$–C$_6$ perfluoroalkyl, heteroaryl, or aryl, multiple degrees of substitution being allowed. Examples of "aryl" groups include, but are not limited to, phenyl, 2-naphthyl, 1-naphthyl, biphenyl, as well as substituted derivatives thereof.

As used herein, the term "arylene" refers to a benzene ring diradical or to a benzene ring system diradical fused to one or more optionally substituted benzene rings, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of "arylene" include, but are not limited to, benzene-1,4-diyl, naphthalene-1,8-diyl, anthracene-1,4-diyl, and the like.

As used herein, the term "aralkyl" refers to an aryl or heteroaryl group, as defined herein, attached through a C$_1$–C$_6$ alkyl linker, wherein C$_1$–C$_6$ alkyl is as defined herein. Examples of "aralkyl" include, but are not limited to, benzyl, phenylpropyl, 2-pyridylmethyl, 3-isoxazolylmethyl, 5-methyl, 3-isoxazolylmethyl, and 2-imidazoyl ethyl.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of C$_1$–C$_6$ alkyl, C$_1$–C$_6$ haloalkyl, C$_1$–C$_6$ alkoxy, C$_1$–C$_6$ alkylsulfanyl, C$_1$–C$_6$ haloalkylsulfanyl, C$_1$–C$_6$ alkylsulfenyl, C$_1$–C$_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, C$_1$–C$_6$ perfluoroalkyl, heteroaryl, or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "heteroarylene" refers to a five—to seven—membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group R$_a$O—, where R$_a$ is alkyl as defined above and the term "C$_1$–C$_6$ alkoxy" refers to an alkoxy group as defined herein wherein the alkyl moiety contains at least 1, and at most 6, carbon atoms. Exemplary C$_1$–C$_6$ alkoxy groups useful in the present invention include, but are not limited to, methoxy, ethoxy, n-propoxy, isopropoxy, n-butoxy, and t-butoxy.

As used herein, the term "haloalkoxy" refers to the group R$_a$O—, where R$_a$ is haloalkyl as defined above and the term "C$_1$–C$_6$ haloalkoxy" refers to an haloalkoxy group as defined herein wherein the haloalkyl moiety contains at least 1, and at most 6, carbon atoms. Exemplary C$_1$–C$_6$ haloalkoxy groups useful in the present invention include, but are not limited to, methoxy, ethoxy, n-propoxy, isopropoxy, n-butoxy, and t-butoxy substituted with one or more halo groups, for instance trifluoromethoxy.

As used herein the term "aralkoxy" refers to the group R$_b$R$_a$O—, where R$_a$ is alkyl and R$_b$ is aryl as defined above.

As used herein the term "aryloxy" refers to the group $R_aO-$, where $R_a$ is aryl as defined above.

As used herein, the term "alkylsulfanyl" refers to the group $R_aS-$, where $R_a$ is alkyl as defined above and the term "$C_1$–$C_6$alkylsulfanyl" refers to an alkylsulfanyl group as defined herein wherein the alkyl moiety contains at least 1, and at most 6, carbon atoms.

As used herein, the term "haloalkylsulfanyl" refers to the group $R_aS-$, where $R_a$ is haloalkyl as defined above and the term "$C_1$–$C_6$ haloalkylsulfanyl" refers to a haloalkylsulfanyl group as defined herein wherein the alkyl moiety contains at least 1, and at most 6, carbon atoms.

As used herein, the term "alkylsulfenyl" refers to the group $R_aS(O)-$, where $R_a$ is alkyl as defined above and the term "$C_1$–$C_6$alkylsulfenyl" refers to an alkylsulfenyl group as defined herein wherein the alkyl moiety contains at least 1, and at most 6, carbon atoms.

As used herein, the term "alkylsulfonyl" refers to the group $R_aSO_2-$, where $R_a$ is alkyl as defined above and the term "$C_1$–$C_6$ alkylsulfonyl" refers to an alkylsulfonyl group as defined herein wherein the alkyl moiety contains at least 1, and at most 6, carbon atoms.

As used herein, the term "oxo" refers to the group =O

As used herein, the term "mercapto" refers to the group —SH.

As used herein, the term "carboxy" refers to the group —COOH.

As used herein, the term "cyano" refers to the group —CN.

As used herein the term "cyanoalkyl" refers to the group —$CNR_a$, wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —$SO_2NH_2$.

As used herein, the term "carbamoyl" refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$— or —$SO_2$—.

As used herein, the term "acyl" refers to the group $R_aC(O)-$, where $R_a$ is alkyl, cycloalkyl, or heterocyclyl as defined herein.

As used herein, the term "aroyl" refers to the group $R_aC(O)-$, where $R_a$ is aryl as defined herein.

As used herein, the term "heteroaroyl" refers to the group $R_aC(O)-$, where $R_a$ is heteroaryl as defined herein.

As used herein, the term "alkoxycarbonyl" refers to the group $R_aOC(O)-$, where $R_a$ is alkyl as defined herein.

As used herein, the term "acyloxy" refers to the group $R_aC(O)O-$, where $R_a$ is alkyl, cycloalkyl, or heterocyclyl as defined herein.

As used herein, the term "aroyloxy" refers to the group $R_aC(O)O-$, where $R_a$ is aryl as defined herein.

As used herein, the term "heteroaroyloxy" refers to the group $R_aC(O)O-$, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or formula (II) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also included within the scope of the invention are the individual isomers of the compounds represented by formulae (I) and (II) above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers of the compounds of formulae (I) or (II) are included within the scope of the compounds of formulae (I) and (II).

It is to be understood that reference to compounds of formula (I) and formula (II) above, following herein, refers to compounds within the scope of formula (I) and formula (II) as defined above with respect to E, X, Z, A, D, M, T, Q, R, $R^1$, $R^2$, $R^3$, $R^4$, $R^5$, $R^6$, $R^7$, or $R^8$ unless specifically limited otherwise. It is also understood that the following embodiments, including uses and compositions, although recited with respect to formula (I) are also applicable to formulae (II), (III), and (IV).

In one embodiment, E is aryl substituted with $R^1$ and $R^2$. In a preferred embodiment, E is phenyl substituted with $R^1$ and $R^2$. In another embodiment, E is unsubstituted heteroaryl, heteroaryl substituted with $R^1$, or heteroaryl substituted with $R^1$ and $R^2$. In a preferred embodiment, E is heteroaryl substituted with $R^1$ or heteroaryl substituted with $R^1$ and $R^2$. In a more preferred embodiment, E is heteroaryl substituted with $R^1$, wherein $R^1$ is preferably $C_1$–$C_6$ alkyl, more preferably —$C(CH_3)_3$, i.e. tert-butyl. In another preferred embodiment, E is selected from

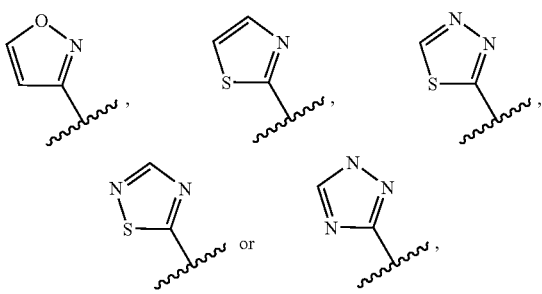

either unsubstituted, substituted by $R^1$ or substituted by $R^1$ and $R^2$.

It is understood that E is attached to the indicated linking group of Formula (I) through the bond of E having an unfilled valence and being indicated by

The appropriate attachments are further illustrated in the working examples recited below.

In another embodiment, E is phenyl and $R^1$ and $R^2$ together with the phenyl ring atoms with which they are attached form a cycloalkyl, preferably cyclopentyl, or aryl, preferably phenyl fused to E.

In one embodiment, the compound of formula (I) is a compound of formula

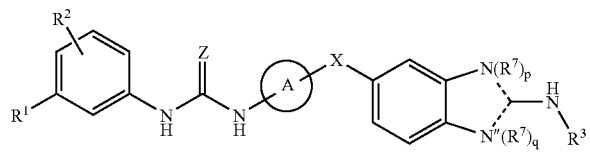

(III)

or salt, solvate, or physiologically functional derivative thereof.

In one embodiment, the compound of formula (I) is a compound of formula (IV):

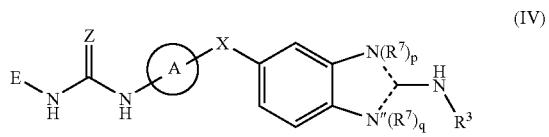

(IV)

wherein E is unsubstituted heteroaryl, heteroaryl substituted with $R^1$, or heteroaryl substituted with $R^1$ and $R^2$, or a salt, solvate, or physiologically functional derivative thereof.

In one embodiment, $R^1$ is $C_1$–$C_6$ alkyl, $C_1$–$C_6$ alkoxy, aryloxy, $C_1$–$C_6$ haloalkyl, $C_1$–$C_6$ haloalkylsulfanyl, $C_1$–$C_6$ alkylsulfanyl, —C(O)$OR^6$, halogen, —CN, or —NO$_2$. In a preferred embodiment, $R^1$ is $C_1$–$C_6$ alkyl, $C_1$–$C_6$ haloalkyl, $C_1$–$C_6$ alkoxy, —NO$_2$, or halogen. In a more preferred embodiment, $R^1$ is —NO$_2$, —OCH$_3$, —CH$_2$CH$_3$, —C(CH$_3$)$_3$, —CF$_3$, —F, —Cl, and —Br. In another preferred embodiment, $R^1$ is $C_1$–$C_6$ haloalkyl, preferably —CF$_3$. In still another preferred embodiment, $R^1$ is $C_1$–$C_6$alkyl, preferably —C(CH$_3$)$_3$.

In one embodiment, $R^2$ is hydrogen, halogen, $C_1$–$C_6$ alkyl, $C_1$–$C_6$ alkoxy, or $C_1$–$C_6$ haloalkyl. In a preferred embodiment, $R^2$ is hydrogen or halogen. In a more preferred embodiment, $R^2$ is hydrogen, —F, —Cl, or —Br. In a most preferred embodiment, $R^2$ is fluorine.

In one embodiment, $R^1$ is $C_1$–$C_6$ alkyl, $C_1$–$C_6$ alkoxy, aryloxy, $C_1$–$C_6$ haloalkyl, $C_1$–$C_6$ haloalkylsulfanyl, $C_1$–$C_6$alkylsulfanyl, —C(O)$OR^6$, halogen, —CN, or NO$_2$and $R^2$ is hydrogen, halogen, $C_1$–$C_6$ alkyl, $C_1$–$C_6$ alkoxy, or $C_1$–$C_6$ haloalkyl. In a preferred embodiment, $R^1$ is $C_1$–$C_6$ haloalkyl and $R^2$ is hydrogen or halogen. In a more preferred embodiment, $R^1$ is NO$_2$, —OCH$_3$, —CH$_2$CH$_3$, —C(CH$_3$)$_3$, —CF$_3$, —F, —Cl, and —Br and $R^2$ is hydrogen, —F, —Cl, or —Br. In a most preferred embodiment, $R^1$ is —CF$_3$ and $R^2$ is fluorine.

In one embodiment Z is S or O. In one embodiment, Z is S. In a preferred embodiment, Z is O.

In one embodiment, A is aryl or heteroaryl. In a preferred embodiment, A is phenyl, 2-pyridyl or 3-pyridyl. In a more preferred embodiment A is phenyl.

In one embodiment, X is S, O, S(O)$_2$, S(O), CH$_2$, CH(OH), or C(O). In a preferred embodiment, X is O or C(O). In a more preferred embodiment, X is O. In another embodiment, X is S.

The side chain —NHC(Z)NHE of the compounds of formula (I) and formula (II) may be linked to any suitable position of the group A. Similarly, the linker group X linking the benzimidazole core to the group A may be linked to any suitable position of the group A. Preferably the group A is linked to the side chain —NHC(Z)NHE and to the linker group X of the benzimidazole core through a (-1,3-) or (-1,4-) linkage. In one preferred embodiment, the group A is linked through a (-1,4-) linkage. In another preferred embodiment, the group A is linked through a (-1,3-) linkage.

The two dotted line bonds represented by "---", which are attached to Q and N' in the five-membered heterocyclic core of Formula I, may represent a single bond or a double bond. When q is 0, the dotted line bond "---" attached to Q is a single bond and the dotted line bond attached to N' is a double bond as illustrated following:

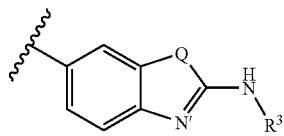

When q is 1, the dotted line bond "---" attached to Q is a double bond and the dotted line bond attached to N' is a single bond as illustrated following:

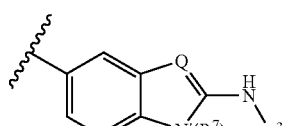

The dotted line within the 6 membered ring containing D, M, and T of Formula I, represents the appropriate aromatic bonds.

In a preferred embodiment, D is CH, T is $CR^8$, M is C and Q is $N(R^7)_p$, wherein p is 0, q is 1, $R^7$ is hydrogen, methyl, or $S(O)_2R^6$ or D is CH, T is $CR^8$, wherein $R^8$ is hydrogen or —Br, M is C and Q is $N(R^7)_p$, wherein p is 1, q is 0, $R^7$ is hydrogen, methyl, —$S(O)_2$ $R^6$, —$NR^4R^5$, —R $R^6$ or aralkyl. In a more preferred embodiment, D is CH, T is $CR^8$, wherein $R^8$ is hydrogen, M is C and Q is $N(R^7)_p$, wherein either p or q is 0, the other is 1 and $R^7$ is hydrogen.

In another embodiment, D is CH, T is $CR^8$, wherein $R^8$ is hydrogen or —Br, M is C and Q is S or O; wherein q is 0. In a further embodiment, D is N, T is $CR^8$, wherein $R^8$ is hydrogen or —Br, M is C and Q is $N(R^7)_p$, wherein either p or q is 0, the other is 1, $R^7$ is hydrogen, methyl, or $S(O)_2R^6$. In an alternative embodiment, D is CH, T is N, M is C and Q is $N(R^7)_p$, wherein either p or q is 0, the other is 1, $R^7$ is hydrogen, methyl, or $S(O)_2R^6$. In a further alternative embodiment, D is CH, T is $CR^8$, wherein $R^8$ is hydrogen or —Br, M is N and Q is CH, wherein q is 0.

In one embodiment, $R^3$ is —$C(O)R^6$, —$C(O)NR^4R^5$, —$C(O)OR^6$, —$C(O)ROR^6$, —$C(O)RC(O)OR^6$, —$C(O)ROR'OR''OR^6$, —$C(O)ROR'OR^6$, —$C(O)NR^4R^5$, —$C(O)RNR^4C(O)R^6$, —$C(O)RNR^4C(O)OR^6$, —$SO_2R^6$, or —$SO_2NR^4R^5$; In a preferred embodiment, $R^3$ is —$C(O)R^6$, —$C(O)NR^4R^5$, or —$C(O)OR^6$. In a more preferred embodiment, $R^3$ is —$C(O)OR^6$. In a most preferred embodiment, $R^3$ is —$C(O)OR^6$ and $R^6$ is methyl.

In one embodiment, A is phenyl; X is O; Z is O; $R^1$ is $C_1$–$C_6$alkyl, $C_1$–$C_6$alkoxy, $C_1$–$C_6$ haloalkyl, or $NO_2$; $R^2$ is hydrogen, halogen, $C_1$–$C_6$ alkyl, or $C_1$–$C_6$alkoxy; and $R^3$ is —$C(O)R$, —$C(O)NR^4R^5$, —$C(O)OR^6$, —$C(O)ROR^6$, —$C(O)RC(O)OR^6$, —$C(O)ROR'OR''OR^6$, —$C(O)ROR'OR^6$, —$C(O)RNR^4R^5$, —$C(O)RNR^4C(O)R^6$, —$C(O)RNR^4C(O)OR^6$, —$SO_2R^6$, or —$SO_2NR^4R^5$. In a preferred embodiment, A is phenyl; X is O; Z is O; $R^1$ is $C_1$–$C_6$ alkyl or $C_1$–$C_6$ haloalkyl; $R^2$ is hydrogen or halogen; and $R^3$ is —$C(O)R^6$, —$C(O)NR^4R^5$, or —$C(O)OR^6$. In a more preferred embodiment, A is phenyl; X is O; Z is O; $R^1$ is $C_1$–$C_6$ haloalkyl; $R^2$ is halogen; and $R^3$ is —$C(O)OR^6$.

In one embodiment, A is phenyl; X is S; Z is O; $R^1$ is $C_1$–$C_6$alkyl, $C_1$–$C_6$alkoxy, $C_1$–$C_6$ haloalkyl, or $NO_2$; $R^2$ is hydrogen, halogen, $C_1$–$C_6$ alkyl, or $C_1$–$C_6$ alkoxy; and $R^3$ is —$C(O)R^6$, —$C(O)NR^4R^5$, —$C(O)OR^6$, —$C(O)ROR^6$, —$C(O)RC(O)OR^6$, —$C(O)ROR'OR''O$ $R^6$, —$C(O)ROR'OR^6$, —$C(O)RNR^4R^5$, —$C(O)RNR^4C(O)R^6$, —$SO_2R^6$, or —$SO_2NR^4R^5$. In a preferred embodiment, A is phenyl; X is S; Z is O; $R^1$ is $C_1$–$C_6$alkyl or $C_1$–$C_6$ haloalkyl; $R^2$ is hydrogen or halogen; and $R^3$ is —$C(O)R^6$ or —$C(O)OR^6$. In a more preferred embodiment, A is phenyl; X is S; Z is O; $R^1$ is $C_1$–$C_6$ haloalkyl; $R^2$ is halogen; and $R^3$ is —$C(O)OR^6$.

In one embodiment, A is pyridyl; X is O; Z is O; $R^1$ is $C_1$–$C_6$ alkyl, $C_1$–$C_6$ alkoxy, $C_1$–$C_6$ haloalkyl, or $NO_2$; $R^2$ is hydrogen, halogen, $C_1$–$C_6$ alkyl, or $C_1$–$C_6$ alkoxy; and $R^3$ is —$C(O)R^6$, —$C(O)NR^4R^5$, —$C(O)OR^6$, —$C(O)ROR^6$, —$C(O)RC(O)OR^6$, —$C(O)ROR'OR''OR^6$, —$C(O)ROR'OR^6$, —$C(O)RNR^4R^5$, —$C(O)RNR^4C(O)R^6$, —$C(O)RNR^4C(O)OR^6$, —$SO_2R^6$, or —$SO_2NR^4R^5$. In a preferred embodiment, A is pyridyl; X is O; Z is O; $R^1$ is $C_1$–$C_6$ alkyl or $C_1$–$C_6$ haloalkyl; $R^2$ is hydrogen or halogen; and $R^3$ is —$C(O)R^6$ or —$C(O)OR^6$. In a more preferred embodiment, A is pyridyl; X is O; Z is O; $R^1$ is $C_1$–$C_6$ haloalkyl; $R^2$ is halogen; and $R^3$ is —$C(O)OR^6$.

In one embodiment, A is pyridyl; X is S; Z is O; $R^1$ is $C_1$–$C_6$ alkyl, $C_1$–$C_6$ alkoxy, $C_1$–$C_6$ haloalkyl, or $NO_2$; $R^2$ is hydrogen, halogen, $C_1$–$C_6$ alkyl, or $C_1$–$C_6$ alkoxy; and $R^3$ is —$C(O)R^6$, —$C(O)NR^4R^5$, —$C(O)OR^6$, —$C(O)ROR^6$, —$C(O)RC(O)OR^6$, —$C(O)ROR'OR''OR^6$, —$C(O)ROR'OR^6$, —$C(O)RNR^4R^5$, —$C(O)RNR^4C(O)R^6$, —$C(O)RNR^4C(O)OR^6$, —$SO_2R^6$, or —$SO_2NR^4R^5$. In a preferred embodiment, A is pyridyl; X is S; Z is O; $R^1$ is $C_1$–$C_6$ alkyl or $C_1$–$C_6$ haloalkyl; $R^2$ is hydrogen or halogen; and $R^3$ is —$C(O)R^6$ or —$C(O)OR^6$. In a more preferred embodiment, A is pyridyl; X is S; Z is O; $R^1$ is $C_1$–$C_6$ haloalkyl; $R^2$ is halogen; and $R^3$ is —$C(O)OR^6$.

In one embodiment, the compound is a compound of formula (IV) where E is unsubstituted heteroaryl, heteroaryl substituted by $R^1$, or heteroaryl substituted by $R^1$ and $R^2$, A is phenyl; X is O; Z is O; $R^1$ is $C_1$–$C_6$ alkyl, aryl, $C_3$–$C_7$cycloalkyl, heterocyclyl, $C_1$–$C_6$haloalkyl, or $C_1$–$C_6$ alkylsulfanyl; $R^2$ is hydrogen, halogen, $C_1$–$C_6$alkyl, or $C_1$–$C_6$haloalkyl; and $R^3$ is —$C(O)R$, —$C(O)NR^4R^5$, —$C(O)OR^6$, —$C(O)ROR^6$, —$C(O)RC(O)OR^6$, —$C(O)ROR'OR''OR^6$, —$C(O)ROR'OR^6$, —$C(O)RNR^4R^5$, —$C(O)RNR^4C(O)R^6$, —$C(O)RNR^4C(O)OR^6$, —$SO_2R^6$, or —$SO_2NR^4R^5$. In a preferred embodiment, E is heteroaryl substituted by $R^1$ or heteroaryl substituted by $R^1$ and $R^2$, A is phenyl; X is O; Z is O; $R^1$ is $C_1$–$C_6$ alkyl; $R^2$ is hydrogen or halogen; and $R^3$ is —$C(O)R^6$, —$C(O)ROR'OR^6$, or —$C(O)OR^6$. In a more preferred embodiment, E is heteroaryl substituted by $R^1$, A is phenyl; X is O; Z is O; $R^1$ is —$C(CH_3)_3$; and $R^3$ is —$C(O)R^6$.

Specific examples of compounds of the present invention include the following:

Methyl N-(5-(4-((3-chlorophenyl)aminocarbonylamino)phenoxy)-1H-benzimidazol-2-yl)carbamate;

Methyl N-(5-(4-((3-(trifluoromethyl)phenyl)aminocarbonylamino)phenylthio)-1H-benzimidazol-2-yl)carbamate;

Methyl N-(5-(4-((3,5-di(trifluoromethyl)phenyl)aminocarbonylamino)phenylthio)-1H-benzimidazol-2-yl)carbamate;

Methyl N-(5-(4-((3-bromophenyl)aminocarbonylamino)phenylthio)-1H-benzimidazol-2-yl)carbamate;

Methyl N-(5-(4-((3,5-dimethoxyphenyl)aminocarbonylamino)phenylthio)-1H-benzimidazol-2-yl)carbamate;

Methyl N-(5-(4-((2-methyl-5-nitrophenyl)aminocarbonylamino)phenylthio)-1H-benzimidazol-2-yl)carbamate;

Methyl N-(5-(4-((3-ethylphenyl)aminocarbonylamino)phenylthio)-1H-benzimidazol-2-yl)carbamate;

Methyl N-(5-(4-((2-fluoro-5-nitrophenyl)aminocarbonylamino)phenylthio)-1H-benzimidazol-2-yl)carbamate;

Methyl N-(5-(4-((2-fluoro-5-(trifluoromethyl)phenyl)aminocarbonylamino)phenylthio)-1H-benzimidazol-2-yl)carbamate;

Methyl N-(5-(4-((2-fluoro-5-(trifluoromethyl)phenyl)aminocarbonylamino)phenoxy)-1H-benzimidazol-2-yl)carbamate;

Methyl N-(5-(4-((3-ethylphenyl)aminocarbonylamino)phenoxy)-1H-benzimidazol-2-yl)carbamate;

Methyl N-(5-(4-((2-fluoro-5-(trifluoromethyl)phenyl)aminocarbonylamino)phenylsulfonyl)-1H-benzimidazol-2-yl)carbamate;

Methyl N-(5-(4-((2-fluoro-5-(trifluoromethyl)phenyl)aminocarbonylamino) phenylsulfinyl)-1H-benzimidazol-2-yl)carbamate;

Methyl (5-(3-((3-chlorophenyl)aminocarbonylamino)phenoxy)-1H-benzimidazol-2-yl)carbamate;

Methyl N-(5-(3-((2-Fluoro-5-(trifluoromethyl)phenyl)aminocarbonylamino)phenoxy)-1H-benzimidazol-2-yl)carbamate;

Methyl N-(5-(3-((3-ethylphenyl)aminocarbonylamino)phenoxy)-1H-benzimidazol-2-yl)carbamate;

Ethyl N-(5-(4-((2-fluoro-5-(trifluoromethyl)phenyl)aminocarbonylamino)phenoxy)-1H-benzimidazol-2-yl)carbamate;

T-butyl N-(5-(4-((2-fluoro-5-(trifluoromethyl)phenyl)aminocarbonylamino)phenoxy)-1H-benzimidazol-2-yl)carbamate;
Methyl N-(5-(4-((3-(trifluoromethyl)phenyl)aminocarbonylamino)phenoxy)-1H-benzimidazol-2-yl)carbamate;
Methyl N-(5-(3-((3-(trifluoromethyl)phenyl)aminocarbonylamino)phenoxy)-1H-benzimidazol-2-yl)carbamate;
Methyl N-(5-(4-((3-t-butylphenyl)aminocarbonylamino)phenoxy)-1H-benzimidazol-2-yl)carbamate;
2-Amino-5-(4-((2-fluoro-5-(trifluoromethyl)phenyl)aminocarbonylamino)phenoxy)-1H-benzimidazole;
(6-(4-((2-Fluoro-5-(trifluoromethyl)phenyl)aminocarbonylamino)phenoxy)-1-(methanesulfonyl)-1H-benzimidazol-2-ylamine;
6-(4-((2-Fluoro-5-(trifluoromethyl)phenyl)aminocarbonylamino)phenoxy)-1-(4-(methyl)phenylsulfonyl)-1H-benzimidazol-2-ylamine;
N-(5-(4-((2-fluoro-5-(trifluoromethyl)phenyl)aminocarbonylamino)phenoxy)-1H-benzimidazol-2-yl)acetamide;
N-(5-(4-((2-fluoro-5-(trifluoromethyl)phenyl)aminocarbonylamino)phenoxy)-1H-benzimidazol-2-yl)cyclopentamide;
N-(5-(4-((2-fluoro-5-(trifluoromethyl)phenyl)aminocarbonylamino)phenoxy)-1H-benzimidazol-2-yl)(2-furyl)formamide;
N-(5-(4-((2-fluoro-5-(trifluoromethyl)phenyl)aminocarbonylamino)phenoxy)-1H-benzimidazol-2-yl)-4-methylpentamide;
N-(5-(4-((2-fluoro-5-(trifluoromethyl)phenyl)aminocarbonylamino)phenoxy)-1H-benzimidazol-2-yl)-2-(N-acetylamino)acetamide;
N-(5-(4-((2-fluoro-5-(trifluoromethyl)phenyl)aminocarbonylamino)phenoxy)-1H-benzimidazol-2-yl)-2-aminoacetamide;
N-(5-(4-((2-fluoro-5-(trifluoromethyl)phenyl)aminocarbonylamino)phenoxy)-1H-benzimidazol-2-yl)-2-methoxyacetamide;
3-(N-(5-(4-((2-fluoro-5-(trifluoromethyl)phenyl)aminocarbonylamino)phenoxy)-1H-benzimidazol-2-yl)carbamoyl)propionic acid;
N-(5-(4-((2-fluoro-5-(trifluoromethyl)phenyl)aminocarbonylamino)phenoxy)-1H-benzimidazol-2-yl)(2-(2-(methoxy)ethoxy)ethoxy)acetamide;
N-(5-(4-((2-fluoro-5-(trifluoromethyl)phenyl)aminocarbonylamino)phenoxy)-1H-benzimidazol-2-yl)(2-(methoxy)ethoxy)acetamide;
N-(5-(4-((2-fluoro-5-(trifluoromethyl)phenyl)aminocarbonylamino)phenoxy)-1H-benzimidazol-2-yl)-2-(N-(t-butoxycarbony)amino)acetamide;
N-(5-(2-((2-fluoro-5-(trifluoromethyl)phenyl)aminocarbonylamino)-5-pyridyloxy)-1H-benzimidazol-2-yl)acetamide;
Methyl N-(5-(5-((2-fluoro-5-(trifluoromethyl)phenyl)aminocarbonylamino)-2-pyridyloxy)-1H-benzimidazol-2-yl)carbamate;
Methyl N-(5-(5-((3-(trifluoromethyl)phenyl)aminocarbonylamino)-2-pyridyloxy)-1H-benzimidazol-2-yl)carbamate; and
Methyl N-(5-(5-((3-ethylphenyl)aminocarbonylamino)-2-pyridyloxy)-1H-benzimidazol-2-yl)carbamate;

or a salt, solvate, or physiologically functional derivative thereof.

Further specific Examples of compounds of the present invention include:
Methyl N-(5-(4-((3-bromophenyl)aminocarbonylamino)phenoxy)-1H-benzimidazol-2-yl)carbamate;
Methyl N-(5-(4-((3-(trifluoromethylthio)phenyl)aminocarbonylamino)phenoxy)-1H-benzimidazol-2-yl)carbamate;
Methyl N-(5-(4-((2,5-dimethoxyphenyl)aminocarbonylamino)phenoxy)-1H-benzimidazol-2-yl)carbamate;
Methyl N-(5-(4-((2-chloro-5-(trifluoromethyl)phenyl)aminocarbonylamino)phenoxy)-1H-benzimidazol-2-yl)carbamate;
Methyl N-(5-(4-((4-chloro-3-(trifluoromethyl)phenyl)aminocarbonylamino)phenoxy)-1H-benzimidazol-2-yl)carbamate;
Methyl N-(5-(4-((2,5-dichlorophenyl)aminocarbonylamino)phenoxy)-1H-benzimidazol-2-yl)carbamate;
Methyl N-(5-(4-((2-fluoro-5-nitrophenyl)aminocarbonylamino)phenoxy)-1H-benzimidazol-2-yl)carbamate;
Methyl N-(5-(4-((2-methyl-5-nitrophenyl)aminocarbonylamino)phenoxy)-1H-benzimidazol-2-yl)carbamate;
Methyl N-(5-(4-(3-methylthiophenyl)aminocarbonylamino)phenoxy)-1H-benzimidazol-2-yl)carbamate;
Methyl N-(5-(4-(3-cyanophenyl)aminocarbonylamino)phenoxy)-1H-benzimidazol-2-yl)carbamate;
Methyl N-(5-(4-((3-fluoro-5-(trifluoromethyl)phenyl)aminocarbonylamino)phenoxy)-1H-benzimidazol-2-yl)carbamate;
Methyl N-(5-(4-((2-chloro-5-(trifluoromethyl)phenyl)aminocarbonylamino)phenylthio)-1H-benzimidazol-2-yl)carbamate;
Methyl N-(5-(3-((2-chloro-5-(trifluoromethyl)phenyl)aminocarbonylamino)phenoxy)-1H-benzimidazol-2-yl)carbamate;
Methyl N-(5-(4-((3-ethoxycarbonylphenyl)aminocarbonylamino)phenoxy)-1H-benzimidazol-2-yl)carbamate;
Methyl N-(5-(4-((3-carboxyphenyl)aminocarbonylamino)phenoxy)-1H-benzimidazol-2-yl)carbamate;
Methyl N-(5-(4-((2-fluoro-5-methylphenyl)aminocarbonylamino)phenoxy)-1H-benzimidazol-2-yl)carbamate;
Methyl N-(5-(4-((2,5-difluorophenyl)aminocarbonylamino)phenoxy)-1H-benzimidazol-2-yl)carbamate;
Methyl N-(5-(4-((2,5-dichlorophenyl)aminocarbonylamino)phenylthio)-1H-benzimidazol-2-yl)carbamate;
Methyl N-(5-(3-((3-(trifluoromethylthio)phenyl)aminocarbonylamino)phenoxy)-1H-benzimidazol-2-yl)carbamate;
Methyl N-(5-(3-((3-bromophenyl)aminocarbonylamino)phenoxy)-1H-benzimidazol-2-yl)carbamate;
Methyl N-(5-(3-((3-(phenoxy)phenyl)aminocarbonylamino)phenoxy)-1H-benzimidazol-2-yl)carbamate;
Methyl N-(5-(3-((4-chlorophenyl)aminocarbonylamino)phenoxy)-1H-benzimidazol-2-yl)carbamate;
Methyl N-(5-(4-((4-methoxyphenyl)aminocarbonylamino)phenoxy)-1H-benzimidazol-2-yl)carbamate;
Methyl N-(5-(4-((4-fluorophenyl)aminocarbonylamino)phenoxy)-1H-benzimidazol-2-yl)carbamate;
Methyl N-(6-(4-((6-fluoro-3-(trifluoromethyl)phenyl)aminocarbonylamino)phenoxy)benzthiazol-2-yl)carbamate;
Methyl N-(4-bromo-6-(4-((6-fluoro-3-(trifluoromethyl)phenyl)aminocarbonylamino)phenoxy)benzthiazol-2-yl)carbamate;
Methyl N-(6-(4-((2-fluoro-5-(trifluoromethyl)phenyl)aminocarbonylamino)phenoxy)-1-methyl-1H-benzimidazol-2-yl)carbamate;
Methyl N-(5-(4-((2-fluoro-5-(trifluoromethyl)phenyl)aminocarbonylamino)phenoxy)-1-methyl-1H-benzimidazol-2-yl)carbamate;
Methyl N-(5-(4-((2-fluoro-5-(trifluoromethyl)phenyl)aminocarbonylamino)phenoxy)-3a-aza-2-indolyl)carbamate;
Methyl N-(5-(4-((2-fluoro-5-(trifluoromethyl)phenyl)aminocarbonylamino)phenoxy)-3,4-diazaindolin-2-yl)carbamate;

Methyl N-(6-(4-((2-fluoro-5-(trifluoromethyl)phenyl)aminocarbonylamino)phenoxy)-1-(2-(dimethylamino)ethyl)-1H-benzimidazol-2-yl)carbamate
Methyl N-(6-(4-((2-fluoro-5-(trifluoromethyl)phenyl)aminocarbonylamino)phenoxy)-1-(2-(4-morpholino)ethyl)-1H-benzimidazol-2-yl)carbamate;
Methyl N-(5-(4-((2-chloro-5-(trifluoromethyl)phenyl)aminocarbonylamino)phenoxy)-3,4-diaza-1H-indole-2-yl)carbamate;
Methyl N-(6-(4-((2-chloro-5-(trifluoromethyl)phenyl)aminocarbonylamino)phenoxy)-3,4-diaza-1H-indole-2-yl)carbamate;
Methyl N-(5-(4-((2,5-dichlorophenyl)aminocarbonylamino)phenoxy)-3,4-diaza-1H-indole-2-yl)carbamate;
Methyl N-(6-(4-((2-fluoro-5-(trifluoromethyl)phenyl)aminocarbonylamino)phenoxy)-3,4-diaza-1H-indole-2-yl)carbamate;
Methyl N-(6-(4-((2-chloro-5-(trifluoromethyl)phenyl)aminocarbonylamino)phenoxy)benzthiazol-2-yl)carbamate;
6-(4-((2-Fluoro-5-(trifluoromethyl)phenyl)aminocarbonylamino)phenoxy)-3,4-dihydro-1,4a,5-triazacarbazol-2-one;
Methyl N-(5-(4-((2-fluoro-5-(trifluoromethyl)phenyl)aminocarbonylamino)phenylcarbonyl)-1H-benzimidazol-2-yl)carbamate;
Methyl N-(5-(4-((2,5-dichlorophenyl)aminocarbonylamino)phenylsulfinyl)-1H-benzimidazol-2-yl)carbamate;
2-(Dimethylamino)ethyl N-(5-(4-((2-fluoro-5-(trifluoromethyl)phenyl)aminocarbonylamino)phenoxy)-1H-benzimidazol-2-yl)carbamate;
Benzyl N-(5-(4-((2-fluoro-5-(trifluoromethyl)phenyl)aminocarbonylamino)phenoxy)-1H-benzimidazol-2-yl)carbamate;
5-(4-((2-Fluoro-5-(trifluoromethyl)phenyl)aminocarbonylamino)phenoxy)-1-(methanesulfonyl)-1H-benzimidazol-2-ylamine;
N-(5-(4-((2-Fluoro-5-(trifluoromethyl)phenyl)aminocarbonylamino)phenoxy)-1H-benzimidazol-2-yl)methanesulfonamide;
5-(4-((2-Fluoro-5-(trifluoromethyl)phenyl)aminocarbonylamino)phenoxy)-1-(4-(methyl)phenylsulfonyl)-1H-benzimidazol-2-ylamine;
N-(5-(4-((2-Fluoro-5-(trifluoromethyl)phenyl)aminocarbonylamino)phenoxy)-1H-benzimidazol-2-yl)-4-methylbenzenesulfonamide;
N-(6-(4-((2-Fluoro-5-(trifluoromethyl)phenyl)aminocarbonylamino)phenoxy)benzthiazol-2-yl)methanesulfonamide;
N-(5-(4-((2-Fluoro-5-(trifluoromethyl)phenyl)aminocarbonylamino)phenoxy)-1H-benzimidazol-2-yl)-4-(4-methyl-1-piperazinomethyl)benzamide;
N-(5-(4-((2-Fluoro-5-(trifluoromethyl)phenyl)aminocarbonylamino)phenoxy)-1H-benzimidazol-2-yl)-3-(pyridine-3-yl)propionamide;
N-(5-(4-((2-Fluoro-5-(trifluoromethyl)phenyl)aminocarbonylamino)phenoxy)-1H-benzimidazol-2-yl)-5-benzimidazolecarboxamide;
N-(5-(4-((2-Fluoro-5-(trifluoromethyl)phenyl)aminocarbonylamino)phenoxy)-1H-benzimidazol-2-yl)-4-(pyrrol-1-yl)benzamide;
N-(5-(4-((2-Fluoro-5-(trifluoromethyl)phenyl)aminocarbonylamino)phenoxy)-1H-benzimidazol-2-yl)-4-(1H-imidazol-1-yl)benzamide;
N-(5-(4-((2-Fluoro-5-(trifluoromethyl)phenyl)aminocarbonylamino)phenoxy)-1H-benzimidazol-2-yl)-4-(dimethylamino)butylamide;
N-(5-(4-((2-Fluoro-5-(trifluoromethyl)phenyl)aminocarbonylamino)phenoxy)-1H-benzimidazol-2-yl)-3-pyridinecarboxamide;
N-(5-(4-((2-Fluoro-5-(trifluoromethyl)phenyl)aminocarbonylamino)phenoxy)-1H-benzimidazol-2-yl)-2-tetrahydrofurancarboxamide;
N-(5-(4-((2-Fluoro-5-(trifluoromethyl)phenyl)aminocarbonylamino)phenoxy)-1H-benzimidazol-2-yl)(1H-indole-3-carboxamide);
N-(5-(4-((2-Fluoro-5-(trifluoromethyl)phenyl)aminocarbonylamino)phenoxy)-1H-benzimidazol-2-yl)(5-(1-pyrrolidino)tetrazol-2-yl)acetamide;
N-(5-(4-((2-Fluoro-5-(trifluoromethyl)phenyl)aminocarbonylamino)phenoxy)-1H-benzimidazol-2-yl)(1-methyl-1H-imidazol-4-yl)acetamide;
N-(5-(4-((2-Fluoro-5-(trifluoromethyl)phenyl)aminocarbonylamino)phenoxy)-1H-benzimidazol-2-yl)(1H-imidazole-4-carboxamide);
N-(5-(4-((2-Fluoro-5-(trifluoromethyl)phenyl)aminocarbonylamino)phenoxy)-1H-benzimidazol-2-yl)benzamide;
N-(5-(4-((2-Fluoro-5-(trifluoromethyl)phenyl)aminocarbonylamino)phenoxy)-1H-benzimidazol-2-yl)-2-thiophenecarboxamide;
N-(5-(4-((2-Fluoro-5-(trifluoromethyl)phenyl)aminocarbonylamino)phenoxy)-1H-benzimidazol-2-yl)(4-methyl-1-piperazino)acetamide;
N-(5-(4-((2-Fluoro-5-(trifluoromethyl)phenyl)aminocarbonylamino)phenoxy)-1H-benzimidazol-2-yl)(dimethylamino)acetamide;
6-(4-((2-Fluoro-5-(trifluoromethyl)phenyl)aminocarbonylamino)phenoxy)-3,4-dihydro-1,4a-diazacarbazol-2-one;
7-(4-((2-Fluoro-5-(trifluoromethyl)phenyl)aminocarbonylamino)phenoxy)-3,4-dihydro-1,4a-diazacarbazol-2-one;
2-(2-(4-Methyl-1-piperazino)ethylamino)-5-(4-((2-Fluoro-5-(trifluoromethyl)phenyl)aminocarbonylamino)phenoxy)-1H-benzimidazole;
2-(2-(Dimethylamino)ethylamino)-5-(4-((2-Fluoro-5-(trifluoromethyl)phenyl)aminocarbonylamino)phenoxy)-1H-benzimidazole;
2-(3-(4-Methyl-1-piperazino)propylamino)-5-(4-((2-Fluoro-5-(trifluoromethyl)phenyl)aminocarbonylamino)phenoxy)-1H-benzimidazole;
Methyl N-(5-(5-((2-fluoro-5-(trifluoromethyl)phenyl)aminocarbonylamino)-1-oxo-2-pyridyloxy)-1H-benzimidazol-2-yl)carbamate;
N-(6-(2-((2-fluoro-5-(trifluoromethyl)phenyl)aminocarbonylamino)-5-pyridyloxy)-1-benzyl-1H-benzimidazol-2-yl)acetamide;
Methyl N-(5-(5-((2-chloro-5-(trifluoromethyl)phenyl)aminocarbonylamino)-2-pyridyloxy)-1H-benzimidazol-2-yl)carbamate;
Methyl N-(5-(5-((2,5-dichlorophenyl)aminocarbonylamino)-2-pyridyloxy)-1H-benzimidazol-2-yl)carbamate;
6-(6-((2-Fluoro-5-(trifluoromethyl)phenyl)aminocarbonylamino)-3-pyridyloxy)-1-benzyl-1H-benzimidazol-2-ylamine;
N-(6-(6-((2-Fluoro-5-(trifluoromethyl)phenyl)aminocarbonylamino)-3-pyridyloxy)-1-benzyl-1H-benzimidazol-2-yl)methanesulfonamide; and
Methyl N-(6-(4-((2-Fluoro-5-(trifluoromethyl)phenyl)aminocarbonylamino)phenoxy)benzoxazol-2-yl)carbamate;

or a salt, solvate, or physiologically functional derivative thereof.

Additional further specific Examples of compounds of the present invention include:

Methyl N-(5-(3-((2-(trifluoromethoxy)phenyl)aminocarbonylamino)phenoxy)-1H-benzimidazol-2-yl)carbamate;
Methyl N-(5-(3-((4-(trifluoromethylthio)phenyl)aminocarbonylamino)phenoxy)-1H-benzimidazol-2-yl)carbamate;
Methyl N-(5-(3-((2-(trifluoromethyl)phenyl)aminocarbonylamino)phenoxy)-1H-benzimidazol-2-yl)carbamate;
Methyl N-(5-(3-((4-chloro-3-(trifluoromethyl)phenyl)aminocarbonylamino)phenoxy)-1H-benzimidazol-2-yl)carbamate;
Methyl N-(5-(3-((3-iodophenyl)aminocarbonylamino)phenoxy)-1H-benzimidazol-2-yl)carbamate; Methyl N-(5-(3-((2,5-dichlorophenyl)aminocarbonylamino)phenoxy)-1H-benzimidazol-2-yl)carbamate;
Methyl N-(5-(4-((3-phenoxyphenyl)aminocarbonylamino)phenylthio)-1H-benzimidazol-2-yl)carbamate;
Methyl N-(5-(4-((3-phenoxyphenyl)aminocarbonylamino)phenoxy)-1H-benzimidazol-2-yl)carbamate;
Methyl N-(5-(3-((2-phenoxyphenyl)aminocarbonylamino)phenoxy)-1H-benzimidazol-2-yl)carbamate;
Methyl N-(5-(3-((4-phenoxyphenyl)aminocarbonylamino)phenoxy)-1H-benzimidazol-2-yl)carbamate;
Methyl N-(5-(3-((5-indanyl)aminocarbonylamino)phenoxy)-1H-benzimidazol-2-yl)carbamate;
Methyl N-(5-(4-((5-indanyl)aminocarbonylamino)phenoxy)-1H-benzimidazol-2-yl)carbamate;
Methyl N-(5-(4-((5-tert-butylisoxazole-3-yl)aminocarbonylamino)phenoxy)-1H-benzimidazol-2-yl)carbamate;
Methyl N-(5-(3-((5-tert-butylisoxazole-3-yl)aminocarbonylamino)phenoxy)-1H-benzimidazol-2-yl)carbamate;
Methyl N-(5-(4-((5-tert-butylisoxazole-3-yl)aminocarbonylamino)phenylthio)-1H-benzimidazol-2-yl)carbamate;
Methyl N-(5-(3-((3-phenyl-1,2,4-thiadiazol-5-yl)aminocarbonylamino)phenoxy)-1H-benzimidazol-2-yl)carbamate;
Methyl N-(5-(3-((1-naphtyl)aminocarbonylamino)phenoxy)-1H-benzimidazol-2-yl)carbamate;
Methyl N-(5-(3-((2,3-dimethylphenyl)aminocarbonylamino)phenoxy)-1H-benzimidazol-2-yl)carbamate;
1-(5-(4-((2-Fluoro-5-(trifluoromethyl)phenyl)aminocarbonylamino)phenoxy)-1H-benzimidazol-2-yl)-3-(2-fluoro-5-(trifluoromethyl)phenyl)urea;
1-(5-(4-((2-Fluoro-5-(trifluoromethyl)phenyl)aminocarbonylamino)phenoxy)-1H-benzimidazol-2-yl)-3-(4-chlorophenyl)urea;
1-(5-(4-((2-Fluoro-5-(trifluoromethyl)phenyl)aminocarbonylamino)phenoxy)-1H-benzimidazol-2-yl)-3-4-(N,N dimethylamino)phenyl)urea;
1-(6-(4-((4Chloro-3-(trifluoromethyl)phenyl)aminocarbonylamino)phenoxy)benzthiazol-2-yl)-3-(butyl)urea;
1-(6-(4-((2-Fluoro-5-(trifluoromethyl)phenyl)aminocarbonylamino)phenoxy)benzthiazol-2-yl)-3-(butyl)urea;
N-(5-(4-((5-Methylisoxazol-3-yl)aminocarbonylamino)phenoxy)-1H-benzimidazol-2-yl)acetamide;
N-(5-(4-(Thiazol-2-yl)aminocarbonylamino)phenoxy)-1H-benzimidazol-2-yl)acetamide;
N-(5-(4-((1,3,4-Thiadiazol-2-yl)aminocarbonylamino)phenoxy)-1H-benzimidazol-2-yl)acetamide;
N-(5-(4-((4-Methylthiazol-2-yl)aminocarbonylamino)phenoxy)-1H-benzimidazol-2-yl)acetamide;
N-(5-(4-((5-Methylthiazol-2-yl)aminocarbonylamino)phenoxy)-1H-benzimidazol-2-yl)acetamide;
N-(5-(4-((5-Methyl-1,3,4-thiadiazol-2-yl)aminocarbonylamino)phenoxy)-1H-benzimidazol-2-yl)acetamide;
N-(5-(4-((5-Ethyl-1,3,4-thiadiazol-2-yl)aminocarbonylamino)phenoxy)-1H-benzimidazol-2-yl)acetamide;
N-(5-(4-((5-Cyclopropyl-1,3,4-thiadiazol-2-yl)aminocarbonylamino)phenoxy)-1H-benzimidazol-2-yl)acetamide;
N-(5-(4-((4-tert-Butyl-thiazol-2-yl)aminocarbonylamino)phenoxy)-1H-benzimidazol-2-yl)acetamide;
N-(5-(4-((5-tert-Butyl-1,3,4-thiadiazol-2-yl)aminocarbonylamino)phenoxy)-1H-benzimidazol-2-yl)acetamide;
N-(5-(4-((4,5-Dimethylthiazol-2-yl)aminocarbonylamino)phenoxy)-1H-benzimidazol-2-yl)acetamide;
N-(5-(4-((5-Morpholino-1,3,4-triazol-2-yl)aminocarbonylamino)phenoxy)-1H-benzimidazol-2-yl)acetamide;
N-(5-(4-((5-Methylisoxazol-3-yl)aminocarbonylamino)phenoxy)-1H-benzimidazol-2-yl)(2-(methoxy)ethoxy)acetamide;
N-(5-(4-((Thiazol-2-yl)aminocarbonylamino)phenoxy)-1H-benzimidazol-2-yl)(2-(methoxy)ethoxy)acetamide;
N-(5-(4-((1,3,4Thiadiazol-2-yl)aminocarbonylamino)phenoxy)-1H-benzimidazol-2-yl)(2-(methoxy)ethoxy)acetamide;
N-(5-(4-((4-Methylthiazol-2-yl)aminocarbonylamino)phenoxy)-1H-benzimidazol-2-yl)(2-(methoxy)ethoxy)acetamide;
N-(5-(4-((5-Methylthiazol-2-yl)aminocarbonylamino)phenoxy)-1H-benzimidazol-2-yl)(2-(methoxy)ethoxy)acetamide;
N-(5-(4-((5-Methyl-1,3,4-thiadiazol-2-yl)aminocarbonylamino)phenoxy)-1H-benzimidazol-2-yl)(2-(methoxy)ethoxy)acetamide;
N-(5-(4-((5-Ethyl-1,3,4-thiadiazol-2-yl)aminocarbonylamino)phenoxy)-1H-benzimidazol-2-yl)(2-(methoxy)ethoxy)acetamide;
N-(5-(4-((5-Cyclopropyl-1,3,4-thiadiazol-2-yl)aminocarbonylamino)phenoxy)-1H-benzimidazol-2-yl)(2-(methoxy)ethoxy)acetamide;
N-(5-(4-((4-tert-Butyl-thiazol-2-yl)aminocarbonylamino)phenoxy)-1H-benzimidazol-2-yl)(2-(methoxy)ethoxy)acetamide;
N-(5-(4-((5-tert-Butyl 1,3,4-thiadiazol-2-yl)aminocarbonylamino)phenoxy)-1H-benzimidazol-2-yl)(2-(methoxy)ethoxy)acetamide;
N-(5-(4-((5-Ethylthio-1,3,4-thiadiazol-2-yl)aminocarbonylamino)phenoxy)-1H-benzimidazol-2-yl)(2-(methoxy)ethoxy)acetamide;
N-(5-(4-((5-Propylthio-1,3,4-thiadiazol-2-yl)aminocarbonylamino)phenoxy)-1H-benzimidazol-2-yl)(2-(methoxy)ethoxy)acetamide;
N-(5-(4-((4,5-Dimethylthiazol-2-yl)aminocarbonylamino)phenoxy)-1H-benzimidazol-2-yl)(2-(methoxy)ethoxy)acetamide;
N-(5-(4-((5-Morpholino-1,3,4-triazol-2-yl)aminocarbonylamino)phenoxy)-1H-benzimidazol-2-yl)(2-(methoxy)ethoxy)acetamide;
N-(5-(4-((5-Methylisoxazol-3-yl)aminocarbonylamino)phenoxy)-1H-benzimidazol-2-yl)(2-furyl)formamide;
N-(5-(4-((Thiazol-2-yl)aminocarbonylamino)phenoxy)-1H-benzimidazol-2-yl)(2furyl)formamide;
N-(5-(4-((1,3,4-Thiadiazol-2-yl)aminocarbonylamino)phenoxy)-1H-benzimidazol-2-yl)(2-furyl)formamide;
N-(5-(4-((4-Methylthiazol-2-yl)aminocarbonylamino)phenoxy)-1H-benzimidazol-2-yl)(2-furyl)formamide;
N-(5-(4-((5-Methylthiazol-2-yl)aminocarbonylamino)phenoxy)-1H-benzimidazol-2-yl)(2-furyl)formamide;
N-(5-(4-((5-Methyl-1,3,4-thiadiazol-2-yl)aminocarbonylamino)phenoxy)-1H-benzimidazol-2-yl)(2-furyl)formamide;
N-(5-(4-((5-Ethyl-1,3,4-thiadiazol-2-yl)aminocarbonylamino)phenoxy)-1H-benzimidazol-2-yl)(2furyl)formamide;

N-(5-(4-((5-Cyclopoyl-1,3,4-thiadiazol-2-yl)aminocarbonylamino)phenoxy)-1H-benzimidazol-2-yl)(2-furyl)formamide;

N-(5-(4-((4-tert-Butylthiazol-2-yl)aminocarbonylamino)phenoxy)-1H-benzimidazol-2-yl)(2-furyl)formamide;

N-(5-(4-((5-tert-Butyl-1,3,4-thiadiazol-2-yl)aminocarbonylamino)phenoxy)-1H-benzimidazol-2-yl)(2-furyl)formamide;

N-(5-(4-((5-Ethylthio-1,3,4-thiadiazol-2-yl)aminocarbonylamino)phenoxy)-1H-benzimidazol-2-yl)(2-furyl)formamide;

N-(5-(4-((4,5-Dimethylthiazol-2-yl)aminocarbonylamino)phenoxy)-1H-benzimidazol-2-yl)(2-furyl)formamide;

N-(5-(4-((5-Morpholino-1,3,4-triazol-2-yl)aminocarbonylamino)phenoxy)-1H-benzimidazol-2-yl)(2-furyl)formamide;

N-(5-(4-(5-Methylthio-1,3,4-thiadiazol-2-yl)aminocarbonylamino)phenoxy)-1H-benzimidazol-2-yl)acetamide;

N-(5-(4-((5-Methylthio-1,3,4-thiadiazol-2-yl)aminocarbonylamino)phenoxy)-1H-benzimidazol-2-yl)(2-(methoxy)ethoxy)acetamide;

N-(5-(4-((5-Methylthio-1,3,4-thiadiazol-2-yl)aminocarbonylamino)phenoxy)-1H-benzimidazol-2-yl)(2-furyl)formamide;

N-(5-(4-((5-Carbamoyl-2-methylphenyl)aminocarbonylamino)phenoxy)-1H-benzimidazol-2-yl)(2-furyl)formamide;

Methyl N-(5-(3-((2,3-dichlorophenyl)aminocarbonylamino)phenoxy)-1H-benzimidazol-2-yl)carbamate;

Methyl N-(5-(3-((2,3-dimethylphenyl)aminocarbonylamino)phenoxy)-1H-benzimidazol-2-yl)carbamate;

1-(5-(4-((2-Fluoro-5-(trifluoromethyl)phenyl)aminocarbonylamino)phenoxy)-1H-benzimidazol-2-yl)-3-(2,3-dimethylphenyl)urea;

Methyl N-(5-(4-((3-chlorophenyl)aminothiocarbonylamino)phenoxy)-1H-benzimidazol-2-yl)carbamate;

Methyl N-(5-(4-((3-methoxyphenyl)aminothiocarbonylamino)phenoxy)-1H-benzimidazol-2-yl)carbamate; and Methyl N-(5-(4-((3-(trifluoromethyl)phenyl)aminothiocarbonylamino)phenoxy)-1H-benzimidazol-2-yl)carbamate;

or a salt, solvate, or physiologically functional derivative thereof.

Typically, the salts of the present invention are pharmaceutically acceptable salts. Salts encompassed within the term "pharmaceutically acceptable salts" refer to. non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula I include the following:

(1) cell cycle specific anti-neoplastic agents include, but are not limited to diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, irinotecan, CPT-11 and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents include, but are not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR, and TIE-2 (other than those VEGFR and TIE-2 inhibitors described in the present invention); and other tyrosine kinase inhibitors such as inhibitors of CDK2 and CDK4 inhibitors.

The compounds of formula (I) and salts, solvates and physiological functional derivatives thereof, are believed to have anticancer activity as a result of inhibition of the protein kinase TIE-2 and its effect on selected cell lines whose growth is dependent on TIE-2 protein kinase activity.

The present invention thus also provides compounds of formula (I) and pharmaceutically acceptable salts or solvates thereof, or physiologically functional derivatives thereof, for use in medical therapy, and particularly in the treatment of disorders mediated by inappropriate TIE-2 activity.

The inappropriate TIE-2 activity referred to herein is any TIE-2 activity that deviates from the normal TIE-2 activity expected in a particular mammalian subject. Inappropriate TIE-2 activity may take the form of, for instance, an abnormal increase in activity, or an aberration in the timing and or control of TIE-2 activity. Such inappropriate activity may result then, for example, from overexpression or mutation of the protein kinase leading to inappropriate or uncontrolled activation. Furthermore, it is also understood that unwanted TIE-2 activity may reside in an abnormal source, such as a malignancy. That is, the level of TIE-2 activity does not have to be abnormal to be considered inappropriate, rather the activity derives from an abnormal source. In a like manner, the inappropriate angiogenesis referred to herein is any angiogenic activity that deviates from the normal angiogenic activity expected in a particular mammalian subject Inappropriate angiogenesis may take the form of, for instance, an abnormal increase in activity, or an aberration in the timing and or control of angiogenic activity. Such inappropriate activity may result then, for example, from overexpression or mutation of a protein kinase leading to inappropriate or uncontrolled activation. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting TIE-2 for the prevention and/or treatment of disorders related to unregulated TIE-2 activity. In particular, the compounds of the present invention can also be used in the treatment of certain forms of cancer. Furthermore, the compounds of the present invention can be used to provide additive or synergistic effects with certain existing cancer chemotherapies, and/or be used to restore effectiveness of certain existing cancer chemotherapies and radiation.

The compounds of the present invention are also useful in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, organ transplant rejection and glomerulopathies; and metabolic disorders include psoriasis, diabetes mellitus, chronic wound healing, inflammation and neurodegenerative diseases.

A further aspect of the invention provides a method of treatment of a mammal suffering from a disorder mediated by inappropriate TIE-2 activity, including susceptible malignancies, which includes administering to said subject an effective amount of a compound of formula (I) or a pharmaceutically acceptable salt, solvate, or a physiologically functional derivative thereof. In a preferred embodiment, the disorder is cancer.

A further aspect of the invention provides a method of treatment of a mammal suffering from cancer which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by inappropriate TIE-2 activity. In a preferred embodiment, the disorder is cancer.

A further aspect of the present invention provides the use of a compound of formula (I), or a pharmaceutically acceptable salt or solvate thereof, or a physiologically functional derivative thereof, in the preparation of a medicament for the treatment of cancer and malignant tumors.

The mammal requiring treatment with a compound of the present invention is typically a human being.

In another embodiment, therapeutically effective amounts of the compounds of formula (I) or salts, solvates or physiologically derived derivatives thereof and agents which inhibit growth factor receptor function may be administered in combination to a mammal for treatment of a disorder mediated by inappropriate TIE-2 activity, for instance in the treatment of cancer. Such growth factor receptors include, for example, EGFR, PDGFR, erbB2, erbB4, VEGFR, and/or TIE-2. Growth factor receptors and agents that inhibit growth factor receptor function are described, for instance, in Kath, John C., Exp. Opin. Ther. Patents (2000) 10(6): 803–818 and in Shawver et al DDT Vol 2, No. 2 February 1997.

The compounds of the Formula (I) or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate angiogenesis, including: administering to said mammal a therapeutically effective amount of a compound of formula (I), or a salt, solvate or physiologically functional derivative thereof. In one embodiment, the inappropriate angiogenic activity is due to at least one of inappropriate VEGFR1, VEGFR2, VEGFR3, or TIE-2 activity. In another embodiment, the inappropriate angiogenesis is due to inappropriate VEGFR2 and TIE-2 activity. In a further embodiment, the method further includes administering a therapeutically effective amount of a VEGFR2 inhibitor along with the compounds of formula (I) or salts, solvates or physiologically functional derivatives thereof. Preferably the disorder is cancer.

In another aspect of the present invention, there is provided the use of a compound of formula (I), or a salt, solvate or physiologically functional derivative thereof in the preparation of a medicament for use in treating a disorder in a mammal, said disorder being characterized by inappropriate angiogenesis. In one embodiment, the inappropriate angiogenic activity is due to at least one of inappropriate VEGFR1, VEGFR2, VEGFR3 or TIE-2 activity. In another embodiment, the inappropriate angiogenesis is due to inappropriate VEGFR2 and TIE-2 activity. In a further embodiment, the use further includes use of a VEGFR2 inhibitor to prepare said medicament.

The combination of a compound of formula (I) or salts, solvates, or physiologically functional derivatives thereof with a VEGFR2 inhibitor may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of Formula (I), wherein $R^3$ is —C(O)OCH$_3$, A is phenyl, and X and Z are oxygen, D and T are CH, M is C, Q is N(R$^7$)$_p$, either p or q is 1, and the other is 0, can be prepared according to the synthetic sequence shown in Scheme 1 and further detailed in the Examples section following. 4-Acetamidophenol (1) in DMF is reacted with 5-chloro-2-nitroaniline (2) in the presence of 60% NaH to provide 5-(4-acetamidophenoxy)-2-nitroaniline (3). The nitroaniline (3) is then refluxed with Na$_2$S$_2$O$_4$ to provide 4-(4-acetamidophenoxy)phenylene-1,2-diamine (4). (It is understood that reduction of nitro group of (3) can be effected in many ways, for example by use of H$_2$, Pd/C; Raney Nickel with hydrazine; SnCl$_4$ in HCl; etc.) Diamine (4) is refluxed with 1,3-bis(methoxycarbonyl)-2-methyl-2-thiopseudourea in ethanol and the acetylated carbamate (5) is obtained. HCl is added to deacetylate the carbamate (5) to give methyl (5-(4-aminophenoxy)-1H-benzimidazol-2-yl) carbamate (7). Alternatively, carbamate (7) may be prepared by refluxing 3,4,4'-triaminodiphenylether (6) with 1,3-bis (methoxycarbonyl)-2-methyl-2-thiopseudourea and then treating with conc. HCl to give carbamate (7). Carbamate (7) is then reacted with the appropriate phenyl isocyanate (8) to give the resultant benzimidazole (9) of the present invention. It is understood that R$^1$ and R$^2$ are as described above. When X of Formula (I) is sulfur and Z of Formula (I) is oxygen, the final compounds are obtained by following the same procedure using a phenylthiol derivative of 1. When X of Formula (I) is sulfur, the compound thus obtained can be oxidized with MCPBA (metachloroperbenzoic acid) to give compounds containing sulfone (SO$_2$) or sulfine (SO) as X. Also, when 3-(3-substitutedphenyl)aminocarbonylamino) phenoxy derivatives of Formula 1 are prepared, 3-acetamidophenol is utilized instead of 4-acetamidophenol.

Scheme 1

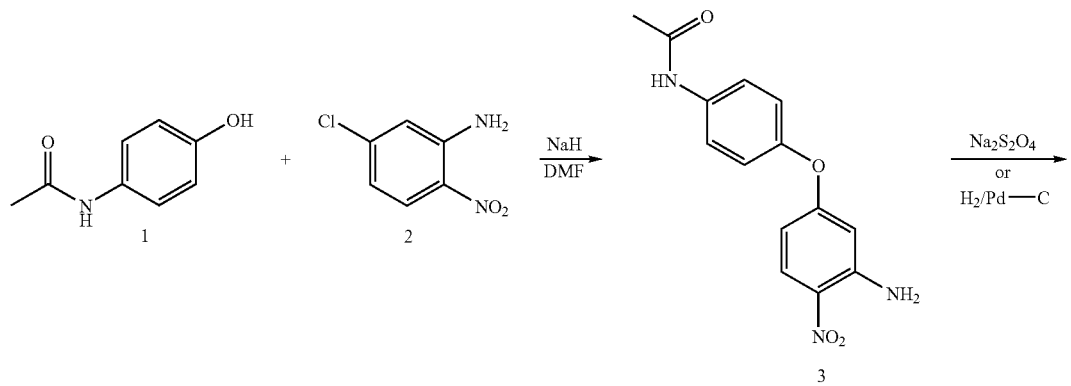

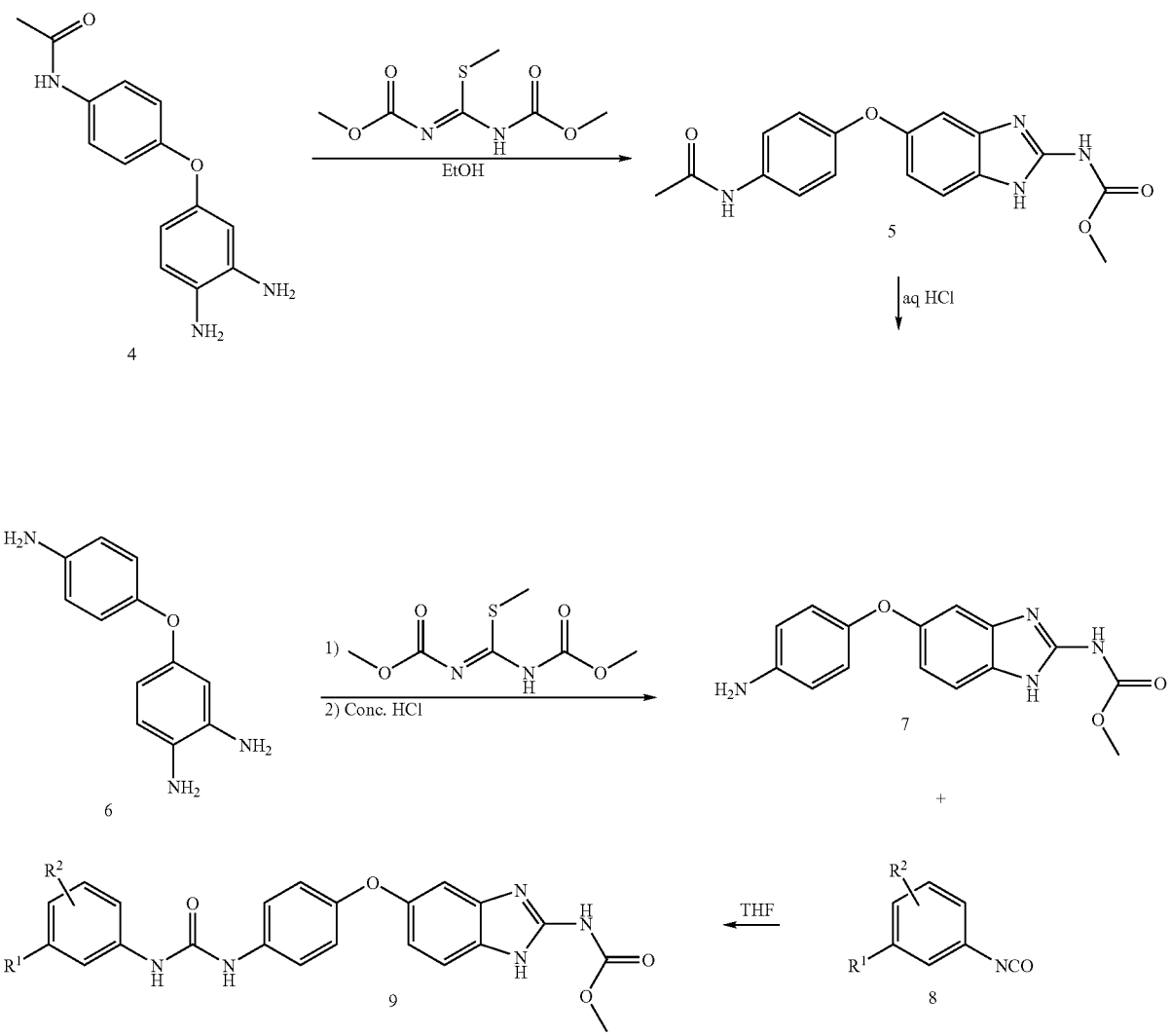

Compounds of Formula (I), wherein A is phenyl, X and Z are oxygen, D and T are CH, M is C, Q is N(R$^7$)$_p$, either p or q is 1, and the other is O, R$^1$ is CF$_3$, R$^2$ is F, and R$^3$ is a substituted carbonyl, can be prepared according to the synthetic sequence shown in Scheme 2 and further detailed in the Examples section following. 4-aminophenol (1) in DMF is reacted with 5-chloro-2-nitroaniline (2) in the presence of 60% NaH to give 5-(4-aminophenoxy)-2-nitroaniline (3). The compound (3) is reacted with 2-fluoro-5-trifluoromethylphenylisocyanate (4) to provide 5-(4-((2-fluoro-5-(trifluoromethyl)phenyl)aminocarbonylamino)phenoxy)-2-nitroaniline (5). The nitroaniline (5) is hydrogenated under an H$_2$ atmosphere in the presence of Pd/C to give the corresponding diamine (6). Diamine (6) is reacted with cyanogen bromide to give benzimidazole (7). Benzimidazole (7) may be reacted with the appropriate carboxylic acid in the presence of triethylamine and HBTU (O-Benzotriazole-1-yl-N,N,N',N'-tetramethyluronium-hexafluorophosphate) to give the corresponding benzimidazole (8). Benzimidazole (7) may also be reacted with J'SO$_2$Cl (J' is methyl or p-tolyl) to give a couple of endo-sulfonated products (9, 10). J'SO$_2$ moiety was migrated to the exo site by heating (11). Further, benzimidazole (7) may be reacted with isocyanate J"NCO to give diurea (12). When X of Formula (I) is sulfur and Z of Formula (I) is oxygen, the final compounds are obtained by following the same procedure except that a phenylthiol derivative of 1 is used. When X of Formula (I) is sulfur, the compound thus obtained can be oxidized with MCPBA (meta-chloroperbenzoic acid) to give compounds containing sulfonyl (—SO$_2$) or sulfenyl (—SO) as X. Also, as indicated above 3-(3-substituted phenyl)aminocarbonylamino)phenoxy derivatives of Formula 1 are prepared using 3-acetamidophenol instead of 4-acetamidophenol. The substituent J may be any substituent attached to C(O) within the scope of the definition of R$^3$ as recited herein. The substituent J" may be any substituent R$^5$ as defined herein.

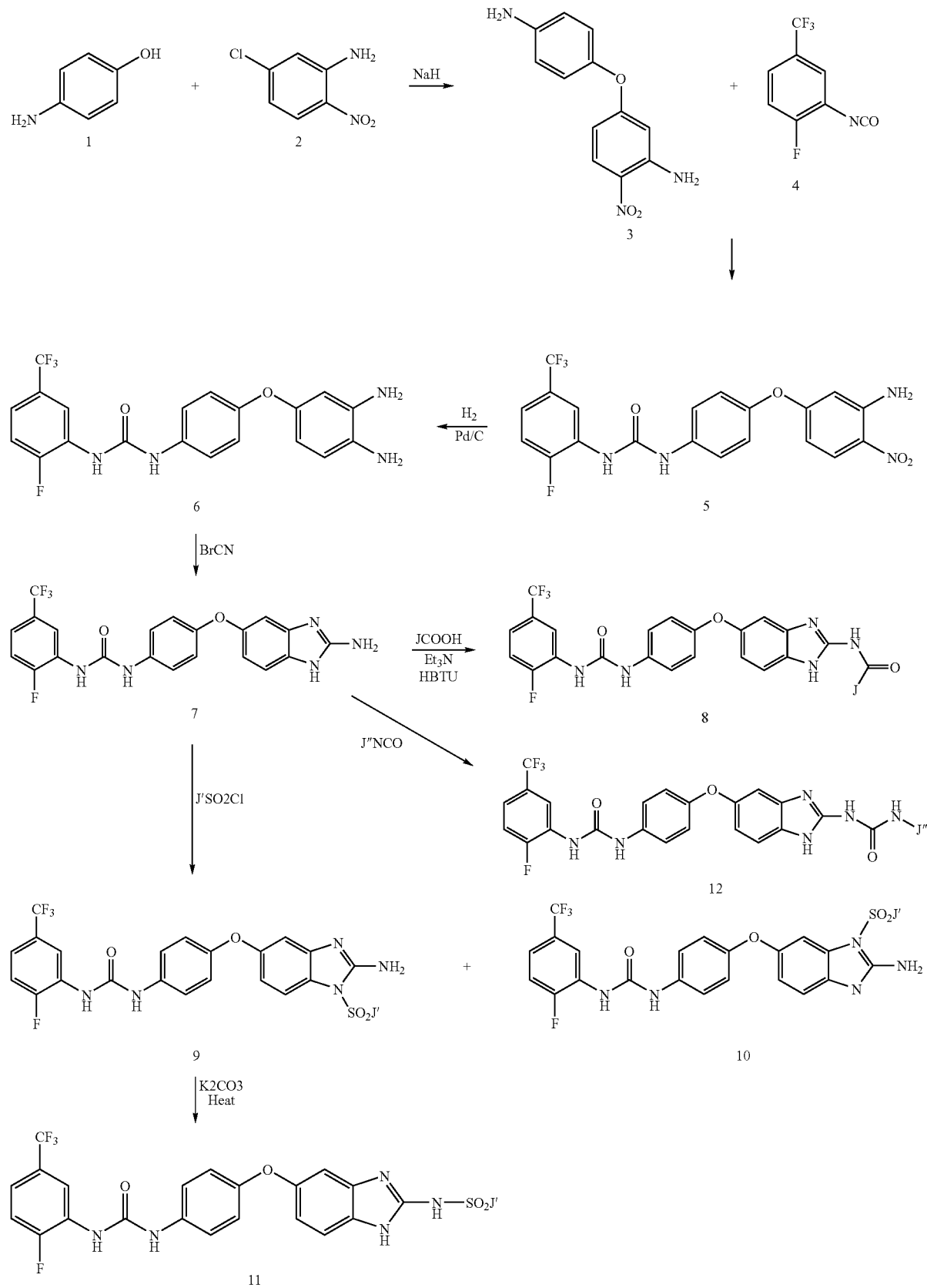

Compounds of Formula I, wherein A is pyridyl, D and T are CH, M is C, Q is $N(R^7)_p$, either p or q is 1, and the other is 0, can be prepared according to the synthetic sequence shown in Scheme 3 and further detailed in the Examples section following. The terms A1 and A2 refer to N and C, or C and N, respectively. 5-Hydroxybenzimdazole derivative (2) with or without a protecting group L is coupled with halonitropyridine (1) in the presence of base e.g. $Cs_2CO_3$ to give compound (3). Subsequent hydrogenation over Pd-C provides aniline derivative (4), followed by coupling with isocyanate (and deprotection if needed) to afford urea (5). ). The intermediate (4) can also be provided by way of triamine (6).

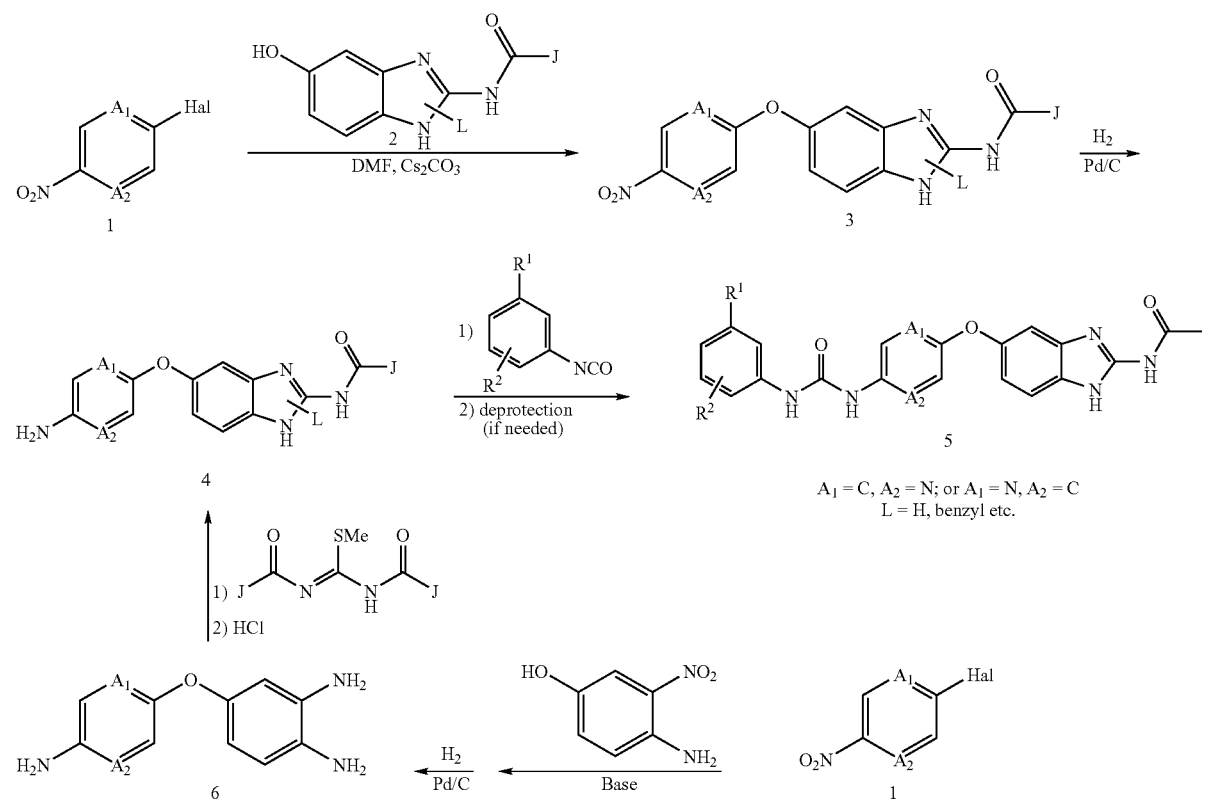

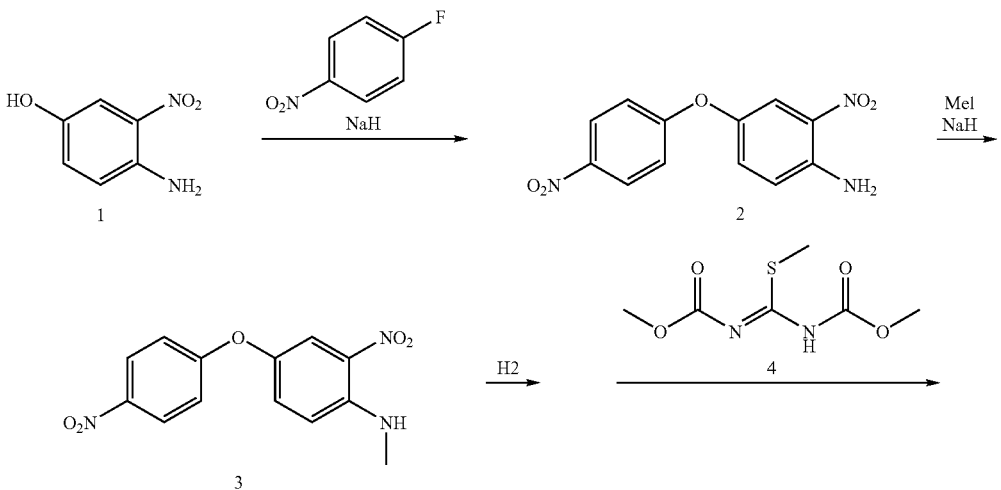

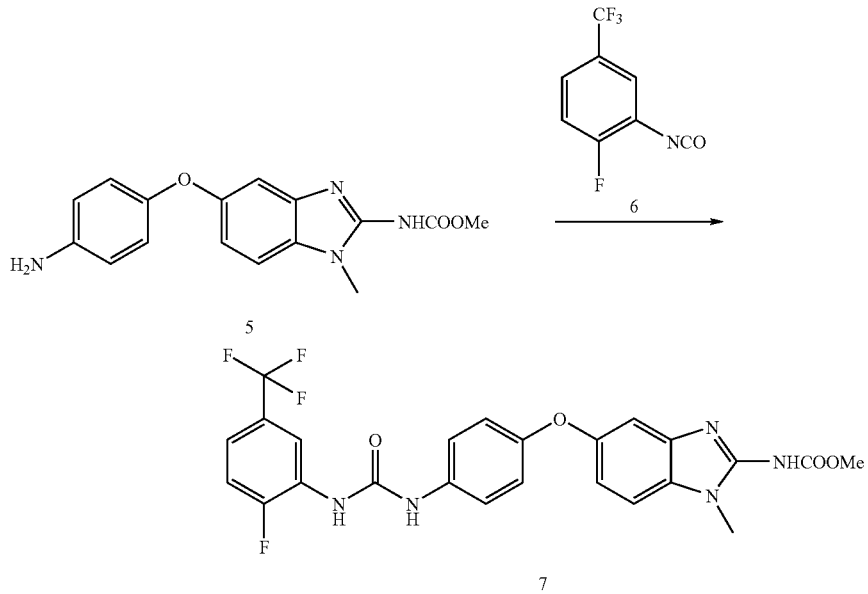

Compounds of Formula I, wherein D is CH, T is C, M is C, Q is N(R⁷)$_p$, R⁷ is CH$_3$, p is 0 and q is 1, can be prepared according to the synthetic sequence shown in Scheme 4 and further detailed in the Examples section following. 4-(4-Nitrophenoxy)-2-nitroaniline (1) was coupled with 1-fluoro-4-nitrobenzene with NaH to give (2). Methylation, hydrogenation proceeding through (3), and subsequent cyclization with (4) afforded (5), followed by coupling with isocyanate (6) to yield urea (7).

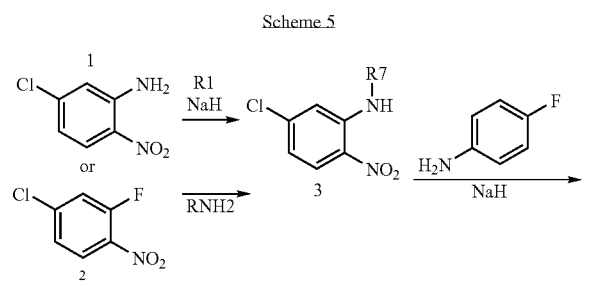

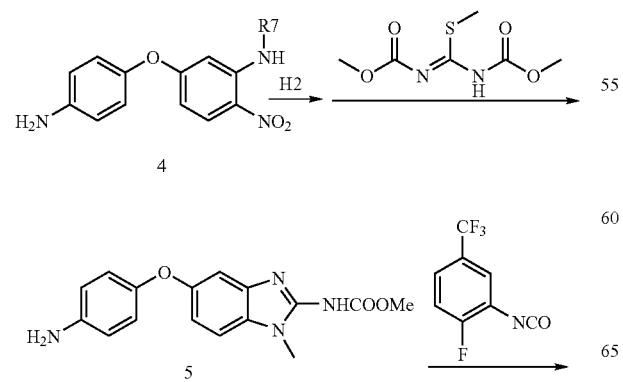

Compounds of Formula I, wherein D is CH, T is CH, M is C, Q is N(R⁷)$_p$ (p is 1; R⁷ is C$_1$–C$_6$ alkyl, —RNR⁴R⁵ or —RR⁶), and q is 0, can be prepared according to the synthetic sequence shown in Scheme 5 and further detailed in the Examples section following. N-alkyl-5-chloro-2-nitroaniline (3), derived from (1) or (2), was coupled with 4-aminophenol to provide (4). Using methods similar to those shown in the previous Schemes, hydrogenation, cyclization through (5), and coupling with isocyanate afforded (6).

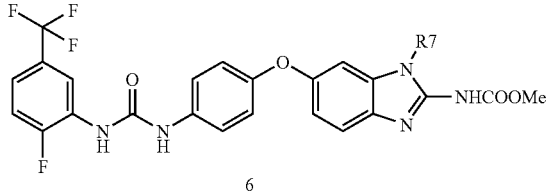

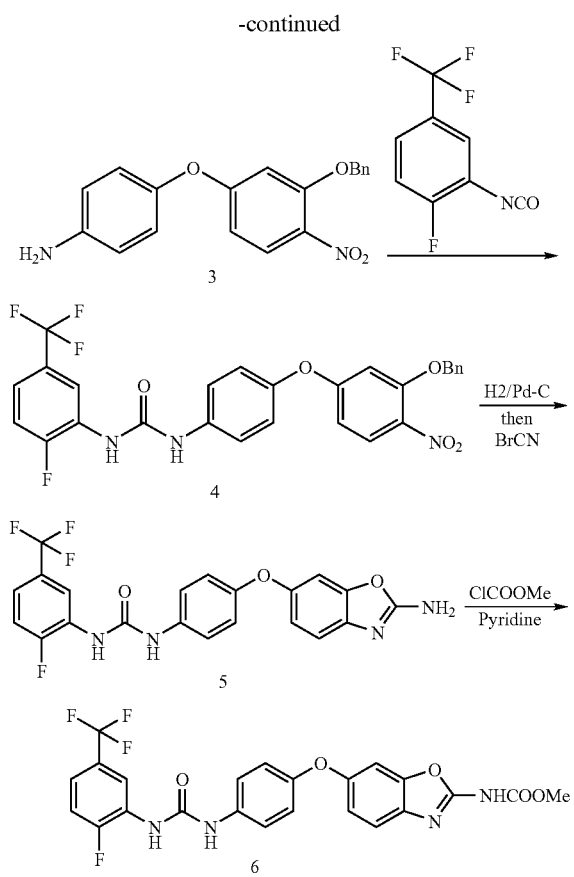
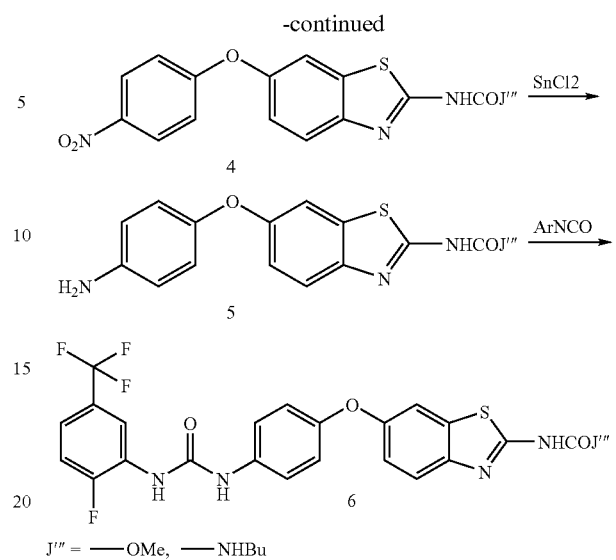

Compounds of Formula I, wherein D is CH, T is CH, M is C, Q is O, and q is 0, can be prepared according to the synthetic sequence shown in Scheme 6 and further detailed in the Examples section following. 4-Aminophenol (1) was coupled with (2) to give ether (3), which was coupled with isocyante to afford (4). Hydrogenation and cyclization with BrCN to give (5), followed by the reaction with ClCOOMe gave oxazole derivative (6).

Compounds of Formula I, wherein D is CH, T is CH, M is C, Q is S, and q is 0, can be prepared according to the synthetic sequence shown in Scheme 7 and further detailed in the Examples section following. 4-(4-Nitrophenoxy) aniline (2), derived from (1) and 4-aminophenol, was cyclized with KSCN and Br₂ in the presence of acid to provide thiazole (3). Subsequent reaction with ClCO₂Me or butylisocyante (BuNCO) to give (4), followed by reduction with SnCl₂ to give (5) and finally coupling with isocyanate afforded (6).

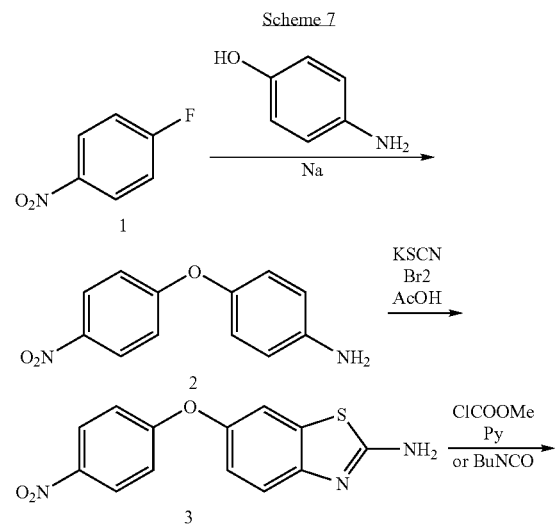
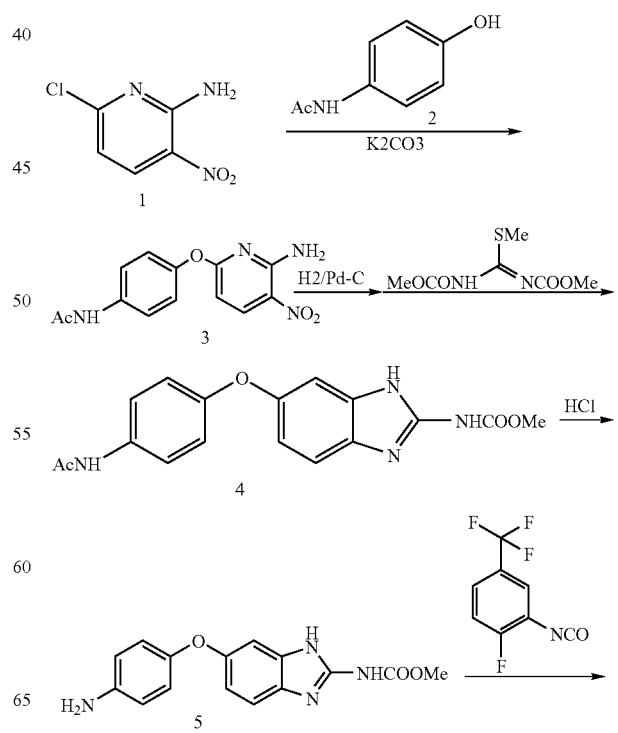

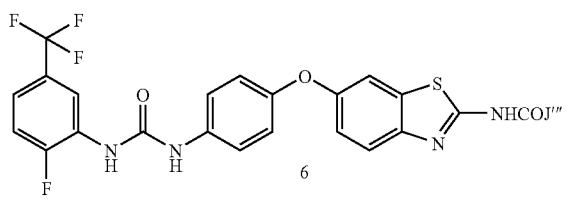
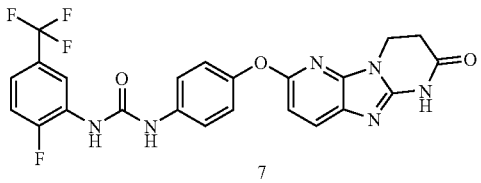

Compounds of Formula I, wherein D is N, T is CH, M is C, Q is N(R⁷)$_p$, R⁷ is H, either p or q is 1, and the other is 0, can be prepared according to the synthetic sequence shown in Scheme 8 and further detailed in the Examples section following. 2-Amino-6-chloro-3-nitropyridine (1) was coupled with 4-acetylaminophenol (2) with $K_2CO_3$ to provide ether (3). Using methods similar to those shown in the previous Schemes, hydrogenation and cyclization to give (4), hydrolysis to give (5), and coupling with isocyanate, were carried out to yield pyridoimidazole (6).

Compounds of Formula I, wherein D is N, T is CH, M is C, Q is N, q is 0 and R³ is COCH$_2$CH$_2$ linked together with the nitrogen at Q, can be prepared according to the synthetic sequence shown in Scheme 9 and further detailed in the Examples section following. 2,6-Dichloro-3-nitropyridine (1) was aminated to give (2) and coupled with 4-acetylaminophenol to give ether (3). After hydrogenation, and subsequent cyclization with BrCN to give (4), compound (4) was cyclized by ester hydrolysis through heating to provide (5). Using methods similar to those shown in the previous Schemes, hydrolysis to give (6) and coupling with isocyanate yielded urea (7).

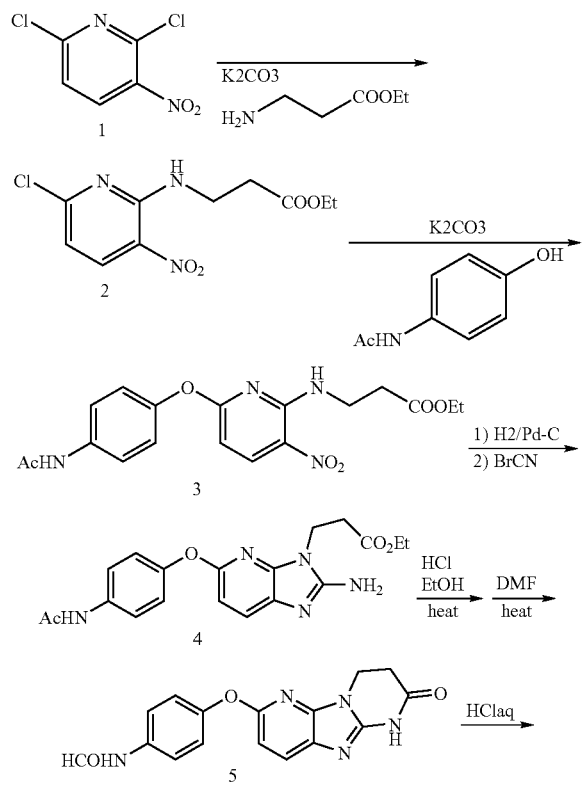
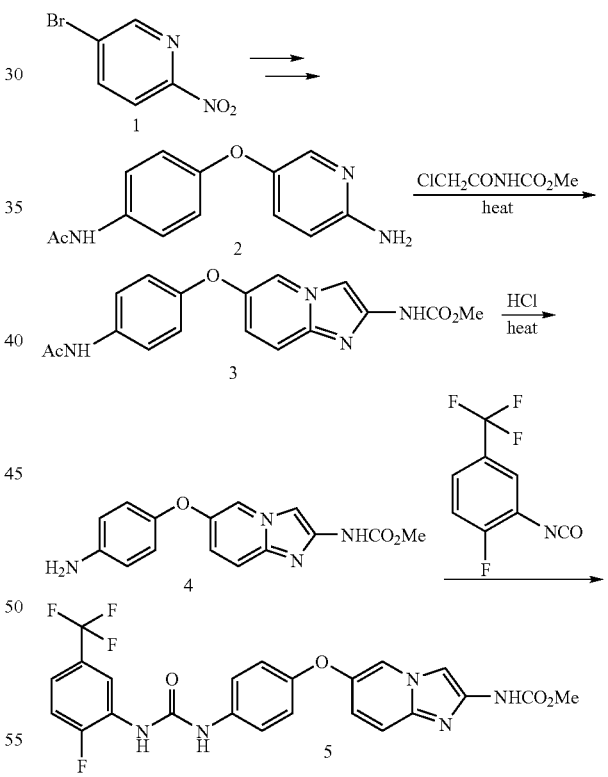

Compounds of Formula I, wherein D is CH, T is CH, M is N, Q is CH, and q is 0, can be prepared according to the synthetic sequence shown in Scheme 10 and further detailed in the Examples section following. Ether (2), derived from 5-bromo-2-nitroaniline (1), was cyclized with ClCH$_2$CONHCO$_2$Me to give pyridoimidazole (3). Using methods similar to those shown in the previous Schemes, hydrolysis to give (4) and coupling with isocyanate yielded urea (5).

Scheme 11

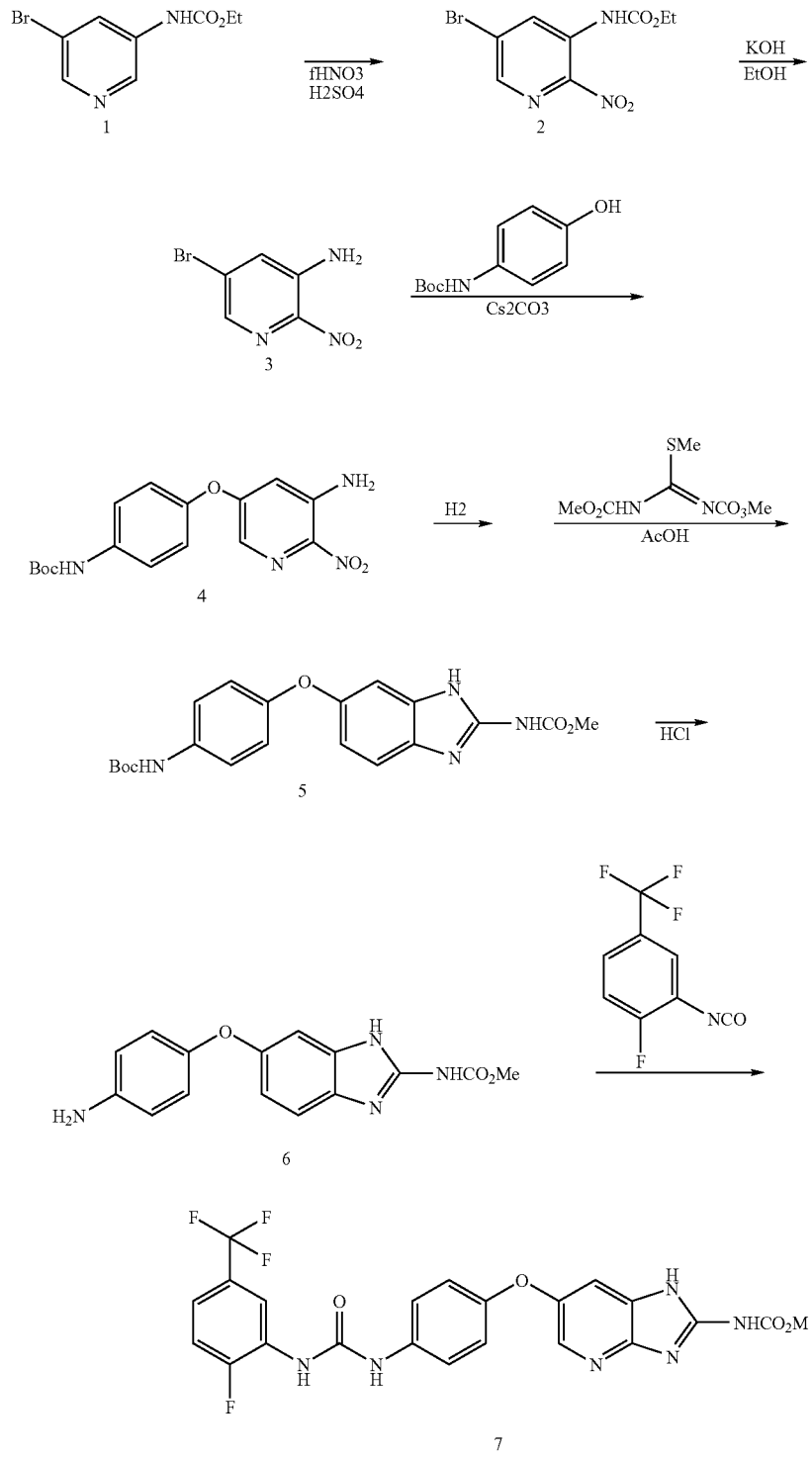

Compounds of Formula I, wherein D is CH, T is N, M is C, Q is $N(R^7)_p$, $R^7$ is H, either p or q is 1, and the other is 0, can be prepared according to the synthetic sequence shown in Scheme 11 and further detailed in the Examples section following. A nitro moiety was added to ethyl N-(5-bromopyridine-3-yl)carbamate (1) to give (2), followed by hydrolysis to give (3). Using methods similar to those shown in the previous Schemes, coupling with phenol derivative gave (4), hydrogenation and cyclization in the presence of acid gave (5), hydrolysis gave (6), and coupling with isocyanate yielded pyridoimidazole (7).

Scheme 12

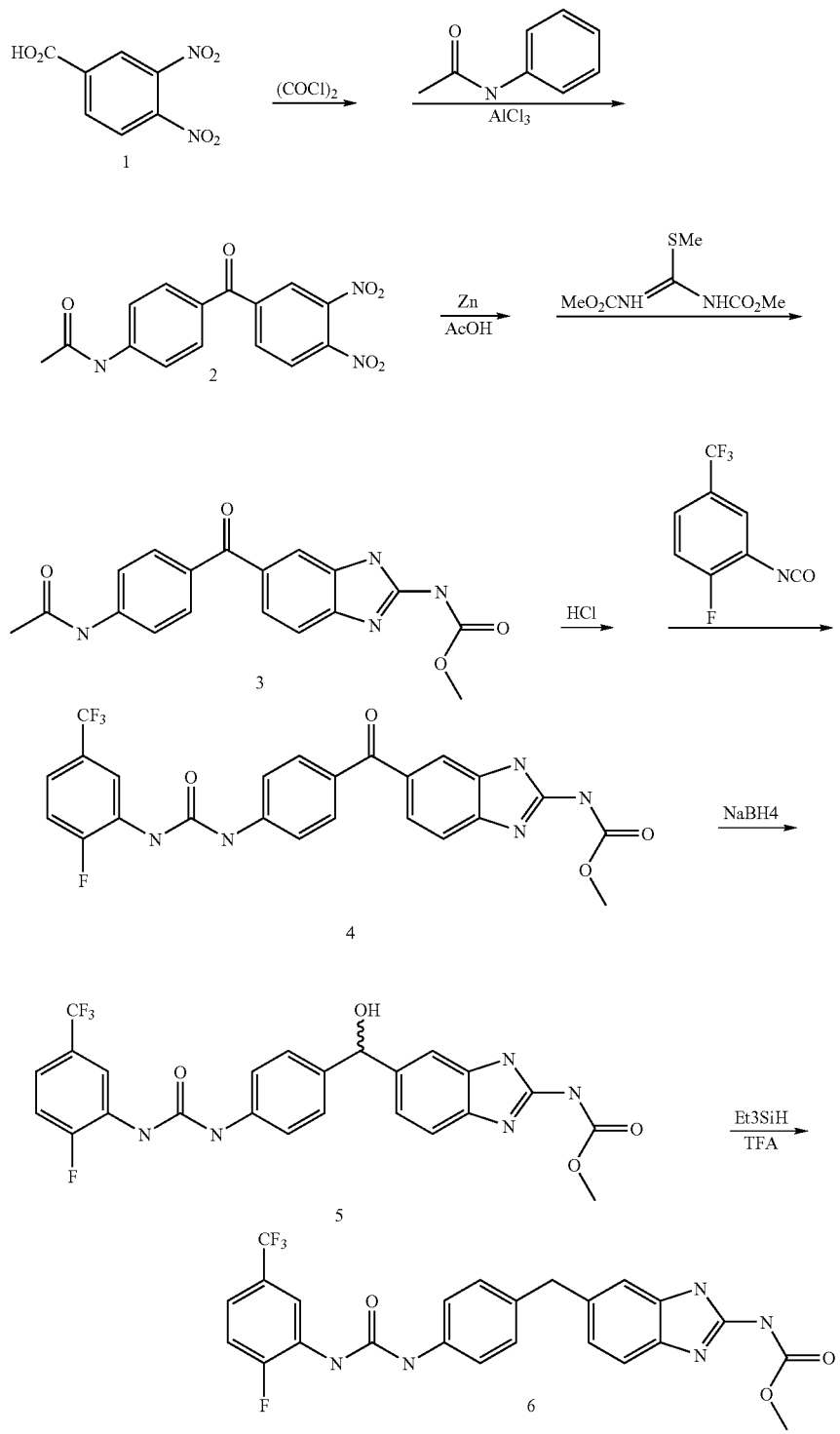

Compounds of Formula I, wherein X is CO, CH$_2$, CH(OH), D is CH, T is CH, M is C, Q is N(R$^7$)$_p$, R$^7$ is H, either p or q is 1, and the other is 0, can be prepared according to the synthetic sequence shown in Scheme 12 and further detailed in the Examples section following. Friedel-Crafts condensation with the halide of (1) and acetoanilide was carried out to give ketone (2). Using methods similar to those shown in the previous Schemes, reduction with zinc and cyclization gave (3), hydrolysis, and coupling with isocyanate yielded pyridoimidazole (4). Also, reduction with NaBH$_4$ gave carbinol (5), followed by further reduction with Et$_3$SiH provided benzyl derivative (6).

Scheme 13

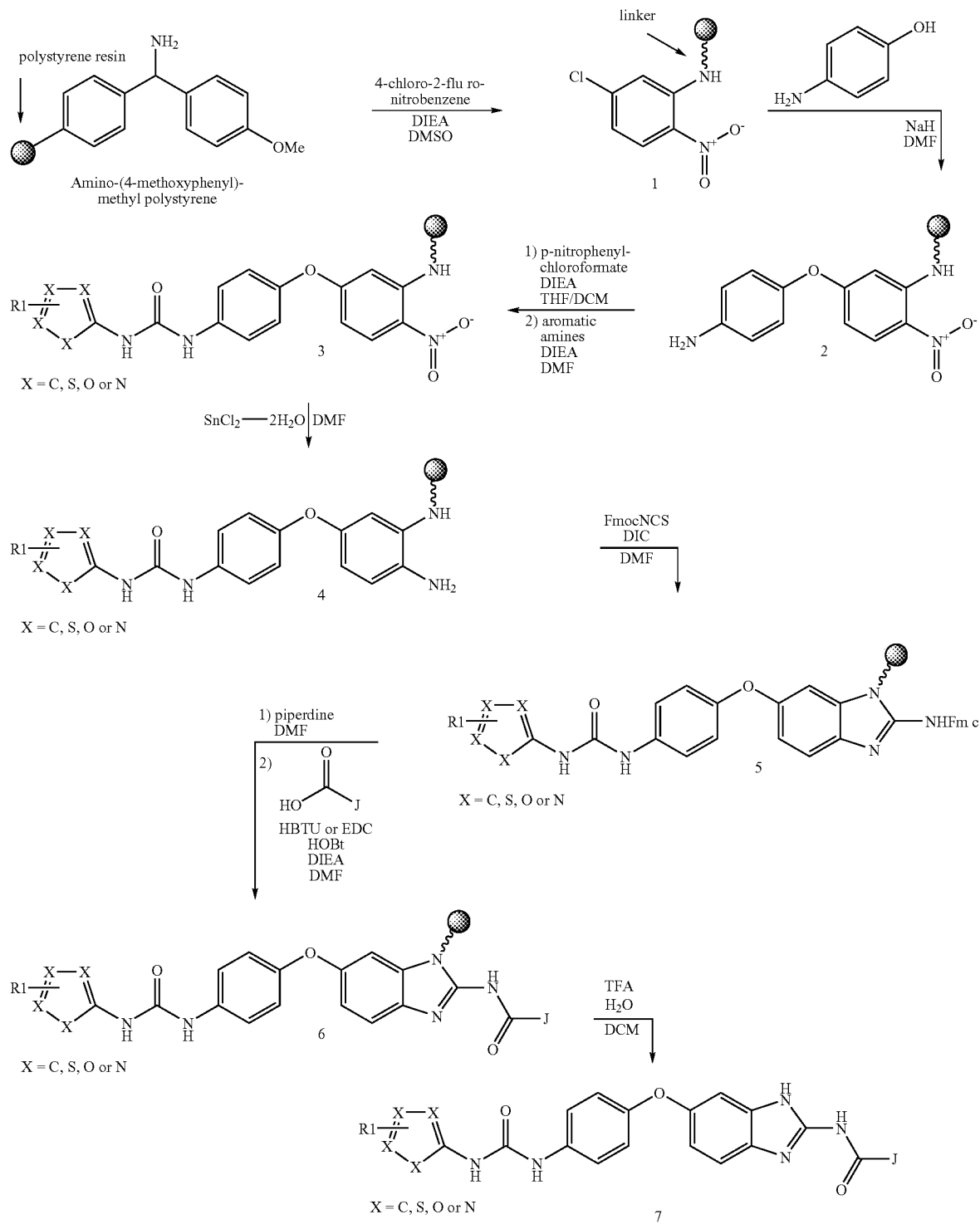

J is as defined above.

According to Scheme 13, amino-(4-methoxyphenyl)-methylpolystyrene resin was first loaded with 4-chloro-2-fluoronitrobenzene in the presence of DIEA. The chlorine of compound (1) was displaced with the oxygen of the 4-aminophenol using NaH as the base to arrive at (2). The free amino group of (2) was then activated with p-nitrophenyl chloroformate, the excess of which was washed away before the amines were added. For this step, the resin was split into 21 equal batches and twenty (20) five-membered heteroaryl amines and one substituted aniline were used to afford (3). The nitro group of (3) was reduced with tin chloride to give diamine (4). Cyclization with Fmoc-NCS resulted in the Fmoc-protected aminobenzimidazole (5). Each resin batch was split again into four even portions. They were deprotected and acylated with four different carboxylic acids. Finally, the resin was treated with 23:2:75 (v/v/v) TFA/H$_2$O/DCM to yield 84 discrete benzimidazoles (7).

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Low-resolution mass spectra (MS) were recorded on a JOEL JMS-AX505HA, JOEL SX-102, or a SCIEX-APIiii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomog (grams);
L (liters);
μL (microliters);
M (molar);
i. v. (intravenous);
MHz (megahertz);
mmol (millimoles);
min (minutes);
mp (melting point);
T$_r$ (retention time);
MeOH (methanol);
TEA (triethylamine);
TFAA (trifluoroacetic anhydride);
DMSO (dimethylsulfoxide);
DME (1,2-dimethoxyethane);
DCE (dichloroethane);
DMPU (N,N'-dimethylpropyleneurea);
IBCF (isobutyl chloroformate);
HOSu (N-hydroxysuccinimide);
mCPBA (meta-chloroperbenzoic acid;
BOC (tert-butyloxycarbonyl);
DCC (dicyclohexylcarbodiimide);
Ac (acetyl);
TMSE (2-(trimethylsilyl)ethyl);
TIPS (triisopropylsilyl);
DMAP (4-dimethylaminopyridine);
ATP (adenosine triphosphate);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
EtOH (Ethanol)
fHNO$_3$ (fumed HNO$_3$);
DIC (1,3-Diisopropylcarbodiimide);
EDC (1-(3-(Dimethylamino)propyl)-3-ethylcarbodiimide hydrochloride;
DIEA (N,N-Diisopropylethylamine); and
EDTA (ethylenediaminetetraacetic acid).

mg (milligrams);
mL (milliliters);
psi (pounds per square inch);
mM (millimolar);
Hz (Hertz);
mol (moles);
rt (room temperature);
h (hours);
TLC (thin layer chromatography);
RP (reverse phase);
i-PrOH (isopropanol);
TFA (trifluoroacetic acid);
THF (tetrahydrofuran);
AcOEt (ethyl acetate);
DCM (dichloromethane);
DMF (N,N-dimethylformamide);
CDI (1,1-carbonyldiimidazole);
HOAc (acetic acid);
HOBT (1-hydroxybenzotriazole);
EDC (ethylcarbodiimide hydrochloride);
FMOC (9-fluorenylmethoxycarbonyl);
CBZ (benzyloxycarbonyl);
atm (atmosphere);
TMS (trimethylsilyl);
TBS (t-butyldimethylsilyl);
BSA (bovine serum albumin)
HRP (horseradish peroxidase);

lybdic acid or p-anisaldehyde solution. Flash column chromatography was performed on silica gel (230–400 mesh, Merck).

A further note on characterization, when $R^7$ is H in a compound of Formula (I) wherein Q is $N(R^7)_p$, it is not identifiable whether p or q is 1 due to the tautomerism.

Preparation of Intermediates

Intermediate 1

5-(4-Acetamidophenoxy)-2-nitroaniline

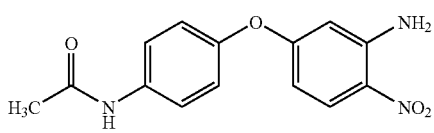

To a solution of 4-acetamidophenol (7.56 g, 50 mmol) in DMF (20 ml) was added 60% NaH (2.2 g) followed by 5-chloro-2-nitroaniline (9.06 g, 50 mmol). The mixture was heated to 120° C. overnight. After cooling, 800 ml of water was added and the resultant solid was collected by filtration. Desiccation in vacuo gave intermediate 1 as a brown solid (13.75 g, 96%): MS m/e 286 (M−1).

Intermediate 1A 5-(3-Acetamidophenoxy)-2-nitroaniline

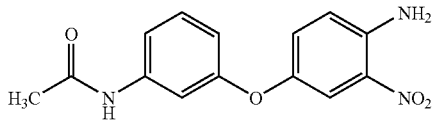

3-Acetamidophenol was utilized instead of 4-acetamidophenol, according to the same procedure for Intermediate 1 to prepare Intermediate 1A: MS m/e 286 (M−1).

Intermediate 2

4-(4-Acetamidophenoxy)phenylene-1,2-diamine

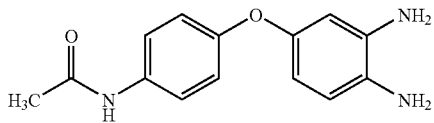

$Na_2S_2O_4$ (28.2 g, 160 mmol) was added to a solution of 5-(4-Acetamidophenoxy)-2-nitroaniline (Intermediate 1) (13.7 g, 48 mmol) in EtOH (600 ml) and $H_2O$ (150 ml). The yellow mixture was refluxed with vigorous stirring until the color disappeared. After cooling, the mixture was washed with brine and the product was extracted with AcOEt. The AcOEt layer was dried over $MgSO_4$, filtered and evaporated to give intermediate 2 as a brown film (10.2 g, 83%): MS m/e 258 (M+1).

Intermediate 2A 4-(3-Acetamidophenoxy)phenylene-1,2-diamine

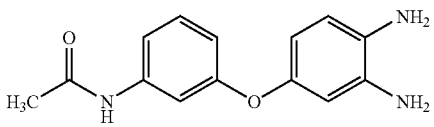

Intermediate 1A was treated instead of Intermediate 1 to give Intermediate 2A: MS m/e 258 (M+1).

Intermediate 3

Methyl (5-(4-aminophenoxy)-1H-benzimidazol-2-yl)carbamate

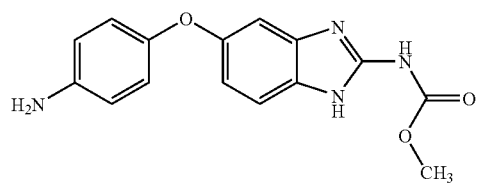

Method A

A mixture of 4-(4-Acetamidophenoxy)phenylene-1,2-diamine (Intermediate 2) (750 mg, 2.9 mmol) and 1,3-bis(methoxycarbonyl)-2-methyl-2-thiopseudourea (600 mg) in EtOH (13 ml) was refluxed overnight. After cooling to rt, diethyl ether was added to form a solid (830 mg), which was collected by filtration. 1N—HCl (150 ml) was poured to this acetylated version of intermediate 3 (7.7 g, 23 mmol). The mixture was heated to reflux (105° C.) for 2 h. After cooling, aq. $NH_3$ (30%, 20 ml) was added. The precipitate thus formed was collected by filtration with suction and dried in vacuo. The solid material was then suspended in MeOH (150 ml) and heated to 70° C. for 30 min. with stirring to dissolve a minor by-product. After cooling, the undissolved material was collected by filtration and dried in vacuo to give intermediate 3 as a brown solid (6.75 g, 99%): MS m/e 299 (M+1).

Method B

A mixture of 3,4,4'-triaminodiphenylether (12.6 g, 59 mmol) and 1,3-bis(methoxycarbonyl)-2-methyl-2-thiopseudourea (26.7 g) was refluxed overnight. After cooling, $Et_2O$ was added to form a precipitate, which was then collected by filtration. The solid thus obtained (4 g) was dissolved in MeOH (20 ml) and treated with 2N—HCl (20 ml) and then with conc.HCl (3 ml). Stirring was continued overnight at rt. The mixture was evaporated to remove MeOH. The resultant material was neutralized with aq. NaOH to give intermediate 3 as an off-white solid: MS m/z 299 (M+1).

Intermediate 3A

Methyl (5-(3-aminophenoxy)-1H-benzimidazol-2-yl)carbamate

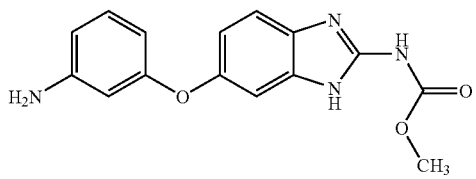

Intermediate 3A was prepared following the Method A procedure for the preparation of Intermediate 3 using Intermediate 2A instead of Intermediate 2: MS m/z 299 (M+1).

Intermediate 3B

Methyl (5-(4-aminophenylthio)-1H-benzimidazol-2-yl)carbamate

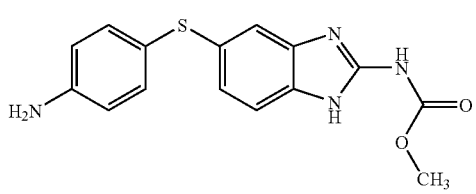

Intermediate 3B was prepared following the Method A procedure for the preparation of Intermediate 3 starting from 4-acetamidophenylthiol: MS m/z 315 (M+1).

Intermediate 3C

Benzyl(5-(4-(N,N'-bis(benzyloxycarbonyl)amidino)aminophenoxy)-1H-benzimidazol-2-yl)carbamate

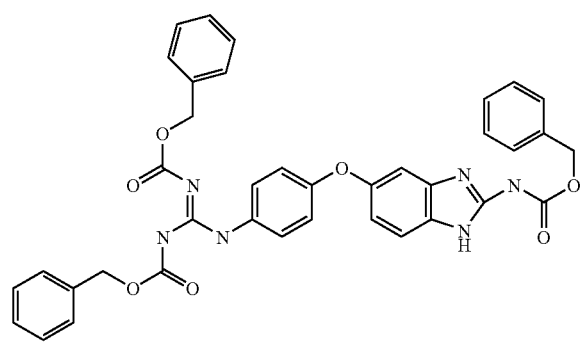

A mixture of 3,4,4'-triaminodiphenyl ether (5.0 g, 23.2 mmol) and 1,3-bis(benzyloxycarbonyl)-2-methyl-2-thiopseudourea (16.5 g, 46.0 mmol) in dry MeOH (100 ml) was refluxed overnight. The reaction mixture was cooled to room temperature and ether was added. An off white solid was generated and collected by filtration and washed with ether and dried in vacuo. 14.3 g of Intermediate 3C was obtained as off white powder. Yield 89.9% $^1$H NMR (DMSO-d$_6$) δ 11.82 (br,1H), 11.40 (br,1H), 7.51–7.27 (m, 20H), 7.03 (s, 1H), 6.93 (d, 2H), 6.80 (dd, 1H), 5.24 (s, 4H), 5.02 (s, 2H); MS m/e 685 (M+1).

Intermediate 3D

Benzyl (5-(4-aminophenoxy)-1H-benzimidazol-2-yl)carbamate

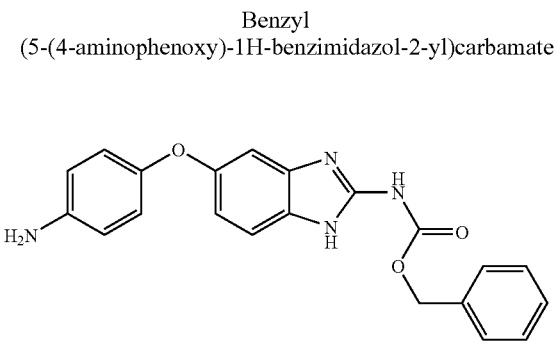

14.3 g of Intermediate 3C was dissolved in 300 ml of MeOH and 300 ml of 2M HCl and stirred for 3 days at 50° C. Then MeOH was removed by evaporation and 2M of NaOH solution was added to pH 9.0. The generated solid was collected by filtration and washed with water and dried in vacuo. Yield 78.0% (7.61 g) $^1$H NMR (DMSO-d$_6$) δ 7.48–7.33 (m, 8H), 7.01–6.94 (m, 3H), 6.89 (d, 2H), 6.78 (dd, 1H), 5.24 (s, 2H); MS m/e 375 (M+1).

Intermediate 4

5-(4-Aminophenoxy)-2-nitroaniline

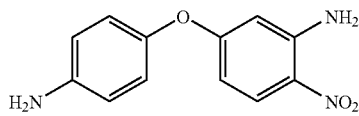

To a solution of 4-aminophenol (5.0 g, 46 mmol) in DMF (120 ml) was slowly added 60% NaH (2.0 g, 50 mmol), followed by 5-chloro-2-nitroaniline (8.7 g). The mixture was heated to 90° C. and stirred overnight. The reaction mixture was poured onto aq. NH$_4$Cl to form a solid, which was collected by filtration, washed with hexane and dried to give intermediate 4 as a yellow solid (12.0 g, >99%): MS m/e 244 (M−1).

Intermediate 5

5-(4-((2-Fluoro-5-(trifluoromethyl)phenyl)aminocarbonylaminophenoxy)-2-nitroaniline

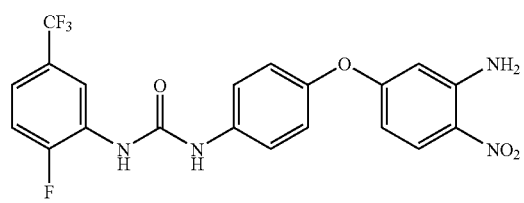

A mixture of 2-fluoro-5-(trifluoromethyl)phenylisocyanate (10.0 g, 48.8 mmol) and 5-(4-Aminophenoxy)-2-nitroaniline (Intermediate 4)(11.6 g, 47.3 mmol) in dry THF (200 ml) was stirred overnight at rt. After treatment with activated carbon, the solvent was evaporated. Purification of the crude material by column chromatography (hexane-AcOEt, 1:2) afforded intermediate 5 as a yellow solid (21.6 g, >98%): MS m/e 449 (M−1).

Intermediate 6

4-(4-((2-Fluoro-5-(trifluoromethyl)phenyl)aminocarbonylamino)phenoxy)phenylene-1,2-diamine

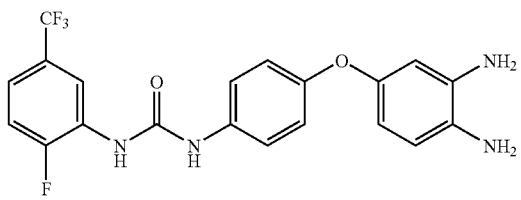

Pd/C (5%, 3.0 g) was introduced to a solution of 5-(4-((2-Fluoro-5-(trifluoromethyl)phenyl)aminocarbonylamino)phenoxy)-2-nitroaniline (Intermediate 5) (21.6 g, 48 mmol) in ethanol (200 ml) under Ar. The starting material was hydrogenated under a $H_2$ atmosphere for 3 days while being stirred. The reaction mixture was then filtered through celite and evaporated to give intermediate 6 as a black film. This crude material was chromatographed through silica gel (hexane-AcOEt, 4:1–3:1–2:1–1:1–0:1) to give purified intermediate 6 (13.0 g, 64%): MS m/e 421 (M+1).

Intermediate 7

N-(5-(2-Nitro-5-pyridyloxy)-1H-benzimidazol-2-yl)acetamide

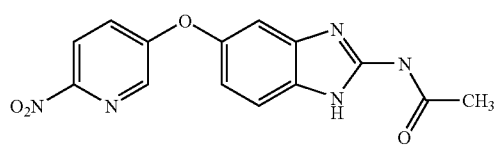

To a mixture of 5-hydroxy-2-acetylaminobenzimidazole (382 mg, 2 mmol) and $Cs_2CO_3$ (978 mg, 3 mmol) in DMF (20 ml) was added 5-bromo-2-nitropyridine (550 mg, 2 mmol) at room temperature. After 2 hours of stirring, the mixture was poured into water and extracted with AcOEt. The organic solvent was washed with water and brine, then evaporated to obtain a crude product. It was purified with silica gel column chromatography ($CHCl_3$—MeOH). The pure fractions were collected to provide intermediate 7, which was then used for the subsequent reduction (314 mg, 50%).

Intermediate 8

N-(5-(2-Amino-5-pyridyloxy)-1H-benzimidazol-2-yl)acetamide

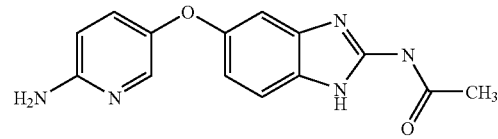

N-(5-(2-Nitro-5-pyridyloxy)-1H-benzimidazol-2-yl)acetamide (Intermediate 7) was hydrogenated under an $H_2$ atmosphere with Pd—C (10%) in MeOH. After the reaction was complete, the solid was filtered off, and the filtrate was evaporated to give intermediate 8 (47 mg, 17%): $^1$H NMR (DMSO-$d_6$) δ 11.56 (brs, 1H) 7.51 (d, 1H), 7.32 (d, 1H), 7.05 (dd, 1H), 6.97 (d, 1H), 6.74 (dd, 1H), 6.70 (d, 1H), 5.02 (br s, 2H), 3.74 (s, 3H), 7.08 (d, 2H), 6.84 (d, 1H), 6.61 (d, 1H), 3.75 (s, 3H); MS m/e 284 (M+1).

Intermediate 8A 4-(4-Nitrophenoxy)-2-nitroaniline

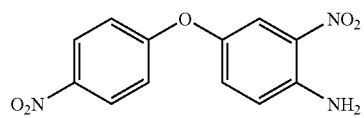

To a solution of 4-hydroxy-2-nitroaniline (3.08 g, 20.0 mmol) in DMF (30 mL) was added NaH (60% oily, 880 mg, 22.0 mmol) followed by 1-fluoro-4-nitrobenzene (2.33 mL, 22.0 mmol). The mixture was stirred at 90° C. overnight. After cooling, the mixture was extracted with ethyl acetate. The organic layer was washed with water and brine, dried over $Na_2SO_4$ then evaporated. Sequence purification on $SiO_2$ column chromatography gave the title compound (4.56 g, 83%): MS m/e 274 (M−1).

Intermediate 8B

N-Methyl-4-(4-nitrophenoxy)-2-nitroaniline

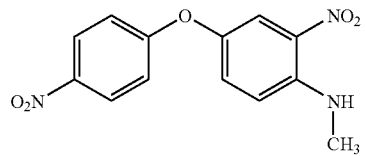

To a mixture of NaH (60% oily, 320 mg, 8.0 mmol) in DMF (30 mL) was added a solution of 4-(4-nitrophenoxy)-2-nitroaniline (Intermediate 8A-2.00 g, 7.3 mmol) in DMF (30 mL) at 0° C. followed by an excess amount of MeI (2.0 mL). The mixture was stirred at 0° C. for 1.5 hrs then at room temperature overnight. The mixture was extracted with ethyl acetate. The organic layer was washed with water and brine, dried over $Na_2SO_4$ then evaporated. Sequence purification on SiO₂ column chromatography gave the title compound (2.10 g, quant). ): ¹H NMR (CDCl₃-d₁) δ 3.08 (d, 3H), 6.94 (d, 1H), 7.00 (d, 2H), 7.30 (dd, 1H), 7.97 (d, 1H), 8.08 (brs, 1H), 8.22 (d, 2H).

Intermediate 8C

Methyl (1-methyl-5-(4-aminophenoxy)-benzimidazol-2-yl)carbamate

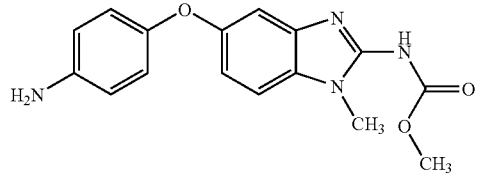

To a mixture of N-methyl-4-(4-nitrophenoxy)-2-nitroaniline (Intermediate 8B -2.10 g, 2.27 mmol) in MeOH (100 mL) was added 5% Pd—C (catalytic amount) and stirred at room temperature under H₂ atmosphere. After 7 hrs, the catalyst was removed by filtration then the solvent was evaporated off. The residual mixture was dissolved into MeOH (50 mL) and added 1,3-bis(methoxycarbonyl)-2-methyl-2-thiopseudourea (3.0 g, 14.5 mmol). The mixture was refluxed overnight. The solvent was removed by evaporation and sequence purification on SiO₂ column chromatography gave title compound (87.3 mg, 4%): MS m/e 313 (M+1).

Intermediate 8D

N-methyl-5-chloro-2-nitroaniline

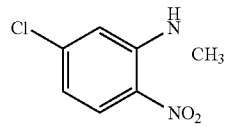

To a solution of 5-chloro-2-nitroaniline (1.73 g, 10.0 mmol) in DMF (40 mL) was added NaH (60% oily, 880 mg, 22.0 mmol) at 0° C. followed by excess amount of MeI (3.0 mL). The mixture was stirred at 0° C. for 1 hr then at room temperature overnight. The mixture was extracted with ethyl acetate. The organic layer was washed with water and brine, dried over Na₂SO₄ then evaporated. Sequence purification on SiO₂ column chromatography gave the title compound (1.86 g, quant): ¹H NMR (DMSO-d₆) δ 2.95 (d, 3H), 6.69 (dd, 1H), 7.03 (d, 1H), 8.08 (d, 1H), 8.28 (br, 1H).

Intermediate 8E

N-(2-(dimethylamino)ethyl)-5-chloro-2-nitroaniline

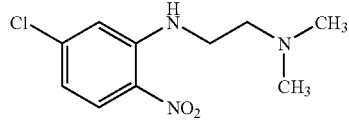

To a solution of 3-fluoro-4-nitro-1-chlorobenzene (1.75 g, 10.0 mmol) in DMSO (50 mL) was added K₂CO₃ (2.76 g, 20.0 mmol) followed by N,N-dimethylaminoethylamine (1.21 mL, 11.0 mmol) at 0° C. The mixture was stirred at 0° C. for 5 min. before being stirred at room temperature overnight. The mixture was poured into water then extracted with ethyl acetate. The organic layer was washed with water and brine, dried over Na₂SO₄ then evaporated. Sequence purification on SiO₂ column chromatography gave the title compound (2.29 g, 94%): MS m/e 244, 246 (M+1).

Intermediate 8F

N-(2-(4-morpholino)ethyl)-5-chloro-2-nitroaniline

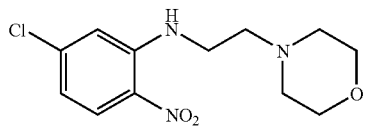

The title compound was prepared following the procedure for Intermediate 8E using 2-(4-morpholino)ethylamine: MS m/e 286, 288 (M+1).

Intermediate 8G 4-(3-Methylamino-4-nitrophenoxy)aniline

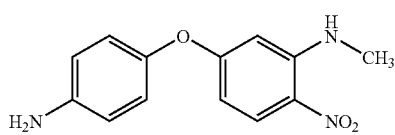

To a mixture of NaH (60% oily, 440 mg, 11.0 mmol) in DMF (30 mL) was added a solution of 4-aminophenol (1.20 g, 11.0 mmol) in DMF (15 mL) followed by N-methyl-5-chloro-2-nitroaniline (Intermediate 8D-2.02 g, 10.0 mmol) in DMF (20 mL). The mixture was stirred at 90° C. overnight. After cooling, the mixture was extracted with ethyl acetate. The organic layer was washed with water and brine, dried over Na₂SO₄ then evaporated. Sequence purification on SiO₂ column chromatography gave the title compound (2.44 g, 94%): MS m/e 260 (M+1).

Intermediate 8H 4-(3-(2-(Dimethylamino)ethylamino)-4-nitrophenoxy)aniline

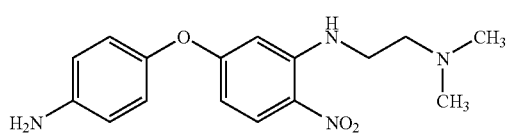

Intermediate 8H is prepared using a procedure similar to Intermediate 8H. MS m/e 317 (M+1).

Intermediate 8I 4-(3-(2-(4-Morpholino)ethylamino)-4-nitrophenoxy)aniline

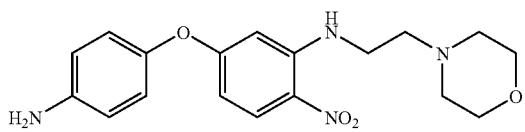

The title compound was prepared following the procedure for Intermediate 8H using Intermediate 8F. MS m/e 359 (M+1).

Intermediate 8J

Methyl (3-methyl-5-(4-aminophenoxy)-benzimidazol-2-yl)carbamate

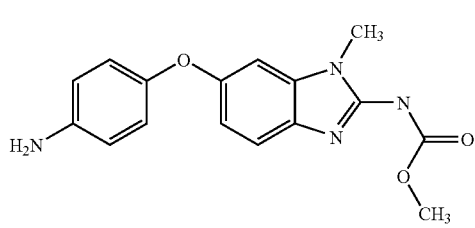

After hydrogenation of 4-(3-methylamino-4-nitrophenoxy)aniline (Intermediate 8G-519.2 mg, 2.0 mmol) with 5% Pd—C in MeOH (20 mL), 1,3-bis(methoxycarbonyl)-2-methyl-2-thiopseudourea (1.03 g, 5.0 mmol) and AcOH (2.0 mL) was added then stirred at 85° C. for 5.5 hrs. After cooling, the mixture was added 2N HClaq. (25 mL) then stirred at 65° C. for 2 hrs. The mixture was passed through celite pad to remove catalyst and the solvent was removed by evaporation. The residue was extracted with ethyl acetate. The organic layer was washed with $NH_4OH$(aq). and brine, dried over $Na_2SO_4$ then evaporated. Sequence purification on $SiO_2$ column chromatography gave the title compound (529.1 mg, 85%): MS m/e 313 (M+1).

Intermediate 8K

Methyl (3-(2-(N,N-dimethylamino)ethyl)-5-(4-aminophenoxy)-benzimidazol-2-yl)carbamate

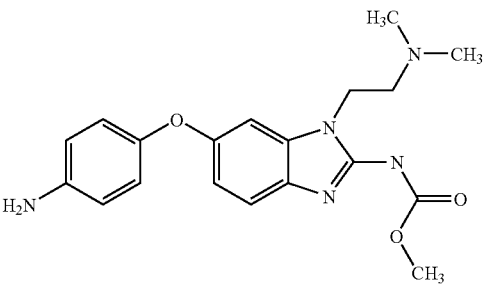

The title compound was prepared following the procedure for Intermediate 8J using Intermediate 8H. MS m/e 370 (M+1).

Intermediate 8L

Methyl (3-(2-(4-morpholino)ethyl)-5-(4-aminophenoxy)-benzimidazol-2-yl)carbamate

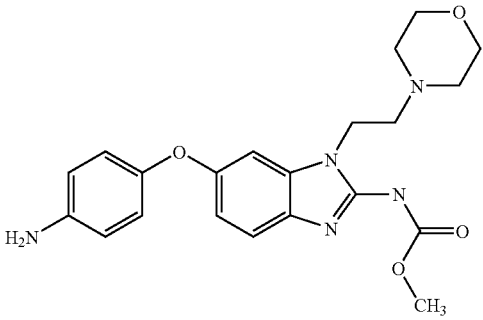

The title compound was prepared following the procedure for Intermediate 8J using Intermediate 8I. MS m/e 412 (M+1).

Intermediate 9

Ethyl N-(5-bromopyridine-3-yl)carbamate

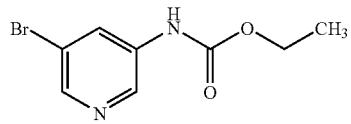

To a solution of 5-bromonicotinic acid (20.0 g, 99.0 mmol) in ethanol (300 mL) was added DPPA (21.6 mL, 100.0 mmol) followed by triethylamine (14.3 mL, 103.0 mmol) then refluxed overnight. After cooling, a half amount of solvent was removed by evaporation. The ethanol solution was extracted with ethyl acetate. The organic layer was washed with $NaHCO_3$ (aq) and brine, dried over $Na_2SO_4$ then evaporated. Sequence purification on $SiO_2$ column chromatography gave the title compound (4.55 g, 19%): MS m/e 245, 246 (M+1).

Intermediate 9A

5-Bromo-2-nitropyridine-3-ylamine

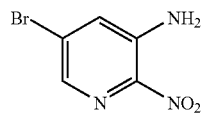

To a mixture of concentrated H₂SO₄ (3.0 mL) and fHNO₃ (2.1 mL), 3-bromo-5-(ethoxycarbonyl)aminopyridine (Intermediate 9—20.0 g, 99.0 mmol) was portionwise added at 0° C. After stirring at 0° C. for 5 min., the mixture was stirred at room temperature overnight. The mixture was poured into ice-water then basified with aqueous NH₄OH. The mixture was extracted with ethyl acetate. The organic layer was washed with aqueous NH₄OH and brine, dried over Na₂SO₄ then evaporated. Sequence purification on SiO₂ column chromatography gave 5-bromo-3-(ethoxycarbonyl)amino-2-nitropyridine (1.57 g, 54%).

To a solution of 5-bromo-3-(ethoxycarbonyl)amino-2-nitropyridine (1.57 g, 5.4 mmol) in ethanol (2.5 mL) was added KOH (813 mg, 14.5 mmol) in water (12.5 mL) and stirred at 90° C. for 1 hr then at room temperature for 1 hr. The mixture was added water. The formed precipitate was collected by filtration, washed with water then dried under reduced pressure to give the title compound (1.08 g, 92%): MS m/e 216, 218 (M−1).

Intermediate 9B

3-Nitro-6-(4-acetamidophenoxy)pyridine-2-ylamine

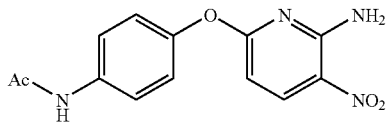

To a solution of 2-amino-6-chloro-3-nitropyridine (2.77 g, 16.0 mmol) in DMF (55 mL) was added 4-acetylaminophenol (2.67 g, 17.5 mmol) followed by K₂CO₃ (3.3 g, 5.0 mmol) and stirred at room temperature for 2 hrs. The solvent was removed by evaporation. To the residue, water was added to form a precipitate. The solid was collected by filtration, washed with water and ethyl acetate then dried under reduced pressure to give the title compound (4.32 g, 94%): MS m/e 289 (M+1).

Intermediate 9C

2-Nitro-5-(4-(tert-butoxycarbonylamino)phenoxy)pyridine-3-ylamine

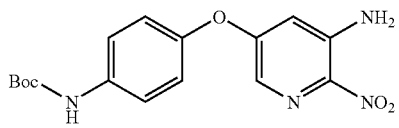

To a solution of 5-bromo-2-nitropyridine-3-ylamine (436 mg, 2.0 mmol) in DMF (10 mL) was added Cs₂CO₃ (977 mg, 3.0 mmol) followed by 4-(t-butoxycarbonyl)aminophenol (459 mg, 2.2 mmol) in DMF (10 mL) at 0° C. then stirred at room temperature for 3 days. The mixture was extracted with ethyl acetate. The organic layer was washed with NaHCO₃ (aq) and brine, dried over Na₂SO₄ then evaporated. Sequence purification on SiO₂ column chromatography gave the title compound (624.2 mg, 90%): MS m/e 347 (M+1).

Intermediate 9D

Methyl (5-(4-aminophenoxy)-3,4-diazaindolin-2-yl)carbamate

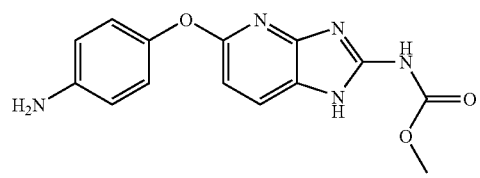

After hydrogenation of 3-nitro-6-(4-acetamidophenoxy)pyridine-2-ylamine (2.02 g, 7.0 mmol) with 5% Pd—C in MeOH (70 mL), catalyst was removed by filtration.

To the MeOH solution, 1,3-bis(methoxycarbonyl)-2-methyl-2-thiopseudourea (1.73 g, 8.4 mmol) was added and stirred at 75° C. After 8 days, AcOH (15 mL) was added and stirred at 80° C. overnight. Additional 1,3-bis(methoxycarbonyl)-2-methyl-2-thiopseudourea (1.73 g, 8.4 mmol) was added then stirred at 80° C. overnight. After cooling, the mixture was poured into NaHCO₃ (aq). Formed precipitate was collected by filtration, washed with ethyl acetate then dried under reduced pressure to give methyl (5-(4-acetoamidophenoxy)-3,4-diazaindolin-2-yl)carbamate (983.0 mg, 41%). To a solution of methyl (5-(4-acetoamidophenoxy)-3,4-diazaindolin-2-yl)carbamate (102.4 mg, 0.3 mmol) in water (3 mL) was added 2N HCl (aq) (3.0 mL) then refluxed for 1 hr and stirred at room temperature for 1 hr. The mixture was extracted with ethyl acetate. The organic layer was washed with NH₄OH (aq), dried over Na₂SO₄ then evaporated. Sequence purification on SiO₂ column chromatography gave the title compound (33.6 mg, 37%): MS m/e 342 (M+1).

Intermediate 9E

Methyl (6-(4-aminophenoxy)-3,4-diazaindolin-2-yl)carbamate

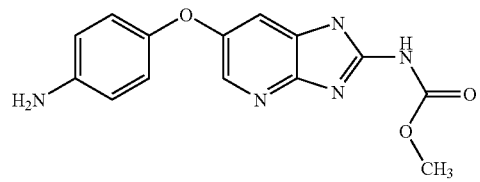

The same procedure described in Intermediate 9D gave methyl (5-(4-(tertbutoxycarbonyl)aminophenoxy)-3,7-diazaindolin-2-yl)carbamate. To a solution of methyl (5-(4-(tert-butoxycarbonyl)aminophenoxy)-3,7-diazaindolin-2- yl)carbamate (160.8 mg, 0.4 mmol) in methanol (10 mL) was added 2N HCl (aq) (10 mL) then stirred at room temperature overnight. The solution was removed by evaporation then the residue was extracted with ethyl acetate. The organic layer was washed with NaHCO₃ (aq) and brine, dried over Na₂SO₄ then evaporated. The residual solid was washed with ethyl acetate then dried under reduced pressure to give the title compound (95.3 mg, 80%): MS m/e 300 (M+1).

Intermediate 9F

Ethyl 3-(6-Chrolo-3-nitropyridine-2-ylamino)propanoate

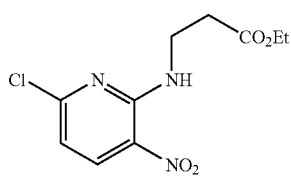

To a solution of 2,6-dichloro-3-nitropyridine (4.83 g, 25.0 mmol) in acetonitrile (100 mL) was added β-alanine hydrochloride (4.61 g, 30.0 mmol) followed by K₂CO₃ (10.4 g, 75.0 mmol). After stirring at room temperature for 3 days, the solvent was removed by evaporation. The residue was extracted with ethyl acetate. The organic layer was washed with water and brine, dried over Na₂SO₄ then evaporated. Sequence purification on SiO₂ column chromatography gave the title compound (5.01 g, 73%): MS m/e 272, 274 (M−1).

Intermediate 9G

Ethyl 3-(6-(4-acetamidophenoxy)-3-nitropyridine-2-ylamino)propanoate

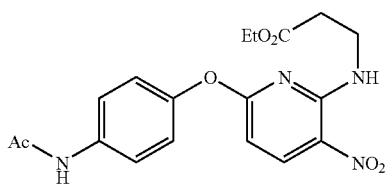

To a solution of ethyl 3-(6-chrolo-3-nitropyridine-2-ylamino)propanoate (Intermediate 9F-2.72 g, 9.94 mmol) in DMF (30 mL) was added 4-acethylaminophenol (1.66 g, 11.0 mmol) followed by K₂CO₃ (2.1 g, 14.9 mmol) then stirred at room temperature for 1 hr. To the mixture, water was added to form precipitate. The solid was collected by filtration, washed with water and ethyl acetate then dried under reduced pressure to give the title compound (3.79 g, 98%): MS m/e 389 (M+1).

Intermediate 9H

2-Amino-3-(2-(ethoxycarbonyl)ethyl)-5-(4-acetamidophenoxy)-3,4-diazaindolidine

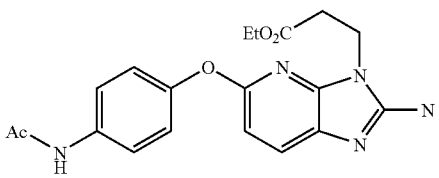

After hydrogenation of ethyl 3-(6-(4-acetamidophenoxy)-3-nitropyridine-2-ylamino)propanoate (Intermediate 9G-1.94 g, 5.0 mmol) with 50% Pd—C in MeOH (25 mL) and evaporation, the residue was added ethanol (65 mL) and BrCN (1.84 g, 17 mmol) and stirred at room temperature overnight. The mixture was extracted with ethyl acetate. The organic layer was washed with NaHCO₃ (aq) and brine, dried over Na₂SO₄ then evaporated. The residue was washed with ethyl acetate then MeOH then dried under reduced pressure to give the title compound (800.0 mg, 42%): MS m/e 384 (M+1).

Intermediate 9I 3,4-Dihydro-6-(4-aminophenoxy)-1,4a,5-triazacarbazol-2-one

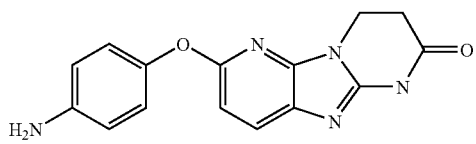

To a solution of 2-amino-3-(2-(ethoxycarbonyl)ethyl)-5-(4-acetamidophenoxy)-3,4-diazaindolidine (Intermediate 9H-200.0 mg, 0.52 mmol) in ethanol (10 mL) was added conc.HCl (1.0 mL) and stirred at 85° C. overnight. After evaporation to remove ethanol, DMF (10 mL) was added to the mixture then heated to 120° C. for 2 hrs. After cooling, the solvent was removed by evaporation then the residue was washed with MeOH. The result solid was added 2M HCl (12 mL) and stirred at room temperature overnight. The mixture was basified with NH₄OH (aq). The formed precipitate was collected, washed with water then dried under reduced pressure to give the title compound (103.4 mg, 67%): MS m/e 296 (M+1).

Intermediate 9J 5-(4-Acetamidophenoxy)pyridine-2-ylamine

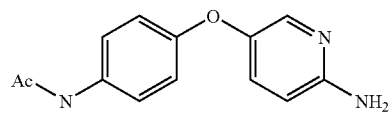

To a solution of 5-bromo2-nitropyridine (2.03 g, 10.0 mmol) in DMF (30 mL) was added $Cs_2CO_3$ (4.9 g, 15.0 mmol) followed by 4-acetylaminophenol (1.66 g, 11.0 mmol) in DMF (30 mL) at 0° C. then stirred at room temperature overnight. The mixture was extracted with ethyl acetate. The organic layer was washed with water and brine, dried over. $Na_2SO_4$ then evaporated. Sequence purification on $SiO_2$ column chromatography and recrystalization from ethyl acetate gave 5-(4-acetamidophenoxy)-2-nitropyridine (1.62 g, 59%). Hydrogenation of 5-(4-acetamidophenoxy)-2-nitropyridine (879.0 mg, 3.22 mmol) with 5% Pd—C in MeOH (80 mL) gave the title compound (575.7 mg, 74%): MS m/e 244 (M+1).

Intermediate 9K

Methyl (5-(4-aminophenoxy)azaindolizine-2-yl)carbamate

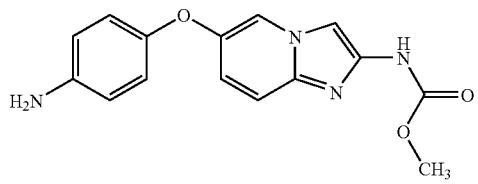

To a solution of 5-(4-acetamidophenoxy)pyridine-2-ylamine (Intermediate 9J170.2 mg, 0.7 mmol) in DMF (2 mL) was added N-(methoxycarbonyl)chloroacetoamide (159.0 mg, 1.1 mmol). The mixture was stirred at 80° C. overnight. Additional N-(methoxycarbonyl)chloroacetoamide (159.0 mg, 1.1 mmol) was added and stirred at 80° C. overnight. After cooling, the mixture was extracted with ethyl acetate. The organic layer was washed with $NaHCO_3$ (aq) and brine, dried over $Na_2SO_4$ then evaporated. Sequence purification on $SiO_2$ column chromatography gave methyl (5-(4-acetoamidophenoxy)azaindolizine-2-yl)carbamate (51.7 mg, 22%). To a solution of methyl (5-(4-acetoamidophenoxy)azaindolizine-2-yl)carbamate (34.0 mg, 0.1 mmol) in water (2 mL) was added 2N HCl (aq) (2.0 mL) then refluxed for 1 hr and stirred at room temperature for 1 hr. The mixture was added $NH_4OH$ (aq). Formed precipitate was collected by filtration, washed with water then dried under reduced pressure to give the title compound (22.0 mg, 74%): MS m/e 299 (M+1).

Intermediate 10

4-(4-Nitrophenoxy)aniline

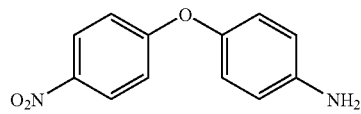

To a mixture of NaH (60% oily, 880 mg, 22.0 mmol) in DMF (40 mL) was added a solution of 4-aminophenol (2.40 g, 22.0 mmol) in DMF (30 mL) followed by 1-fluoro-4-nitrobenzene (2.12 mL, 20.0 mmol). The mixture was stirred at 90° C. overnight. After cooling, the mixture was extracted with ethyl acetate. The organic layer was washed with water and brine, dried over $Na_2SO_4$ then evaporated. Sequence purification on $SiO_2$ column chromatography gave the title compound (4.60 g, quant): MS m/e 229 (M−1).

Intermediate 10A 6-(4-Nitrophenoxy)benzthiazole-2-ylamine

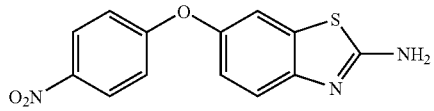

See the procedure following for Intermediate 10B.

Intermediate 10B

4-Bromo-6-(4-nitrophenoxy)benzthiazole-2-ylamine

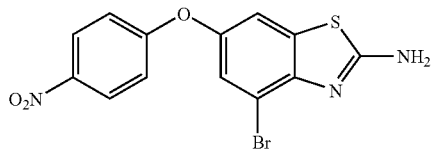

To a solution of 4-(4-nitrophenoxy)aniline (Intermediate 10–1.15 g, 5.0 mmol) in AcOH (5 mL) was added KSCN (729 mg, 7.5 mmol). The mixture was cooled to 0° C. and added a solution of $Br_2$ (256 μL, 5.0 mmol) in AcOH (6 mL) then stirred at room temperature overnight. The mixture was poured into $H_2O$, basified with $NH_4OH$ (aq), then extracted with ethyl acetate. The organic layer was washed with water and brine, dried over $Na_2SO_4$ then evaporated. Sequence purification on $SiO_2$ column chromatography gave Intermediate 10A (941.5 mg, 66%): MS m/e 288 (M+1) and Intermediate 10B (223.7 mg, 12%): MS m/e 366, 368 (M+1).

Intermediate 10C

N-(6-(4-Nitrophenoxy)benzthiazole-2-yl)methanesulfonamide

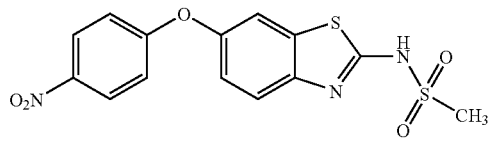

To a solution of Intermediate 10A (1.15 g, 4.0 mmol) in pyridine (10 ml) was added mesyl chloride (1.55 ml, 20 mmol) at 0° C. and stirred over night at 0° C.—room temperature. Then potassium carbonate (5.5 g, 40 mmol) in water (20 ml) and MeOH (20 ml) was added and stirred 4 days at 60° C. MeOH was removed by evaporated and desired compound was extracted with AcOEt ×3 and organic layer was washed with water and brine and dried over with $MgSO_4$. And purified by column chromatography (AcOEt-DCM, 1:1,3:1) and crystallized from AcOEt-Hexane. 300 mg of Intermediate 10C was obtained as yellow solid. Yield 20.5% MS m/e 366 (M+1).

Intermediate 10D

N-(6-(4-Aminophenoxy)benzthiazole-2-yl)methane-sulfonamide

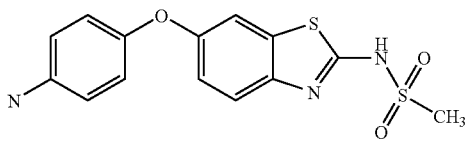

To a solution of Intermediate 10C (100 mg, 0.27 mmol) in acetic acid (1 ml) was added Zn (54 mg, 0.81 mmol) and stirred over night at room temperature. Acetic acid was removed by evaporation and residue was dissolved in DMF and filtrated. Filtrate was purified by SPE(SCX) tube (washed with MeOH/DMF and eluted with $NH_3$/MeOH). $NH_3$/MeOH eluent was collected and 72 mg of Intermediate 10D was obtained. Yield 79.5% MS m/e 336 (M+1).

Intermediate 10E

Methyl (6-(4-nitrophenoxy)benzthiazole-2-yl)carbamate

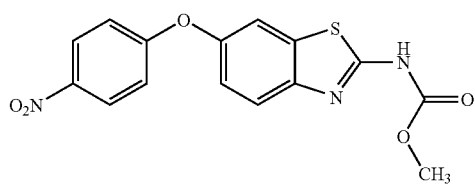

To a mixture of 5-(4-nitrophenoxy)benz-3-thiazole-2-ylamine (430.5 mg, 1.5 mmol) in pyridine (6 mL) and DMF (9 mL) was dropwise added an excess amount of $ClCO_2Me$ (ca 0.8 mL) at room temperature. The mixture was added water. The formed precipitate was collected by filtration, washed with water and MeOH and dried under reduced pressure to give the title compound (503.7 mg, 97%): MS m/e 346 (M+1).

Intermediate 10F

Methyl (4-bromo-6-(4-nitrophenoxy)benzthiazole-2-yl)carbamate

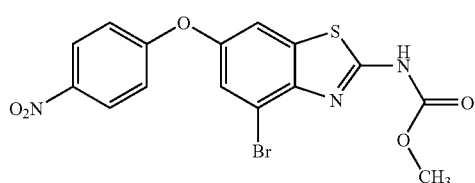

The title compound was prepared following the procedure for Intermediate 10E using Intermediate 10A. MS m/e 424, 426 (M+1)

Intermediate 10G

Methyl (6-(4-aminophenoxy)benzthiazole-2-yl)carbamate

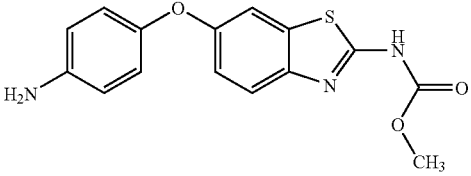

To a solution of methyl (6-(4-nitrophenoxy)benzthiazole-2-yl)carbamate (Intermediate 10E-172.7 mg, 0.5 mmol) in DMF (5 mL) was added $SnCl_2$ (474.0 mg, 2.5 mmol) and stirred at room temperature for 4 days. The mixture was extracted with ethyl acetate, and the organic layer was washed with $NaHCO_3$aq. and dried over $Na_2SO_4$ then evaporated to remove solvent. The residue dissolved in small amount of DMF was charged on SCX column chromatography then washed with MeOH then eluted with $NH_3$—MeOH to give the title compound (69.2 mg, 44%): MS m/e 316 (M+1).

Intermediate 10H

Methyl (4-bromo-6-(4-aminophenoxy)benzthiazole-2-yl)carbamate

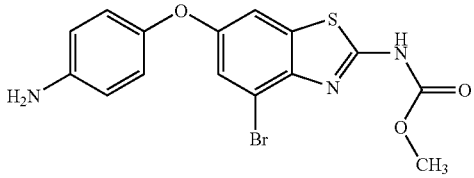

To a solution of methyl (4-bromo-6-(4-nitrophenoxy)benzthiazole-2-yl)carbamate (Intermediate 10F-65.3 mg, 0.15 mmol) in AcOH (2 mL) was added Zn powder (300 mg) and stirred at room temperature for 2 hrs. The insoluble materials were removed by filtration. The solvent was removed by evaporation. The residue was charged on SCX column chromatography then washed with MeOH then eluted with $NH_3$—MeOH to give the title compound (39.6 mg, 65%): MS m/e 394, 396 (M+1).

Intermediate 11

4-(3-Benzyloxy-4-nitrophenoxy)aniline

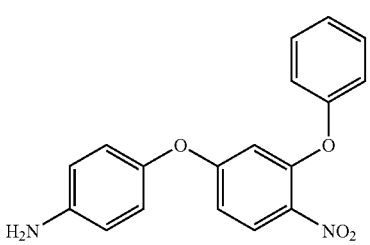

To a solution of 5-fluoro-2-notrophenol (9.43 g, 60.0 mmol) in acetone (100 mL) was added $K_2CO_3$ (12.4 g, 90.0 mmol) followed by benzylbromide (8.6 mL, 72.0 mmol) and acetone (60 mL) then stirred at room temperature overnight. The mixture was extracted with ethyl acetate, and the organic layer was washed with water and brine, dried over $Na_2SO_4$ then evaporated. Sequence purification on $SiO_2$ column chromatography gave 2-benzyloxy-4-nitro-1-fluorobenzene (11.97 g, 81%).

To a mixture of NaH (60% oily, 440.0 mg, 11.0 mmol) in DMF (20 mL) was dropwise added 4-aminophenol (1.20 g, 11.0 mmol) in DMF (15 mL) followed by 2-benzyloxy-4-nitro-1-fluorobenzene (2.47 g, 10.0 mmol) in DMF (15 mL). The mixture was stirred at room temperature for 10 min then at 80°0 C. overnight. After cooling, the mixture was extracted with ethyl acetate. The organic layer was washed with water and brine, dried over $Na_2SO_4$ then evaporated. Sequence purification on $SiO_2$ column chromatography gave the title compound (3.30 g, 98%): MS m/e 337 (M+1).

Intermediate 11A

N-(4-(3-Benzyloxy-4-nitrophenoxy)phenyl)(2-fluoro-5-(trifluoromethyl)phenylamino)formamide

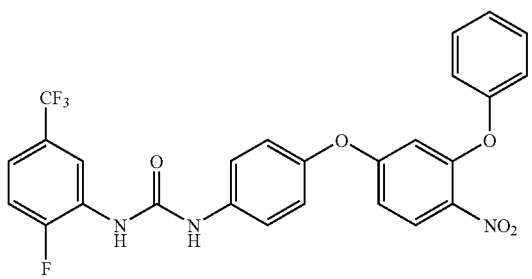

To a mixture of 4-(3-benzyloxy-4-nitrophenoxy)aniline (Intermediate 11–1.34 g, 4.0 mmol) in THF (40 mL) was added 5-fluoro-3-trifruolomethylphenyl isocyanate (636 µL, 4.4 mmol) and stirred at room temperature overnight. The mixture was added MeOH then the solvent was removed by evaporation. The residue was purified on $SiO_2$ column chromatography gave the title compound (2.17 g, quant): MS m/e 542 (M+1).

Intermediate 11B 6-(4-((2-Fluoro-5-(trifluoromethyl)phenyl)aminocarbonylamino)phenyloxy)benzoxazol-2-ylamine

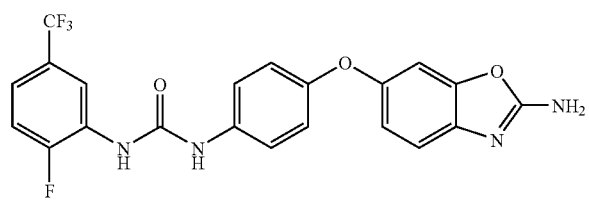

After hydrogenation of N-(4-(3-benzyloxy-4-nitrophenoxy)phenyl)(2-fluoro-5-(trifluoromethyl)phenylamino)formamide (Intermediate 11A-542 mg, 1.0 mmol) with 5% Pd—C in MeOH (10 mL), BrCN (800 mg, 7.6 mmol) was added and stirred at room temperature for 4 days. The mixture was added $NaHCO_3$ (aq) and stirred for 1 day. The mixture was extracted with ethyl acetate. The organic layer was washed with $NaHCO_3$ (aq) and brine, dried over $Na_2SO_4$ then evaporated. Sequence purification on $SiO_2$ column chromatography gave the title compound (237 mg, 53%): MS m/e 447 (M+1).

Intermediate 11C 4-(4-(Acetamido)phenylcarbonyl)-1,2-dinitrobenzene

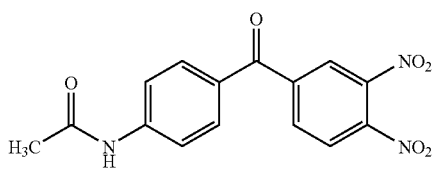

A mixture of 3,4-dinitrobenzoyl chloride (4 mmol), acetoanilide (540 mg, 4 mmol), and $AlCl_3$ (1.6 g) in $CH_2Cl_2$ was heated at 40° C. for 24 h. The slurry was washed with HCl (aq) and the product was extracted with ether. It was washed with $K_2CO_3$ (aq), dried, and evaporated. Purification by column-chromatography on silica-gel (hexane:AcOEt=1:3) provided 87 mg of the title compound; MS m/e 328 (M−1).

Intermediate 11D 4-(4-Aminophenylcarbonyl)-1,2-dinitrobenzene

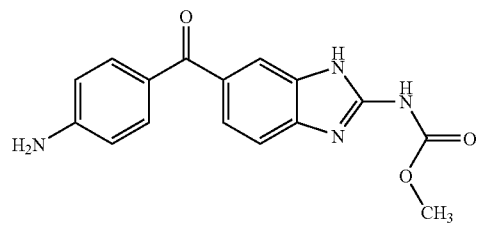

Using the methods of Intermediate 2 and then Intermediate 3 (Method A), Intermediate 11D was prepared from Intermediate 11C; MS m/e 311 (M+1).

Intermediate 12

4-Nitro-3-fluorophenyl tetrahydropyranyl ether

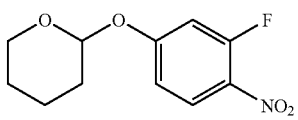

To the mixture of 3-fluoro-4-nitrophenol (25 g, 0.160 mol) and 3,4-dihydro-2H-pyran (14 g, 0.167 mol)in dicloromethane (200 ml), pyridinium p-toluenesulfonate (4.0 g, 16 mol) was added portionly under ice-water bath. After overnight at room temperature, the reaction mixture was pored to Si-column chromatography. Eluting by Hexane Ethyl acetate (3:1), the desired product was obtained at 35.5 g (92%) as light yellow solid.

Intermediate 12A

3-Benzylamino-4-nitrophenyl tetrahydropyranyl ether

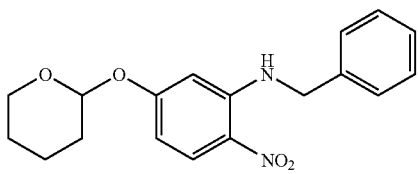

To the solution of Intermediate 12 (20 g, 0.083 mol) in DMSO (150 ml), benzylamine (8.9 g, 0.083 mol) and $K_2CO_3$ (23 g) were added at room temperature. $NH_2$-TLC by eluted Hexane-AcOEt showed reaction complete. Water was added to the mixture, then, extracted by AcOEt at twice. All organic layer was evaporated. The residue is used to the next reduction. MS m/e 329 (M+1).

Intermediate 12B

3-Benzylamino-4-nitrophenyl tetrahydropyranyl ether

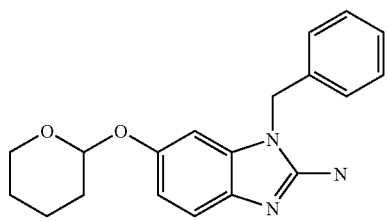

The product of Intermediate 12A was reduced in a usual manner to give 2-benzylaminoaniline derivative (see Intermediate 2). To the suspension of crude diamino phenylene (26.3 g, 88 mmol) derivatives in methanol (300 ml), bromocyanide (9.35 g, 1 equiv.) was added at 0° C. After 15 min, the ice-bath was removed and stirred for 1 hr at room temperature. After evaporation of the methanol solution, saturated $NaHCO_3$ (300 ml) and AcOEt (100 ml) were added to the residue. Generated precipitates were filtered and washed with water to give a crude powder (21.68 g). MS m/e 324 (M+1).

Intermediate 12C

N-(1-Benzyl-6-hydroxy-1H-benzimidazol-2-yl)acetamide

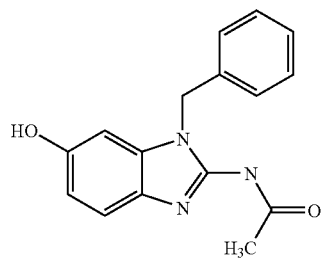

To the suspension of Intermediate 12B (2 g, 6.1 mmol) in THF (5 ml), acetic anhydride (2.3 ml) was added at room temperature. After 3 hr at room temperature, THF was evaporated. Ice-water was added to the residue, then conc. HCl and methanol were added carefully at 0 C. After 30 min' stirring, the acidic solution was neutralized by NaOH and $NaHCO_3$. The generated precipitate was collected, washed with $Et_2O$, and dried to give the title compound. MS m/e 282 (M+1).

Intermediate 12D

1-Benzyl-6-hydroxy-2-(tert-butoxycarbonylamino)-1H-benzimidazole

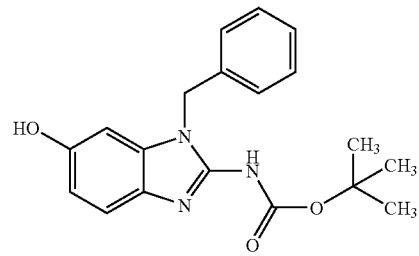

1-Benzyl-6-hydroxy-2-amino-1H-benzimidazole was treated with $BOC_2O$ in pyridine, followed by hydrolysis with NaOH (aq) to give the title compound; MS m/e 340 (M+1).

Intermediate 12E

Tert-Butyl N-(1-benzyl-6-(6-aminopyridin-3-yloxy)-1H-benzimidazol-2-yl)

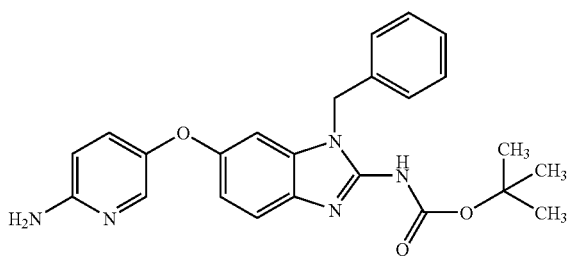

Coupling of Intermediate 12D with 3-bromo-6-nitropyridine and subsequent hydrogenation over Pd/C gave the title compound; MS m/e 432 (M+1).

Intermediate 13A 1-(6-(4-Nitrophenoxy)benzthiazol-2-yl)-3-butylurea

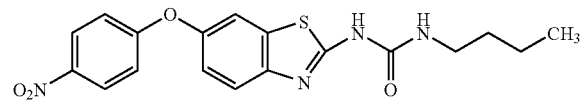

Intermediate 13A was prepared following a similar procedure for Example 1 using Intermediate 10A. MS m/e 387 (M+1)

Intermediate 13B 1-(6-(4-Aminophenoxy)benzthiazol-2-yl)-3-butylurea

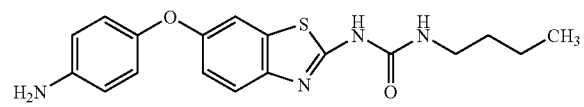

Intermediate 13B was prepared following a similar procedure for Intermediate 10D using Intermediate 13A. MS m/e 357 (M+1)

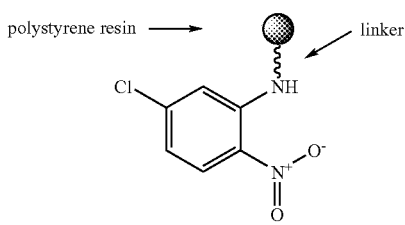

Intermediate 14A

Resin-Bound 5-Chloro-2-nitroaniline

Amino-(4-methoxyphenyl)-methylpolystyrene (loading 1.69 mmol/g, 7.00 g, 11.8 mmol) was soaked in DMSO in a peptide vessel for 30 min. The solvent was then drained. DIEA (11.3 mL, 65.1 mmol) in DMSO (88 mL) was added to the resin, followed by 4-chloro-2-fluoronitrobenzene (10.4 g, 59.2 mmol). The mixture was shaken at room temperature for 19 h, at which point it was drained. The resin was washed with DMSO (3x), EtOH (3x), DMF (3x), MeOH (3x) and DCM (3x). It was then dried under vacuum overnight. A small sample (approx. 10 mg) was treated with 23:2:75 (v/v/v) TFA/H₂O/DCM (0.5 mL) for ca. 1 h. The solution containing the released material was concentrated and analyzed with LC/MS. UV (254 nm): 97% @ 5.65 min. MS: m/e 171 (M−1).

Intermediate 14B

Resin-bound 5-(4-Aminophenoxy)-2-nitroaniline

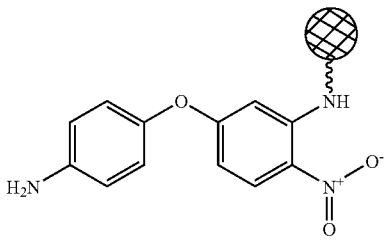

4-Aminophenol (4.71 g, 43.2 mmol) was dissolved in degassed DMF (108 mL) and bubbled with Ar for 10 min in a dry, 300-mL pear-shaped flask. Sodium hydride (60% in mineral, 1.78 g, 44.5 mmol) was added. The mixture was bubbled and stirred for an additional 15 min. Resin-bound 5-chloro-2-nitroaniline 1 (4.3 g, theoretically 5.75 mmol) was added to the now dark mixture. After the evolution of gas had minimized, the flask was stoppered and shaken at room temperature for ca. 4.5 days. The mixture was filtered and the salts washed away with water. The black resin was washed with H₂O (3x), 1:1 DMF/H₂O (3x), DMF (3x), MeOH (3x) and DCM (3x). The reaction was repeated on the same resin batch the same way. After drying in vacuo, a small sample (approx. 10 mg) was treated with 23:2:75 (v/v/v) TFA/H₂O/DCM (0.5 mL) for ca. 1 h. The solution containing the released material was concentrated and analyzed with LC/MS. UV (254 nm): 90% @ 6.08 min. MS: m/e 244 (M−1).

Intermediate 14C (Library)

Resin-bound 5-(4-((Heteroaryl)aminocarbonylamino)phenoxy)-2-nitroaniline

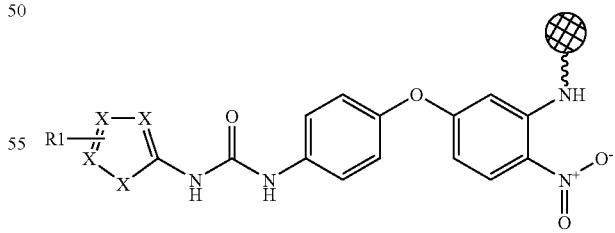

X = C, S, O or N

Intermediate 14B (approx. 224 mg, theoretically 0.273 mmol) was rinsed with 1:1 (v/v) THF/DCM in a 25-mL Alltech tube. p-Nitrophenyl chloroformate (551 mg, 2.73 mmol) and DIEA (476 μL, 2.73 mmol) in 1:1 (v/v) THF/DCM (5.5 mL) was added. The mixture was shaken for 18–22 h. After draining, the resin was washed with 1:1 (v/v) THF/DCM (3–4x). The heteroaryl amine (2.73 mmol) and DIEA (476 µL, 2.73 mmol) in DMF (5.5 mL) were added. (Twice the equivalent of DIEA was used for the amines that were monohydrochloride salts.) The yellow mixtures were shaken for ca. 16 h. and then drained. The resin was washed thoroughly with DMF (3×), 10:90 DIEA/DMF (10×), DMF (3×), 1:1 DMF/H₂O (3×), MeOH (3×), DCM (3×) to wash away most of the p-nitrophenol that slowly leached away from the resin. After drying, a small sample (approx. 5 mg) was treated with 23:2:75 (v/v/v) TFA/H₂O/DCM (0.5 mL) for ca. 1 h. The solution containing the released material was concentrated and analyzed with LC/MS.

Intermediate 14D (Library)

Resin-Bound 4-(4-((Heteroaryl)aminocarbonylamino)phenoxy)-1,2-phenylenediamine

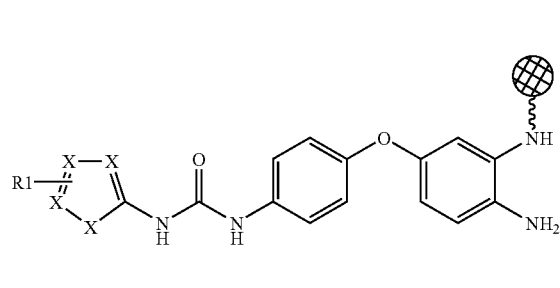

X = C, S, O or N

Intermediate 14C (theoretically 0.273 mmol) was soaked in NMP for at least 30 min in a 25-mL Alltech tube. Tin (II) chloride dihydrate (1.85 g, 8.20 mmol) in NMP (8.20 mL) was added and the mixture was shaken for ca. 5.5 days. After filtration, the resin was washed with NMP (3×), 30:70 ethylene diamine/NMP (10×), NMP (3×), MeOH (3×) and DCM (3×). It was dried under vacuum and a small sample (approx. 5 mg) was treated with 23:2:75 (v/v/v) TFA/H₂O/DCM (0.5 mL) for ca. 1 h. The solution containing the released material was concentrated and analyzed with LC/MS.

Intermediate 14E (Library)

1-Resin-bound-2-(Fmoc-amino)-6-(4-((heteroaryl) aminocarbonylamino)phenoxy)-1H-benzimidazoles

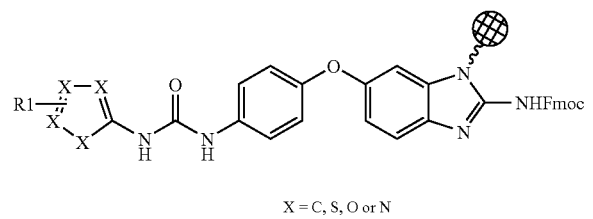

X = C, S, O or N

Intermediate 14D (theoretically 0.273 mmol) was rinsed with DMF in a 25-mL Alltech tube. DIC (1.71 mL, 10.9 mmol) was added to a solution of Fmoc-NCS (1.54 g, 5.47 mmol) in DMF (5.5 mL) and the mixture was immediately added to the resin. The Alltech tube was vortexed vigorously for ca. 6.75 days. The mixture was drained and the precipitate formed during the reaction was washed away with DCM. The resin was then washed with DCM (3×), DMF (3×), 1:1 DMF/H₂O (3×), MeOH (3×) and DCM (3×) and dried in vacuo. A small sample (approx. 5 mg) was treated with 23:2:75 (v/v/v) TFA/H₂O/DCM (0.5 mL) for ca. 1 h. The solution containing the released material was concentrated and analyzed with LC/MS.

Intermediate 14F (Library)

1-Resin-Bound-2-(R2-carbonylamino)-6-(4-((heteroaryl)aminocarbonylamino)phenoxy)-1H-benzimidazoles

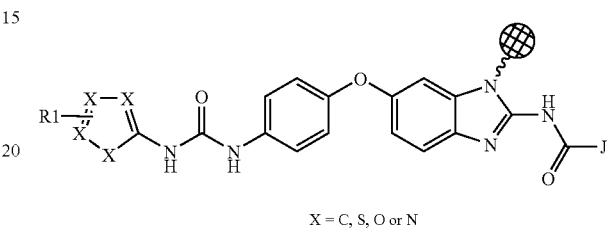

X = C, S, O or N

Intermediate 14E (theoretically 0.0401 mmol) was treated with 20% piperidine in DMF (1 mL) in a 6-mL Alltech tube for 30 min. The mixture was drained and the resin washed with DMF (3×). The piperidine treatment and the succeeding DMF wash were repeated for a second time.

Coupling Procedure A (for acetic acid and 4-dimethylaminobutyric acid hydrochloride): To a mixture of DIEA (69.9 µL, 0.400 mmol) and EDC (38.5 mg, 0.200 mmol) in DMF (0.67 mL) was added a solution of HOBt-H₂O (30.7 mg, 0.200 mmol) and the acid (0.200 mmol) also dissolved in DMF (1.33 mL). (The equivalent of DIEA was doubled for the butyric acid coupling.) The acid was activated for ca. 5 min. and then added to the deprotected resin. The reaction mixture was vortexed for ca. 15 h. The solvent was removed by vacuum and the resin washed with DMF (3×), 1:1 DMF/H₂O (3×), MeOH (3×) and DCM (3×).

Coupling Procedure B (for 2-furoic and 2-(2-methoxyethoxy)acetic acids): To a solution of the acid (0.202 mmol) in DMF (0.67 mL) was added HOBt-H₂O (30.9 mg, 0.202 mmol) in DMF (0.67 mL), DIEA (70.4 µL, 0.404 mmol) and then HBTU (75.1 mg, 0.198 mmol) in DMF (0.67 mL). The reaction mixture was vortexed for ca. 20 h. After filtration, the resin was washed with DMF (3×), 1:1 DMF/H₂O (3×), MeOH (3×) and DCM (3×).

Intermediate 15A

5-Amino-2-(3,4-diaminophenoxy)pyridine

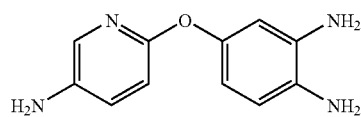

2-Nitro-4-hydroxyaniline was reacted with 2-chloro-5-nitropyridine and K₂CO₃ in DMF at rt, followed by hydrogenation over Pd/C in MeOH, afforded the title compound; MS m/e 217 (M+1).

Intermediate 15B

Methyl N-(5-(5-aminopyridine-2-yl)-1H-benzimidazol-2-yl)carbamate

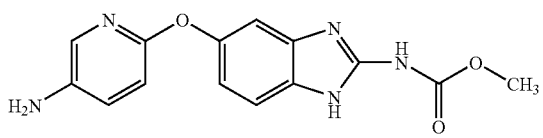

The title compound was obtained according to procedures for Intermediate 3C and 3D, using the product of Intermediate 15A instead of 3,4,4'-triaminodiphenylether; MS m/e 300 (M+1).

Example 1

Methyl N-(5-(4-((3-chlorophenyl) aminocarbonylamino) phenoxy)-1H-benzimidazol-2-yl)carbamate

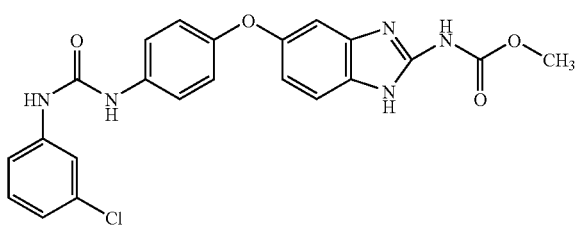

A mixture of methyl (5-(4aminophenoxy)-1H-benzimidazol-2-yl)carbamate (Intermediate 3) (80 mg, 0.27 mmol) and 3-chlorophenylisocyanate (49 mg, 0.32 mmol) in dry THF (2 ml) was heated to 45° C. overnight. After cooling, diethyl ether was added to form a precipitate. The solid was collected by filtration to provide the title compound (83 mg, 69%): $^1$H NMR (DMSO-d$_6$) δ 11.60 (brs, 2H), 9.00 (s, 1H), 8.83 (s, 1H), 7.70 (m, 1H), 7.42 (d, 2H), 7.38 (d, 1H), 7.32–7.24 (m, 2H), 7.01 (m, 2H), 6.93 (d, 2H), 6.80 (dd, 1H) 3.75 (s, 3H); MS m/e 452 (M+1).

Examples 2–11, 14–16, 19–21, 40–78, 81, and 86 were prepared according to the procedures described above for Example 1. Intermediates 3, 3A, and 3B, were used or other precursors as indicated. The free bases obtained may be transformed into their pharmaceutically acceptable salts (e.g. HCl salts) by standard procedures known in the art.

Example 2

Methyl N-(5-(4-((3-(trifluoromethyl)phenyl)aminocarbonylamino) phenylthio)-1H-benzimidazol-2-yl)carbamate

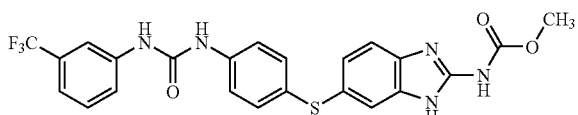

$^1$H NMR (DMSO-d$_6$) δ 11.61 (brs, 1H), 9.01 (s, 1H), 8.85 (s, 1H), 7.76 (s, 1H), 7.08–7.52 (m, 8H), 6.90 (d, 1H), 6.53 (d, 1H), 5.35 (s, 1H), 3.71 (s, 3H); MS m/e 502 (M+1).

Example 3

Methyl N-(5-(4-((3,5-di(trifluoromethyl)phenyl) aminocarbonylamino) phenylthio)-1H-benzimidazol-2-yl)carbamate

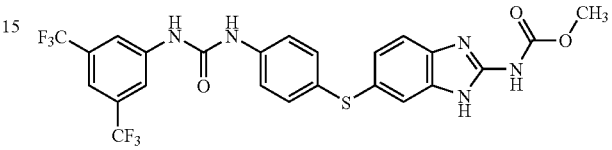

$^1$H NMR (DMSO-d$_6$) δ 11.65 (brs, 1H), 10.00 (s, 1H), 9.45 (s, 1H), 8.07 (s, 2H), 7.59 (s, 1H), 7.31–7.48 (m, 4H), 7.05–7.20 (m, 4H), 3.72 (s, 3H); MS m/e 570 (M+1).

Example 4

Methyl N-(5-(4-((3-bromophenyl)aminocarbonylamino)phenylthio)-1H-benzimidazol-2-yl)carbamate

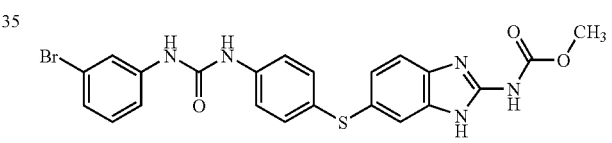

$^1$H NMR (DMSO-d$_6$) δ 11.61 (brs, 1H), 9.25 (s, 1H), 9.17 (s, 1H), 7.79 (s, 1H), 7.40 (d, 2H), 7.16–7.36 (m, 6H), 7.10 (d, 1H), 7.05 (d, 1H), 5.72 (s, 1H), 3.71 (s, 3H); MS m/e 513 (M+1).

Example 5

Methyl N-(5-(4-((3,5-dimethoxyphenyl)aminocarbonylamino) phenylthio)-1H-benzimidazol-2-yl)carbamate

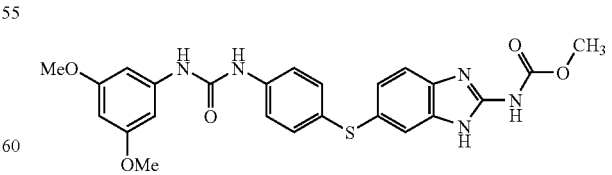

$^1$H NMR (DMSO-d$_6$) δ 11.60 (brs, 1H), 9.13 (s, 1H), 9.05 (s, 1H), 7.40 (d, 2H), 7.05–7.36 (m, 5H), 6.64 (d, 2H), 6.09 (s, 1H), 5.72 (s, 1H), 3.71 (s, 3H), 3.67 (s, 6H); MS m/e 494 (M+1).

Example 6

Methyl N-(5-(4-((2-methyl-5-nitrophenyl)aminocarbonylamino) phenylthio)-1H-benzimidazol-2-yl) carbamate

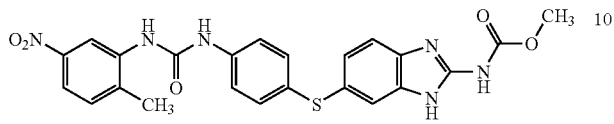

$^1$H NMR (DMSO-d$_6$) δ 11.24 (brs, 1H), 9.32 (s, 1H), 8.93 (dd, 1H), 8.27 (s, 1H), 7.79 (dd, 1H), 7.48–7.38 (m, 5H), 7.22 (dd, 2H), 7.12 (dd, 1H), 3.75 (s, 3H), 2.35 (s, 3H); MS m/e 493 (M+1).

Example 7

Methyl N-(5-(4-((3-ethylphenyl)aminocarbonylamino)phenylthio)-1H-benzimidazol-2-yl)carbamate

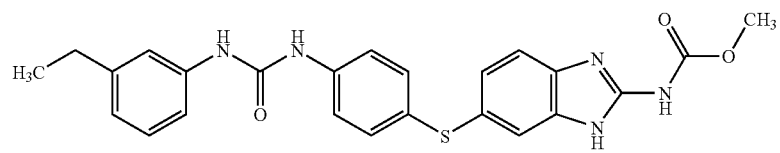

$^1$H NMR (DMSO-d$_6$) δ 11.86 (brs, 1H), 8.72 (s, 1H), 8.58 (s, 1H), 7.46–7.34 (m, 4H), 7.29 (dd, 1H), 7.23–7.14 (m, 4H), 7.08 (dd, 1H), 6.81 (dd, 1H), 3.74 (s, 3H), 2.56 (q, 2H), 1.17 (t, 3H); MS m/e 462 (M+1).

Example 8

Methyl N-(5-(4-((2-fluoro-5-nitrophenyl)amino carbonylamino) phenylthio)-1H-benzimidazol-2-yl) carbamate

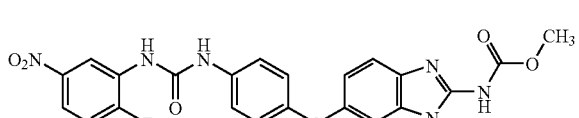

$^1$H NMR (DMSO-d$_6$) δ 11.81 (brs, 1H), 9.26 (s, 1H), 9.13 (dd, 1H), 8.99 (s, 1H), 7.90 (m, 1H), 7.54 (dd, 1H), 7.46–7.38 (m, 4H), 7.21 (dd, 2H), 7.12 (dd, 1H), 3.75 (s, 3H); MS m/e 497 (M+1).

Example 9

Methyl N-(5-(4-((2-fluoro-5-(trifluoromethyl)phenyl) aminocarbonylamino) phenylthio)-1H-benzimidazol-2-yl)carbamate $^1$H NMR (DMSO-d$_6$) δ 11.70 (brs, 2H), 9.25 (s, 1H), 8.89 (d, 1H), 8.60 (dd, 1H), 7.53–736 (m, 6H), 7.22 (d, 2H), 7.12 (dd, 1H), 3.75 (s, 3H); MS m/e 520 (M+1).

Example 9A

Methyl N-(5-(4-((2-fluoro-5-(trifluoromethyl)phenyl) aminocarbonylamino) phenylthio)-1H-benzimidazol-2-yl)carbamate methanesulfonic acid

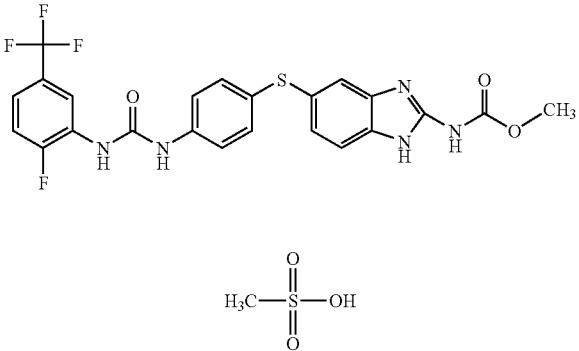

$^1$H NMR (DMSO-d$_6$) δ 9.38 (s, 1H), 8.97 (s, 1H), 8.60 (s, 1H), 7.58–7.48 (m, 4H), 7.44–7.35 (m, 3H), 7.34 (d, 1H), 7.27 (dd, 1H), 3.85 (s, 3H), 2.34 (s, 3H); MS m/e 520 (M+1).

Example 9B

Methyl N-(5-(4-((2-fluoro-5-(trifluoromethyl)phenyl) aminocarbonylamino)phenylthio)-1H-benzimidazol-2-yl)carbamate sulfuric acid

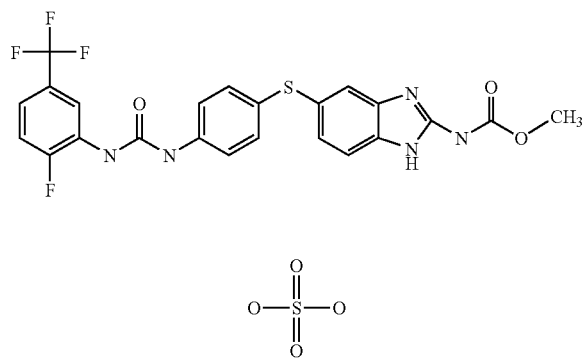

$^1$H NMR (DMSO-d$_6$) δ 9.38(s, 1H), 8.96 (s, 1H), 8.60 (s, 1H), 7.58–7.48 (m, 4H), 7.44–7.34 (m, 4H), 7.26 (dd, 1H), 3.84 (s, 3H); MS m/e 520 (M+1).

Example 10

Methyl N-(5-(4-((2-fluoro-5-(trifluoromethyl)phenyl) aminocarbonylamino) phenoxy)-1H-benzimidazol-2-yl)carbamate

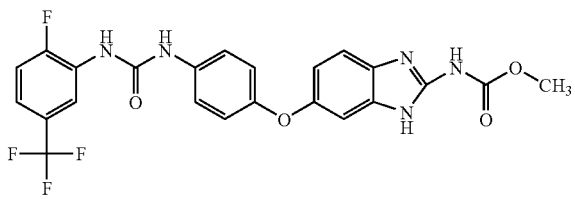

$^1$H NMR (DMSO-d$_6$) δ11.60 (brs, 2H), 9.13 (s, 1H), 8.85 (d, 1H), 8.62 (dd, 1H), 7.49 (m, 1H), 7.44 (d, 2H), 7.40–7.35 (m, 2H), 7.01 (d, 1H), 6.94 (d, 2H), 6.79 (dd, 1H) 3.74 (s, 3H); MS m/e 504 (M+1).

Example 11

Methyl N-(5-(4-((3-ethylphenyl)aminocarbonylamino)phenoxy)-1H-benzimidazol-2-yl)carbamate

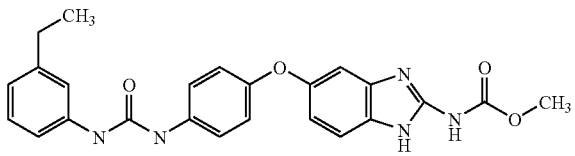

$^1$H NMR (DMSO-d$_6$) δ11.60 (brs, 2H), 8.71 (s, 1H), 8.67 (s, 1H), 7.42 (d, 2H), 7.37 (d, 1H), 7.31–6.98 (m, 4H), 6.92 (d, 2H), 6.83–6.77 (m, 2H), 3.75 (s, 3H), 2.57 (q, 2H), 1.17 (t, 3H); MS m/e 446 (M+1).

Example 12

Methyl N-(5-(4-((2-fluoro-5-(trifluoromethyl)phenyl) aminocarbonylamino) phenylsulfonyl)-1H-benzimidazol-2-yl)carbamate

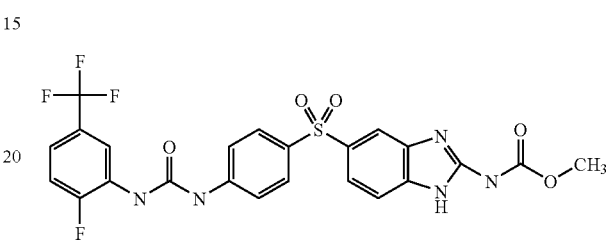

To a solution of methyl N-(5-(4-((2-fluoro-5-(trifluoromethyl)phenyl) aminocarbonylamino) phenylthio)-1H-benzimidazol-2-yl)carbamate (Product of Example 9, 100 mg, 0.19 mmol) in acetic acid (2ml) was added mCPBA (92 mg, 0.53 mmol) in DCM (1 ml) and stirred over night. Aqueous NaHCO3 solution was added and off-white solid was generated. Solid was collected by filtration and washed with water and dried in vacuo. 80 mg of off-white compound was obtained: Yield 76.3%; $^1$H NMR (DMSO-d$_6$) δ12.29 (brs, 1H), 11.60 (brs, 1H), 9.70 (s, 1H), 9.07 (d, 1H), 8.56 (dd, 1H), 7.95 (br, 1H), 7.85 (d, 2H), 7.66 (d, 2H), 7.64–7.61 (m, 1H), 7.59–7.47 (m, 2H), 7.45–7.40 (m, 1H), 3.78 (s, 3H); MS m/e 552 (M+1).

Example 13

Methyl N-(5-(4-((2-fluoro-5-(trifluoromethyl)phenyl) aminocarbonylamino) phenylsulfinyl)-1H-benzimidazol-2-yl)carbamate

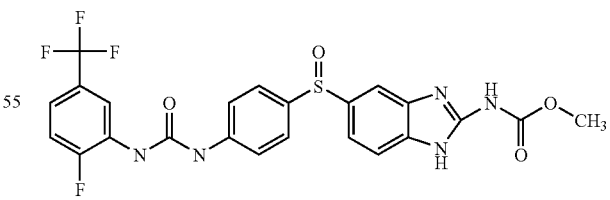

Reduced amount of mCPBA in Example 12 also afforded the title compound. $^1$H NMR (DMSO-d$_6$) δ12.12 (brs, 1H), 11.49 (br, 1H), 9.46 (s, 1H), 8.96 (d, 1H), 8.58 (dd, 1H), 7.73 (s, 1H), 7.60 (s, 4H), 7.54–7.47 (m, 2H), 7.43–7.38 (m, 1H), 7.34 (dd, 1H), 3.76 (s, 3H); MS m/e 536 (M+1).

Example 14

Methyl (5-(3-((3-Chlorophenyl)aminocarbonylamino)phenoxy)-1H-benzimidazol-2-yl)carbamate hydrochloride

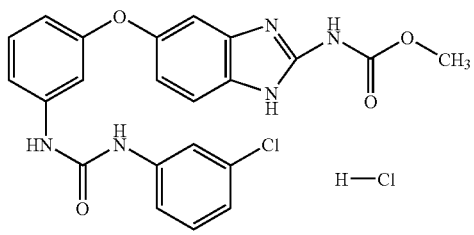

$^1$H NMR (DMSO-d$_6$) δ 10.70 (brs, 1H), 8.82 (s, 1H), 8.79 (s, 1H), 7.64 (m, 1H), 7.40 (d, 1H), 7.23 (m, 3H), 7.11 (m, 2H), 7.07 (m, 1H), 7.00 (d, 1H), 6.82 (dd, 1H), 6.57 (d, 1H), 3.75 (s, 3H); MS m/e 452 (M+1).

Example 15

Methyl N-(5-(3-((2-Fluoro-5-(trifluoromethyl)phenyl)aminocarbonylamino)phenoxy)-1H-benzimidazol-2-yl)carbamate

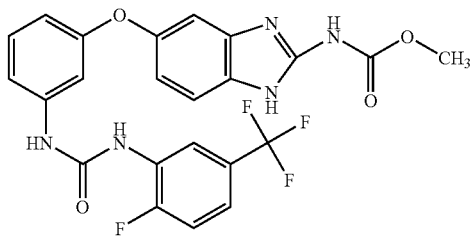

$^1$H NMR (DMSO-d$_6$) δ 11.67 (brs, 2H), 9.23 (s, 1H), 8.80 (s, 1H), 8.54 (d, 1H), 7.48 (t, 1H), 7.41 (m, 2H), 7.26 (t, 1H), 7.14 (d, 1H), 7.08 (d, 2H), 6.84 (d, 1H), 6.61 (d, 1H), 3.75 (s, 3H); MS m/e 504 (M+1).

Example 16

Methyl N-(5-(3-((3-ethylphenyl)aminocarbonylamino)phenoxy)-1H-benzimidazol-2-yl)carbamate

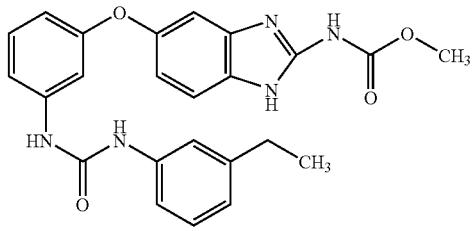

$^1$H NMR (DMSO-d$_6$) δ 11.62 (br, 2H), 8.71 (s, 1H), 8.50 (s, 1H), 7.40 (d, 1H), 7.25–7.15 (m, 5H), 7.09 (d, 2H), 6.81 (t, 2H), 6.55 (d, 1H), 3.75 (s, 3H), 2.54 (q, 2H), 1.15 (t, 3H); MS m/e 446 (M+1).

Example 17

Ethyl N-(5-(4-((2-fluoro-5-(trifluoromethyl)phenyl)aminocarbonylamino)phenoxy)-1H-benzimidazol-2-yl)carbamate

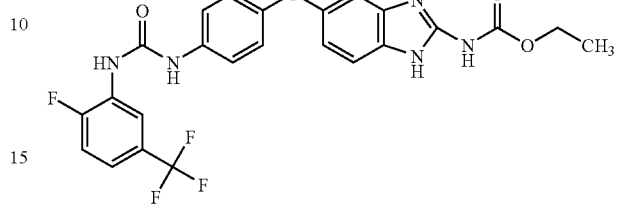

The title compound was prepared by heating a mixture of the product of Example 10 and NaOEt in ethanol:
$^1$H NMR (DMSO-d$_6$) δ 11.50 (brs, 2H), 9.13 (s, 1H), 8.85 (s, 1H), 8.62 (d, 1H), 7.49 (t, 1H), 7.43 (d, 2H), 7.37 (m, 2H), 7.01 (s, 1H), 6.93 (d, 2H), 6.79 (d, 1H), 4.21 (q, 2H), 1.27 (t, 3H); MS m/e 518 (M+1).

Example 18 t-Butyl N-(5-(4-((2-fluoro-5-(trifluoromethyl)phenyl)aminocarbonylamino)phenoxy)-1H-benzimidazol-2-yl)carbamate

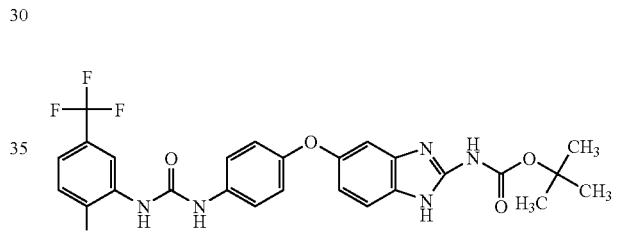

Utilizing the method described for preparing Intermediate 3, but using 1,3-bis(tert-butoxycarbonyl)-2-methyl-2-thiopseudourea instead of 1,3-bis(methoxycarbonyl)-2-methyl-2-thiopseudourea afforded the title compound.
$^1$H NMR (DMSO-d$_6$) δ 11.80 (brs, 1H), 10.94 (brs, 1H), 9.12 (s, 1H), 8.85 (s, 1H), 8.62 (dd, 1H), 7.50 (t, 1H), 7.42 (d, 2H), 7.37 (m, 2H), 7.00 (brs, 1H), 6.91 (d, 2H), 6.76 (dd, 1H), 1.51 (s, 9H); MS m/e 546 (M+1).

Example 19

Methyl N-(5-(4-((3-(trifluoromethyl)phenyl)aminocarbonylamino)phenoxy)-1H-benzimidazol-2-yl)carbamate

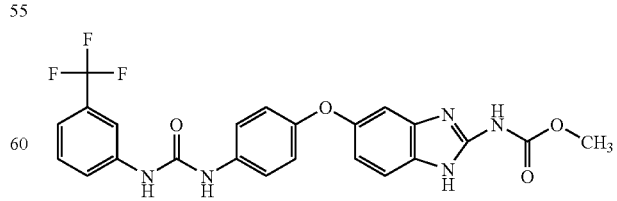

$^1$H NMR (DMSO-d$_6$) δ 11.80 (brs, 2H), 9.04 (s, 1H), 8.78 (s, 1H), 8.01 (s, 1H), 7.57 (d, 1H), 7.50 (t, 1H), 7.43 (d, 2H), 7.37 (d, 1H), 7.29 (d, 1H), 7.00 (s, 1H), 6.92 (d, 2H), 6.79 (dd, 1H), 3.74 (s, 3H); MS m/e 486 (M+1).

Example 20

Methyl N-(5-(3-((3-(trifluoromethyl)phenyl)aminocarbonylamino)phenoxy)-1H-benzimidazol-2-yl)carbamate

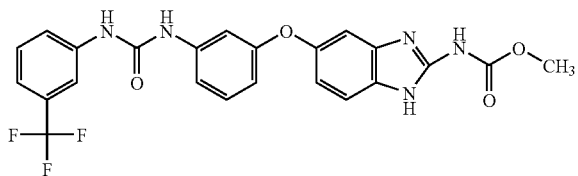

$^1$H NMR (DMSO-d$_6$) δ 11.60 (brs, 2H), 8.98 (s, 1H), 8.89 (s, 1H), 7.94 (s, 1H), 7.54 (d, 1H), 7.49 (t, 1H), 7.41 (d, 1H), 7.29 (d, 1H), 7.24 (t, 1H), 7.14 (s, 1H), 7.09 (d, 2H), 6.83 (dd, 1H), 6.59 (d, 1H), 3.75 (s, 3H); MS m/e 486 (M+1).

Example 21

Methyl N-(5-(4-((3-t-butylphenyl)aminocarbonylamino)phenoxy)-1H-benzimidazol-2-yl)carbamate

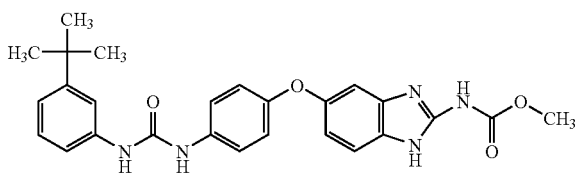

$^1$H NMR (DMSO-d$_6$) δ12.2–11.0 (brs, 2H), 8.61 (s, 1H), 8.59 (s, 1H), 7.45 (m, 3H), 7.36 (d, 1H), 7.27 (d, 1H), 7.19 (t, 1H), 6.99 (m, 2H), 6.91 (d, 2H), 6.78 (dd, 1H), 3.75 (s, 3H), 1.27 (s, 9H); MS m/e 474 (M+1).

Example 22

2-Amino-5-(4-((2-fluoro-5-(trifluoromethyl)phenyl)aminocarbonylamino)phenoxy)-1H-benzimidazole.

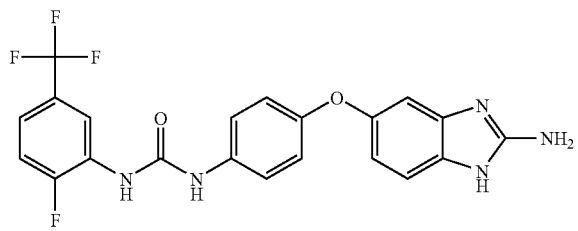

The title compound was prepared from intermediates 4, 5, and 6 described above. To a solution of 4-(4-((2-fluoro-5-(trifluoromethyl)phenyl)aminocarbonylamino)phenoxy)phenylene-1,2-diamine (Intermediate 6) (1.5, 3.6 mmol) in MeOH (20 ml) was added cyanogen bromide (490 mg, 4.6 mmol). The reaction mixture was stirred for 1 h and then washed with aq. NaOH. The product was extracted with AcOEt, dried over MgSO$_4$ and the solvent evaporated. Purification with SCX Ion exchange column chromatography (eluted first with MeOH then with aq. NH$_3$ in MeOH) yielded the title compound (1.53 g, 96%); $^1$H NMR (DMSO-d$_6$) δ 10.63 (brs, 1H), 9.08 (s, 1H), 8.83 (s, 1H), 8.62 (d, 1H), 7.49 (t, 1H), 7.40 (d, 2H), 7.38 (m, 1H), 7.05 (d, 1H), 6.89 (d, 2H), 6.74 (s, 1H), 6.55 (d, 1H), 6.15 (s, 2H); MS m/e 446 (M+1).

Example 23

(6-(4-((2-Fluoro-5-(trifluoromethyl)phenyl)aminocarbonylamino)phenoxy)-3-(methanesulfonyl)-1H-benzimidazol-2-ylamine

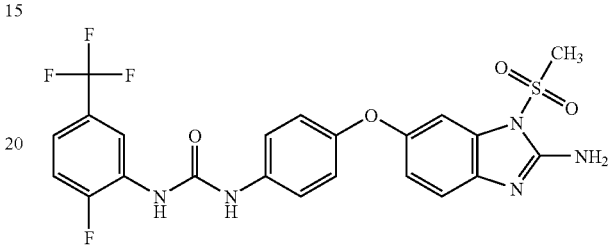

To a mixture of 2-amino-5-4-((2-fluoro-5-trifluoromethylphenyl) aminocarbonylamino) phenoxy)-1H-benzimidazole (90 mg, 0.20 mmol) (prepared according to similar procedures as described for Intermediates 4, 5, and 6 and Example 22) and triethylamine (30 mg, 0.30 mmol) in DMF/CHCl$_3$ (3 ml/1 ml) was added methanesulfonyl chloride (30 mg, 0.26 mmol). After stirring for 3 h at rt, the reaction mixture was washed with water and extracted with CHCl$_3$. The organic layer was dried over MgSO$_4$ and evaporated. The crude material was purified with silica gel column chromatography (AcOEt) to give the title compound (22.0 mg, 15%): $^1$H NMR (DMSO-d$_6$) δ 9.14 (s, 1H), 8.85 (s, 1H), 8.62 (d, 1H), 7.50 (t, 1H), 7.48 (d, 2H), 7.38 (m, 1H), 7.22 (d, 1H), 7.18 (s, 1H), 6.97 (d, 2H), 6.87 (s, 1H), 6.86 (d, 1H), 3.49 (s, 3H); MS m/e 524 (M+1).

Example 24

6-(4-((2-Fluoro-5-(trifluoromethyl)phenyl)aminocarbonylamino)phenoxy)-1-(4-(methyl)phenylsulfonyl)-1H-benzimidazol-2-ylamine

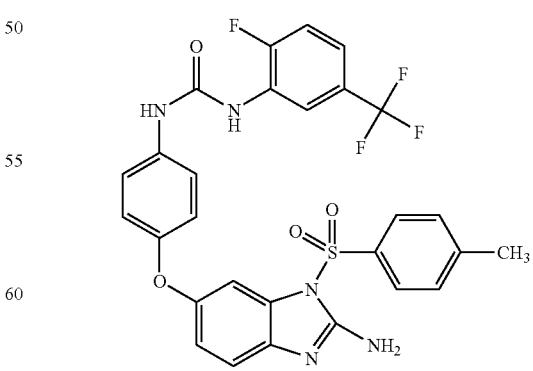

Example 24 was prepared according to procedures similar to the one described above in Example 23. They can be transformed into their pharmaceutically acceptable salts (e.g. HCl salts) by standard procedures. ¹H NMR (DMSO-d₆) δ9.18 (s, 1H), 8.88 (d, 1H), 8.63 (dd, 1H), 7.85 (d, 2H), 7.51–7.46 (m, 5H), 7.43–7.36 (m, 1H), 7.25 (d, 1H), 7.14–7.11 (m, 3H), 6.94 (d, 2H), 6.84 (dd 1H), 2.38 (s 3H); MS m/e 600 (M+1).

Example 25

N-(5-(4-((2-Fluoro-5-(trifluoromethyl)phenyl)aminocarbonylamino)phenoxy)-1H-benzimidazol-2-yl)acetamide

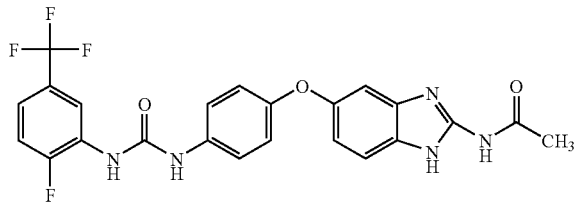

To a mixture of 2-amino-5–4-((2-fluoro-5-(trifluoromethyl)phenyl) aminocarbonylamino)phenoxy)-1H-benzimidazole (prepared according to similar procedures as described for Intermediates 4, 5, and 6 and Example 22) (72 mg, 0.165 mmol), acetic acid (15 mg, 0.24 mmol) and triethylamine (50 mg) in DMF was added HBTU (91 mg, 0.24 mmol) and HOBT (20 mg). The reaction mixture was stirred for 4 h, poured into water, washed and extracted with AcOEt The organic layer was dried over MgSO₄ and evaporated. Purification of the residue by column chromatography on silica gel (AcOEt as an eluant) afforded the title compound (28 mg, 36%): ¹H NMR (DMSO-d₆) δ 11.99 (brs, 1H), 11.51 (br, 1H), 9.15 (s, 1H), 8.87 (s, 1H), 8.62 (d, 1H), 7.50 (t, 1H), 7.43 (d, 2h), 7.38 (m, 2H), 7.04 (d, 1H), 6.93 (d, 2H), 6.80 (dd, 1H), 2.15 (s, 3H); MS m/e 488 (M+1).

Examples 26–35 and 87–102 were prepared according to procedures similar to that described above. They can be transformed into their pharmaceutically acceptable salts (e.g. HCl salts) by standard procedures.

Example 26

N-(5-(4-((2-Fluoro-5-(trifluoromethyl)phenyl)aminocarbonylamino)phenoxy)-1H-benzimidazol-2-yl)cyclopentamide

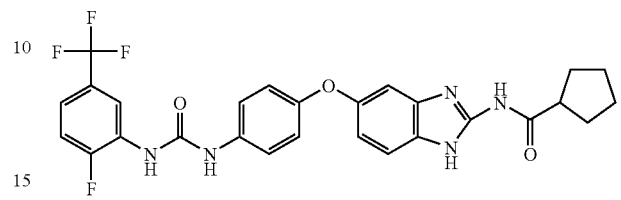

¹H NMR (DMSO-d₆) δ12.05 (brd, 1H), 11.51 (d, 1H), 9.13 (s, 1H), 8.85 (s, 1H), 8.62 (d, 1H), 7.50 (t, 1H), 7.43 (d, 2H), 7.39 (m, 2H), 6.99 (d. 1H), 6.93 (d, 2H), 6.80 (dd, 1H), 2.93 (quint, 1H), 1.88 (m, 2H), 1.70 (M, 4H), 1.57 (m, 2H); MS m/e 542 (M+1).

Example 27

N-(5-(4-((2-Fluoro-5-(trifluoromethyl)phenyl)aminocarbonylamino)phenoxy)-1H-benzimidazol-2-yl)(2-fury)formamide

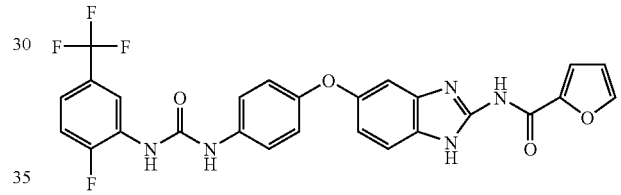

¹H NMR (DMSO-d₆) δ12.20 (brs, 2H), 9.16 (s, 1H), 8.88 (s, 1H), 8.62 (d, 1H), 7.95 (s, 1H), 7.45 (m, 5H), 7.39 (m, 1H), 7.05 (s, 1H), 6.96 (d, 2H), 6.86 (dd, 1H), 6.70 (m, 1H); MS m/e 540 (M+1).

Example 28

N-(5-(4-((2-Fluoro-5-(trifluoromethyl)phenyl)aminocarbonylamino)phenoxy)-1H-benzimidazol-2-yl)-4-methylpentamide

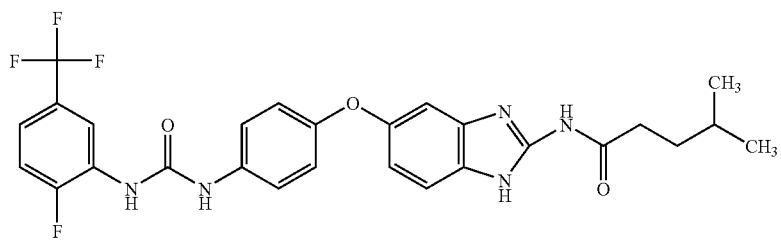

¹H NMR (DMSO-d₆) δ 12.08 (brd, 1H), 11.51 (d, 1H), 9.13 (s, 1H), 8.85 (s, 1H), 8.62 (d, 1H), 7.50 (t, 1H), 7.43 (d, 2H), 7.38 (m, 2H), 7.05 (d, 1H), 6.93 (d, 2H), 6.80 (dd, 1H), 2.44 (t, 2H), 1.53 (m, 2H), 0.90 (d, 6H); MS m/e 544 (M+1).

Example 29

N-(5-(4-((2-Fluoro-5-(trifluoromethyl)phenyl)aminocarbonylamino)phenoxy)-1H-benzimidazol-2-yl)-2-(N-acetylamino)acetamide

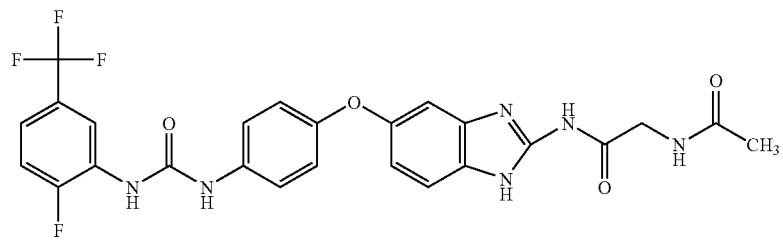

¹H NMR (DMSO-d₆) δ 12.03 (brs, 1H), 11.58 (s, 1H), 9.14 (s, 1H), 8.85 (s, 1H), 8.62 (d, 1H), 8.29 (t, 1H), 7.52 (t, 1H), 7.44 (d, 2H), 7.42 (m, 1H), 7.39 (m, 1H), 7.05 (br, 1H), 6.94 (d, 2H), 6.82 (dd, 1H), 3.96 (d, 2H), 1.90 (s, 3H); MS m/e 545 (M+1).

Example 30

N-(5-(4-((2-Fluoro-5-(trifluoromethyl)phenyl)aminocarbonylamino)phenoxy)-1H-benzimidazol-2-yl)-2-aminoacetamide dihydrochloride

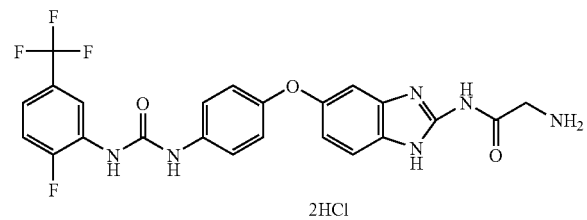

¹H NMR (DMSO-d₆) δ 9.76 (s, 1H), 9.15 (d, 2H), 8.62 (d, 1H), 8.40 (br, 2H), 7.56 (d, 2H), 7.54 (d, 2H), 7.39 (m, 1H), 7.10 (s, 1H), 7.02 (m, 1H), 7.01 (d, 2H), 3.97 (m, 2H); MS m/e 503 (M+1).

Example 31

N-(5-(4-((2-Fluoro-5-(trifluoromethyl)phenyl)aminocarbonylamino)phenoxy)-1H-benzimidazol-2-yl)-2-methoxyacetamide ¹H NMR (DMSO-d₆) δ 12.09 (brs, 1H), 11.41 (br, 1H), 9.13 (s, 1H), 8.86 (s, 1H), 8.62 (dd, 1H), 7.50 (m, 2H), 7.44 (d, 2H), 7.39 (m, 1H), 7.05 (br, 1H), 6.94 (d, 2H), 6.82 (dd, 1H), 4.14 (s, 2H), 3.39 (s, 3H); MS m/e 518 (M+1).

Example 32

3-(N-(5-(4-((2-Fluoro-5-(trifluoromethyl)phenyl)aminocarbonylamino)phenoxy)-1H-benzimidazol-2-yl)carbamoyl)propionic acid

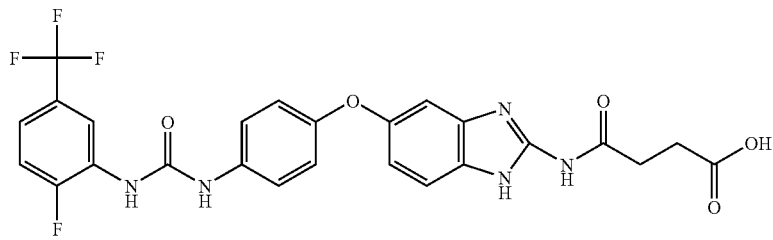

¹H NMR (DMSO-d₆) δ 12.10 (brs, 1H), 11.60 (brs, 1H), 9.22 (s, 1H), 8.92 (s, 1H), 8.61 (dd, 1H), 7.60–7.40 (m, 3H), 7.44 (d, 2H), 7.05 (brs, 1H), 6.93 (d, 2H), 6.80 (dd, 1H), 2.67 (t, 2H), 2.55 (t, 2H); MS m/e 546 (M+1).

Example 33

N-(5-(4-((2-Fluoro-5-(trifluoromethyl)phenyl)aminocarbonylamino)phenoxy)-1H-benzimidazol-2-yl)(2-(2-(methoxy)ethoxy)ethoxy)acetamide

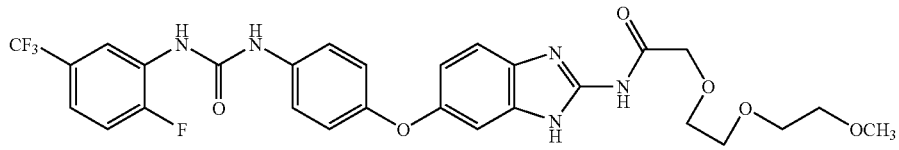

¹H NMR (DMSO-d₆) δ 12.11 (brs, 1H), 11.29 (brs, 1H), 9.15 (s, 1H), 8.86 (d, 1H), 8.61 (dd, 1H), 7.43–7.50 (m, 5H), 6.98–7.14 (brm, 1H), 6.94 (d, 2H), 6.82 (dd, 1H), 4.23 (s, 2H), 3.68–3.70 (m, 2H), 3.56–3.61 (m, 4H), 3.49–3.47 (m, 2H), 3.24 (s, 3H); MS m/e 606 (M+1).

Example 34

N-(5-(4-((2-Fluoro-5-(trifluoromethyl)phenyl)aminocarbonylaminophenoxy)-1H-benzimidazol-2-yl)(2-(methoxy)ethoxy)acetamide

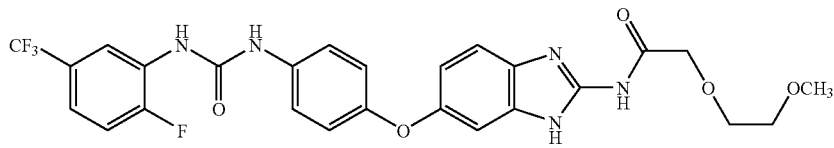

¹H NMR (DMSO-d₆) δ12.11 (brs, 1H), 11.28 (brs, 1H), 9.14 (s, 1H), 8.86 (d, 1H), 8.61 (dd, 1H), 7.38–7.52 (m, 5H), 6.98–7.14 (brs, 1H), 6.94 (d, 2H), 6.82 (dd, 1H), 4.22 (s, 2H), 3.68–3.71 (m, 2H), 3.51–3.54 (m, 2H), 3.30 (s, 3H); MS m/e 562 (M+1).

Example 35

N-(5-(4-((2-Fluoro-5-(trifluoromethyl)phenyl)aminocarbonylamino)phenoxy)-1H-benzimidazol-2-yl)-2-(N-(t-butoxycarbony)amino)acetamide

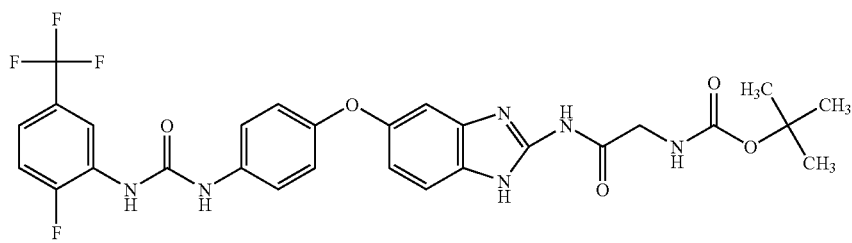

1H NMR (DMSO-d₆) δ 12.06 (d, 1H), 11.56 (brs, 1H), 9.13 (s, 1H), 8.85 (s, 1H), 8.62 (s, 1H), 7.50 (t, 1H), 7.44 (d, 2H), 7.41 (m, 1H), 7.39 (m, 1H), 7.17 (t, 1H), 7.04 (br, 1H), 6.97 (d, 2H), 6.81 (dd, 1H), 3.82 (d, 2H), 1.40 (s, 9H); MS m/e 603 (M+1).

Example 36

N-(5-(2-((2-fluoro-5-(trifluoromethyl)phenyl)aminocarbonylamino)-5-pyridyloxy)-1H-benzimidazol-2-yl)acetamide dihydrochloride

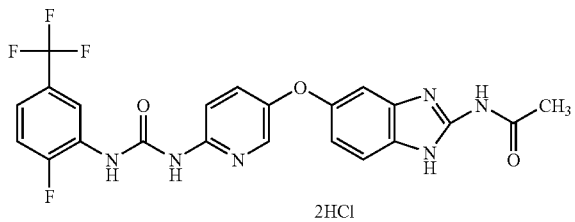

The title compound was synthesized according to similar procedures as described for Intermediates 7 and 8 and for Example 1 (13.0 mg 14%): $^1$H NMR (DMSO-$d_6$) δ 12.42 (brs, 1H), 10.64 (brs, 1H), 9.97 (s, 1H), 8.66 (dd, 1H), 8.11 (d, 1H), 7.68–7.61 (m, 1H), 7.60–7.48 (m, 3H), 7.47–7.41 (m, 1H), 7.17 (d, 1H), 7.04 (dd, 1H), 2.24 (s, 3H); MS m/e 489 (M+1).

The compounds of Examples 37 to 39 were prepared according to procedures similar to that described for Example 36 above. They can be transformed into their pharmaceutically acceptable salts (e.g. HCl salts) by standard procedures.

Example 37

Methyl N-(5-(5-((2-fluoro-5-(trifluoromethyl)phenyl)aminocarbonylamino)-2-pyridyloxy)-1H-benzimidazol-2-yl)carbamate

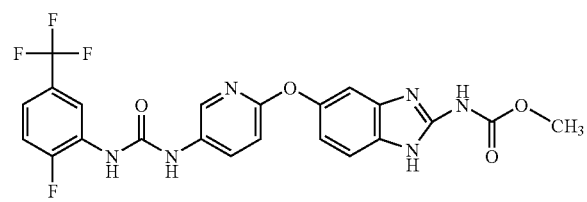

$^1$H NMR (DMSO-$d_6$) δ 12.0–11.1 (brm, 2H), 9.21 (s, 1H), 8.96 (d, 1H), 8.58 (dd, 1H), 8.15 (d, 1H), 8.00 (dd, 1H), 7.52–7.48 (m, 1H), 7.41–7.38 (m, 2H), 7.11 (d, 1H), 6.94 (d, 1H), 6.82 (dd, 1H), 3.75 (s, 3H); MS m/e 505 (M+1).

Example 38

N-(5-(5-((3-(trifluoromethyl)phenyl)aminocarbonylamino)-2-pyridyloxy)-1H-benzimidazol-2-yl)acetamide

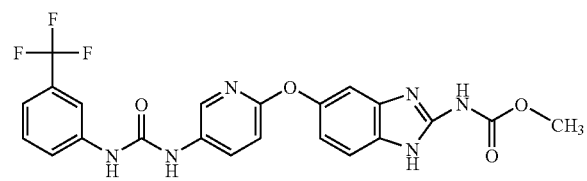

hu 1H NMR (DMSO-$d_6$) δ 11.70 (brs, 2H), 9.17 (s, 1H), 8.88 (s, 1H), 8.17 (d, 1H), 7.99 (s, 1H), 7.96 (d, 1H), 7.59 (d, 1H), 7.51 (t, 1H), 7.39 (d, 1H), 7.31 (d, 1H), 7.11 (s, 1H), 6.92 (d, 1H), 6.83 (dd, 1H), 3.75 (s, 3H); MS m/e 487 (M+1).

Example 39

Methyl N-(5-(5-((3-ethylphenyl)aminocarbonylamino)-2-pyridyloxy)-1H-benzimidazol-2-yl)carbamate

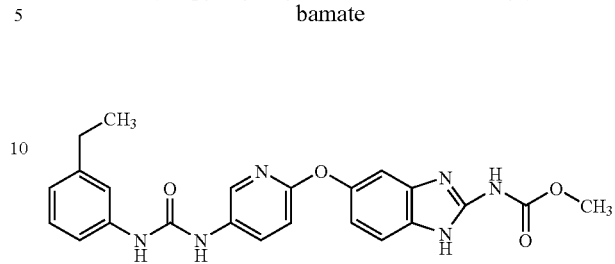

$^1$H NMR (DMSO-$d_6$) δ 11.82 (brs, 1H), 11.30 (brs, 1H), 8.71 (d, 2H), 8.15 (d, 1H), 7.95 (d, 1H), 7.38 (d, 1H), 7.31 (s, 1H), 7.24 (d, 1H), 7.17 (t, 1H), 7.09 (brs, 1H), 6.91 (d, 1H), 6.83–6.80 (m, 2H), 3.75 (s, 3H), 2.56 (q, 2H), 1.17 (t, 3H); MS m/e 447 (M+1).

Example 40

Methyl N-(5-(4-((3-bromophenyl)aminocarbonylamino)phenoxy)-1H-benzimidazol-2-yl)carbamate

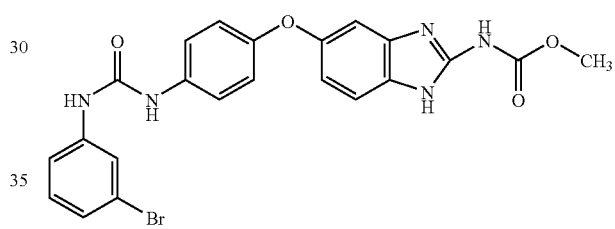

$^1$H NMR (DMSO-$d_6$) δ 12.2–11.0 (brs, 2H), 9.11 (s, 1H), 8.93 (s, 1H), 7.84 (t, 1H), 7.42 (d, 2H), 7.37 (d, 1H), 7.31 (d, 1H), 7.22 (t, 1H), 7.13 (d, 1H), 7.00 (d, 1H), 6.92 (d, 2H), 6.79 (dd, 1H), 3.74 (s, 3H); MS m/e 496 (m), 498 (M+2).

Example 41

Methyl N-(5-(4-((3-(trifluoromethylthio)phenyl)aminocarbonylamino)phenoxy)-1H-benzimidazol-2-yl)carbamate

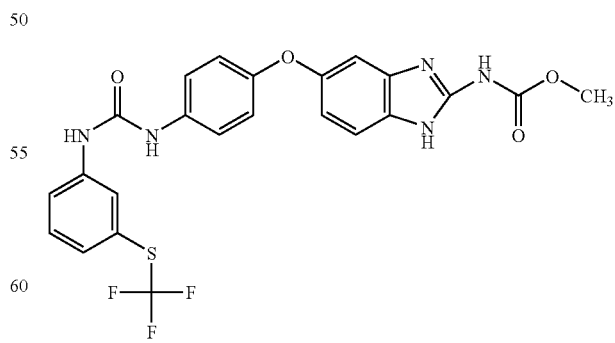

$^1$H NMR (DMSO-$d_6$) δ 12.2–11.2 (brs, 2H), 8.96 (s, 1H), 8.73 (s, 1H), 7.98 (s, 1H), 7.55 (d, 1H), 7.46–7.42 (m, 1H), 7.43 (d, 2H), 7.37 (d, 1H), 7.29 (d, 1H), 7.00 (d, 1H), 6.92 (d, 2H), 6.79 (dd, 1H), 3.74 (s, 3H); MS m/e 518 (M+1).

Example 42

Methyl N-(5-(4-((2,5-dimethoxyphenyl)aminocarbonylamino)phenoxy)-1H-benzimidazol-2-yl)carbamate

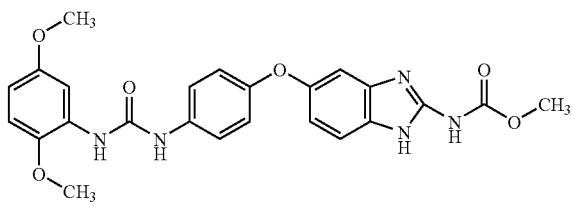

$^1$H NMR (DMSO-$d_6$) δ 12.0–11.2 (brs, 2H), 9.31(s, 1H), 8.20 (s, 1H), 7.85 (d, 1H), 7.42 (d, 2H), 7.36 (d, 1H), 6.99 (s, 1H), 6.91 (m, 3H), 6.78 (dd, 1H), 6.48 (dd, 1H), 3.82 (s, 3H), 3.74 (s, 3H), 3.68 (s, 3H), δ; MS m/e 478 (M+1).

Example 43

Methyl N-(5-(4-((2-chloro-5-(trifluoromethylphenyl)aminocarbonylaminophenoxy)-1H-benzimidazol-2-yl)carbamate

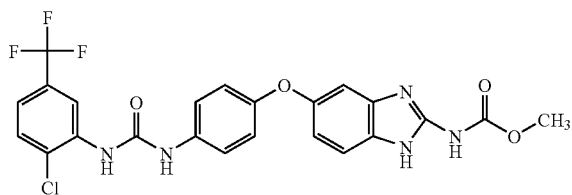

$^1$H NMR (DMSO-$d_6$) δ 12.0–11.2 (brs, 2H), 9.53 (s, 1H), 8.65 (d, 1H), 8.57 (s, 1H), 7.71 (d, 1H), 7.45 (d, 2H), 7.37 (m, 2H), 7.01 (s, 1H), 6.94 (d, 2H), 6.80 (dd, 1H), 3.75 (s, 3H); MS m/e 520 (M+1), 522 (M+3).

Example 44

Methyl N-(5-(4-((4-chloro-3-(trifluoromethyl)phenyl)aminocarbonylamino)phenoxy)-1H-benzimidazol-2-yl)carbamate

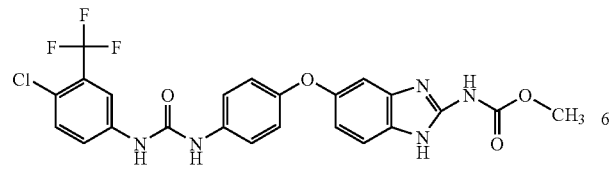

$^1$H NMR (DMSO-$d_6$) δ 12.0–11.2 (brs, 2H), 9.13 (s, 1H), 8.80 (s, 1H), 8.11 (d, 1H), 7.65–7.59 (m, 2H), 7.43 (d, 2H), 7.37 (d, 1H), 7.00 (d, 1H), 6.92 (d, 2H), 6.79 (dd, 1H), 3.74 (s, 3H); MS m/e 520 (M+1)), 522 (M+3).

Example 45

Methyl N-(5-(4-((2,5-dichlorophenyl)aminocarbonylamino)phenoxy)-1H-benzimidazol-2-yl)carbamate

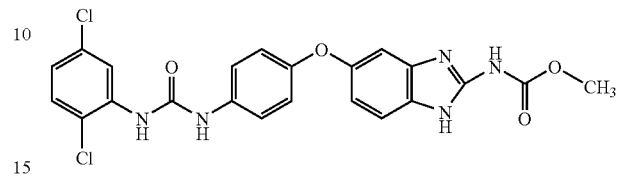

$^1$H NMR (DMSO-$d_6$) δ 12.2–11.2 (brs, 2H), 9.50 (s, 1H), 8.42 (s, 1H), 8.33 (m, 1H), 7.49 (d, 1H), 7.43 (d, 2H), 7.38 (d, 1H), 7.08 (dd, 1H), 7.01 (d, 1H), 6.94 (d, 2H), 6.80 (dd, 1H), 3.75 (s, 3H); MS m/e 486 (M+1).

Example 46

Methyl N-(5-(4-((2-fluoro-5-nitrophenyl)aminocarbonylamino)phenoxy)-1H-benzimidazol-2-yl)carbamate

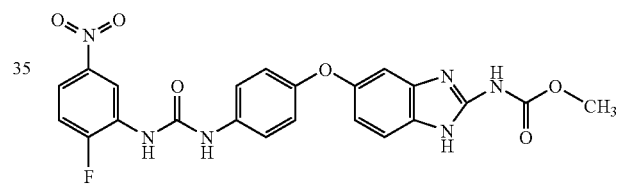

$^1$H NMR (DMSO-$d_6$) δ 12.2–11.2 (brs, 2H), 9.16 (m, 2H), 8.97 (s, 1H), 7.90 (m, 1H), 7.55 (t, 1H), 7.45 (d, 2H), 7.38 (d, 1H), 7.01 (d, 1H), 6.94 (d, 2H), 6.80 (dd, 1H), 3.75 (s, 3H); MS m/e 481 (M+1).

Example 47

Methyl N-(5-(4-((2-methyl-5-nitrophenyl)aminocarbonylamino)phenoxy)-1H-benzimidazol-2-yl)carbamate

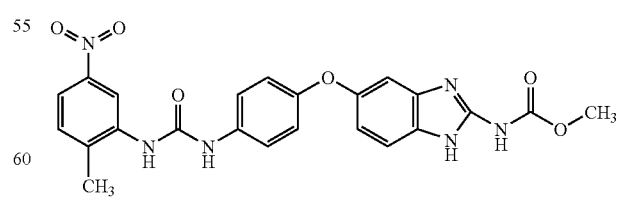

$^1$H NMR (DMSO-$d_6$) δ 12.2–11.2 (brs, 2H), 9.22 (s, 1H), 8.96 (d, 1H), 8.23 (s, 1H), 7.79 (dd, 1H), 7.47 (m, 1H), 7.46 (d, 2H), 7.38 (d, 1H), 7.01 (d, 1H), 6.94 (d, 2H), 6.80 (dd, 1H), 3.75 (s, 3H), 2.37 (s, 3H); MS m/e 477 (M+1).

Example 48

Methyl N-(5-(4-(3-methylthiophenyl)aminocarbonylamino)phenoxy)-1H-benzimidazol-2-yl)carbamate

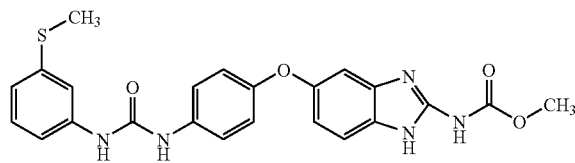

$^1$H NMR (DMSO-d$_6$) δ 12.2–11.2 (brs, 2H), 8.67 (s, 1H), 8.64 (s, 1H), 7.46 (t, 1H), 7.41 (d, 2H), 7.36 (d, 1H), 7.21 (t, 1H), 7.13 (d, 1H), 6.99 (d, 1H), 6.92 (d, 2H), 6.84 (d, 1H), 6.78 (dd, 1H), 3.74 (s, 3H), 2.45 (s, 3H); MS m/e 464 (M+1).

Example 49

Methyl N-(5-(4-(3-cyanophenyl)aminocarbonylamino)phenoxy)-1H-benzimidazol-2-yl)carbamate

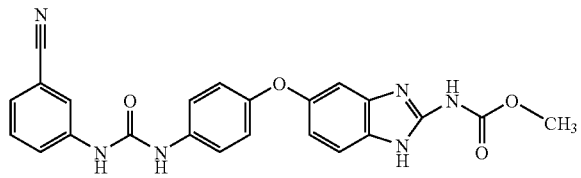

$^1$H NMR (DMSO-d$_6$) δ 12.2–11.2 (brs, 2H), 9.02 (s, 1H), 8.83 (s, 1H), 7.97 (s, 1H), 7.67 (d, 1H), 7.49 (t, 1H), 7.43 (d, 2H), 7.42 (t, 1H), 7.37 (d, 1H), 7.00 (d, 1H), 6.93 (d, 2H), 6.79 (dd, 1H), 3.74 (s, 3H); MS m/e 443 (M+1).

Example 50

Methyl N-(5-(4-((3-fluoro-5-(trifluoromethyl)phenyl)aminocarbonylamino)phenoxy)-1H-benzimidazol-2-yl)carbamate

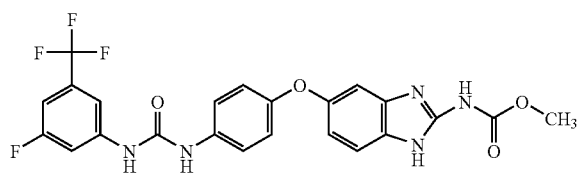

$^1$H NMR (DMSO-d$_6$) δ 12.2–11.2 (brs, 2H), 9.21 (s, 1H), 8.87 (s, 1H), 7.70 (s, 1H), 7.61 (d, 1H), 7.43 (d, 2H), 7.37 (d, 1H), 7.22 (d, 1H), 7.00 (d, 1H), 6.93 (d, 2H), 6.79 (dd, 1H), 3.74 (s, 3H); MS m/e 504 (M+1).

Example 51

Methyl N-(5-(4-((2-chloro-5-(trifluoromethyl)phenyl)aminocarbonylamino)phenylthio)-1H-benzimidazol-2-yl)carbamate hydrochloride

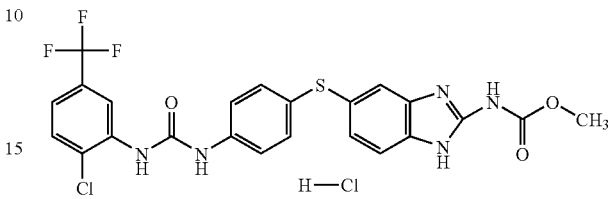

$^1$H NMR (DMSO-d$_6$) δ 9.82 (s, 1H), 6.69 (s, 1H), 8.62 (d, 1H), 7.71 (d, 1H), 7.46 (d, 2H), 7.42–7.36 (m, 3H), 7.21 (d, 2H), 7.12 (dd, 1H), 3.75 (s, 3H); MS m/e 536 (M+1), 538 (M+3).

Example 52

Methyl N-(5-(3-((2-chloro-5-(trifluoromethyl)phenyl)aminocarbonylamino)phenoxy)-1H-benzimidazol-2-yl)carbamate hydrochloride

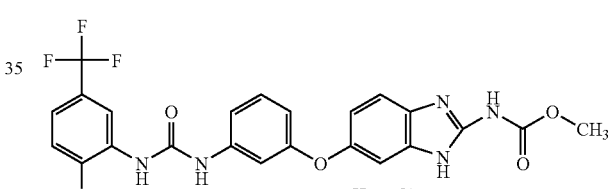

$^1$H NMR (DMSO-d$_6$) δ 9.67 (s, 1H), 8.57 (s, 1H), 8.56 (s, 1H), 7.70 (d, 1H), 7.41 (d, 1), 7.36 (dd, 1H), 7.27 (t, 1H), 7.18 (d, 1H), 7.09 (d, 1H), 7.03 (t, 1H), 6.84 (dd, 1H), 6.62 (dd, 1H), 3.75 (s, 3H); MS m/e 520 (M+1), 522 (M+3).

Example 53

Methyl N-(5-(4-((3-ethoxycarbonylphenyl)aminocarbonylamino)phenoxy)-1H-benzimidazol-2-yl)carbamate

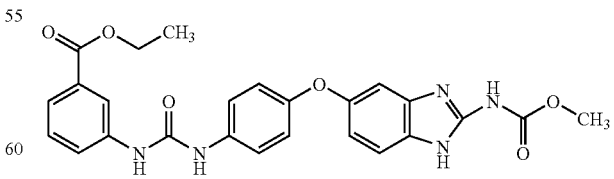

$^1$H NMR (DMSO-d$_6$) δ 12.0–11.2 (brs, 2H), 8.91 (s, 1H), 8.64 (s, 1H), 8.15 (t, 1H), 7.65 (d, 1H), 7.55 (d, 1H), 7.44–7.40 (m, 3H), 7.37 (d, 1H), 7.00 (s, 1H), 6.92 (d, 2H), 6.79 (dd, 1H), 4.31 (q, 2H), 3.74 (s, 3H), 1.32 (t, 3H); MS m/e 490 (M+1).

Example 54

Methyl N-(5-(4-((3-carboxyphenyl)aminocarbonylamino)phenoxy)-1H-benzimidazol-2-yl)carbamate

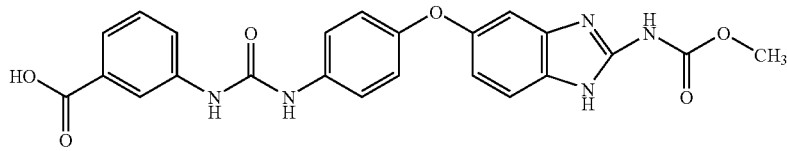

Hydrolysis of the product of Example 53 with NaOH gave the title compound. ¹H NMR (DMSO-d₆) δ 12.2–11.2 (brs, 2H), 8.97 (brs, 1H), 8.77 (brs, 1H), 8.12 (s, 1H), 7.64 (d, 1H), 7.54 (d, 1H), 7.44 (d, 2H), 7.38 (m, 2H), 7.00 (d, 1H), 6.92 (d, 2H), 6.79 (dd, 1H), 3.74 (s, 3H); MS m/e 462 (M+1).

Example 55

Methyl N-(5-(4-((2-fluoro-5-methylphenyl)aminocarbonylamino)phenoxy)-1H-benzimidazol-2-yl)carbamate hydrochloride

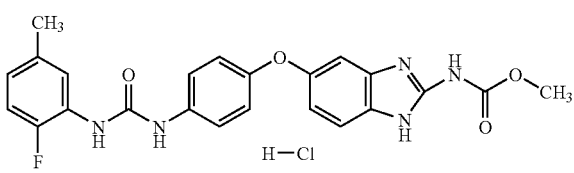

¹H NMR (DMSO-d₆) δ 9.56 (s, 1H), 8.66 (s, 1H), 7.96 (d, 1H), 7.58 (d, 1H), 7.51 (d, 2H), 7.12–7.06 (m, 3H), 7.01 (d, 2H), 6.79 (m, 1H), 3.86 (s, 3H), 2.27 (s, 3H); MS m/e 450 (M+1).

Example 56

Methyl N-(5-(4-((2,5-difluorophenyl)aminocarbonylamino)phenoxy)-1H-benzimidazol-2-yl)carbamate

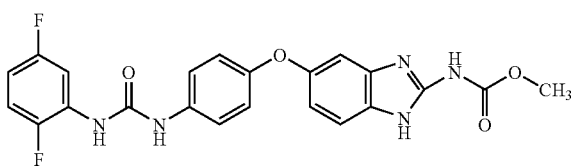

¹H NMR (DMSO-d₆) δ 12.0–11.0 (brs, 2H), 9.09 (s, 1H), 8.71 (s, 1H), 8.04 (m, 1H), 7.42 (d, 2H), 7.37 (d, 1H), 7.29 (m, 1H), 7.00 (d, 1H), 6.93 (d, 2H), 6.82 (m, 1H), 6.79 (dd, 1H), 3.74 (s, 3H); MS m/e 454 (M+1).

Example 57

Methyl N-(5-(4-((2,5-dichlorophenyl)aminocarbonylamino)phenylthio)-1H-benzimidazol-2-yl)carbamate

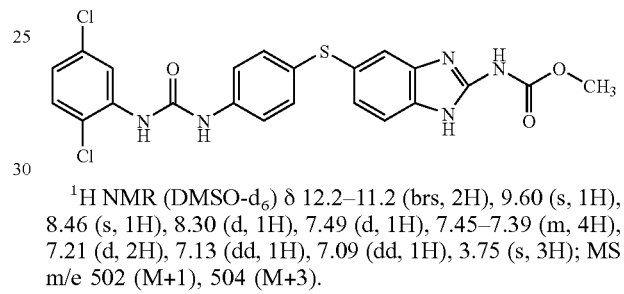

¹H NMR (DMSO-d₆) δ 12.2–11.2 (brs, 2H), 9.60 (s, 1H), 8.46 (s, 1H), 8.30 (d, 1H), 7.49 (d, 1H), 7.45–7.39 (m, 4H), 7.21 (d, 2H), 7.13 (dd, 1H), 7.09 (dd, 1H), 3.75 (s, 3H); MS m/e 502 (M+1), 504 (M+3).

Example 58

Methyl N-(5-(3-((3-trifluoromethylthio)phenyl)aminocarbonylamino)phenoxy)-1H-benzimidazol-2-yl)carbamate

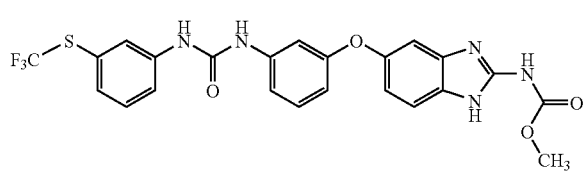

¹H NMR (DMSO-d₆) δ 12.2–11.2 (brs, 2H), 9.02 (s, 1H), 8.94 (s, 1H), 7.90 (s, 1H), 7.52 (d, 1H), 7.44–7.40 (m, 2H), 7.30–7.21 (m, 2H), 7.12–7.07 (m, 3H), 6.84 (dd, 1H), 6.57 (d, 1H), 3.75 (s, 3H); MS m/e 518 (M+1).

Example 59

Methyl N-(5-(3-((3-bromophenyl)aminocarbonylamino)phenoxy)-1H-benzimidazol-2-yl)carbamate

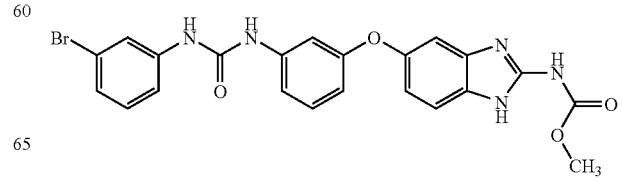

¹H NMR (DMSO-d₆) δ 12.0–11.5 (brs, 2H), 7.78 (s, 1H), 7.41 (d, 1H), 7.30–7.00 (m, 9H), 6.83 (dd, 1H), 6.57 (dd, 1H), 3.75 (s, 3H); MS m/e 496 (M), 498 (M+2).

Example 60

Methyl N-(5-(3-((3-(phenoxy)phenyl)aminocarbonylamino)phenoxy)-1H-benzimidazol-2-yl)carbamate

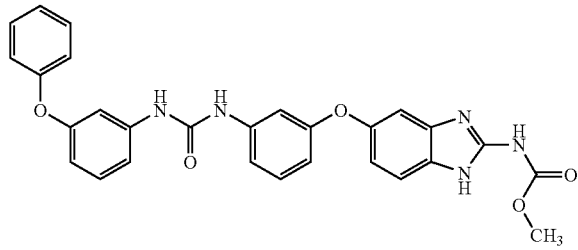

¹H NMR (DMSO-d₆) δ 12.0–11.5 (brs, 2H), 8.94 (s, 1H), 8.91 (s, 1H), 7.39 (m, 3H), 7.30–7.21 (m, 2H), 7.19 (t, 1H), 7.11–7.00 (m, 7H), 6.83 (dd, 1H), 6.59 (d, 1H), 6.54 (d, 1H) 3.75 (s, 3H); MS m/e 510 (M+1).

Example 61

Methyl N-(5-(3-((4-chlorophenyl)aminocarbonylamino)phenoxy)-1H-benzimidazol-2-yl)carbamate

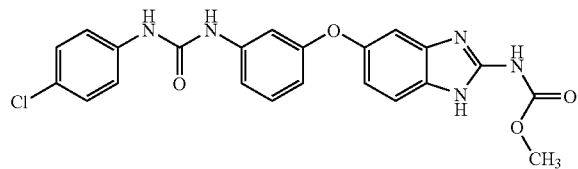

¹H NMR (DMSO-d₆) δ 12.0–11.2 (brs, 2H), 8.94 (s, 1H), 8.91 (s, 1H), 7.44–7.40 (m, 3H), 7.29 (d, 2H), 7.23 (t, 1H), 7.14 (t, 1H), 7.07 (s, 2H), 6.82 (dd, 1H), 6.57 (dd, 1H), 3.75 (s, 3H), δ; MS m/e 452 (M+1).

Example 62

Methyl N-(5-(4-((4-methoxyphenyl)aminocarbonylamino)phenoxy)-1H-benzimidazol-2-yl)carbamate

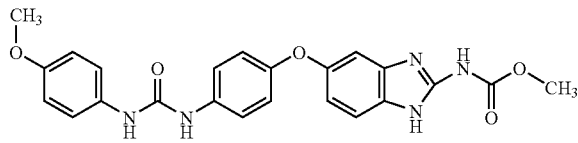

¹H NMR (DMSO-d₆) δ 12.0–11.0 (brs, 2H), 8.53 (s, 1H), 8.42 (s, 1H), 7.40 (d, 2H), 7.36 (d, 1H), 7.34 (d, 2H), 6.99 (d, 1H), 6.90 (d, 2H), 6.86 (d, 2H), 6.78 (dd, 1H), 3.74 (s, 3H), 3.71 (s, 3H); MS m/e 448 (M+1).

Example 63

Methyl N-(5-(4-((4-fluorophenyl)aminocarbonylamino)phenoxy)-1H-benzimidazol-2-yl)carbamate

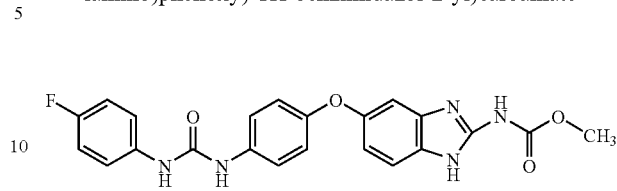

¹H NMR (DMSO-d₆) δ 12.2–11.2 (brs, 2H), 8.66 (s, 1H), 8.61 (s, 1H), 7.46–7.40 (m, 5H), 7.36 (d, 1H), 7.11 (t, 2H), 7.00 (d, 1H), 6.91 (d, 2H), 6.78 (dd, 1H), 3.74 (s, 3H), δ; MS m/e 436 (M+1).

Example 64

Methyl N-(6-(4-((6-fluoro-3-(trifluoromethyl)phenyl)aminocarbonylamino)phenoxy)-benzthiazol-2-yl)carbamate

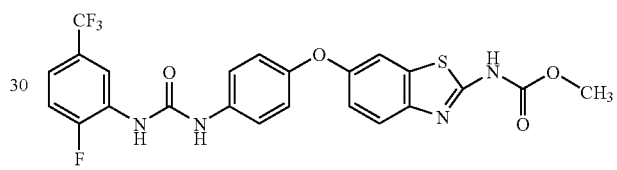

This example was prepared according to the procedure of Example 1 except that Intermediate 10G was used as a precursor in lieu of Intermediate 1.

¹H NMR (DMSO-d₆) δ 12.05 (brs, 1H), 9.18 (s, 1H), 8.87 (d, 1H), 8.62 (dd, 1H), 7.66 (d, 1H), 7.60 (s, 1H), 7.50 (m, 1H), 7.47 (d, 2H), 7.38 (m, 1H), 7.07 (dd, 1H), 7.00 (d, 2H), 3.77 (s, 3H); MS m/e 521 (M+1).

Example 65

Methyl N-(4-bromo-6-(4-((6-fluoro-3-(trifluoromethylphenyl)aminocarbonylamino)phenoxy)benzthiazol-2-yl)carbamate hydrochloride

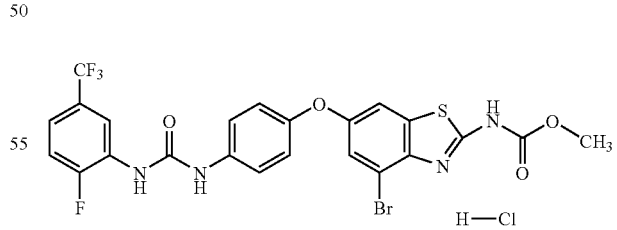

This example was prepared according to the procedure of Example 1 except that Intermediate 10H was used as a precursor in lieu of Intermediate 1.

¹H NMR (DMSO-d₆) δ 12.39 (brs, 1H), 9.27 (brs, 1H), 8.91 (d, 1H), 8.62 (dd, 1H), 7.67 (d, 1H), 7.50 (d, 2H), 7.50 (m, 1H), 7.39 (m, 1H), 7.32 (d, 1H), 7.05 (d, 2H), 3.78 (s, 3H); MS m/e 599, 601 (M+1).

Example 66

Methyl N-(6-(4-((2-fluoro-5-(trifluoromethyl)phenyl)aminocarbonylamino)phenoxy)-1-methyl-1H-benzimidazol-2-yl)carbamate

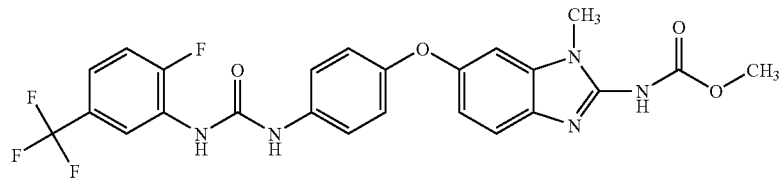

This example was prepared according to the procedure of Example 1 except that Intermediate 8J was used as a precursor in lieu of Intermediate 1.

$^1$H NMR (DMSO-$d_6$) δ 9.22 (brs, 1H), 8.92 (brs, 1H), 8.61 (d, 1H), 7.50 (m, 1H), 7.45 (d, 2H), 7.43–7.36 (m, 2H), 7.15 (d, 1H), 6.96 (d, 2H), 6.83 (dd, 1H), 3.62 (s, 3H), 3.46 (s, 3H); MS m/e 518 (M+1).

Example 67

Methyl N-(5-(4-((2-fluoro-5-(trifluoromethyl)phenyl)aminocarbonylamino)phenoxy)-1-methyl-1H-benzimidazol-2-yl)carbamate

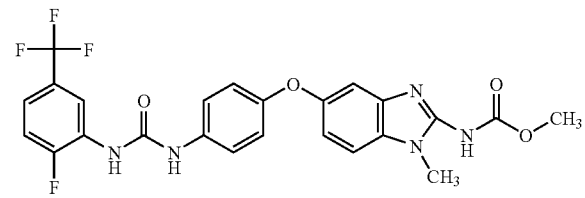

This example was prepared according to the procedure of Example 1 except that Intermediate 8C was used as a precursor in lieu of Intermediate 1.

$^1$H NMR (chloroform-$d_1$) δ 8.65 (brd, 1H), 7.43 (d, 2H), 7.22 (m, 1H), 7.14 (m, 1H), 7.12 (d, 1H), 6.99–6.90 (m, 4H), 3.78 (s, 3H), 3.59 (s, 3H); MS m/e 518 (M+1).

Example 68

Methyl N-(5-(4-((2-fluoro-5-(trifluoromethyl)phenyl)aminocarbonylamino)phenoxy)-3a-aza-2-indolyl)carbamate

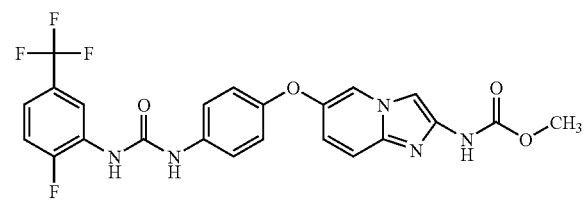

This example was prepared according to the procedure of Example 1 except that Intermediate 9K was used as a precursor in lieu of Intermediate 1.

$^1$H NMR (DMSO-$d_6$) δ 10.28 (brs, 1H), 9.26 (s, 1H), 8.95 (s, 1H), 8.60 (dd, 1H), 8.47 (d, 1H), 7.87 (s, 1H), 7.48 (m, 1H), 7.47 (d, 2H), 7.42 (d, 1H), 7.38 (m, 1H), 7.05 (dd, 1H), 7.02 (d, 2H), 3.68 (s, 3H); MS m/e 504 (M+1).

Example 69

Methyl N-(5-(4-((2-fluoro-5-(trifluoromethyl)phenyl)aminocarbonylamino)phenoxy)-3,4-diazaindolin-2-yl)carbamate dihydrochloride

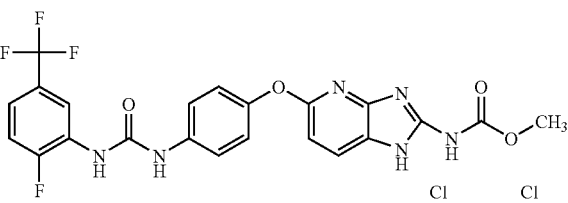

This example was prepared according to the procedure of Example 1 except that Intermediate 9D was used as a precursor in lieu of Intermediate 1.

$^1$H NMR (DMSO-$d_6$) δ 9.21 (s, 1H), 8.89 (d, 1H), 8.63 (dd, 1H), 7.79 (d, 1H), 7.49 (d, 1H), 7.47 (d, 2H), 7.38 (m, 1H), 7.05 (d, 2H), 6.73 (d, 1H), 3.76 (s, 3H); MS m/e 505 (M+1).

Example 70

Methyl N-(6-(4-((2-fluoro-5-(trifluoromethyl)phenyl)aminocarbonylamino)phenoxy)-1-(2-(dimethylamino)ethyl)-1H-benzimidazol-2-yl)carbamate

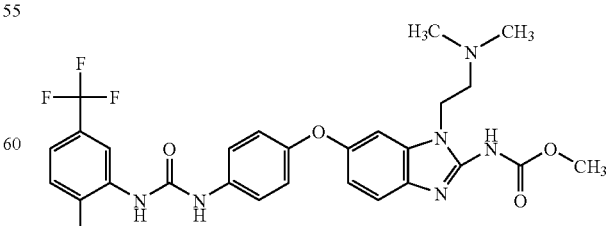

This example was prepared according to the procedure of Example 1 except that Intermediate 8K was used as a precursor in lieu of Intermediate 1.

¹H NMR (chloroform-d₁) δ 9.02 (brs, 1H), 8.59 (dd, 1H), 8.48 (brs, 1H), 7.38 (d, 2H), 7.17 (d, 1H), 7.13 (m, 1H), 7.03 (dd, 1H), 6.86 (d, 2H), 6.84 (d, 1H), 6.76 (dd, 1H), 4.06 (t, 2H), 3.79 (s, 3H), 2.70 (t, 2H), 2.32 (s, 6H); MS m/e 573 (M−1).

Example 71

Methyl N-(6-(4-((2-fluoro-5-(trifluoromethyl)phenyl)aminocarbonylamino)phenoxy)-1-(2-(4-morpholino)ethyl)-1H-benzimidazol-2-yl)carbamate

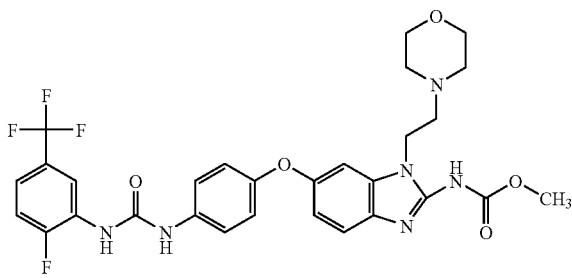

This example was prepared according to the procedure of Example 1 except that Intermediate 8L was used as a precursor in lieu of Intermediate 1.

¹H NMR (chloroform-d₁) δ 8.66–8.59 (br, 2H), 8.15 (d, 1H), 7.38 (d, 2H), 7.19 (d, 1H), 7.18 (m, 1H), 7.07 (dd, 1H), 6.90 (d, 2H), 6.86 (d, 1H), 6.81 (dd, 1H), 4.09 (t, 2H), 3.82 (s, 3H), 3.64 (brs, 4H), 2.70 (t, 2H), 2.50 (brs, 4H); MS m/e 615 (M−1).

Example 72

Methyl N-(5-(4-((2-chloro-5-(trifluoromethyl)phenyl)aminocarbonylamino)phenoxy)-3,4-diaza-1H-indole-2-yl)carbamate dihydrochloride

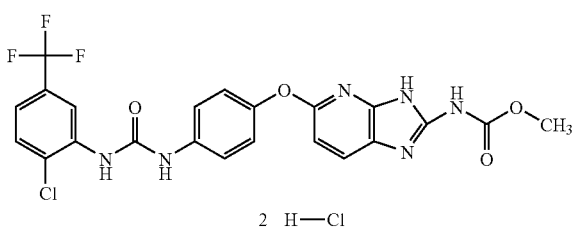

This example was prepared according to the procedure of Example 1 except that Intermediate 9D was used as a precursor in lieu of Intermediate 1.

¹H NMR (DMSO-d₆) δ 9.60 (s, 1H), 8.65 (d, 1H), 8.61 (s, 1H), 7.80 (d, 1H), 7.22 (d, 1H), 7.48 (d, 2H), 7.37 (dd, 1H), 7.05 (d, 2H), 6.73 (d, 1H), 3.76 (s, 3H); MS m/e 521 (M+1), 523 (M+3).

Example 73

Methyl N-(6-(4-((2-chloro-5-(trifluoromethyl)phenyl)aminocarbonylamino)phenoxy)-3,4-diaza-1H-indole-2-yl)carbamate dihydrochloride

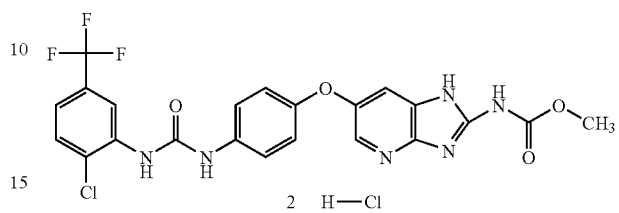

This example was prepared according to the procedure of Example 1 except that Intermediate 9E was used as a precursor in lieu of Intermediate 1.

¹H NMR (DMSO-d₆) δ 9.62 (s, 1H), 8.64 (d, 1H), 8.60 (s, 1H), 8.09 (d, 1H), 7.72 (d, 1H), 7.49 (d, 2H), 7.47 (d, 1H), 7.37 (dd, 1H), 7.01 (d, 2H), 3.78 (s, 3H); MS m/e 521, 523 (M+1).

Example 74

Methyl N-(5-(4-((2,5-dichlorophenyl)aminocarbonylamino)phenoxy)-3,4-diaza-1H-indole-2-yl)carbamate dihydrochloride

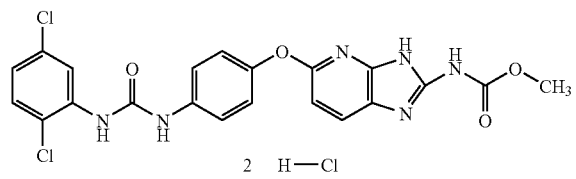

This example was prepared according to the procedure of Example 1 except that Intermediate 9D was used as a precursor in lieu of Intermediate 1.

¹H NMR (DMSO-d₆) δ 9.56 (s, 1H), 8.46 (s, 1H), 8.34 (d, 1H), 7.80 (d, 1H), 7.51 (d, 1H), 7.47 (d, 2H), 7.09 (dd, 1H), 7.05 (d, 2H), 6.73 (d, 1H), 3.76 (s, 3H); MS m/e 487 (M+1), 489 (M+3).

Example 75

Methyl N-(6-(4-((2-fluoro-5-(trifluoromethyl)phenyl)aminocarbonylamino)phenoxy)-3,4-diaza-1H-indole-2-yl)carbamate dihydrochloride

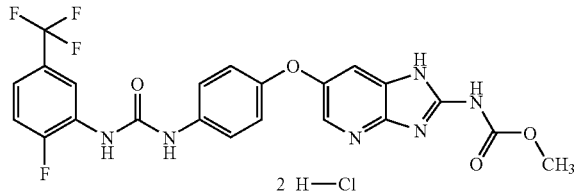

This example was prepared according to the procedure of Example 1 except that Intermediate 9E was used as a precursor in lieu of Intermediate 1.

¹H NMR (DMSO-d₆) δ 9.22 (s, 1H), 8.89 (d, 1H), 8.61 (dd, 1H), 8.08 (s, 1H), 7.53–7.42 (m, 4H), 7.38 (m, 1H), 7.01 (d, 2H), 3.78 (s, 3H); MS m/e 505 (M+1).

Example 76

Methyl N-(6-(4-((2-chloro-5-(trifluoromethyl)phenyl)aminocarbonylamino)phenoxy)benzthiazol-2-yl)carbamate

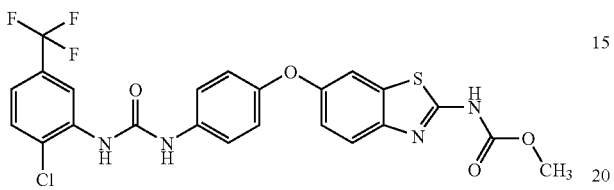

This example was prepared according to the procedure of Example 1 except that Intermediate 10G was used as a precursor in lieu of Intermediate 1.

¹H NMR (DMSO-d₆) δ 12.06 (s, 1H), 9.57 (s, 1H), 8.65 (d, 1H), 8.59 (s, 1H), 7.22 (d, 1H), 7.67 (d, 1H), 7.62 (d, 1H), 7.50 (t, 1H), 7.48 (t, 1H), 7.37 (dd, 1H), 7.09 (dd, 1H), 7.02 (t, 1H), 7.00 (t, 1H), 3.77 (s, 3H), δ; MS m/e 537 (M+1), 539 (M+3).

Example 77

6-(4-((2-Fluoro-5-(trifluoromethylphenyl)aminocarbonylamino)phenoxy)-3,4-dihydro-1,4a,5-triazacarbazol-2-one

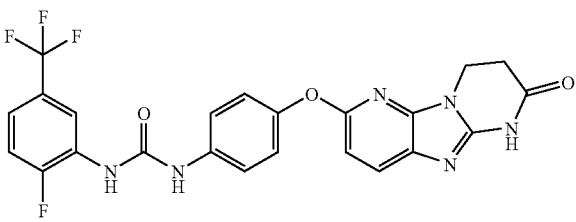

This example was prepared according to the procedure of Example 1 except that Intermediate 9I was used as a precursor in lieu of Intermediate 3.

¹H NMR (DMSO-d₆) δ 9.22 (d, 1H), 8.92 (s, 1H), 8.62 (d, 1H), 7.83 (d, 1H), 7.50 (m, 1H), 7.48 (d, 2H), 7.38 (m, 1H), 7.07 (d, 2H), 6.71 (d, 1H), 4.12 (t, 2H), 2.83 (t, 2H); MS m/e 501 (M+1).

Example 78

Methyl N-(5-(4-((2-fluoro-5-(trifluoromethyl)phenyl)aminocarbonylamino)phenylcarbonyl)-1H-benzimidazol-2-yl)carbamate

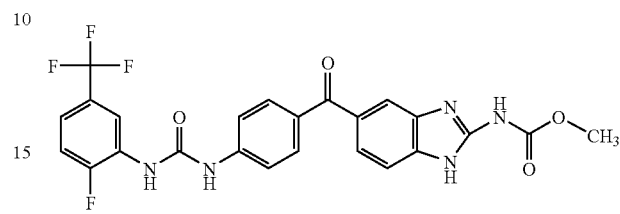

This example was prepared according to the procedure of Example 1 except that Intermediate 11D was used as a precursor in lieu of Intermediate 3.

¹H NMR (DMSO-d₆) δ 12.5–11.2 (brs, 2H), 9.59 (s, 1H), 9.04 (s, 1H), 8.62 (d, 1H), 7.83 (brs, 1H), 7.75 (d, 2H), 7.65 (d, 2H), 7.55–7.50 (m, 3H), 7.44 (m, 1H), 3.78 (s, 3H); MS m/e 516 (M+1).

Example 79

Methyl N-(5-(4-((2,5-dichlorophenyl)aminocarbonylamino)phenylsulfinyl)-1H-benzimidazol-2-yl)carbamate

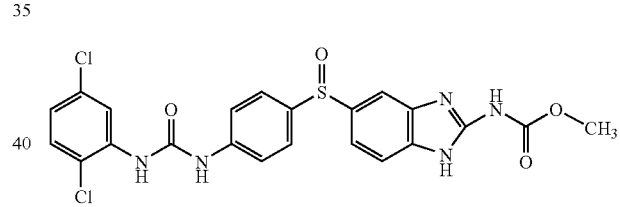

The title compound was prepared following the procedure for Example 12 except that the product of Example 57 was used as a precursor.

¹H NMR (DMSO-d₆) δ 12.4–11.3 (brs, 2H), 9.80 (s, 1H), 8.52 (s, 1H), 8.29 (d, 1H), 7.73 (s, 1H), 7.60 (s, 4H), 7.51 (m, 1H), 7.50 (d, 1H), 7.34 (dd, 1H), 7.11 (dd, 1H), 3.76 (s, 3H); MS m/e 518 (M+1).

Example 80

2-(Dimethylamino)ethyl N-(5-(4-((2-fluoro-5-(trifluoromethyl)phenyl)aminocarbonylamino)phenoxy)-1H-benzimidazol-2-yl)carbamate

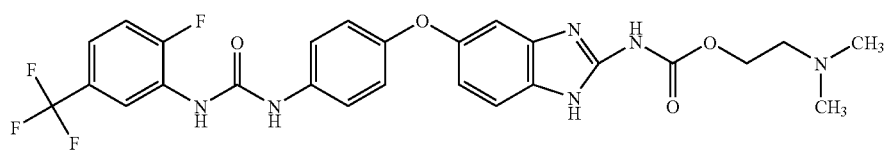

Heating of a mixture of Example 10 and NaH, 2-(dimethylamino)ethanol gave the title compound:

$^1$H NMR (DMSO-d$_6$) δ 11.62 (br, 2H), 9.13 (s, 1H), 8.85 (s, 1H), 8.62 (d, 1H), 7.54–7.34 (m, 5H), 7.01 (d, 1H), 6.93 (d, 2H), 6.78 (dd, 1H), 4.25 (dd, 2H), 2.54 (t, 2H), 2.20 (s, 6H); MS m/e 561 (M+1).

Example 81

Benzyl N-(5-(4-((2-fluoro-5-(trifluoromethyl)phenyl)aminocarbonylamino)phenoxy)-1H-benzimidazol-2-yl)carbamate

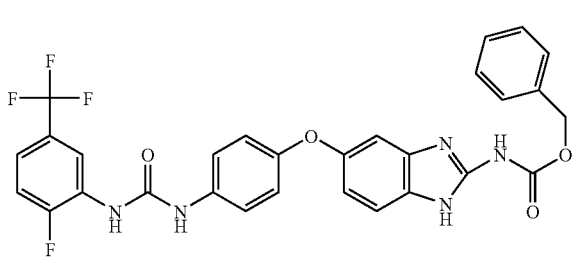

Following the method for Example 1 using Intermediate 3D instead of Intermediate 3 afforded the title compound.

$^1$H NMR (DMSO-d$_6$) δ 11.73 (br, 2H), 9.17 (s, 1H), 8.87 (s, 1H), 8.62 (d, 1H), 7.53–7.33 (m, 10H), 7.01 (d, 1H), 6.93 (d, 2H), 6.79 (dd, 1H), 5.24 (s, 2H); MS m/e 580 (M+1).

Example 82

5-(4-((2-Fluoro-5-(trifluoromethyl)phenyl)aminocarbonylamino)phenoxy)-1(methanesulfonyl)-1H-benzimidazol-2-ylamine

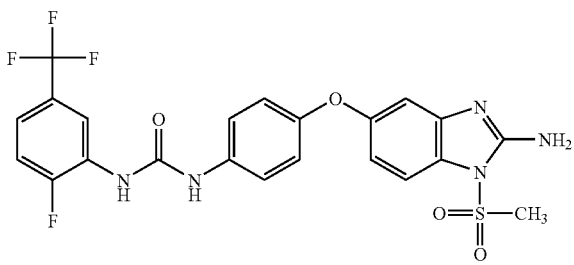

To a mixture of 2-amino-5-(4-((2-fluoro-5-(trifluoromethyl)phenyl)aminocarbonylamino)phenoxy)-1H-benzimidazole (90 mg, 0.20 mmol) (prepared according to similar procedures as described for Intermediates 4, 5, and 6 and Example 22) and triethylamine (30 mg, 0.30 mmol) in DMF/CHCl$_3$ (3 ml/1 ml) was added methanesulfonyl chloride (30 mg, 0.26 mmol). After stirring for 3 h at rt, the reaction mixture was washed with water and extracted with CHCl$_3$. The organic layer was dried over MgSO$_4$ and evaporated. The crude material was purified with silica gel column chromatography (AcOEt) to give the product of Example 23 (11.0 mg, 11%) and the title compound (34 mg, 25%): $^1$H NMR (DMSO-d$_6$) δ 9.14 (s, 1H), 8.85 (s, 1H), 8.62 (d, 1H), 7.51 (d, 1H), 7.47 (d, 1H), 7.46 (d, 2H), 7.38 (m, 1H), 7.02 (brs, 2H), 6.97 (d, 2H), 6.82 (d, 1H), 6.70 (dd, 1H), 3.49 (s, 3H); MS m/e 524 (M+1).

Example 83

N-(5-(4-((2-Fluoro-5-(trifluoromethyl)phenyl)aminocarbonylamino)phenoxy)-1H-benzimidazol-2-yl)methanesulfonamide

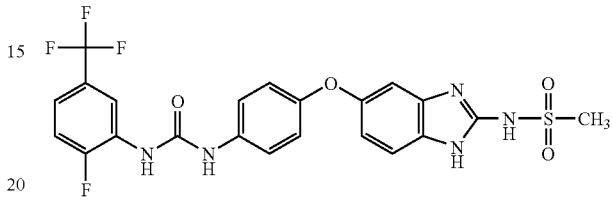

2-amino-5-(4-((2-fluoro-5-(trifluoromethyl)phenyl)aminocarbonylamino)phenoxy)-1H-benzimidazole (the product of Example 22–600 mg) and methanesulfonyl chloride (5 equiv.) in pyridine was stirred at room temperature for 2 days. The resulting mixture was treated with K$_2$C$_{03}$ (10 equiv.) and H$_2$O (10 mL) and MeOH (10 mL), and heated at 60 C. for 7 days. The crude solid was collected by filtration. Recrystallization from hot MeOH afforded the title compound (280 mg, 40%);

$^1$H NMR (DMSO-d$_6$) δ 11.69 (br, 2H), 9.16 (s, 1H), 8.86 (s, 1H), 8.62 (d, 1H), 7.54–7.43 (m, 3H), 7.41–7.36 (m, 1H), 7.23 (d, 1H), 6.97 (d, 2H), 6.86 (d, 1H), 6.80 (dd, 1H), 2.92 (s, 3H); MS m/e 524 (M+1).

Example 84

5-(4-((2-Fluoro-5-(trifluoromethyl)phenyl)aminocarbonylamino)phenoxy)-1-(4-(methyl)phenylsulfonyl)-1H-benzimidazol-2-ylamine

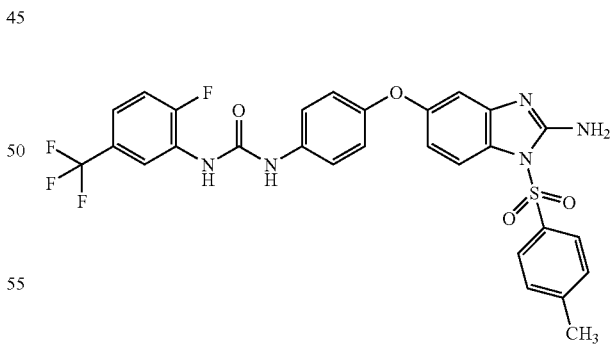

The title compound was prepared following for Example 24. The products of Example 24 and 84 are separated by columnchromatography.

$^1$H NMR (DMSO-d$_6$) δ 9.16 (s, 1H), 8.86 (s, 1H), 8.62 (d, 1H), 7.93 (d, 2H), 7.62 (d, 1H), 7.53–7.42 (m, 5H), 7.41–7.36 (m, 1H), 7.25 (br, 2H), 6.96 (d, 2H), 6.70 (d, 1H), 6.66 (dd, 1H), 2.37 (s, 3H); MS m/e 600 (M+1).

Example 85

N-(5-(4-((2-Fluoro-5-(trifluoromethy)phenyl)aminocarbonylamino)phenoxy)-1H-benzimidazol-2-yl)-4-methylbenzenesulfonamide

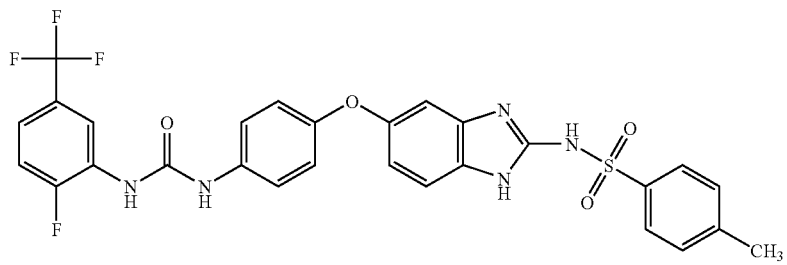

To a mixture of Intermediate 6 (105 mg, 0.25 mmol) and N',N''-bis-p-tolyl sulfonyl-S-methylisothiourea (100 mg, 0.25 mmol; prepared from p-toluene sulfonamide, cf. *J.Org.Chem.*, 1998, 53, 3120–3122; Zh.Org.Khim., 1975, 11, (3), 574–576) in THF (3ml) was added acetic acid (0.5 ml) and stirred for 4 days at 90° C. Reaction mixture was treated with SPE (NH$_2$) tube (washed with MeOH and eluted with NH$_3$/MeOH), NH3/MeOH eluent was collected and purified by column chromatography (hexane-AcOEt, 1:1) and desired compound was obtained as off-white solid. (2.3 mg, yield 1.53%)

$^1$H NMR (DMSO-d$_6$) δ 11.89 (br, 1H), 11.84 (br, 1H), 9.16 (s, 1H), 8.85 (s, 1H), 8.61 (d, 1H), 7.76 (d, 2H), 7.53–7.43 (m, 3H), 7.41–7.36 (m, 1H), 7.31 (d, 2H), 7.24 (d, 1H), 6.97 (d, 2H), 6.86 (d, 1H), 6.82 (dd, 1H), 2.33 (s, 3H); MS m/e 600 (M+1).

Example 86

N-(6-(4-((2-Fluoro-5-(trifluoromethyl)phenyl)aminocarbonylamino)phenoxy)benzthiazol-2-yl)methanesulfonamide

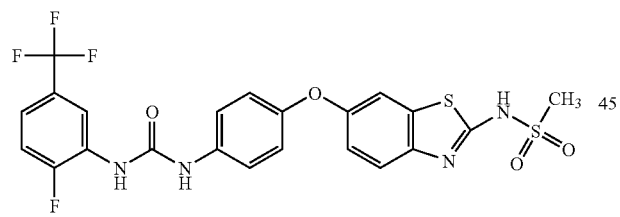

A mixture of 2-fluoro-5-(trifluoromethyl)phenylisocyanate (47.4 mg, 0.23 mmol) and Intermediate 10D (72 mg, 0.21 mmol) in THF (3 ml) was stirred over night at 45° C. The reaction mixture was cooled to room temperature and ether was added and a pale brown solid was generated. The solid was collected by filtration and washed with ether and dried in vacuo. 55 mg of desired compound was obtained.

(50% yield)

$^1$H NMR (DMSO-d$_6$) δ 12.95 (br, 1H), 9.18 (s, 1H), 8.86 (s, 1H), 8.61 (d, 1H), 7.54–7.44 (m, 4H), 7.41–7.36 (m, 1H), 7.30 (d, 1H), 7.05 (dd, 1H), 6.99 (d, 2H), 2.99 (s, 3H); MS m/e 541 (M+1).

Examples 87–102 were prepared according to procedure similar to Example 25.

Example 87

N-(5-(4-((2-Fluoro-5-(trifluoromethyl)phenyl)aminocarbonylamino)phenoxy)-1H-benzimidazol-2-yl)-4-(4-methyl-1-piperazinomethyl)benzamide

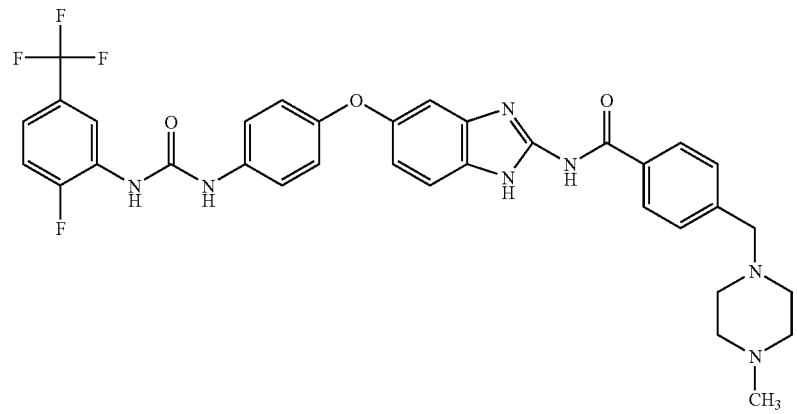

¹H NMR (DMSO-d₆) δ 12.20 (brs, 2H), 9.15 (s, 1H), 8.86 (d, 1H), 8.62 (dd, 1H), 8.08 (d, 2H), 7.44–7.53 (m, 4H), 7.35–7.42 (m, 1H), 7.22–7.34 (brs, 1H), 7.08 (d, 1H), 6.96 (d, 2H), 6.86 (dd, 1H), 6.64–6.76 (brs, 1H), 3.54 (s, 2H), 2.25–2.48 (brs, 4H), 2.18 (s, 4H), 1.76 (s, 3H); MS m/e 663 (M+2).

Example 88

N-(5-(4-((2-Fluoro-5-(trifluoromethyl)phenyl)aminocarbonylamino)phenoxy)-1H-benzimidazol-2-yl)-3-(pyridine-3-yl)propionamide

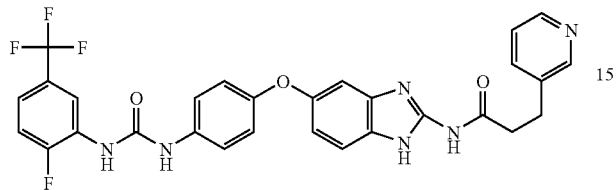

¹H NMR (DMSO-d₆) δ 12.04 (brd, 1H), 11.57 (brd, 1H), 9.15 (s, 1H), 8.86 (d, 1H), 8.62 (dd, 1H), 8.50 (d, 1H), 8.40 (dd, 1H), 7.69 (d, 1H), 7.35–7.53 (m, 5H), 7.32 (dd, 1H), 7.03 (d, 1H), 6.93 (d, 2H), 6.80 (dd, 1H), 2.96 (t, 2H), 2.80 (t, 2H); MS m/e 579 (M+1).

Example 89

N-(5-(4-((2-Fluoro-5-(trifluoromethyl)phenyl)aminocarbonylamino)phenoxy)-1H-benzimidazol-2-yl)-5-benzimidazolecarboxamide

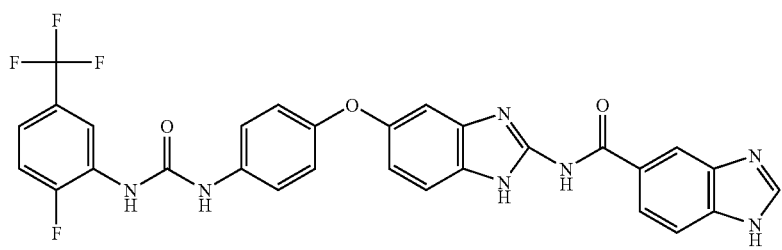

¹H NMR (DMSO-d₆) δ 12.80 (brs, 1H), 12.40 (brs, 2H), 9.16 (s, 1H), 8.88 (s, 1H), 8.62 (d, 1H), 8.45 (brs, 1H), 8.39 (dd, 1H), 8.01 (d, 1H), 7.69 (brs, 1H), 7.44–7.53 (m, 4H), 7.36–7.41 (m, 1H), 7.09 (brs, 1H), 6.96 (d, 2H), 6.85 (dd, 1H); MS m/e 590 (M+1).

Example 90

N-(5-(4-((2-Fluoro-5-(trifluoromethyl)phenyl)aminocarbonylamino)phenoxy)-1H-benzimidazol-2-yl)-4-(pyrrol-1-yl)benzamide

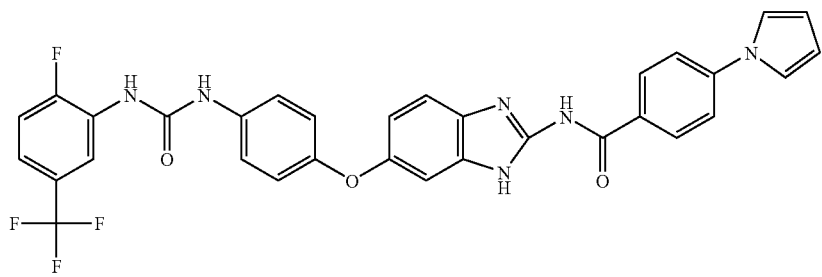

¹H NMR (DMSO-d₆) δ 12.26 (brs, 2H), 9.17 (s, 1H), 8.88 (s, 1H), 8.62 (d, 1H), 8.22 (d, 2H), 7.77 (d, 2H), 7.54 (t, 2H), 7.42–7.52 (m, 4H), 7.36–7.41 (m, 1H), 7.08 (brs, 1H), 6.97 (d, 2H), 6.86 (dd, 1H), 6.33 (t, 2H); MS m/e 615 (M+1).

Example 91

N-(5-(4-((2-Fluoro-5-(trifluoromethyl)phenyl)aminocarbonylamino)phenoxy)-1H-benzimidazol-2-yl)-4-(1H-imidazol-1-yl)benzamide

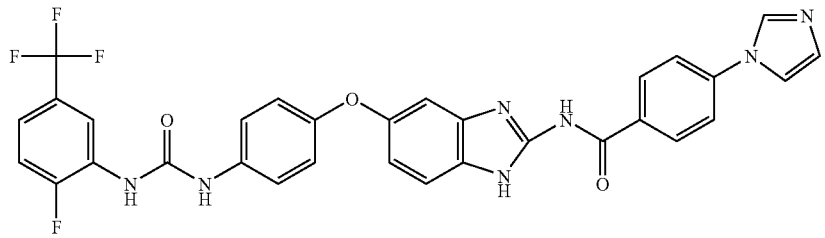

¹H NMR (DMSO-d₆) δ 12.40 (brs, 2H), 9.17 (s, 1H), 8.86 (d, 1H), 8.62 (dd, 1H), 8.43 (s, 1H), 8.27 (d, 2H), 8.05 (d, 1H), 7.80–7.96 (m, 3H), 7.45–7.54 (m, 3H), 7.33–7.42 (m, 1H), 7.16 (s, 1H), 7.07 (brs, 1H), 6.98 (d, 2H), 6.88 (dd, 1H); MS m/e 616 (M+1).

Example 92

N-(5-(4-((2-Fluoro-5-(trifluoromethyl)phenyl)aminocarbonylamino)phenoxy)-1H-benzimidazol-2-yl)-4-(dimethylamino)butylamide

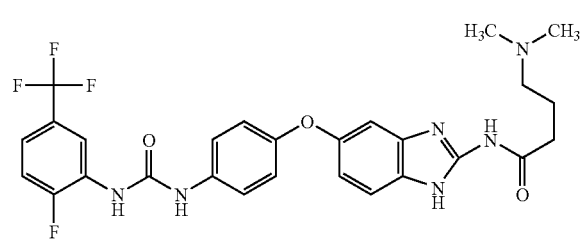

¹H NMR (DMSO-d₆) δ 12.02 (br, 1H), 11.56 (br, 1H), 9.18 (s, 1H), 8.90 (s, 1H), 8.62 (s, 1H), 7.53–7.35 (m, 5H), 7.16–6.97 (m, 1H), 6.93 (d, 2H), 6.80 (dd, 1H), 2.45 (t, 2H), 2.24 (t, 2H), 2.13 (s, 6H), 1.75 (m, 2H); MS m/e 559 (M+1).

Example 93

N-(5-(4-((2-Fluoro-5-(trifluoromethyl)phenyl)aminocarbonylamino)phenoxy)-1H-benzimidazol-2-yl)-3-pyridinecarboxamide

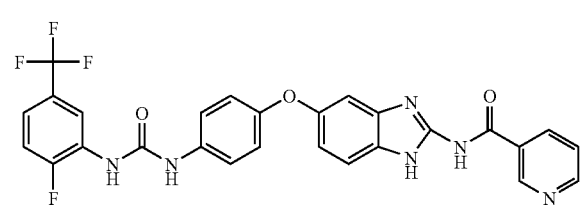

¹H NMR (DMSO-d₆) δ 12.41 (br, 2H), 9.26 (d, 1H), 9.16 (s, 1H), 8.87 (s, 1H), 8.74 (s, 1H), 8.62 (dd, 1H), 8.43 (m, 1H), 7.57–7.42 (m, 5H), 7.42–7.36 (m, 1H), 7.05 (d, 1H), 6.98 (d, 2H), 6.88 (dd, 1H); MS m/e 551 (M+1).

Example 94

N-(5-(4-((2-Fluoro-5-(trifluoromethylphenyl)aminocarbonylamino)phenoxy)-1H-benzimidazol-2-yl)-2-tetrahydrofurancarboxamide

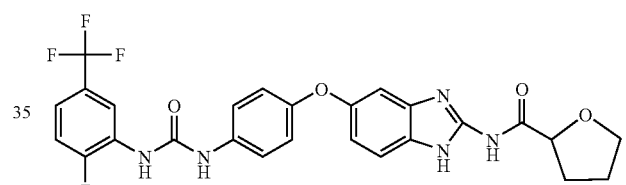

¹H NMR (DMSO-d₆) δ 12.08 (br, 1H), 11.26 (br, 1H), 9.14 (s, 1H), 8.86 (s, 1H), 8.62 (d, 1H), 7.53–7.41 (m, 4H), 7.41–7.35 (m, 1H), 7.06(br, 1H), 6.94 (d, 2H), 6.83 (dd, 1H), 4.53 (dd, 1H), 3.99 (q, 1H), 3.83 (q, 1H), 2.28–2.18 (m, 1H), 2.04–1.83 (m, 3H); MS m/e 544 (M+1).

Example 95

N-(5-(4-((2-Fluoro-5-(trifluoromethyl)phenyl)aminocarbonylamino)phenoxy)-1H-benzimidazol-2-yl)(1H-indole-3-carboxamide)

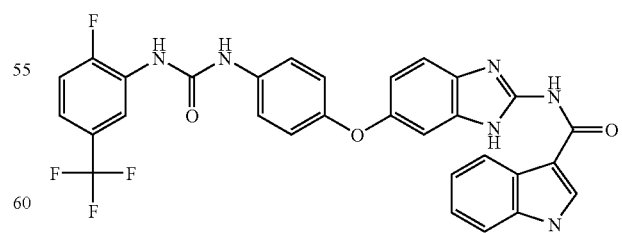

¹H NMR (DMSO-d₆) δ 12.25 (brs, 1H), 11.77 (s, 1H), 9.18 (s, 1H), 8.88 (d, 1H), 8.62 (dd, 1H), 7.70 (d, 1H), 7.60 (brs, 1H), 7.43–7.55 (m, 6H), 7.35–7.41 (m, 1H), 7.25 (t, 1H), 7.05–7.12 (m, 2H), 6.97 (d, 2H), 6.86 (dd, 1H); MS m/e 589 (M+1).

Example 96

N-(5-(4-((2-Fluoro-5-(trifluoromethyl)phenyl)aminocarbonylamino)phenoxy)-1H-benzimidazol-2-yl)(5-(1-pyrrolidino)tetrazol-2-yl)acetamide

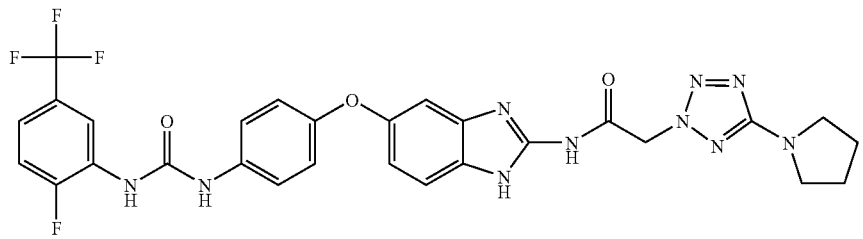

$^1$H NMR (DMSO-d$_6$) δ 12.17 (brs, 2H), 9.14 (s, 1H), 8.85 (d, 1H), 8.61 (dd, 1H), 7.36–7.53 (m, 5H), 7.01 (d, 1H), 6.96 (d, 2H), 6.85 (dd, 1H), 5.49 (s, 2H), 3.30–3.40 (m, 4H, overlap with d6-DMSO water peak), 1.88–1.97 (m, 4H); MS m/e 625 (M+1).

Example 97

N-(5-(4-((2-Fluoro-5-(trifluoromethyl)phenyl)aminocarbonylamino)phenoxy)-1H-benzimidazol-2-yl)(1methyl-1H-imidazol-4-yl)acetamide

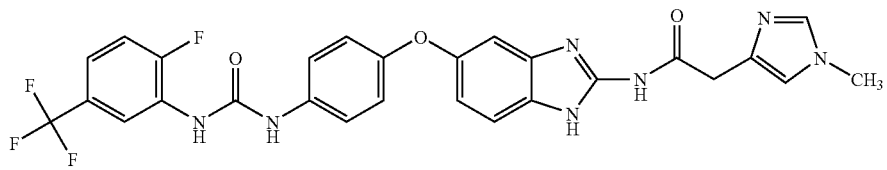

$^1$H NMR (DMSO-d$_6$) δ 12.10 (brs, 1H), 11.85 (brs, 1H), 9.39 (s, 1H), 9.07 (dd, 2H), 7.62–7.84 (m, 7H), 7.33 (s, 1H), 7.21 (d, 2H), 7.11 (dd, 1H), 3.99 (s, 5H); MS m/e 568 (M+1).

Example 98

N-(5-(4-((2-Fluoro-5-(trifluoromethyl)phenyl)aminocarbonylamino)phenoxy)-1H-benzimidazol-2-yl)(1H-imidazole-4-carboxamide)dihydrochloride

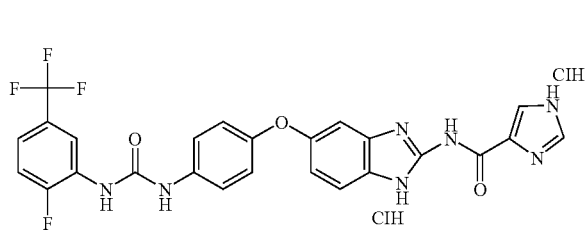

$^1$H NMR (DMSO-d$_6$) δ 9.74 (s, 1H), 9.13 (s, 1H), 8.62 (d, 2H), 8.24 (s, 1H), 7.60 (d, 1H), 7.53 (d, 2H), 7.48 (d, 1H), 7.40 (m, 1H), 7.17 (d, 1H), 7.08 (m, 1H), 7.04 (d, 2H), 3.88 (s, 3H); MS m/e 540 (M+1).

Example 99

N-(5-(4-((2-Fluoro-5-(trifluoromethyl)phenyl)aminocarbonylamino)phenoxy)-1H-benzimidazol-2-yl)benzamide

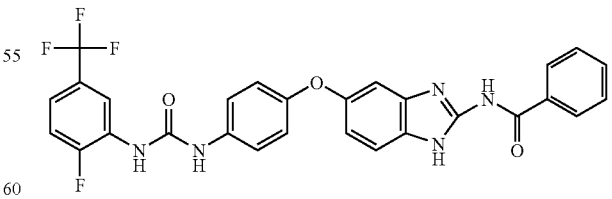

$^1$H NMR (DMSO-d$_6$) δ 12.6–12.2 (brs, 2H), 9.15 (s, 1H), 8.87 (d, 1H), 8.62 (dd, 1H), 8.13 (d, 2H), 7.95 (s, 2H), 7.64–7.50 (m, 4H), 7.45 (d, 2H), 7.39 (brm, 1H), 6.97 (d, 2H), 6.86 (dd, 1H); MS m/e 550 (M+1).

Example 100

N-(5-(4-((2-Fluoro-5-(trifluoromethyl)phenyl)aminocarbonylamino)phenoxy)-1H-benzimidazol-2-yl)-2-thiophenecarboxamide

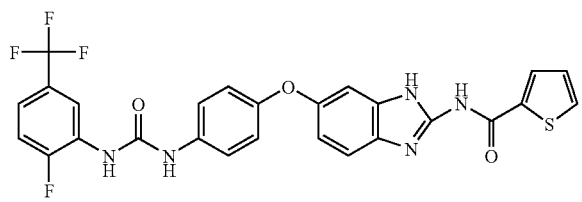

¹H NMR (DMSO-d₆) δ 12.23 (br, 2H), 9.16 (s, 1H), 8.86 (s, 1H), 8.62 (d, 1H), 8.02 (br, 1H), 7.84 (br, 1H), 7.54–7.34 (m, 5H), 7.20 (t, 1H), 7.03(br, 1H), 6.97 (d, 2H), 6.86 (dd, 1H); MS m/e 556 (M+1).

Example 101

N-(5-(4-((2-Fluoro-5-(trifluoromethyl)phenyl)aminocarbonylamino)phenoxy)-1H-benzimidazol-2-yl)(4-methyl-1-piperazino)acetamide

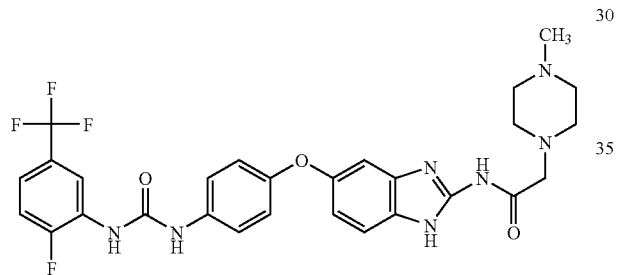

¹H NMR (DMSO-d₆) δ 11.90–12.25 (brd, 1H), 10.90–11.30 (brs, 1H), 9.13 (s, 1H), 8.85 (d, 1H), 8.62 (dd, 1H), 7.33–7.53 (m, 5H), 6.97–7.18 (brd, 1H), 6.93 (d, 2H), 6.81 (dd, 1H), 3.26 (s, 2H), 2.5–42.62 (bs, 4H), 2.28–2.42 (bs, 4H), 2.16 (s, 3H); MS m/e 584 (M−1).

Example 102

N-(5-(4-((2-Fluoro-5-(trifluoromethylphenyl)aminocarbonylamino)phenoxy)-1H-benzimidazol-2-yl)(dimethylamino)acetamide

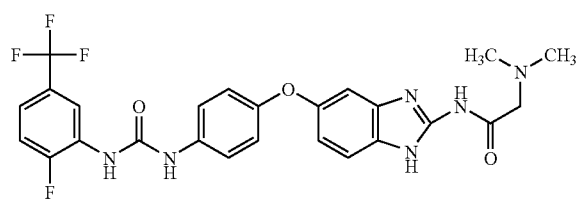

¹H NMR (DMSO-d₆) δ 12.10 (brs, 1H), 9.14 (s, 1H), 8.85 (d, 1H), 8.62 (dd, 1H), 7.35–7.53 (m, 6H), 6.96 (brs, 1H), 6.95 (d, 2H), 6.85 (dd, 1H), 3.60–3.80 (brs, 2H), 2.55–2.67 (brs, 6H); MS m/e 529 (M−1).

Example 103

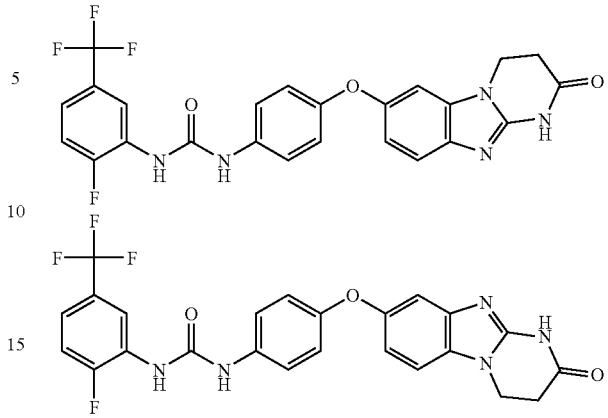

Prepared as described by the coupling reaction in Example 25 using 1-piperidine propionic acid. Using these reaction conditions, elimination of piperidine followed by cyclization to the two regioisomeric products in a 1:1 ratio occurred in situ without isolation of the intermediates.

¹H NMR (DMSO-d₆) δ 11.45 (brs, 1H), 11.42 (brs, 1H), 9.12 (s, 2H), 8.84 (d, 2H), 8.61 (dd, 2H), 7.35–7.53 (m, 10H), 7.15 (d, 1H), 7.03 (d, 1H), 6.93 (d, 2H), 6.91 (d, 2H), 6.85 (dd, 1H), 6.80 (dd, 1H), 4.25 (t, 2H), 4.21 (t, 2H), 2.89 (t, 2H), 2.86 (t, 2H); MS m/e 500 (M+1).

The two regioisomers were separated by successive recrystallizations from 2-butanone followed by methanol.

Example 103A 6-(4-((2-Fluoro-5-(trifluoromethyl)phenyl)aminocarbonylamino)phenoxy)-3,4-dihydro-1,4a-diazacarbazol-2-one

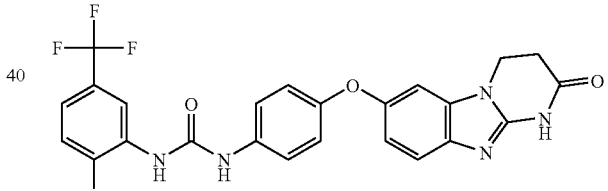

¹H NMR (DMSO-d₆) δ 9.16 (s, 1H), 8.88 (d, 1H), 8.61 (d, 1H), 7.35–7.53 (m, 5H), 7.15 (d, 1H), 6.93 (d, 2H), 6.80 (dd, 1H), 4.21 (t, 2H), 2.86 (t, 2H); MS m/e 500 (M+1).

Example 103B 7-(4-((2-Fluoro-5-(trifluoromethyl)phenyl)aminocarbonylamino)phenoxy)-3,4-dihydro-1,4a-diazacarbazol-2-one

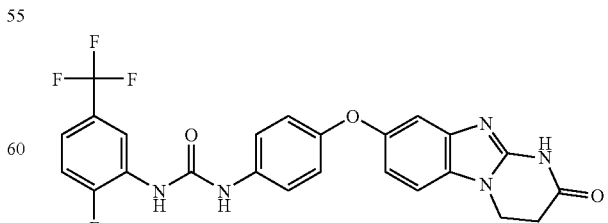

¹H NMR (DMSO-d₆) δ 11.42 (brs, 1H), 9.17 (s, 1H), 8.90 (s, 1H), 8.61 (dd, 1H), 7.35–7.53 (m, 5H), 7.03 (d, 1H), 6.91 (d, 2H), 6.84 (dd, 1H), 4.25 (t, 2H), 2.89 (t, 2H); MS m/e 500 (M+1).

Example 104

2-(2-(4-Methyl-1-piperazino)ethylamino)-5-(4-((2-fluoro-5-(trifluoromethyl)phenyl)aminocarbonylamino)phenoxy)-1H-benzimidazole

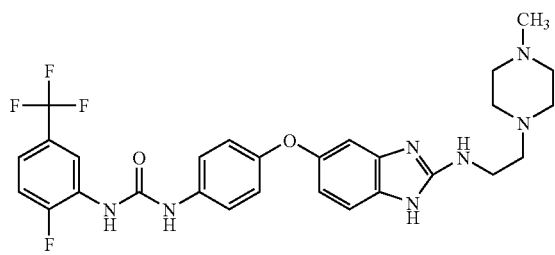

To a stirred solution of N-(5-(4-((2-fluoro-5-(trifluoromethyl)phenyl)aminocarbonylamino)phenoxy)-1H-benzimidazol-2-yl)(N-4-methyl-1-piperazino)acetamide (the product of Example 101, 150 mg, 0.26 mmol) in dry THF (10 ml) under nitrogen was added dropwise a solution of lithium aluminium hydride in THF (5 ml of a 1M solution, 5 mmol). The reaction was stirred at room temperature for 5h and then quenched by slow dropwise addition of ethyl acetate, followed by methanol and water. The resulting white precipitate was filtered off through a celite pad and washed well with methanol. The filtered solution was evaporated to dryness and partioned between ethyl acteate and water. The aqueous phase was further extracted by ethyl acetate three times and then combined ethyl acetate solutions were dried over magnesium sulfate and concentrated to give the crude product as an oil. Purification of the crude material by column chromatography (eluting with AcOEt and incremental amounts of methanolic ammonia up to 10%) afforded the product as an oil (86 mg, 58% yield).

$^1$H NMR (DMSO-$d_6$) δ 10.80 (brs, 1H), 9.10 (s, 1H), 8.84 (d, 1H), 8.61 (dd, 1H), 7.49 (t, 1H), 7.35–7.43 (m, 4H), 7.08 (d, 1H), 6.88 (d, 2H), 6.70 (d, 1H), 6.41 (brs, 1H), 2.25–2.45 (m, 4), 2.15 (s, 4H), 1.76 (s, 7H); MS m/e 572 (M+1).

Example 105

2-(2-(Dimethylamino)ethylamino)-5-(4-((2-fluoro-5-(trifluoromethyl)phenyl)aminocarbonylamino)phenoxy)-1H-benzimidazole

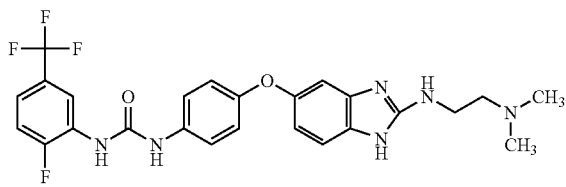

The title compound was prepared as described in Example 104 using the product of Example 102;

$^1$H NMR (DMSO-$d_6$) δ 10.75 (brs, 1H), 9.10 (s, 1H), 8.85 (d, 1H), 8.61 (dd, 1H), 7.49 (t, 1H), 7.34–7.44 (m, 4H), 7.08 (d, 1H), 6.88 (d, 2H), 6.55 (dd, 1H), 6.43 (brs, 1H), 3.53 (t, 2H, overlap with d6-DMSO water peak), 2.44 (t, 2H), 3.19 (s, 6H); MS m/e 517 (M+1).

Example 106

2-(3-(4-methyl-1-piperazino)propylamino)-5-(4-((2-fluoro-5-(trifluoromethyl)phenyl)aminocarbonylamino)phenoxy)-1H-benzimidazole

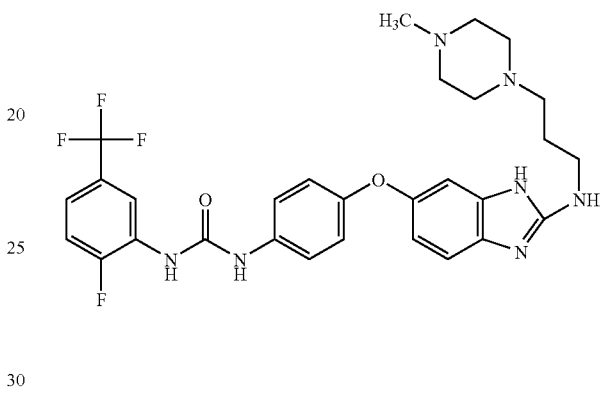

To a stirred solution of thiophosgene (1.47 g, 12.8 mmol) in acetone (10 ml) and dichloromethane (10 ml), cooled in an ice bath under nitrogen, was added dropwise a solution of 1-(3-aminopropyl)-4-methylpiperazine (1.0 g, 6.4 mmol) in acetone (5 ml) and dichloromethane (5 ml) over 10 minutes. The reaction was stirred at room tempertaure for 3h and then diluted with dichloromethane (50 ml) and washed with aqueous sodium bicarbonate solution (25 ml). The aqueous phase was further extracted by dichloromethane twice and then combined dichloromethane solutions were dried over magnesium sulfate and concentrated to give a brown oil (0.37 g, 1.86 mmol, 0.29% yield) which was used without purification. The crude oil was dissolved in acetonitrile (30 ml) and 4-(4-((2-fluoro-5-(trifluoromethyl)phenyl)aminocarbonylamino)phenoxy)phenylene-1,2-diamine (intermediate 6) (0.20 g, 0.47 mmol) was added. The stirred reaction was heated to reflux for 24 hours. On cooling, the reaction solution was decanted off to leave behind an insoluble dark oil residue. The acetonitrile was evaporated off to give a crude oil. Purification of the crude material was achieved by two column chromatographic separations. The first eluting with dichloromethane and incremental amounts of methanolic ammonia up to 15%, and the second eluting with AcOEt and incremental amounts of methanolic ammonia up to 15%, to afford the product as an oil (79 mg, 28% yield) which solidified on standing.

$^1$H NMR (DMSO-$d_6$) δ 10.76 (brs, 1H), 9.09 (s, 1H), 8.83 (d, 1H), 8.61 (dd, 1H), 7.49 (t, 1H), 7.35–7.43 (m, 3H), 7.07 (d, 1H), 6.88 (d, 2H), 6.76 (d, 1H), 6.63 (brs, 1H), 6.56 (brs, 1H), 2.22–2.43 (m, 10H), 2.15 (s, 4H), 1.65–1.78 (m, 3H); MS m/e 586 (M+1).

Example 107

Methyl N-(5-(5-((2-fluoro-5-(trifluoromethyl)phenyl)aminocarbonylamino)-1-oxo-2-pyridyloxy)-1H-benzimidazol-2-yl)carbamate

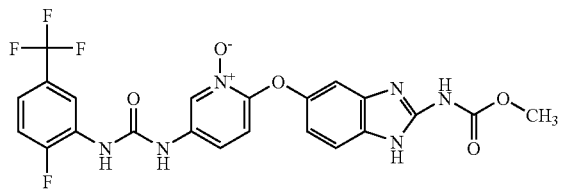

The title compound was prepared following the procedure for Example 12 using the compound of Example 37.

$^1$H NMR (DMSO-d$_6$) δ 12.2–11.2 (brs, 2H), 9.42 (s, 1H), 9.06 (s, 1H), 8.68 (s, 1H), 8.53 (d, 1H), 7.53 (t, 1H), 7.45 (brs, 1H), 7.39 (d, 1H), 7.30 (d, 1H), 7.11 (d, 1H), 7.02 (s, 1H), 6.80 (d, 1H), 3.75 (s, 3H); MS m/e 521 (M+1).

Example 108

Methyl N-(5-(5-((2-fluoro-5-(trifluoromethyl)phenyl)aminocarbonylamino)-2-pyridyloxy)-1H-benzimidazol-2-yl)carbamate dimethanesulfonic acid

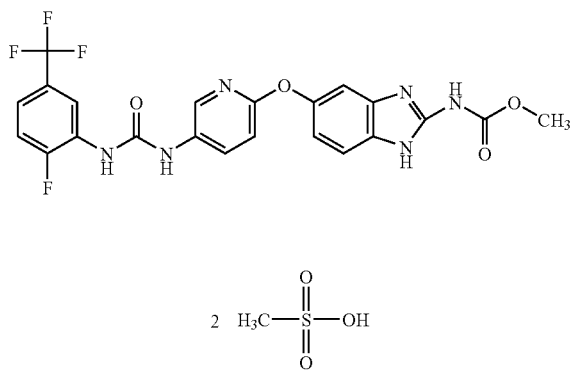

The product of Example 37 was converted into the salt form.

$^1$H NMR (DMSO-d$_6$) δ 9.31 (brs, 1H), 9.02 (d, 1H), 8.56 (dd, 1H), 8.21 (d, 1H), 8.05 (dd, 1H), 7.62 (d, 1H), 7.51 (m, 1H), 7.41 (m, 2H), 7.42 (m, 1H), 7.33 (d, 1H), 7.17 (dd, 1H), 7.08 (d, 1H), 3.89 (s, 6H); MS m/e 505 (M+1).

Example 109

Methyl N-(5-(5-((2-fluoro-5-(trifluoromethyl)phenyl)aminocarbonylamino)-2-pyridyloxy)-1H-benzimidazol-2-yl)carbamate maleate

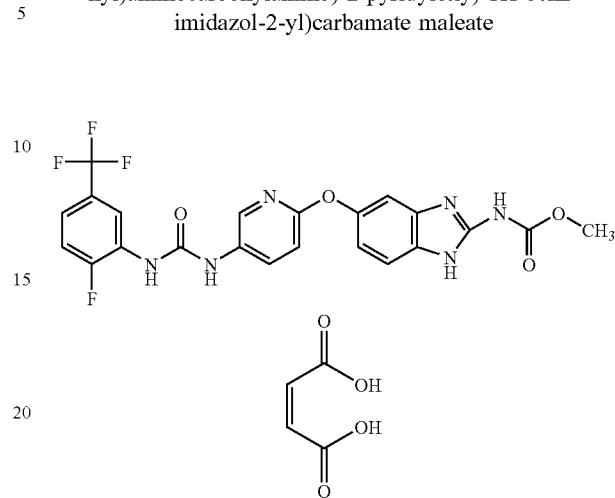

The product of Example 37 was converted into the salt form.

$^1$H NMR (DMSO-d$_6$) δ 9.21 (s, 1H), 8.95 (d, 1H), 8.57 (dd, 1H), 8.15 (d, 1H), 8.00 (dd, 1H), 7.51 (m, 1H), 7.41 (m, 2H), 7.13 (d, 1H), 6.95 (d, 1H), 6.86 (dd, 1H), 6.24 (s, 2H), 3.77 (s, 3H); MS m/e 505 (M+1).

Example 110

N-(6-(2-((2-fluoro-5-(trifluoromethylphenyl)aminocarbonylamino)-5-pyridyloxy)-1-benzyl-1H-benzimidazol-2-yl)acetamide

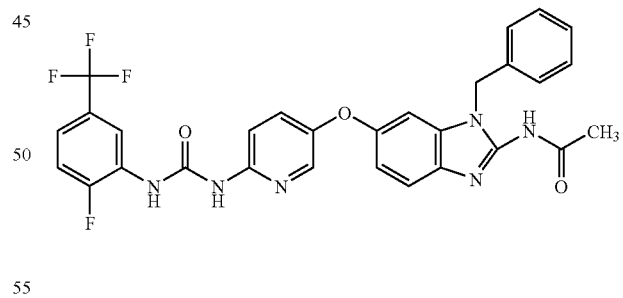

Coupling of Intermediate 12C with 2-nitro-5-bromopyridine and subsequent hydrogenation gave N-(6-(2-amino-5-pyridyloxy)-1-benzyl-1H-benzimidazol-2-yl)acetamide. Following the procedure for Example 1 provides the title compound.

$^1$H NMR (DMSO-d$_6$) δ 10.62 (brs, 1H), 9.92 (s, 1H), 8.67 (dd, 1H), 8.02 (dd, 1H), 7.41–7.62 (m, 5H), 7.22–7.34 (m, 3H), 7.16 (brs, 2H), 6.91 (dd, 1H), 5.30 (s, 2H), 2.10 (s, 3H); MS m/e 579 (M+1).

Examples 111 and 112 are prepared according to the procedure for

Example 1 using Intermediate 15B.

Example 111

Methyl-N-(5-(5-((2-chloro-5-(trifluoromethyl)phenyl)aminocarbonylamino)-2-pyridyloxy)-1H-benzimidazol-2-yl)carbamate

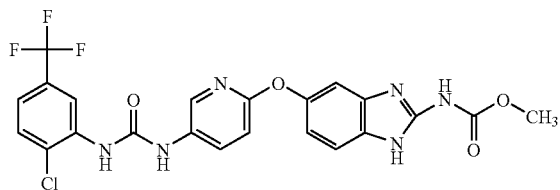

¹H NMR (DMSO-d₆) δ 12.2–11.2 (brs, 2H), 9.61 (s, 1H), 8.66 (s, 1H), 8.61 (d, 1H), 8.15 (d, 1H), 8.01 (dd, 1H), 7.72 (dd, 1H), 7.38 (m, 2H), 7.11 (d, 1H), 6.94 (d, 1H), 6.83 (dd, 1H), 3.76 (s, 3H); MS m/e 521 (M+1).

Example 112

Methyl N-(5-(5-((2,5-dichlorophenyl)aminocarbonylamino)-2-pyridyloxy)-1H-benzimidazol-2-yl)carbamate dihydrochloride

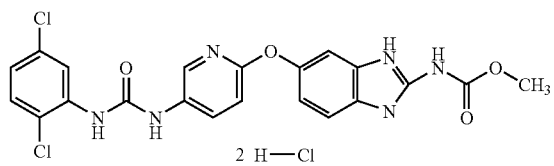

¹H NMR (DMSO-d₆) δ 10.35 (s, 1H), 8.76 (s, 1H), 8.29 (d, 1H), 8.24 (d, 1H), 8.03 (dd, 1H), 7.63 (d, 1H), 7.50 (d, 1H), 7.35 (d, 1H), 7.16 (dd, 1H), 7.11–7.07 (m, 2H), 3.88 (s, 3H); MS m/e 487 (M+1).

Example 113

6-(6-((2-Fluoro-5-(trifluoromethyl)phenyl)aminocarbonylamino)-3-pyridyloxy)-1-benzyl-1H-benzimidazol-2-ylamine

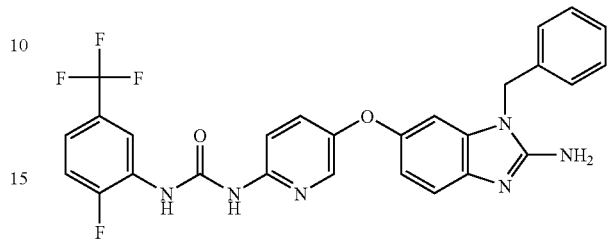

The title compound was prepared according to the procedure for Example 1 using Intermediate 12E, followed by acidic hydrolysis.

¹H NMR (DMSO-d₆) δ 10.69 (brs, 1H), 9.87 (brs, 1H), 8.65 (dd, 1H), 7.92 (d, 1H), 7.51 (m, 2H), 7.41 (m, 2H), 7.31 (m, 2H), 7.23 (m, 1H), 7.18 (m, 1H), 7.12 (d, 1H), 6.89 (d, 1H), 6.67 (d, 1H), 6.56 (brs, 2H), 5.23 (s, 2H); MS m/e 537 (M+1).

Example 114

N-(6-(6-((2-Fluoro-5-(trifluoromethyl)phenyl)aminocarbonylamino)-3-pyridyloxy)-1-benzyl-1H-benzimidazol-2-yl)methanesulfonamide

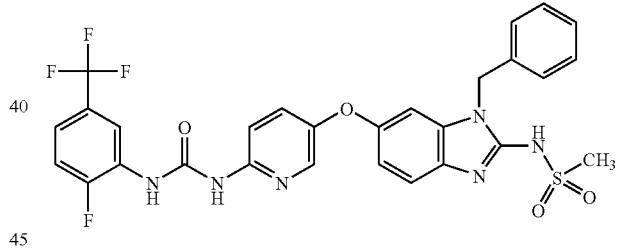

To the suspension of the product of Example 113 in dry THF, BOC₂O (2 eq.) was added at room temperature. The solution becomes clear. After the reaction completion, the solvent was removed then Si-column cromathograpy was performed by CHCl₃—MeOH (1–3%) as eluent. 5-(6-((2-fluloro-5-(trifluoromethyl)phenyl)aminocarbonylamino)-3-pyridyloxy)-3-benzyl-1-tert-butoxycarbonyl-2-imino benzimidazolidine was obtained as amorphous in good yield.

The compound (100 mg) was dissolved to pyridine, and mesylchloride was dropped slowly (5–7 drops) to it at 0° C. After overnight stirring, the mixture was quenched to the ice-water and extracted with AcOEt then solvent was removed. To the obtained crude mixture. TFA (1 ml) was added. After stirring 30 min at room temperature, TFA was removed. The obtained residue was charged to the aminocolumn chromatography. 5–7% MeOH—CHCl₃ eluent was used to get the title compound.

¹H NMR (DMSO-d₆) δ 11.84 (brs, 1H), 10.64 (brs, 1H), 9.92 (brs, 1H), 8.66 (dd, 1H), 8.00 (brs, 1H), 7.48 (m, 4H), 7.33 (m, 5H), 7.17 (m, 1H), 5.86 (dd, 1H), 5.18 (s, 2H), 2.98 (s, 3H); MS m/e 615 (M+1).

Example 115

Methyl N-(6-(4-((2-fluoro-5-(trifluoromethyl)phenyl)aminocarbonylamino)phenoxy)benzoxazol-2-yl)carbamate

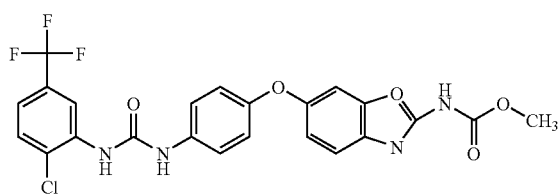

To a mixture of 5-(4-((2-fluoro-5-(trifluoromethyl)phenyl)aminocarbonylamino)phenyloxy)benz-3-oxazol-2-ylamine (Intermediate 11B-67.0 mg, 0.15 mmol) in pyridine (2 mL) was dropwise added excess amount of ClCO$_2$Me (ca 0.23 mL) at room temperature. The mixture was added water and stirred at room temperature overnight. The mixture was extracted with ethyl acetate. The organic layer was washed with NaHCO$_3$(aq) and brine then dried over Na$_2$SO$_4$. After evaporation, residual solid was washed with MeOH and dried under reduced pressure to give the title compound (46.1 mg, 61%):

$^1$H NMR (DMSO-d$_6$) δ 9.17 (brs, 1H), 8.86 (d, 1H), 8.62 (dd, 1H), 7.49 (m, 2H), 7.46 (d, 2H), 7.38 (m, 1H), 7.26 (brs, 1H), 6.99 (d, 2H), 6.92 (dd, 1H), 3.70 (s, 3H); MS m/e 505 (M+1).

The following compounds (Example 116–132) were prepared according to the procedures described for Example 1.

Example 116

Methyl N-(5-(3-((2-(trifluoromethoxy)phenyl)aminocarbonylamino)phenoxy)-1H-benzimidazol-2-yl)carbamate

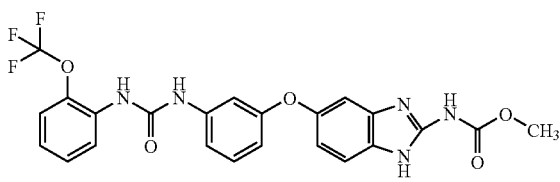

$^1$H NMR (DMSO-d$_6$) δ 12.2–11.2 (brs, 2H), 9.39 (s, 1H), 8.42 (s, 1H), 8.19 (d, 1H), 7.41 (d, 1H), 7.36 (d, 1H), 7.31 (t, 1H), 7.26 (t, 1H), 7.09 (m, 1H), 6.83 (dd, 1H), 6.60 (dd, 1H), 3.75 (t, 3); MS m/e 502 (M+1)

Example 117

Methyl N-(5-(3-((4-(trifluoromethylthio)phenyl)aminocarbonylamino)phenoxy)-1H-benzimidazol-2-yl)carbamate

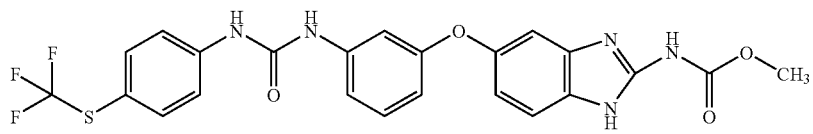

$^1$H NMR (DMSO-d$_6$) δ 12.2–11.2 (brs, 2H), 9.17 (s, 1H), 9.04 (s, 1H), 7.58 (q, 4H), 7.41 (d, 1H), 7.24 (t, 1H), 7.15 (s, 1H), 7.08 (m, 2H), 6.83 (dd, 1H), 6.59 (dd, 1H), 3.75 (s, 3H); MS m/e 518 (M+1)

Example 118

Methyl N-(5-(3-((2-(trifluoromethyl)phenyl)aminocarbonylamino)phenoxy)-1H-benzimidazol-2-yl)carbamate

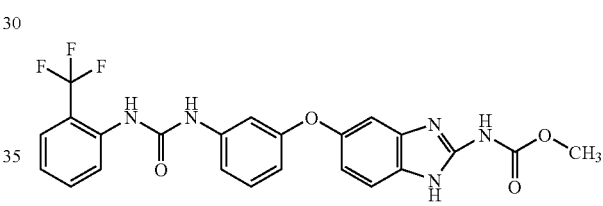

$^1$H NMR (DMSO-d$_6$) δ 12.2–11.2 (brs, 2H), 9.49 (s, 1H), 8.04 (s, 1H), 7.87 (d, 1H), 7.65 (d, 1H), 7.60 (t, 1H), 7.39 (d, 1H), 7.27–7.22 (m, 2H), 7.12–7.07 (m, 3H), 6.82 (dd, 1H), 6.60 (dd, 1H), 3.74 (s, 3H); MS m/e 486 (M+1)

Example 119

Methyl N-(5-(3-((4chloro-3-(trifluoromethyl)phenyl)aminocarbonylamino)phenoxy)-1H-benzimidazol-2-yl)carbamate

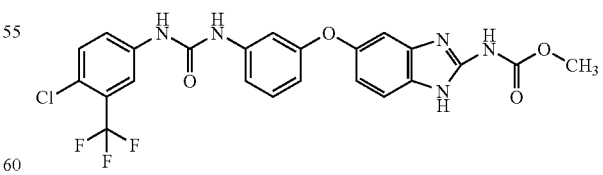

$^1$H NMR (DMSO-d$_6$) δ 12.2–11.2 (brs, 2H), 9.29 (s, 1H), 9.08 (dd, 1H), 8.94 (d, 1H), 7.90 (m, 1H), 7.53 (t, 1H), 7.42 (d, 1H), 7.27 (t, 1H), 7.14 (d, 1H), 7.09 (m, 2H), 6.84 (dd, 1H), 6.62 (dd, 1H), 3.75 (s, 3H); MS m/e 520 (M+1)

Example 120

Methyl N-(5-(3-((3-iodophenyl)aminocarbonylamino)phenoxy)-1H-benzimidazol-2-yl)carbamate

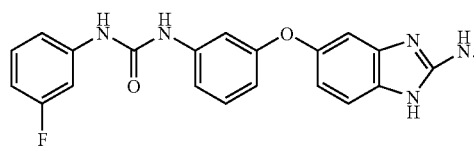

$^{1}$H NMR (DMSO-d$_6$) δ 12.2–11.2 (brs, 2H), 8.87 (s, 1H), 8.79 (s, 1H), 7.94 (s, 1H), 7.41 (d, 1H), 7.31 (d, 2H), 7.23 (t, 1H), 7.11–7.03 (m, 4H), 6.83 (dd, 1H), 6.57 (d, 1H), 3.75 (s, 3H); MS m/e 544 (M+1)

Example 121

Methyl N-(5-(3-((2,5-dichlorophenyl)aminocarbonylamino)phenoxy)-1H-benzimidazol-2-yl)carbamate

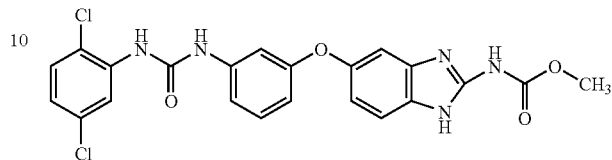

$^{1}$H NMR (DMSO-d$_6$) δ 12.2–11.2 (brs, 2H), 9.57 (s, 1H), 8.38 (s, 1H), 8.26 (d, 1H), 7.48 (d, 1H), 7.41 (d, 1H), 7.27 (t, 1H), 7.14 (d, 1H), 7.08 (m, 2H), 7.04 (s, 1H), 6.84 (dd, 1H), 6.62 (d, 1H), 3.75 (s, 1H); MS m/e 486 (M+1), 488 (M+3)

Example 122

Methyl N-(5-(4-((3-phenoxyphenyl)aminocarbonylamino)phenylthio)-1H-benzimidazol-2-yl)carbamate

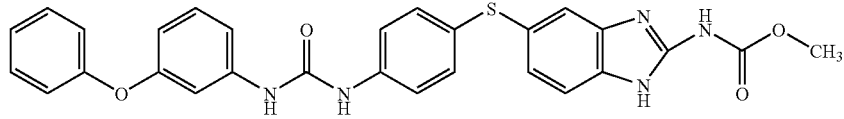

$^{1}$H NMR (DMSO-d$_6$) δ; 12.0–11.5 (brs, 2H), 9.00 (s, 1H), 8.94 (s, 1H), 7.41–7.38 (m, 6H), 7.27 (t, 1H), 7.25 (t, 1H), 7.20 (d, 2H), 7.16–7.08 (m, 3H), 7.03 (d, 2H), 6.60 (dd, 1H), 3.73 (s, 3H), MS m/e 526 (M+1)

Example 123

Methyl N-(5-(4-((3-phenoxyphenyl)aminocarbonylamino)phenoxy)-1H-benzimidazol-2-yl)carbamate

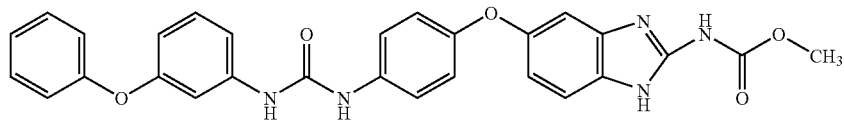

$^{1}$H NMR (DMSO-d$_6$) δ; 12.0–11.2 (brs, 2H), 8.76 (s, 1H), 8.60 (s, 1H), 7.42–7.35 (m, 5H), 7.27 (t, 1H), 7.25 (s, 1H), 7.17–7.10 (m, 2H), 7.03 (d, 2H), 6.98 (d, 1H), 6.90 (d, 2H), 6.78 (dd, 1H), 6.60 (dd, 1H), 3.75 (s, 3H), MS m/e 510 (M+1)

Example 124

Methyl N-(5-(3-((2-phenoxyphenyl)aminocarbony-lamino)phenoxy)-1H-benzimidazol-2-yl)carbamate

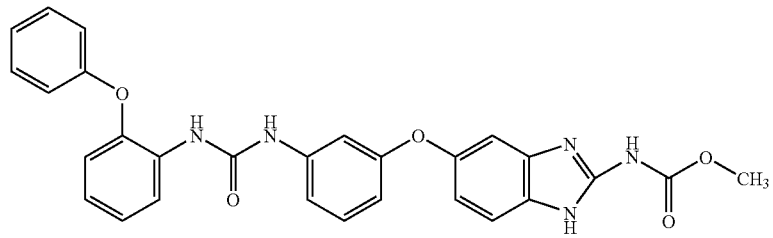

$^1$H NMR (DMSO-d$_6$) δ; 12.0–11.2 (brs, 2H), 9.34 (s, 1H), 8.40 (s, 1H), 7.42–7.36 (m, 3H), 7.22 (t, 1H), 7.14 (t, 1H), 7.10–7.05 (m, 4H), 7.01 (d, 2H), 6.94 (td, 1H), 6.82 (m, 2H), 6.57 (d, 1H), 3.75 (s, 3H), MS m/e 510 (M+1)

Example 125

Methyl N-(5-(3-((4-phenoxyphenyl)aminocarbony-lamino)phenoxy)-1H-benzimidazol-2-yl)carbamate

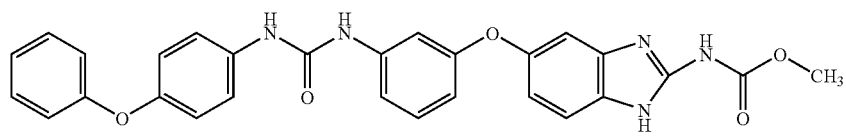

$^1$H NMR (DMSO-d$_6$) δ; 12.0–11.2 (brs, 2H), 8.90 (s, 1H), 8.78 (s, 1H), 7.43–7.40 (m, 3H), 7.36 (d, 1H), 7.34 (d, 1H), 7.22 (t, 1H), 7.16 (d, 1H), 7.08 (m, 3H), 6.97–6.93 (m, 4H), 6.83 (dd, 1H), 6.55 (dd, 1H), 3.75 (s, 3H), MS m/e 510 (M+1)

Example 126

Methyl N-(5-(3-((5-indanyl)aminocarbonylamino)phenoxy)-1H-benzimidazol-2-yl)carbamate

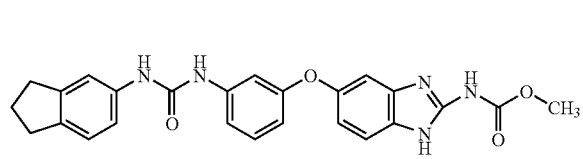

$^1$H NMR (DMSO-d$_6$) δ; 12.0–11.2 (brs, 2H), 8.68 (s, 1H), 8.43 (s, 1H), 7.40 (d, 1H), 7.32 (s, 1H), 7.21 (t, 1H), 7.11 (t, 1H), 7.08 (m, 4H), 6.82 (dd, 1H), 6.55 (d, 1H), 3.75 (s, 3H), 2.79 (m, 4H), 1.98 (m, 2H), MS m/e 458 (M+1)

Example 127

Methyl N-(5-(4-((5-indanyl)aminocarbonylamino)phenoxy)-1H-benzimidazol-2-yl)carbamate

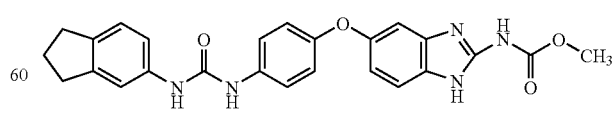

$^1$H NMR (DMSO-d$_6$) δ; 12.0–11.2 (brs, 2H), 8.57 (s, 1H), 8.48 (s, 1H), 7.41 (d, 2H), 7.37 (m, 2H), 7.11 (m, 2H), 6.99 (d, 1H), 6.90 (d, 2H), 6.78 (dd, 1H), 3.75 (s, 3H), 2.80 (quint, 4H), 1.99 (m, 2H), MS m/e 458 (M+1)

Example 128

Methyl N-(5-(4-((5-tert-butylisoxazole-3-yl)aminocarbonylamino)phenoxy)-1H-benzimidazol-2-yl)carbamate

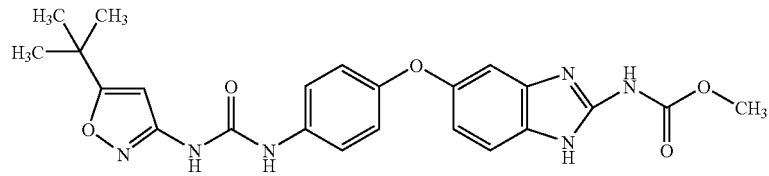

$^1$H NMR (DMSO-$d_6$) δ 11.8–11.4 (brs, 2H), 9.46 (s, 1H), 8.76 (s, 1H), 7.42 (d, 2H), 7.38 (d, 1H), 7.01 (d, 1H), 6.92 (d, 2H), 6.79 (dd, 1H), 6.48 (s, 1H), 3.74 (s, 3H), 1.29 (s, 9H); MS m/e 465 (M+1)

Example 129

Methyl N-(5-(3-((5-tert-butylisoxazole-3-yl)aminocarbonylamino)phenoxy)-1H-benzimidazol-2-yl)carbamate

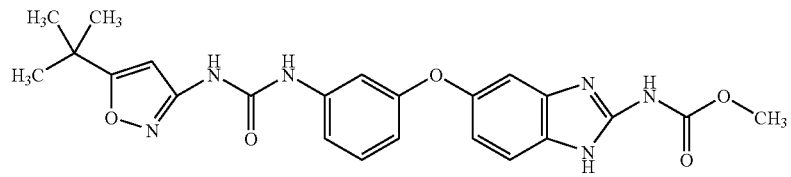

$^1$H NMR (DMSO-$d_6$) δ 12.0–11.2 (brs, 2H), 9.40 (s, 1H), 8.88 (s, 1H), 7.40 (d, 1H), 7.25 (t, 1H), 7.13 (t, 1H), 7.07 (m, 2H), 6.82 (dd, 1H), 6.61 (dd, 1H), 6.46 (s, 1H), 3.75 (s, 3H), 1.27 (s, 9H); MS m/e 465 (M+1)

Example 130

Methyl N-(5-(4-((5-tert-butylisoxazole-3-yl)aminocarbonylamino)phenylthio)-1H-benzimidazol-2-yl)carbamate

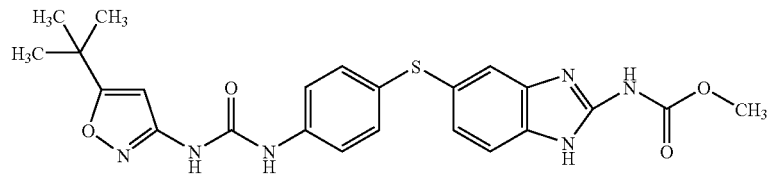

$^1$H NMR (DMSO-$d_6$) δ 12.2–11.2 (brs, 2H), 9.49 (s, 1H), 8.89 (s, 1H), 7.42 (d, 2H), 7.40 (m, 2H), 7.20 (d, 2H), 7.11 (dd, 1H), 6.49 (s, 1H), 3.75 (s, 3H), 1.28 (s, 9H); MS m/e 481 (M+1)

Example 131

Methyl N-(5-(3-((3-phenyl-1,2,4-thiadiazol-5-yl)aminocarbonylamino)phenoxy)-1H-benzimidazol-2-yl)carbamate

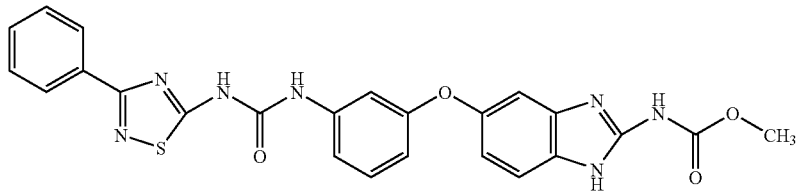

$^1$H NMR (DMF-d$_7$) δ 12.4–11.2 (brs, 2H), 9.84 (brs, 1H), 8.22–8.20 (m, 2H), 7.50 (m, 4H), 7.38 (brs, 1H), 7.36–7.34 (m, 2H), 7.22 (brs, 1H), 6.92 (dd, 1H), 6.71 (m, 1H), 3.81 (s, 1H); MS m/e 502 (M+1)

Example 132

Methyl N-(5-(3-((1-naphtyl)aminocarbonylamino)phenoxy)-1H-benzimidazol-2-yl)carbamate

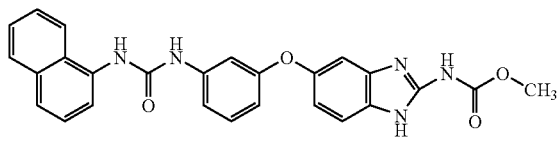

$^1$H NMR (DMSO-d$_6$) δ 12.0–11.2 (brs, 2H), 9.14 (s, 1H), 8.70 (s, 1H), 8.08 (d, 1H), 7.95 (d, 1H), 7.92 (d, 1H), 7.62 (d, 1H), 7.55 (m, 2H), 7.45 (t, 1H), 7.41 (d, 1H), 7.62 (t, 1H), 7.16–7.14 (m, 2H), 7.10 (d, 1H), 6.84 (dd, 1H), 6.59 (d, 1H), 3.75 (s, 3H); MS m/e 468 (M+1)

The compound of Example 22 was treated with 2-fluoro-5-trifluoromethylphenyl, 4-chrolophenyl, and N,N-dimethylaminophenyl isocyanate in THF to give compounds of Example 133, 134, and 135 respectively.

Example 133

1-(5-(4-((2-Fluoro-5-(trifluoromethyl)phenyl)aminocarbonylamino)phenoxy)-1H-benzimidazol-2-yl)-3-(2-fluoro-5-(trifluoromethyl)phenyl)urea

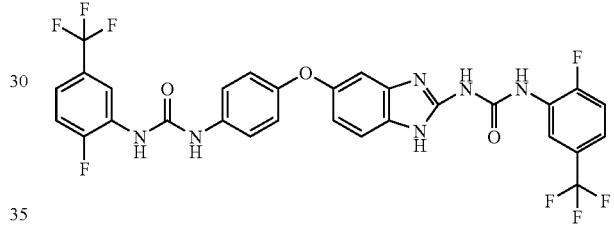

$^1$H NMR (DMSO-d$_6$) δ; 12.0–11.3 (brs, 1H), 10.7–10.1 (brs, 1H), 8.92 (s, 1H), 8.63 (s, 1H), 8.46 (d, 1H), 8.39 (d, 1H), 7.29 (m, 4H), 7.22 (d, 2H), 7.18–7.14 (m, 3H), 6.72 (d, 2H), 6.58 (dd, 1H), MS m/e 651 (M+1)

Example 134

1-(5-(4-((2-Fluoro-5-(trifluoromethyl)phenyl)aminocarbonylamino)phenoxy)-1H-benzimidazol-2-yl)-3-(4-chlorophenyl)urea

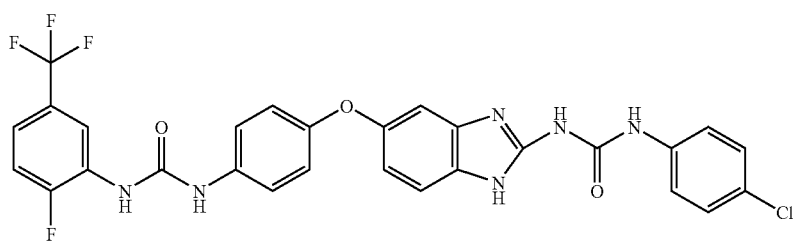

$^1$H NMR (DMSO-d$_6$) δ; 9.77 (brs, 1H), 9.14 (s, 1H), 8.86 (brs, 1H), 8.62 (d, 1H), 7.61 (d, 2H), 7.50 (m, 1H), 7.44 (d, 2H), 7.39 (m, 2H), 7.34 (d, 2H), 6.99 (d, 1H), 6.95 (d, 2H), 6.79 (dd, 1H), MS m/e 599 (M+1), 601 (M+3)

Example 135

1-(5-(4-((2-Fluoro-5-(trifluoromethyl)phenyl)aminocarbonylamino)phenoxy)-1H-benzimidazol-2-yl)-3-(4-(N,N-dimethylamino)phenyl)urea

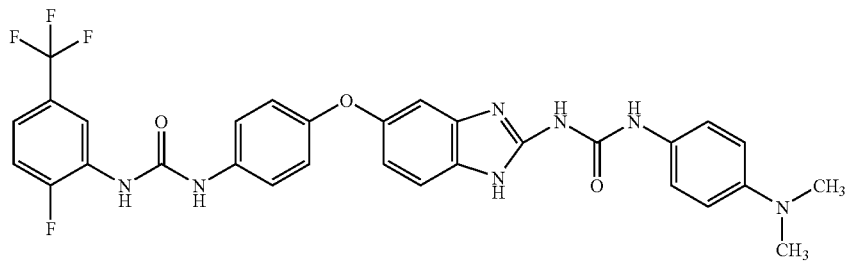

$^1$H NMR (DMSO-$d_6$) δ; 9.30 (brs 1H), 9.13 (s, 1H), 8.85 (s, 1H), 8.62 (d, 1H), 7.50 (t, 1H), 7.43 (d, 2H), 7.37 (brm, 2H), 7.34 (d, 2H), 7.00 (s, 1H), 6.93 (d, 2H), 6.76 (d, 1H), 6.72 (d, 2H), 2.85 (s, 6H), MS m/e 608 (M+1)

Example 136

1-(6-(4-((4-Chloro-3-(trifluoromethyl)phenyl)aminocarbonylamino)phenoxy)benzthiazol-2-yl)-3-(butyl)urea

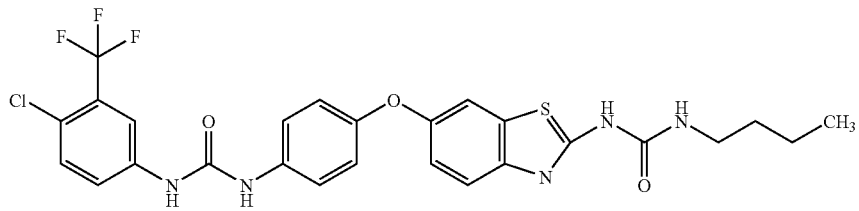

The title compound and the next compound (Example 137) were prepared according to the procedures described for Example 1, using Intermediate 13B.

$^1$H NMR (DMSO-$d_6$) δ; 10.57 (s, 1H), 9.15 (s, 1H), 8.84 (s, 1H), 8.11 (d, 1H), 7.65–7.63 (m, 2H), 7.58 (d, 1H), 7.46 (d, 2H), 7.02 (dd, 1H), 6.98 (d, 2H), 6.72 (brs, 1H), 3.15 (q, 2H), 1.46 (quint, 2H), 1.31 (sextet, 2H), MS m/e 578 (M+1), 580 (M+3).

Example 137

1-(6-(4-((2-Fluoro-5-(trifluoromethyl)phenyl)aminocarbonylamino)phenoxy)benzthiazol-2-yl)-3-(butyl)urea

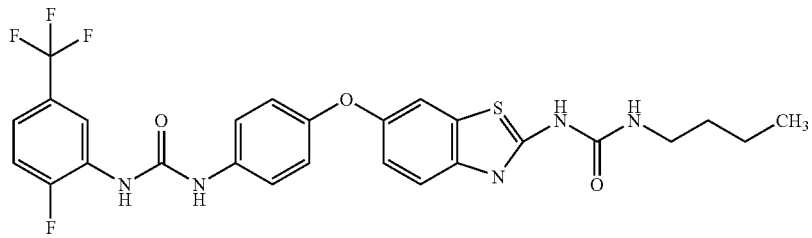

$^1$H NMR (DMSO-$d_6$) δ; 10.58 (brs, 1H), 9.17 (s, 1H), 8.87 (s, 1H), 8.62 (dd, 1H), 7.59 (d, 1H), 7.54 (d, 1H), 7.52–7.47 (m, 1H), 7.47 (d, 2H), 7.39 (m, 1H), 7.03 (dd, 1H), 6.99 (d, 2H), 6.74 (brs, 1H), 3.15 (q, 2H), 1.47 (quint, 2H), 1.31 (sextet, 2H), MS m/e 562 (M+1).

Example 138

N-(5-(4-((5-Methylisoxazol-3-yl)aminocarbonylamino)phenoxy)-1H-benzimidazol-2-yl)acetamide

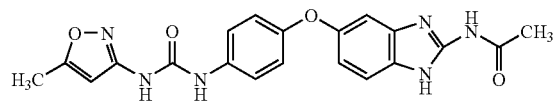

Intermediate 14F was treated with 23:2:75 (v/v/v) TFA/H$_2$O/DCM (1 mL) for ca. 1 h. The solution containing the released material was collected. The resin was washed with DCM (3×, 1 mL each). The washings were collected and combined with the original filtrate. Evaporation of the solvent in vacuo yielded a dark sticky solid. The cleaving was repeated two more times and the materials obtained after each time were combined. The crude material was dissolved in DMSO and purified with reverse-phase preparative Gilson HPLC system to yield the desired benzimidazole.

$^1$H NMR (DMF-d$_7$) δ 10.79 (br s, 1H), 10.40 (br s, 1H), 7.64 (d, J=8.8 Hz, 2H), 7.49 (br s, 1H), 7.15 (br s, 1H), 6.96 (d, J=8.8 Hz, 2H), 6.87 (dd, J=8.6, 2.5 Hz, 1H), 6.62 (s, 1H), 2.38 (s, 3H), 2.24 (s, 3H); MS m/e 407 (M+1).

The following compounds (Example 139–180) were prepared in a combinatorial chemistry format using the same procedure as Example 138. In most cases, the benzimidazoles thus obtained were light colored after HPLC purification.

Example 139

N-(5-(4-((Thiazol-2-yl)aminocarbonylamino)phenoxy)-1H-benzimidazol-2-yl)acetamide

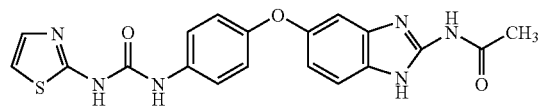

$^1$H NMR (DMF-d$_7$) δ 12.12 (br s, 1H), 11.61 (br s, 1H), 9.58 (br s, 1H), 7.60 (d, J=8.8 Hz, 2H), 7.50 (br s, 1H), 7.39 (d, J=3.5 Hz, 1H), 7.27–7.06 (m, 2H), 7.00 (d, J=8.8 Hz, 2H), 6.88 (dd, J=8.6, 2.5 Hz, 1H), 2.25 (s, 3H); MS m/e 409 (M+1).

Example 140

N-(5-(4-((1,3,4-Thiadiazol-2-yl)aminocarbonylamino)phenoxy)-1H-benzimidazol-2-yl)acetamide

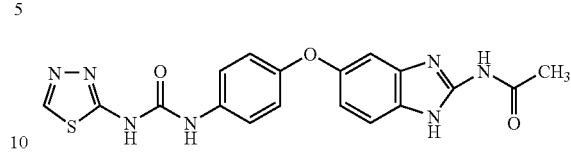

$^1$H NMR (DMF-d$_7$) δ 12.12 (br s, 1H), 11.56 (br s, 1H), 9.80 (br s, 1H), 9.09 (s, 1H) 7.66 (m, 2H), 7.50 (br s, 1H), 7.19 (br s, 1H), 7.01 (d, J=8.8 Hz, 2H), 6.88 (dd, J=8.6, 2.3 Hz, 1H), 2.25 (s, 3H); MS m/e 410 (M+1).

Example 141

N-(5-(4-((4-Methylthiazol-2-yl)aminocarbonylamino)phenoxy)-1H-benzimidazol-2-yl)acetamide

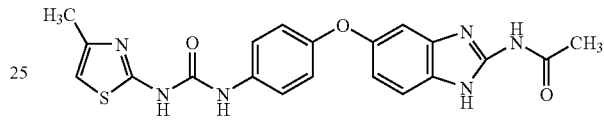

$^1$H NMR (DMF-d$_7$) δ 9.61 (s, 1H), 7.60 (d, J=9.0 Hz, 2H), 7.50 (br s, 1H), 7.16 (br s, 1H), 7.00 (d, J=9.0 Hz, 2H), 6.88 (dd, J=8.6, 2.5 Hz, 1H), 6.65 (s, 1H), 2.24 (m, 6H); MS m/e 423 (M+1).

Example 142

N-(5-(4-((5-Methylthiazol-2-yl)aminocarbonylamino)phenoxy)-1H-benzimidazol-2-yl)acetamide

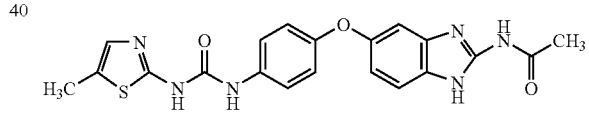

$^1$H NMR (DMF-d$_7$) δ 9.56 (s, 1H), 7.60 (d, J=8.8 Hz, 2H), 7.51 (br s, 1H), 7.16 (br s, 1H), 7.04 (s, 1H), 6.99 (d, J=8.8 Hz, 2H), 6.88 (dd, J=8.5, 2.4 Hz, 1H), 2.35 (s, 3H), 2.25 (s, 3H); MS m/e 423 (M+1).

Example 143

N-(5-(4-((5-Methyl-1,3,4-thiadiazol-2-yl)aminocarbonylamino)phenoxy)-1H-benzimidazol-2-yl)acetamide

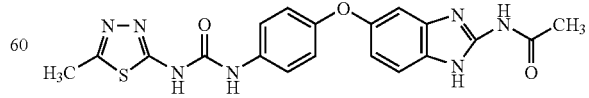

$^1$H NMR (DMF-d$_7$) δ 12.12 (br s, 1H), 11.59 (br s, 1H), 9.70 (br s, 1H), 7.65 (m, 2H), 7.50 (br s, 1H), 7.21 (br s, 1H), 7.00 (d, J=8.8 Hz, 2H), 6.88 (dd, J=8.6, 2.3 Hz, 1H), 2.62 (s, 3H), 2.25 (s, 3H); MS m/e 424 (M+1).

Example 144

N-(5-(4-((5-Ethyl-1,3,4-thiadiazol-2-yl)aminocarbonylamino)phenoxy)-1H-benzimidazol-2-yl)acetamide

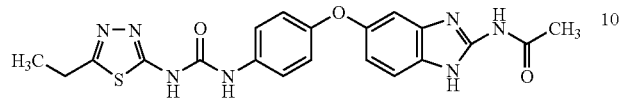

$^1$H NMR (DMF-d$_7$) δ 12.15 (br s, 1H), 11.59 (br s, 1H), 9.29 (s, 1H), 7.60 (d, J=8.8 Hz, 2H), 7.53 (br s, 1H), 7.19 (br s, 1H), 7.01 (d, J=8.8 Hz, 2H), 6.89 (dd, J=8.6, 2.3 Hz, 1H), 3.00 (q, J=7.6 Hz, 2H), 2.25 (s, 3H), 1.34 (t, J=7.6 Hz, 3H); MS m/e 438 (M+1).

Example 145

N-(5-(4-((5-Cyclopropyl-1,3,4-thiadiazol-2-yl)aminocarbonylamino)phenoxy)-1H-benzimidazol-2-yl)acetamide

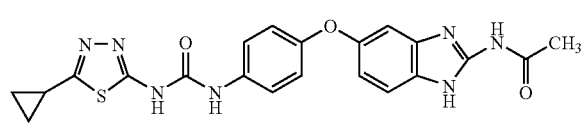

$^1$H NMR (DMF-d$_7$) δ 11.63 (br s, 1H), 9.28 (s, 1H), 7.59 (d, J=9.0 Hz, 2H), 7.53 (br d, J=8.4 Hz, 1H), 7.18 (br s, 1H), 7.01 (d, J=9.0 Hz, 2H), 6.89 (dd, J=8.6, 2.3 Hz, 1H), 2.38 (m, 1H), 2.25 (s, 3H), 1.16 (m, 2H), 0.99 (m, 2H); MS m/e 450 (M+1).

Example 146

N-(5-(4-((4-tert-Butylthiazol-2-yl)aminocarbonylamino)phenoxy)-1H-benzimidazol-2-yl)acetamide

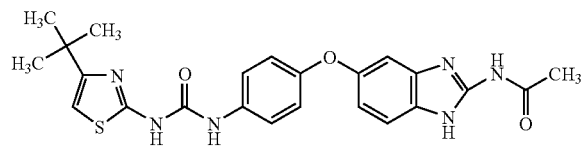

$^1$H NMR (DMF-d$_7$) δ 12.13 (br s, 1H), 9.50 (br s, 1H), 7.60 (d, J=8.9 Hz, 2H), 7.46 (m, 1H), 7.21–7.13 (m, 1H), 7.01 (d, J=8.9 Hz, 2H), 6.89 (dd, J=8.6, 2.5 Hz, 1H), 6.68 (s, 1H), 2.25 (s, 3H), 1.27 (s, 9H); MS m/e 465 (M+1).

Example 147

N-(5-(4-((5-tert-Butyl-1,3,4-thiadiazol-2-yl)aminocarbonylamino)phenoxy)-1H-benzimidazol-2-yl)acetamide

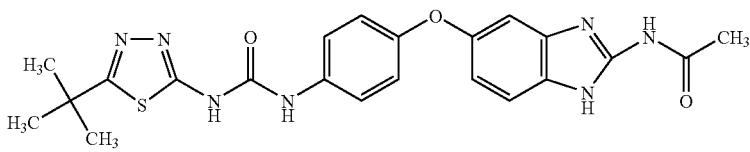

$^1$H NMR (DMF-d$_7$) δ 12.09 (br s, 1H), 11.57 (br s, 1H), 9.42 (s, 1H), 7.62 (d, J=8.8 Hz, 2H), 7.51 (br s, 1H), 7.17 (br s, 1H), 7.01 (d, J=8.8 Hz, 2H), 6.88 (dd, J=8.6, 2.3 Hz, 1H), 2.25 (s, 3H), 1.42 (s, 9H); MS m/e 466 (M+1).

Example 148

N-(5-(4-((4,5-Dimethylthiazol-2-yl)aminocarbonylamino)phenoxy)-1H-benzimidazol-2-yl)acetamide

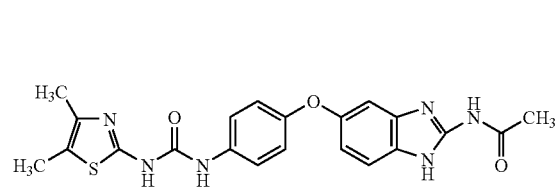

$^1$H NMR (DMF-d$_7$) δ 12.10 (br s, 1H), 11.58 (br s, 1H), 9.60 (br s, 1H), 7.60 (d, J=8.8 Hz, 2H), 7.50 (br s, 1H), 7.16 (br s, 1H), 6.99 (d, J=8.8 Hz, 2H), 6.87 (dd, J=8.6, 2.3 Hz, 1H), 2.24 (m, 6H), 2.13 (s, 3H); MS m/e 437 (M+1).

Example 149

N-(5-(4-((5-Morpholino-1,3,4-triazol-2-yl)aminocarbonylamino)phenoxy)-1H-benzimidazol-2-yl)acetamide

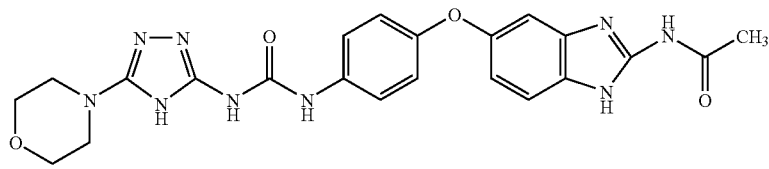

$^1$H NMR (DMF-d$_7$) δ 12.14 (br s, 1H), 11.60 (br s, 1H), 9.67 (s, 1H), 7.73 (d, J=9.1 Hz, 2H), 7.51 (br s, 1H), 7.38 (br s, 1H), 7.31–7.07 (m, 1H), 7.02 (d, J=9.1 Hz, 2H), 6.89 (dd, J=8.6, 2.3 Hz, 1H), 3.69 (m, 4H), 3.33 (m, 4H), 2.25 (s, 3H); MS m/e 478 (M+1).

Example 150

N-(5-(4-((5-Methylisoxazol-3-yl)aminocarbonylamino)phenoxy)-1H-benzimidazol-2-yl)(2-(methoxy)ethoxy)acetamide

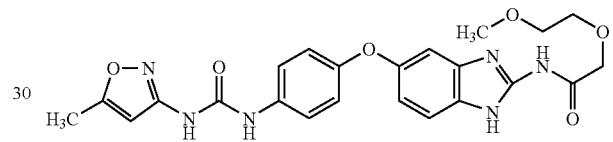

$^1$H NMR (DMF-d$_7$) δ 9.85 (s, 1H), 9.43 (s, 1H), 7.59 (d, J=8.9 Hz, 2H), 7.52 (br s, 1H), 7.17 (br s, 1H), 6.99 (d, J=9.1 Hz, 2H), 6.90 (dd, J=8.6, 2.3 Hz, 1H), 6.61 (s, 1H), 4.33 (s, 2H), 3.81 (m, 2H), 3.61 (m, 2H), 3.41 (s, 3H), 2.40 (s, 3H); MS m/e 481 (M+1).

Example 151

N-(5-(4-((Thiazol-2-yl)aminocarbonylamino)phenoxy)-1H-benzimidazol-2-yl)(2-(methoxy)ethoxy)acetamide

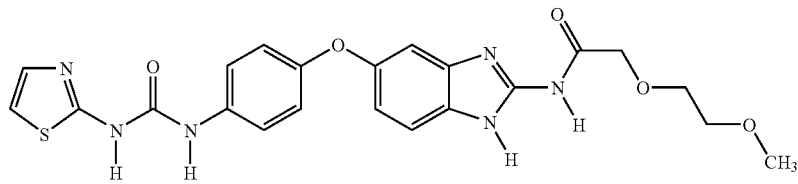

$^1$H NMR (DMF-d$_7$) δ 12.10 (br s, 1H), 11.04 (br s, 1H), 9.54 (s, 1H), 7.61 (d, J=9.0 Hz, 2H), 7.53 (br s, 1H), 7.39 (d, J=3.5 Hz, 1H), 7.19 (br s, 1H), 7.13 (d, J=3.5 Hz), 7.02 (d, J=9.0 Hz, 2H), 6.91 (dd, J=8.6, 2.5 Hz, 1H), 4.32 (s, 2H), 3.81 (m, 2H), 3.61 (m, 2H), 3.41 (s, 3H); MS m/e 483 (M+1).

Example 152

N-(5-(4-((1,3,4-Thiadiazol-2-yl)aminocarbonylamino)phenoxy)-1H-benzimidazol-2-yl)(2-(methoxy)ethoxy)acetamide

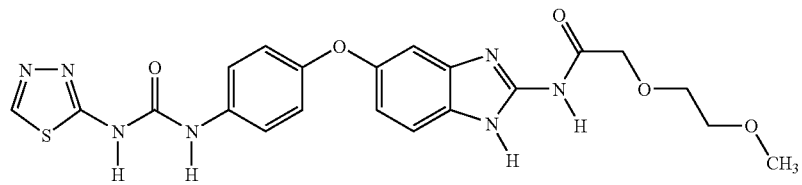

$^1$H NMR (DMF-d$_7$) δ 12.23 (br s, 1H), 11.19 (br s, 1H), 9.45 (br s, 1H), 9.12 (s, 1H), 7.62 (d, J=9.1 Hz, 2H), 7.54 (br d, J=8.4 Hz, 1H), 7.19 (br s, 1H), 7.03 (d, J=9.1 Hz, 2H), 6.91 (dd, J=8.6, 2.3 Hz, 1H), 4.32 (s, 2H), 3.82 (m, 2H), 3.61 (m, 2H), 3.41 (s, 3H); MS m/e 484 (M+1).

Example 153

N-(5-(4-((4-Methylthiazol-2-yl)aminocarbonylamino)phenoxy)-1H-benzimidazol-2-yl)(2-(methoxy)ethoxy)acetamide

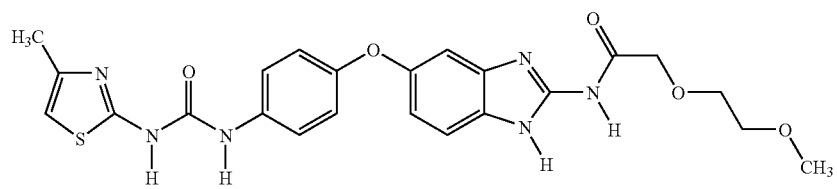

$^1$H NMR (DMF-d$_7$) δ 12.20 (br s, 1H), 10.95 (br s, 1H), 9.38 (s, 1H), 7.60 (d, J=9.0 Hz, 2H), 7.53 (br d, J=8.2 Hz 1H), 7.18 (br s, 1H), 7.01 (d, J=9.0 Hz, 2H), 6.91 (dd, J=8.6, 2.3 Hz, 1H), 6.67 (s, 1H), 4.32 (s, 2H), 3.81 (m, 2H), 3.61 (m, 2H), 3.41 (s, 3H), 2.24 (s, 3H); MS m/e 497 (M+1).

Example 154

N-(5-(4-((5-Methylthiazol-2-yl)aminocarbonylamino)phenoxy)-1H-benzimidazol-2-yl)(2-(methoxy)ethoxy)acetamide

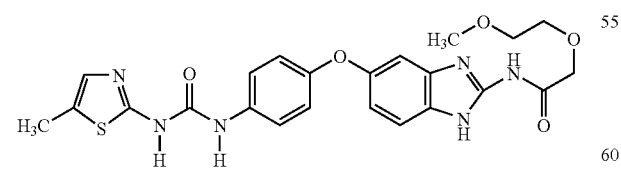

$^1$H NMR (DMF-d$_7$) δ 9.35 (s, 1H), 7.59 (d, J=9.1, 2H), 7.53 (br d, J=8.4, 1H), 7.18 (br s, 1H), 7.04 (app d 1H), 7.01 (d, J=9.1, 2H), 6.90 (dd, J=8.4, 2.3, 1H), 4.32 (s, 2H), 3.81 (m, 2H), 3.61 (m, 2H), 3.41 (s, 3H), 2.35 (app d, 3H); MS m/e 497 (M+1).

Example 155

N-(5-(4-((5-Methyl-1,3,4-thiadiazol-2-yl)aminocarbonylamino)phenoxy)-1H-benzimidazol-2-yl)(2-(methoxy)ethoxy)acetamide

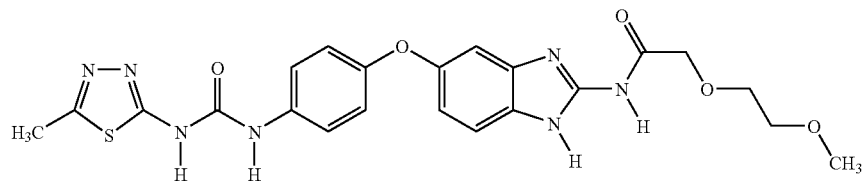

$^1$H NMR (DMF-$d_7$) δ 12.23 (br s, 1H), 11.07 (br s, 1H), 9.32 (s, 1H), 7.61 (d, J=9.0 Hz, 2H), 7.55 (d, J=8.5 Hz, 1H), 7.20 (br s, 1H), 7.02 (d, J=9.0 Hz, 2H), 6.92 (dd, J=8.5, 2.5 Hz, 1H), 4.32 (s, 2H), 3.82 (m, 2H), 3.65 (m, 2H), 3.41 (s, 3H), 2.63 (s, 3H); MS m/e 498 (M+1).

Example 156

N-(5-(4-((5-Ethyl-1,3,4-thiadiazol-2-yl)aminocarbonylamino)phenoxy)-1H-benzimidazol-2-yl)(2-(methoxy)ethoxy)acetamide

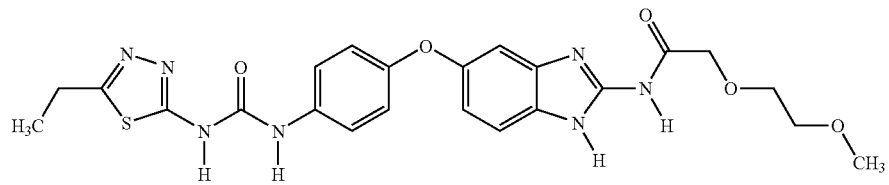

$^1$H NMR (DMF-$d_7$) δ 12.14 (br s, 1H), 11.16 (br s, 1H), 9.38 (s, 1H), 7.62 (d, J=9.0 Hz, 2H), 7.51 (d, J=8.6 Hz, 1H), 7.19 (br s, 1H), 7.02 (d, J=9.0 Hz, 2H), 6.91 (dd, J=8.6, 2.3 Hz, 1H), 4.32 (s, 2H), 3.82 (m, 2H), 3.61 (m, 2H), 3.41 (s, 3H), 3.00 (q, J=7.6 Hz, 2H), 1.34 (t, J=7.6 Hz, 3H); MS m/e 512 (M+1).

Example 157

N-(5-(4-((5-Cyclopropyl-1,3,4-thiadiazol-2-yl)aminocarbonylamino)phenoxy)-1H-benzimidazol-2-yl)(2-(methoxy)ethoxy)acetamide

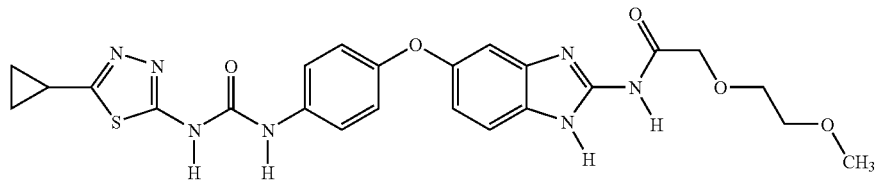

$^1$H NMR (DMF-$d_7$) δ 12.13 (br s, 1H), 11.24 (br s, 1H), 9.44 (s, 1H), 7.63 (d, J=8.8 Hz, 2H), 7.54 (d, J=8.6, 1H), 7.19 (br s, 1H), 7.02 (d, J=8.8 Hz, 2H), 6.91 (dd, J=8.6, 2.5 Hz, 1H), 4.32 (s, 2H), 3.81 (m, 2H), 3.61 (m, 2H), 3.41 (s, 3H), 2.38 (m, 1H), 1.15 (m, 2H), 1.00 (m, 2H); MS m/e 524 (M+1).

Example 158

N-(5-(4-((4-tert-Butylthiazol-2-yl)aminocarbonylamino)phenoxy)-1H-benzimidazol-2-yl)(2-(methoxy)ethoxy)acetamide

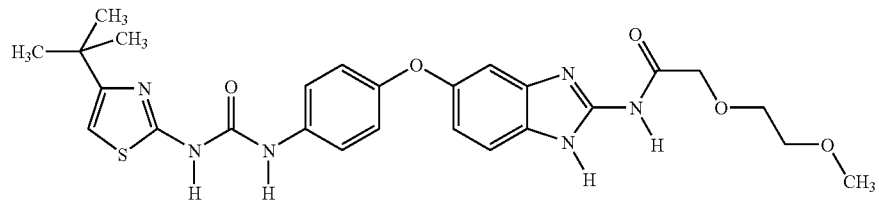

$^1$H NMR (DMF-$d_7$) δ 9.54 (s, 1H), 7.61 (d, J=8.8 Hz, 2H), 7.55 (br d, J=8.4 Hz, 1H), 7.20 (br s, 1H), 7.02 (d, J=8.8 Hz, 2H), 6.92 (dd, J=8.4, 2.5 Hz, 1H), 6.69 (s, 1H), 4.33 (s, 2H), 3.82 (m, 2H), 3.61 (m, 2H), 3.41 (s, 3H), 1.28 (s, 9H); MS m/e 539 (M+1).

Example 159

N-(5-(4-((5-tert-Butyl-1,3,4-thiadiazol-2-yl)aminocarbonylamino)phenoxy)-1H-benzimidazol-2-yl)(2-(methoxy)ethoxy)acetamide

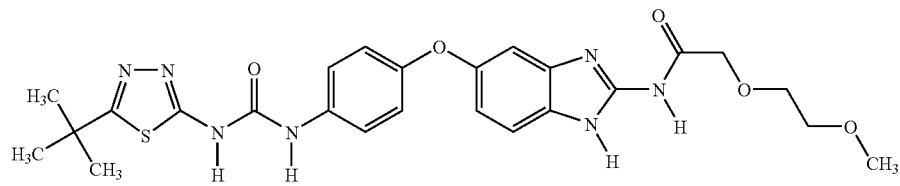

$^1$H NMR (DMF-$d_7$) δ 12.20 (br s, 1H), 11.24 (br s, 1H), 9.59 (br s, 1H), 7.65 (d, J=8.9 Hz, 2H), 7.54 (br d, J=8.4 Hz, 1H), 7.19 (br s, 1H), 7.02 (d, J=8.9 Hz, 2H), 6.91 (dd, J=8.4, 2.3 Hz, 1H), 4.32 (s, 2H), 3.81 (m, 2H), 3.61 (m, 2H), 3.41 (s, 3H), 1.43 (s, 9H); MS m/e 540 (M+1).

Example 160

N-(5-(4-((5-Ethylthio-1,3,4-thiadiazol-2-yl)aminocarbonylamino)phenoxy)-1H-benzimidazol-2-yl)(2-(methoxy)ethoxy)acetamide

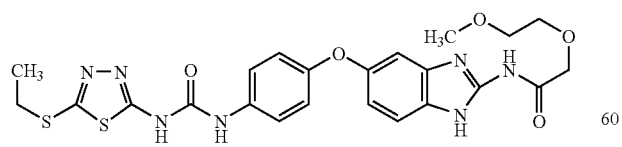

$^1$H NMR (DMF-$d_7$) δ 9.76 (s, 1H), 7.64 (d, J=8.8 Hz, 2H), 7.54 (d, J=8.6, 1H), 7.19 (br s, 1H), 7.02 (d, J=8.8 Hz, 2H), 6.91 (dd, J=8.6, 2.3 Hz, 1H), 4.32 (s, 2H), 3.81 (m, 2H), 3.61 (m, 2H), 3.41 (s, 3H), 3.25 (q, J=7.2 Hz, 2H) 1.39 (t, J=7.3 Hz, 3H); MS m/e 544 (M+1).

Example 161

N-(5-(4-((5-Propylthio-1,3,4-thiadiazol-2-yl)aminocarbonylamino)phenoxy)-1H-benzimidazol-2-yl)(2-(methoxy)ethoxy)acetamide

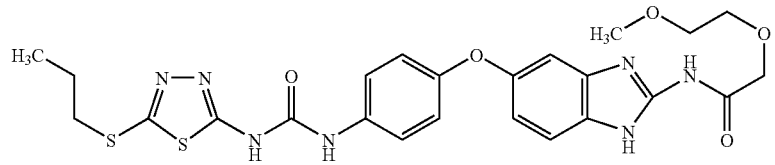

$^1$H NMR (DMF-$d_7$) δ 12.19 (br s, 1H), 7.77 (m, 2H), 7.52 (br s, 1H), 7.19 (br s, 1H), 7.01 (d, J=8.8 Hz, 2H), 6.91 (dd, J=8.6, 2.3 Hz, 1H), 4.31 (s, 2H), 3.81 (m, 2H), 3.61 (m, 2H), 3.41 (s, 3H), 3.20 (t, J=7.1 Hz, 2H), 1.77 (m, 2H), 1.02 (t, J=7.3 Hz, 3H); MS m/e 588 (M+1).

Example 162

N-(5-(4-((4,5-Dimetylthiazol-2-yl)aminocarbonylamino)phenoxy)-1H-benzimidazol-2-yl)(2-(methoxy)ethoxy)acetamide

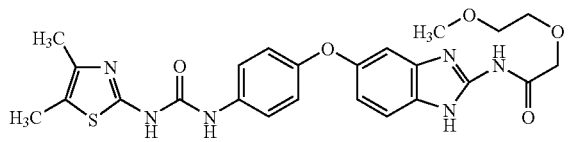

$^1$H NMR (DMF-$d_7$) δ 9.57 (s, 1H), 7.60 (d, J=9.1 Hz, 2H), 7.53 (br d, J=8.3, 1H), 7.18 (br s, 1H), 7.00 (d, J=9.1 Hz, 2H), 6.90 (dd, J=8.3, 2.3 Hz, 1H), 4.32 (s, 2H), 3.81 (m, 2H), 3.61 (m, 2H), 3.41 (s, 3H), 2.24 (s, 3H), 2.14 (s, 3H); MS m/e 511 (M+1).

Example 163

N-(5-(4-((5-Morpholino-1,3,4-triazol-2-yl)aminocarbonylamino)phenoxy)-1H-benzimidazol-2-yl)(2-(methoxy)ethoxy)acetamide

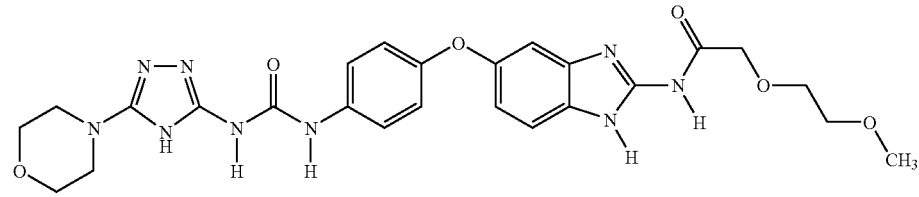

$^1$H NMR (DMF-$d_7$) δ 11.22 (br s, 1H), 9.68 (s, 1H), 7.75 (d, J=9.0 Hz, 2H), 7.55 (d, J=8.7 Hz, 1H), 7.38 (br s, 1H), 7.22 (br s, 1H), 7.03 (d, J=9.0 Hz, 2H), 6.93 (dd, J=8.7, 2.5 Hz, 1H), 4.33 (s, 2H), 3.82 (m, 2H), 3.70 (m, 4H), 3.61 (m, 2H), 3.41 (s, 3H), 3.34 (m, 4H); MS m/e 552 (M+1).

Example 164

N-(5-(4-((5-Methylisoxazol-3-yl)aminocarbonylamino)phenoxy)-1H-benzimidazol-2-yl)(2-furyl)formamide

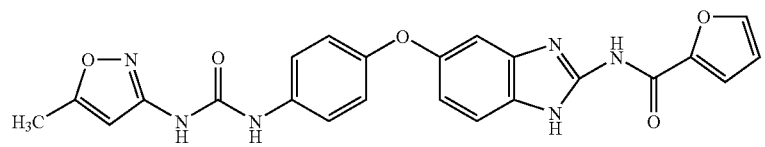

¹H NMR (DMF-d₇) δ 9.80 (s, 1H), 9.38 (s, 1H), 8.00 (s, 1H), 7.59 (m, 3H), 7.54 (d, J=8.6 Hz, 1H), 7.19 (d, J=2.3 Hz, 1H), 7.02 (d, J=8.8 Hz, 2H), 6.92 (dd, J=8.6, 2.3 Hz, 1H), 6.75 (m, 1H), 6.62 (s, 1H), 2.41 (s, 3H); MS m/e 459 (M+1).

Example 165

N-(5-(4-((Thiazol-2-yl)aminocarbonylamino)phenoxy)-1H-benzimidazol-2-yl)(2-furyl)formamide

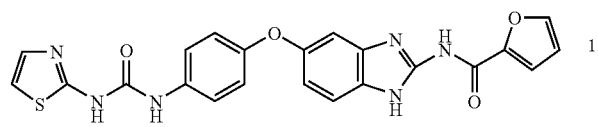

¹H NMR (DMF-d₇) δ 9.56 (br s, 1H), 8.00 (s, 1H), 7.62 (d, J=8.8 Hz, 2H), 7.58 (m, 1H), 7.54 (d, J=8.5 Hz, 1H), 7.39 (d, J=3.5 Hz, 1H), 7.20 (d, J=2.2 Hz, 1H), 7.13 (d, J=35 Hz, 1H), 7.04 (d, J=8.8 Hz, 2H), 6.93 (dd, J=8.5, 2.2 Hz, 1H), 6.75 (m, 1H); MS m/e 461 (M+1).

Example 166

N-(5-(4-((1,3,4-Thiadiazol-2-yl)aminocarbonylamino)phenoxy)-1H-benzimidazol-2-yl)(2-furyl)formamide

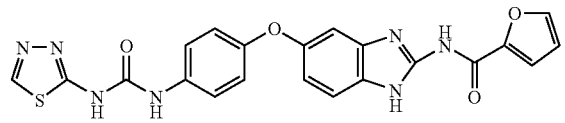

¹H NMR (DMF-d₇) δ 11.95 (br s, 1H), 9.56 (br s, 1H), 9.12 (s, 1H), 8.00 (s, 1H), 7.65 (d, J=8.9 Hz, 2H), 7.59 (m, 1H), 7.55 (d, J=8.6 Hz, 1H), 7.21 (d, J=2.4 Hz, 1H), 7.05 (d, J=8.9 Hz, 2H), 6.93 (dd, J=8.6, 2.4 Hz, 1H), 6.75 (m, 1H); MS m/e 462 (M+1).

Example 167

N-(5-(4-((4-Methylthiazol-2-yl)aminocarbonylamino)phenoxy)-1H-benzimidazol-2-yl)(2-furyl)formamide

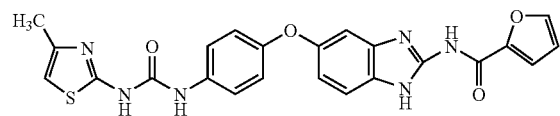

¹H NMR (DMF-d₇) δ 9.41 (s, 1H), 8.00 (s, 1H), 7.61 (d, J=9.0 Hz, 2H), 7.58 (m, 1H), 7.54 (d, J=8.7 Hz, 1H), 7.20 (d, J=2.4 Hz, 1H), 7.03 (d, J=9.0 Hz, 2H), 6.92 (dd, J=8.7, 2.4 Hz, 1H), 6.75 (m, 1H), 6.67 (s, 1H), 2.24 (s, 3H); MS m/e 475 (M+1).

Example 168

N-(5-(4-((5-Methylthiazol-2-yl)aminocarbonylamino)phenoxy)-1H-benzimidazol-2-yl)(2-furyl)formamide

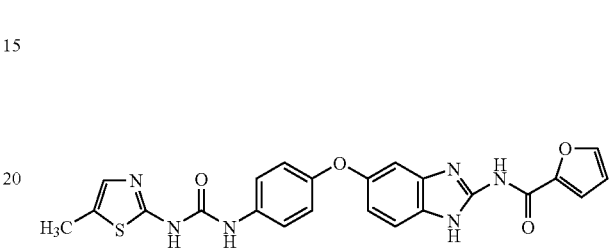

¹H NMR (DMF-d₇) δ 9.48 (s, 1H), 8.00 (s, 1H), 7.61 (d, J=9.0 Hz, 2H), 7.58 (d, J=3.8 Hz, 1H), 7.54 (d, J=8.6 Hz, 1H), 7.19 (d, J=2.3 Hz, 1H), 7.03 (m, 3H), 6.93 (dd, J=8.6, 2.3 Hz, 1H), 6.75 (m, 1H), 2.35 (s, 3H); MS m/e 475 (M+1).

Example 169

N-(5-(4-((5-Methyl-1,3,4-thiadiazol-2-yl)aminocarbonylamino)phenoxy)-1H-benzimidazol-2-yl)(2-furyl)formamide

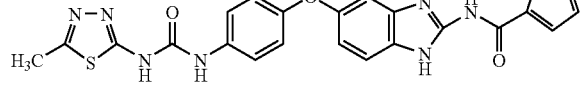

¹H NMR (DMF-d₇) δ 11.99 (br s, 1H), 9.45 (br s, 1H), 8.00 (s, 1H), 7.63 (d, J=8.8 Hz, 2H), 7.59 (br d, J=3.3 Hz, 1H), 7.54 (d, J=8.6 Hz, 1H), 7.20 (d, J=2.3 Hz, 1H), 7.04 (d, J=8.8 Hz, 2H), 6.93 (dd, J=8.6, 2.3 Hz, 1H), 6.75 (m, 1H), 2.62 (s, 3H); MS m/e 476 (M+1).

Example 170

N-(5-(4-((5-Ethyl-1,3,4-thiadiazol-2-yl)aminocarbonylamino)phenoxy)-1H-benzimidazol-2-yl)(2-furyl)formamide

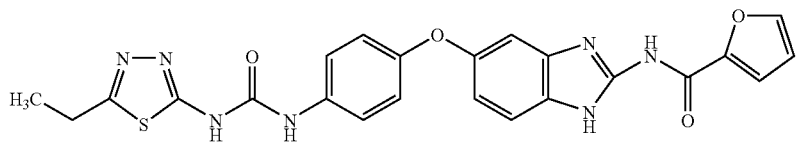

$^1$H NMR (DMF-d$_7$) δ 11.93 (br s, 1H), 9.37 (br s, 1H), 8.00 (s, 1H), 7.63 (d, J=9.1 Hz, 2H), 7.59 (br d, J=3.3 Hz, 1H), 7.54 (d, J=8.6 Hz, 1H), 7.20 (d, J=2.3 Hz, 1H), 7.04 (d, J=9.1 Hz, 2H), 6.93 (dd, J=8.6, 2.3 Hz, 1H), 6.75 (m, 1H), 3.00 (q, J=7.5 Hz, 2H), 1.33 (t, J=7.5 Hz, 3H); MS m/e 490 (M+1).

Example 171

N-(5-(4-((5-Cyclopropyl-1,3,4-thiadiazol-2-yl)aminocarbonylamino)phenoxy)-1H-benzimidazol-2-yl)(2-furyl)formamide

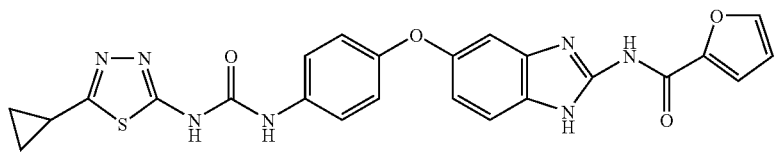

$^1$H NMR (DMF-d$_7$) δ 11.92 (br s, 1H), 9.42 (br s, 1H), 8.00 (s, 1H), 7.62 (d, J=9.1 Hz, 2H), 7.59 (br d, J=3.3 Hz, 1H), 7.54 (d, J=8.6 Hz, 1H), 7.20 (d, J=2.3 Hz, 1H), 7.04 (d, J=9.1 Hz, 2H), 6.93 (dd, J=8.6, 2.3 Hz, 1H), 6.75 (m, 1H), 2.38 (m, 1H), 1.15 (m, 2H), 0.99 (m, 2H); MS m/e 502 (M+1).

Example 172

N-(5-(4-((4-tert-Butylthiazol-2-yl)aminocarbonylamino)phenoxy)-1H-benzimidazol-2-yl)(2-furyl)formamide

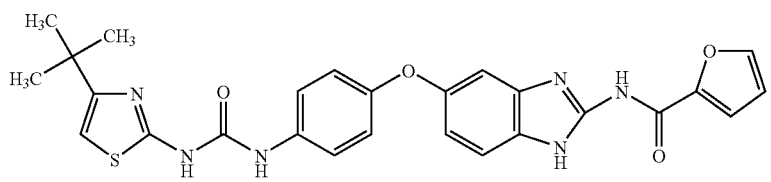

$^1$H NMR (DMF-d$_7$) δ 10.60 (br s, 1H), 9.41 (br s, 1H), 8.00 (s, 1H), 7.61 (d, J=8.8 Hz, 2H), 7.58 (br d, J=3.5 Hz, 1H), 7.55 (d, J=8.6 Hz, 1H), 7.20 (d, J=2.3 Hz, 1H), 7.04 (d, J=8.8 Hz, 2H), 6.93 (dd, J=8.6, 2.3 Hz, 1H), 6.75 (m, 1H), 6.69 (s, 1H), 1.27 (s, 9H); MS m/e 517 (M+1).

Example 173

N-(5-(4-((5-tert-Butyl-1,3,4-thiadiazol-2-yl)aminocarbonylamino)phenoxy)-1H-benzimidazol-2-yl)(2-furyl)formamide

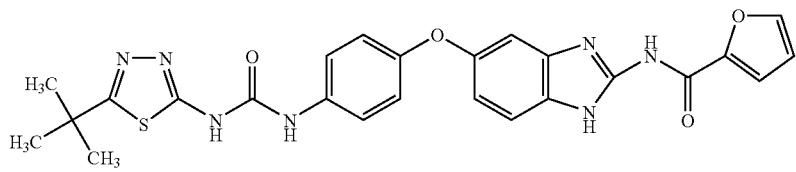

$^1$H NMR (DMF-d$_7$) δ 11.96 (br s, 1H), 9.39 (br s, 1H), 8.00 (s, 1H), 7.64 (d, J=9.1 Hz, 2H), 7.59 (m, 1H), 7.54 (d, J=8.5 Hz, 1H), 7.20 (d, J=2.3 Hz, 1H), 7.04 (d, J=9.1 Hz, 2H), 6.93 (dd, J=8.5, 2.3 Hz, 1H), 6.75 (m, 1H), 1.43 (s, 9H); MS m/e 518 (M+1).

Example 174

N-(5-(4-((5-Ethylthio-1,3,4-thiadiazol-2-yl)aminocarbonylamino)phenoxy)-1H-benzimidazol-2-yl)(2-furyl)formamide

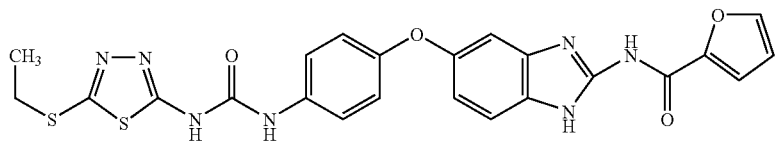

$^1$H NMR (DMF-d$_7$) δ 12.20 (br s, 1H), 8.00 (s, 1H), 7.75 (m, 2H), 7.58 (br s, 1H), 7.54 (d, J=8.6 Hz, 1H), 7.20 (d, J=2.3 Hz, 1H), 7.04 (d, J=8.8 Hz, 2H), 6.93 (dd, J=8.6, 2.3 Hz, 1H), 6.75 (m, 1H), 3.25 (q, J=7.2 Hz, 2H), 1.40 (t, J=7.2 Hz, 3H); MS m/e 522 (M+1).

Example 175

N-(5-(4-((4,5-Dimethylthiazol-2-yl)aminocarbonylamino)phenoxy)-1H-benzimidazol-2-yl)(2-furyl)formamide

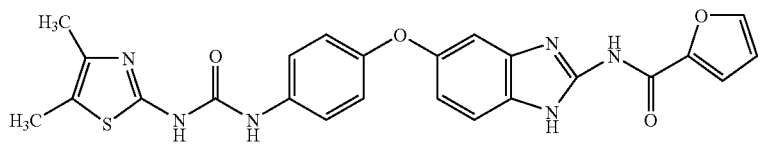

$^1$H NMR (DMF-d$_7$) δ 9.37 (br s, 1H), 8.00 (s, 1H), 7.60 (d, J=8.8 Hz, 2H), 7.58 (m, 1H), 7.54 (d, J=8.6 Hz, 1H), 7.19 (d, J=2.4 Hz, 1H), 7.03 (d, J=8.8 Hz, 2H), 6.93 (dd, J=8.6, 2.4 Hz, 1H), 6.75 (m, 1H), 2.24 (s, 3H), 2.14 (s, 3H); MS m/e 489 (M+1).-

Example 176

N-(5-(4-((5-Morpholino-1,3,4-triazol-2-yl)aminocarbonylamino)phenoxy)-1H-benzimidazol-2-yl)(2-furyl)formamide

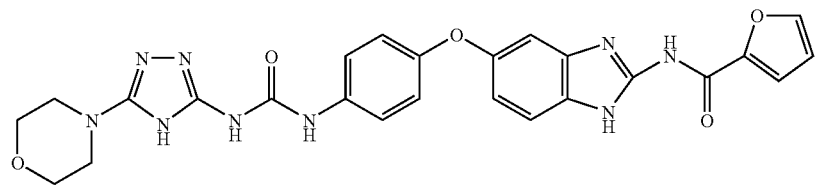

¹H NMR (DMF-d₇) δ 9.69 (s, 1H), 8.00 (s, 1H), 7.76 (d, J=8.9 Hz, 2H), 7.60 (br d, J=3.3 Hz, 1H), 7.56 (d, J=8.6 Hz, 1H), 7.38 (br s, 1H), 7.23 (d, J=2.4 Hz, 1H), 7.05 (d, J=8.9 Hz, 2H), 6.94 (dd, J=8.6, 2.4 Hz, 1H), 6.75 (m, 1H), 3.70 (m, 4H), 3.33 (m, 4H); MS m/e 530 (M+1).

Example 177

N-(5-(4-((5-Methylthio-1,3,4-thiadiazol-2-yl)aminocarbonylamino)phenoxy)-1H-benzimidazol-2-yl)acetamide

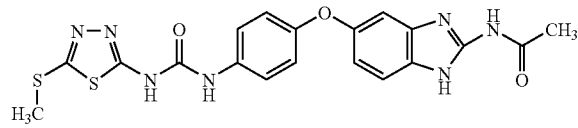

¹H NMR (DMF-d₇) δ 12.11 (br s, 1H), 11.57 (br s, 1H), 10.58 (br s, 1H), 7.74 (m, 2H), 7.52 (br s, 1H), 7.30–7.07 (m, 1H), 7.00 (d, J=9.1 Hz, 2H), 6.88 (dd, J=8.6, 2.5 Hz, 1H), 2.95–2.72 (m, 3H), 2.24 (s, 3H); MS m/e 456 (M+1).

Example 178

N-(5-(4-((5-Methylthio-1,3,4-thiadiazol-2-yl)aminocarbonylamino)phenoxy)-1H-benzimidazol-2-yl)(2-(methoxy)ethoxy)acetamide

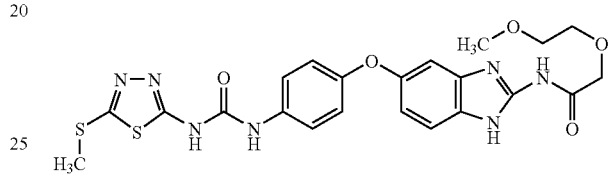

¹H NMR (DMF-d₇) δ 12.20 (br s, 1H), 7.77 (m, 2H), 7.52 (br s, 1H), 7.18 (br s, 1H), 7.06 (d, J=9.1 Hz, 2H), 6.91 (dd, J=8.6, 2.5 Hz, 1H), 4.31 (s, 2H), 3.81 (m, 2H), 3.61 (m, 2H), 3.41 (s, 3H), 2.95–2.72 (m, 3H); MS m/e 530 (M+1).

Example 179

N-(5-(4-((5-Methylthio-1,3,4-thiadiazol-2-yl)aminocarbonylamino)phenoxy)-1H-benzimidazol-2-yl)(2-furyl)formamide

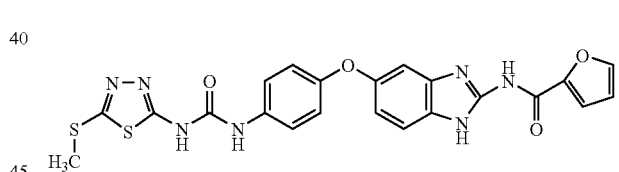

¹H NMR (DMF-d₇) δ 12.12 (br s, 1H), 9.91 (br s, 1H), 8.00 (s, 1H), 7.69 (m, 2H), 7.58 (m, 1H), 7.54 (d, J=8.6 Hz, 1H), 7.20 (d, J=2.3 Hz, 1H), 7.04 (d, J=9.1 Hz, 2H), 6.93 (dd, J=8.6, 2.3 Hz, 1H), 6.75 (m, 1H), 2.95–2.72 (m, 3H); MS m/e 508 (M+1).

Example 180

N-(5-(4-((5-Carbamoyl-2-methylphenyl)aminocarbonylamino)phenoxy)-1H-benzimidazol-2-yl)(2-furyl)formamide

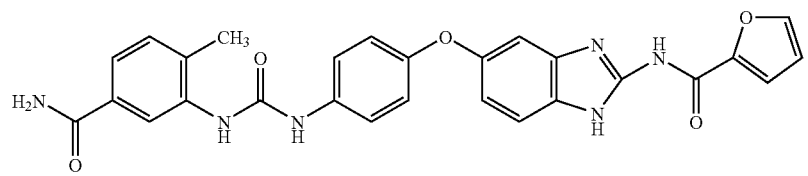

This compound was prepared according to procedure for Example 138i by way of Intermediate 14F, although left-hand ring is not heteroarylic.

$^1$H NMR (DMF-d$_7$) δ 12.26 (br s, 1H), 9.23 (s, 1H), 8.57 (d, J=1.8 Hz, 1H), 8.00 (s, 1H), 7.61–7.58 (m, 4H), 7.53 (d, J=8.6 Hz, 1H), 7.27 (d, J=7.8 Hz, 1H), 7.23 (br s, 1H), 7.19 (d, J=2.3 Hz, 1H), 7.02 (d, J=8.8 Hz, 2H), 6.92 (dd, J=8.6, 2.3 Hz, 1H), 6.74 (m, 1H), 2.34 (s, 3H); MS m/e 511 (M+1).

Examples 181–182 were prepared according to the procedures described for Example 1 using intermediate 3A.

Example 181

Methyl N-(5-(3-((2,3-dichlorophenyl)aminocarbonylamino)phenoxy)-1H-benzimidazol-2-yl)carbamate

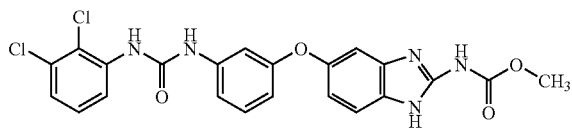

$^1$H NMR (DMSO-d$_6$) δ 12.0–11.2 (br s, 2H), 9.53 (s, 1H), 8.40 (s, 1H), 8.10 (dd, 1H), 7.41 (d, 1H), 7.30–7.24 (m, 3H), 7.13–7.07 (m, 3H), 6.83 (dd, 1H), 6.62 (dd, 1H), 3.75 (s, 3H); MS m/e 486 (M+1), 488 (M+3).

Example 182

Methyl N-(5-(3-((2,3-dimethylphenyl)aminocarbonylamino)phenoxy)-1H-benzimidazol-2-yl)carbamate

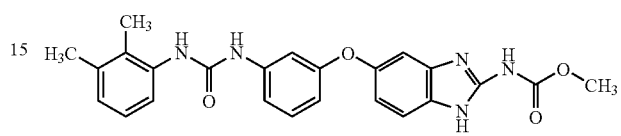

$^1$H NMR (DMSO-d$_6$) δ 12.0–11.2 (brs, 2H), 8.98 (s, 1H), 7.86 (s, 1H), 7.48 (d, 1H), 7.40 (d, 1H), 7.22 (t, 1H), 7.10 (d, 1H), 7.07 (m, 2H), 7.00 (t, 1H), 6.88 (d, 1H), 6.82 (dd, 1H), 3.75 (s, 3H), 2.23 (s, 3H), 2.09 (s, 3H); MS m/e 446 (M+1)

Example 183

1-(5-(4-((2-Fluoro-5-(trifluoromethylphenyl)aminocarbonylamino)phenoxy)-1H-benzimidazol-2-yl)-3-(2,3-dimethylphenyl)urea

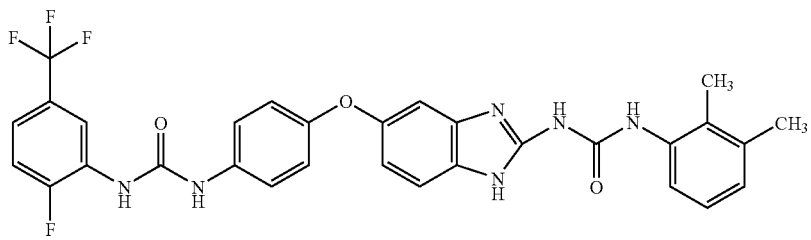

The compound of Example 22 was treated with 2,3-dimethylphenylisocyanate in THF to give the title compound.

$^1$H NMR (DMSO-d$_6$) δ; 11.5 (brs, 1H), 10.4 (brs, 1H), 9.6 (brs, 1H), 9.13 (s, 1H), 8.85 (s, 1H), 8.62 (d, 1H), 7.68 (d, 1H), 7.50 (t, 1H), 7.44 (d, 2H), 7.38 (m, 2H), 7.08 (t, 1H), 7.02 (brs, 1H), 6.94 (d, 2H), 6.94 (d, 1H), 6.79 (dd, 1H), 2.28 (s, 3H), 2.22 (s, 3H), MS m/e 593 (M+1)

The following compounds (Example 184–186) are synthesized according to the similar procedure for Example 1 using corresponding isothiocyanate in lieu of isocyanate.

Example 184

Methyl N-(5-(4-((3-chlorophenyl)aminothiocarbonylamino)phenoxy)-1H-benzimidazol-2-yl)carbamate

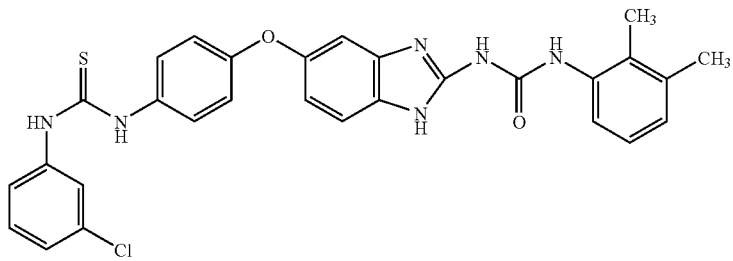

$^1$H NMR (DMSO-d$_6$) δ; 12.0–11.2 (brs, 2H), 9.89 (s, 1H), 9.85 (s, 1H), 7.70 (t, 1H), 7.42–7.32 (m, 5H), 7.16 (d, 1H), 7.06 (d, 1H), 6.92 (d, 2H), 6.81 (dd, 1H), 3.75 (s, 3H); MS m/e 468 (M+1), 470 (M+3).

Example 185

Methyl N-(5-(4-((3-methoxyphenyl)aminothiocarbonylamino)phenoxy)-1H-benzimidazol-2-yl)carbamate

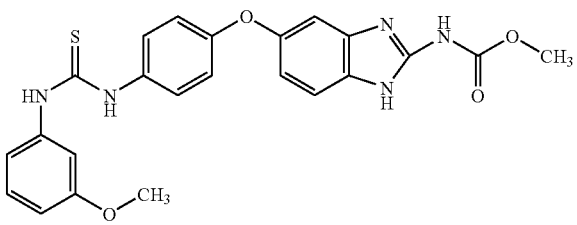

$^1$H NMR (DMSO-d$_6$) δ; 12.0–11.2 (brs, 2H), 9.73 (s, 1H), 9.71 (s, 1H), 7.40 (m, 1H), 7.39 (d, 2), 7.22 (t, 1H), 7.18 (s, 1H), 7.05 (s, 1H), 7.01 (d, 1H), 6.91 (d, 2), 6.80 (dd, 1H), 6.70 (dd, 1H), 3.75 (s, 3H), 3.74 (s, 3H); MS m/e 464 (M+1).

Example 186

Methyl N-(5-(4-((3-(trifluoromethyl)phenyl)aminothiocarbonylamino)phenoxy)-1H-benzimidazol-2-yl)carbamate

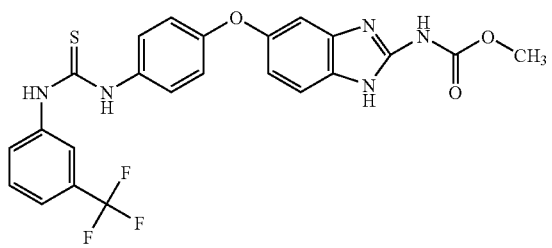

$^1$H NMR (DMSO-d$_6$) δ; 12.0–11.2 (brs, 2H), 9.95 (s, 1H), 9.92 (s, 1H), 7.95 (s, 1H), 7.75 (d, 1H), 7.55 (t, 1H), 7.44 (d, 1H), 7.39 (m, 1H), 7.38 (d, 2H), 7.06 (s, 1H), 6.93 (d, 2H), 6.81 (dd, 1H), 3.75 (s, 3H); MS m/e 502 (M+1).

Biological Data

TIE-2 Enzyme Assay (TIE2-E)

The TIE-2 enzyme assay used the LANCE method (Wallac) and GST-TIE2, baculovirus expressed recombinant constructs of the intracellular domains of human TIE2 (amino acids 762–1104, GenBank Accession # L06139) tagged by GST). The method measured the ability of the purified enzymes to catalyse the transfer of the γ-phosphate from ATP onto tyrosine residues in a biotinylated synthetic peptide, D1-15 (biotin-C6-LEARLVAYEGWVAGKKKamide). This peptide phosphorylation was detected using the following procedure: for enzyme preactivation, GST-TIE2 was incubated for 30 mins at room temperature with 2 mM ATP, 5 mM MgCl$_2$ and 12.5 mM DTT in 22.5 mM HEPES buffer (pH7.4). Preactivated GST-TIE2 was incubated for 30 mins at room temperature in 96 well plates with 1 µM D1-15 peptide, 80 uM ATP, 10 mM MgCl$_2$, 0.1 mg/ml BSA and the test compound (diluted from a 10 mM stock in DMSO, final DMSO concentration was 2.4%) in 1 mM HEPES (pH7.4). The reaction was stopped by the addition of EDTA (final concentration 45 mM). Streptavidin linked-APC (allophycocyanin, Molecular Probe) and Europium-labeled anti-phosphorylated tyrosine antibody (Wallac) were then added at the final concentration of 17 µg/well and 2.1 µg/well, respectively. The APC signal was measured using an ARVO multilabel counter. (Wallac Berthold Japan). The percent inhibition of activity was calculated relative to blank control wells. The concentration of test compound that inhibits 50% of activity (IC$_{50}$) was interpolated using nonlinear regression (Levernberg-Marquardt) and the equation, y=Vmax (1−x/(K+x))+Y2, where "K" was equal to the IC$_{50}$. The IC$_{50}$ values were converted to pIC$_{50}$ values, i.e., −log IC$_{50}$ in Molar concentration. The results are represented in Table 1 below.

TIE-2 Autophosphorylation Assay (TIE2-C)

The TIE-2 autophosphorylation assay used an ELISA method and a TIE2 intracellular domain/c-fms extracellular domain (TIE2/c-fms) chimeric protein expressing mouse 3T3 cells. This assay measured the autophosphorylation level of TIE2 protein expressed in cells. The cells were cultured in high glucose DMEM (Sigma) containing 10% serum at 37° C. in a humidified 10% CO$_2$, 90% air incubator.

The test compound (diluted from a 10 mM stock in DMSO, final DMSO concentration was 0.1%) was incubated with TIE2/c-fms expressing cells for 1 hr in serum free DMEM in 96 well plates followed by the activation of TIE2/c-fms receptor using c-fms ligand, MCSF (macrophage colony stimulating factor). The culture media was removed by aspiration and the cells incubated for at least 30 mins on ice with lysis buffer containing 137 mM NaCl, 2 mM EDTA, 10% glycerol, 0.09 ml sodium ortho vanadate and complete protease inhibitor cocktail (Roche) in 20 mM Tris-HCl (pH8.0). The cell extracts were transferred into Rat anti-c-fms antibody coated 96 well plates and incubated for 12 hrs at 4° C. The extracts were removed by aspiration and the plate was incubated with biotinylated anti-phosphotyrosine antibody, PT66 (Sigma) and then with HRP (Horseradish Peroxidase)-labeled streptavidin (PIERCE). The optical density at 450 nm derived from HRP catalyzed TMB was measured with an ARVO multilabel counter. (Wallac Berthold Japan). The percent inhibition of activity was calculated relative to blank control wells. The concentration of test compound that inhibits 50% of activity ($IC_{50}$) was interpolated using nonlinear regression (Levernberg-Marquardt) and the equation, y=Vmax (1−x/(K+x))+Y2, where "K" was equal to the $IC_{50}$. The $IC_{50}$ values were converted to $pIC_{50}$ values, i.e., −log $IC_{50}$ in Molar concentration. The results are represented in Table 1 below.

Tie2 Fluorescence Polarization Kinase Activity Assay: (TIE2-FP)

Activation of Recombinant Tie2 Activation:

Recombinant GST-Tie2 was activated by incubating the enzyme in 20 mM Tris-HCl, pH 7.5, 12 mM $MgCl_2$, 100 mM NaCl, 20 μM sodium vanidate, 1 mM DTT and 300 μM ATP at room temperature for 2 hours. The activation mixture was then passed through a NAP-25 desalting column (Pharmacia Biotech cat. no. 17-0852-02) to remove the free ATP. The activated enzyme was stored as aliquots at −80° C. in 20 mM Tris-HCl, pH 7.5 and 100 mM NaCl.

Assay Conditions:

The final assay conditions were 50 mM HEPES, pH 7.5, 5% DMSO (when screening compounds), 200 μM ATP, 5 mM $MgCl_2$, 1 mM DTT, 50 μM sodium vanidate, 1 nM activated enzyme, and 200 μM peptide. $IC_{50}$'s of compounds were measured under subsaturating ATP (200 μM) and varing concentrations of activated Tie2 and peptide substrate (RFWKYEFWR-OH; MW 1873 Da, TFA salt). Panvera Antiphosphotyrosine antibody (Cat#P2840) and PTK Green Tracer (Cat#P2842) were used to detect the phosphorylated peptide. Polarization was measured on a TECAN Polarion in 138-second cycles for 30 minutes at room temperature. $IC_{50}$'s were then determined from the % polarization using normal calculation methods. Results are indicated below.

VEGF-R2 Enzyme Assay (VEGF-E)

The VEGF enzyme assay used the LANCE method (Wallac) and GST-VEGFR2, baculovirus expressed recombinant constructs of the intracellular domains of human TIE2 tagged by GST. The method measured the ability of the purified enzymes to catalyse the transfer of the γ-phosphate from ATP onto tyrosine residues in a biotinylated synthetic peptide, (biotin-aminohexyl-EEEEYFELVAKKKK-$NH_2$). This peptide phosphorylation was detected using the following procedure: GST-VEGFR2 was incubated for 40–60 mins at room temperature with 75 μM ATP, 5 mM $MgCl_2$, 0.1 mM DTT, 0.1 mg/mL BSA and the test compound (diluted from a 10 mM stock in DMSO for desired concentration) in 100 mM HEPES buffer. The reaction was stopped by the addition of EDTA (final concentration 50 mM). Streptavidin linked-APC (allophycocyanin, Molecular Probe) and Europium-labeled anti-phosphorylated tyrosine antibody (Wallac) were then added at the final concentration of 15 nM and 1 nM, respectively. The APC signal was measured using an ARVO multilabel counter (Wallac Berthold, Japan). The percent inhibition of activity was calculated relative to blank control wells. The concentration of test compound that inhibits 50% of activity ($IC_{50}$) was interpolated using nonlinear regression (Levernberg-Marquardt) and the equation, y=Vmax (1−x/(K+x))+Y2, where "K" was equal to the $IC_{50}$. The $IC_{50}$ values were converted to $pIC_{50}$ values, i.e., −log $IC_{50}$ in Molar concentration. The results are represented in Table 1 below.

VFGF-driven Cellular Proliferation Assay: BrdU Incorporation Assay (VEGF-C)

Human umbilical cord endothelial cells (HUVEC, Clonetics, CC2519) were passaged in Type I collagen-coated 100-mm petridishes in EGM-MV medium (Clonetics, CC3125) at 37° C. in a humidified 5% $CO_2$, 95% air incubator. (HUVEC passaged more than 6 times in vitro were discarded and not subjected to assaying.) The cells were harvested using trypsin/EDTA, counted using a haemocytometer and plated at 5000 cells/well in a Type I-collagen coated 96-well plate (Becton Dickinson, 354407) in M199 medium (Gibco BRL, 12340-030) containing 5% FBS (Hyclone, A 1115-L) and gentamicin (at 50 μg/ml, Gibco BRL). After incubation overnight at 37° C., the media were replaced with 100 μl of M199 serum-free medium containing compounds at various concentrations with 0.6% DMSO and gentamicin. The compounds were diluted in serum-free M199 medium from 10 mM stock solutions prepared in 100% DMSO. After a 30 min incubation at 37° C., the cells were fed with 100 μl of serum-free M199 medium containing gentamicin, 0.2% culture-grade bovine serum albumin (BSA, Sigma A1993) and 20 ng/ml of VEGF (R&D systems, 293-VE) or 0.6 ng/ml of basic FGF (R&D systems, 233-FB), and cultured at 37° C. for another 24 h. The cells were pulsed with bromodeoxyuridine (BrdU at 10 μM in serum-free M199) at 37° C. for an additional 24 h. The incorporation of BrdU into the proliferating HUVEC were analyzed using BrdU Cell Proliferation ELISA (Roche Molecular Biochemicals, 1647229) according to the manufacturer's protocols. The optical density at 450 nm was measured with a multilabel counter (ARVO SX, Wallac). The percent inhibition of cell growth was calculated relative to blank control wells. The concentration of test compound that inhibits 50% of cell growth ($IC_{50}$) was interpolated using nonlinear regression (Levernberg-Marquardt) and the equation, y=Vmax (1−x/(K+x))+Y2, where "K" was equal to the $IC_{50}$. The $IC_{50}$, values were converted to $pIC_{50}$ values, i.e., −log $IC_{50}$ in Molar concentration. The results are represented in Table 1 below.

Test compounds are employed in free or salt form.

TABLE I

| Ex. No | TIE2-E | TIE2-C | VEGF-E | VEGF-C |
|---|---|---|---|---|
| 1 | +++ | ++ | +++ | − |
| 2 | +++ | +++ | +++ | + |
| 3 | ++ | | +++ | − |
| 4 | +++ | + | ++ | − |
| 5 | ++ | +++ | + | − |
| 6 | +++ | | + | − |
| 7 | +++ | | − | − |

TABLE I-continued

| Ex. No | TIE2-E | TIE2-C | VEGF-E | VEGF-C |
|---|---|---|---|---|
| 8 | +++ |  | +++ | − |
| 9 | +++ | +++ | +++ | − |
| 10 | +++ | +++ | +++ | +++ |
| 11 | +++ | ++ | +++ | − |
| 12 | ++ | +++ | + | − |
| 13 | +++ | ++ | ++ | − |
| 14 | ++ | ++ | +++ | ++ |
| 15 | +++ | +++ | +++ | ++ |
| 16 | +++ | +++ | +++ |  |
| 17 | +++ | +++ | +++ | +++ |
| 18 | +++ | +++ | +++ | +++ |
| 19 | +++ | +++ | +++ | − |
| 20 | +++ | ++ |  | +++ |
| 21 | +++ | +++ |  | − |
| 22 | +++ | + | +++ | + |
| 23 | +++ | +++ |  | ++ |
| 24 | +++ | ++ | +++ | − |
| 25 | +++ | +++ | +++ | +++ |
| 26 | +++ | ++ | +++ | ++ |
| 27 | +++ | +++ | +++ | ++ |
| 28 | +++ | +++ | +++ | ++ |
| 29 | +++ | +++ | +++ | ++ |
| 30 | +++ | +++ | +++ | ++ |
| 31 | +++ | +++ | +++ | +++ |
| 32 | +++ | ++ |  | + |
| 33 | +++ | +++ | +++ | +++ |
| 34 | +++ | +++ | +++ | − |
| 35 | +++ | ++ | +++ | + |
| 36 | +++ | +++ |  | − |
| 37 | +++ | +++ | +++ | − |
| 38 | +++ | +++ | +++ | − |
| 39 | ++ | ++ | ++ |  |
| 40 | +++ | +++ | +++ | − |
| 41 | +++ | +++ | +++ | − |
| 42 | +++ | +++ | +++ | ++ |
| 43 | +++ | +++ | +++ | + |
| 44 | +++ | ++ | +++ | − |
| 45 | +++ | +++ | +++ | − |
| 46 | +++ | +++ | +++ | − |
| 47 | +++ | +++ | +++ | − |
| 48 | +++ | +++ | +++ | − |
| 49 | ++ | ++ | +++ | − |
| 50 | +++ | +++ | +++ | ++ |
| 51 | +++ | +++ | +++ | − |
| 52 | +++ | ++ | +++ |  |
| 55 | +++ | +++ | +++ | − |
| 56 | ++ | +++ | +++ | − |
| 57 | +++ | ++ |  |  |
| 58 |  |  | +++ |  |
| 59 |  |  | +++ |  |
| 60 |  |  | +++ |  |
| 61 |  |  | +++ |  |
| 62 | + |  | +++ |  |
| 63 | − |  | +++ |  |
| 64 | +++ | +++ | +++ | +++ |
| 65 | +++ | +++ | +++ | − |
| 68 | +++ | +++ | +++ | +++ |
| 69 | +++ | +++ | +++ | ++ |
| 70 | +++ | ++ | +++ | + |
| 71 | +++ | ++ | +++ | + |
| 72 | +++ | +++ | +++ | + |
| 73 | ++ | ++ | +++ |  |
| 74 | +++ | +++ | +++ | − |
| 75 | ++ | +++ | +++ | − |
| 76 | +++ | +++ | +++ | − |
| 77 | +++ | +++ | +++ | ++ |
| 78 |  |  | +++ |  |
| 79 | ++ | ++ |  |  |
| 80 | +++ | +++ | +++ | +++ |
| 81 | +++ | +++ | +++ | − |
| 87 | +++ | +++ | +++ | ++ |
| 88 | +++ | +++ | +++ | +++ |
| 89 | +++ | +++ | +++ | ++ |
| 90 | +++ | + | +++ |  |
| 91 | +++ | +++ | +++ | − |
| 92 | +++ | +++ | +++ | +++ |
| 93 | +++ | +++ | +++ | + |
| 94 | +++ | +++ | +++ | + |
| 95 | +++ | ++ | +++ |  |
| 96 | +++ | +++ | +++ | ++ |
| 97 | +++ | +++ | +++ | +++ |
| 98 | +++ | +++ | +++ | ++ |
| 99 | +++ | ++ | +++ |  |
| 100 | +++ | +++ | +++ |  |
| 101 | +++ | +++ | +++ | +++ |
| 102 | +++ | +++ | +++ | +++ |
| 103 | +++ | +++ | +++ | + |
| 104 | ++ | ++ | +++ |  |
| 105 | ++ | + | +++ |  |
| 106 | ++ | ++ | +++ |  |
| 107 | +++ | ++ | ++ |  |
| 110 | +++ | ++ | ++ |  |
| 111 | +++ | +++ | +++ | − |
| 112 | ++ | ++ | ++ |  |
| 113 | +++ |  |  |  |
| 115 | +++ | +++ | +++ | +++ |
| 116 |  |  | +++ |  |
| 117 |  |  | +++ |  |
| 118 |  |  | ++ |  |
| 119 |  |  | +++ |  |
| 120 |  |  | +++ |  |
| 121 |  |  | ++ |  |
| 123 |  |  | ++ |  |
| 124 |  |  | +++ |  |
| 125 |  |  | +++ |  |
| 127 |  |  | +++ |  |
| 128 |  |  | +++ |  |
| 129 |  |  | +++ |  |
| 130 |  |  | +++ |  |
| 133 |  |  | +++ |  |
| 134 |  |  | +++ |  |
| 136 |  |  | +++ |  |
| 137 |  |  | +++ |  |
| 146* | ++ |  | +++ |  |
| 151* | + |  | ++ |  |
| 152* | + |  | + |  |
| 153* | + |  | ++ |  |
| 155* | + |  | ++ |  |
| 156* | ++ |  | +++ |  |
| 158* | ++ |  | +++ |  |
| 159* | +++ |  | +++ |  |
| 163 |  |  | + |  |
| 184 | + | + | +++ |  |
| 185 |  |  | ++ | + |
| 186 | + | ++ | +++ |  |

+ = $pIC_{50}$ of 5.0–6.0;
++ = $pIC_{50}$ of 6.0–7.0;
+++ = $pIC_{50}$ of > 7.0;
− = a negative or inconclusive result;
blank = not tested
*Tie-2 activities run utilizing Tie2-FP assay described above.

We claim:
1. A compound of Formula (I):

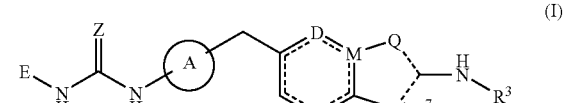

or a salt or solvate, thereof:
wherein:
E is
  unsubstituted heteroaryl, or
  heteroaryl substituted with $R^1$, or
  heteroaryl substituted by $R^1$ and $R^2$, or R¹ and R² together with the atoms of E to which they are attached form a cycloalkyl, aryl, or heterocyclic ring fused to E;

A is aryl, heteroaryl, or heterocyclic;

X is S, O, S(O)$_2$, S(O), C(H)$_2$, C(H)(OH), or C(O);

Z is O or S;

p is 0 or 1;

q is 0 or 1;

the dotted line bonds "---" attached to Q and N' represent a single bond or a double bond wherein when q is 0 the dotted line bond "---" attached to Q is a single bond and the dotted line bond attached to N' is a double bond, and when q is 1 the dotted line bond "---" attached to Q is a double bond and the dotted line bond attached to N' is a single bond; and the dotted line within the 6 membered ring containing D, M, and T represents appropriate aromatic bonds;

D is CH, T is CR⁸, M is C and Q is N(R⁷)$_p$, wherein p is 0 and q is 1; or

D is CH, T is CR⁸, M is C and Q is N(R⁷)$_p$, wherein p is 1 and q is 0;

R¹ is $C_1$–$C_6$ alkyl, $C_1$–$C_6$ haloalkyl, aryl, heteroaryl, heterocyclic, halogen, $C_1$–$C_6$ alkoxy, $C_1$–$C_6$ haloalkoxy, aralkyl, aralkoxy, aryloxy, $C_1$–$C_6$ alkylsulfanyl, $C_1$–$C_6$ haloalkylsulfanyl, $C_1$–$C_6$ alkylsulfenyl, $C_1$–$C_6$ alkylsulfonyl, —NO$_2$, —NR⁴R⁵, —C(O)R⁶, —CN, —C(O)NR⁴R⁵, —S(O)$_2$NR⁴R⁵, or cyanoalkyl;

R² is hydrogen, $C_1$–$C_6$ alkyl, $C_1$–$C_6$ haloalkyl, aryl, heteroaryl, heterocyclic, aralkyl, aralkoxy, aryloxy, halogen, $C_1$–$C_6$ alkoxy, $C_1$–$C_6$ haloalkoxy, $C_1$–$C_6$ alkylsulfanyl, $C_1$–$C_6$ haloalkylsulfanyl, $C_1$–$C_6$ alkylsulfenyl, $C_1$–$C_6$ alkylsulfonyl, oxo, hydroxy, —NO$_2$, —NR⁴R⁵, —C(O)OR⁶, —CN, —C(O)NR⁴R⁵, —S(O)$_2$NR⁴R⁵, or cyanoalkyl;

R³ is hydrogen, $C_1$–$C_6$ alkyl, aryl, aralkyl, aralkoxy, heteroaryl, heterocyclic, —RR⁶, —RNR⁴R⁵, —C(O)R⁶, —C(O)NR⁴R⁵, —C(O)OR⁶, —C(O)RO R⁶, —C(O)RC(O)OR⁶, —C(O)R R⁶, —C(O)RR'R⁶, —C(O)ROR'OR''O R⁶, —C(O)ROR'O R⁶, —C(O)RNR⁴R⁵, —C(O)RNR⁴C(O) R⁶, —C(O)RNR⁴C(O)OR⁶, —C(O)ORNR⁴R⁵, —S(O)$_2$ R⁶, or —S(O)$_2$NR⁴R⁵; or R³ is $C_1$–$C_6$ alkylene or $C_1$–$C_6$ alkylene substituted with oxo, and is linked together with the nitrogen to which it is attached and to one of the benzimidazole nitrogens to form a heterocylic compound fused to the benzimidazole;

R, R', and R", are each independently selected from $C_1$–$C_6$ alkylene, arylene, heteroarylene, $C_3$–$C_7$cycloalkylene, or heterocyclylene;

R''' is $C_1$–$C_6$ alkyl, aryl, heteroaryl, aralkyl, $C_3$–$C_7$ cycloalkyl, or heterocyclic;

R⁴ and R⁵ are each independently selected from hydrogen, $C_1$–$C_6$ alkyl, $C_1$–$C_6$ haloalkyl, $C_1$–$C_6$ alkylsulfanyl, $C_1$–$C_6$ alkylsulfenyl, $C_1$–$C_6$ alkylsulfonyl, aryl, heteroaryl, aralkyl, heterocyclic, $C_3$–$C_7$ cycloalkyl, —C(O)OR⁶, —C(O)NR'''R''', —C(O)NR'''H, —C(O)NH$_2$, or —S(O)$_2$NR'''R''';

R⁶ is hydrogen, $C_1$–$C_6$ alkyl, $C_1$–$C_6$ haloalkyl, aryl, heteroaryl, aralkyl, heterocyclic, or $C_3$–$C_7$ cycloalkyl;

R⁷ is hydrogen, $C_1$–$C_6$ alkyl, —S(O)$_2$ R⁶, —RNR⁴R⁵, —RR⁶, or aralkyl; and

R⁸ is hydrogen or halogen.

2. A compound as claimed in claim 1, wherein the compound of formula (I) is a compound of formula (IV):

(IV)

wherein E is, heteroaryl substituted with R¹, or heteroaryl substituted with R¹ and R², or a salt or solvate thereof.

3. A compound as claimed in claim 1, wherein the group A is linked to the side chain —NHC(Z)NHE and to the linker group X of the benzimidazole core through a (-1,3-) or a (-1,4-) linkage.

4. A compound as claimed in claim 1, wherein R¹ is $C_1$–$C_6$ alkyl, aryloxy, $C_1$–$C_6$ alkoxy, $C_1$–$C_6$ haloalkyl, $C_1$–$C_6$ haloalkylsulfanyl, $C_1$–$C_6$ alkylsulfanyl, —C(O)OR⁶, halogen, —CN, or —NO$_2$.

5. A compound as claimed in claim 1, wherein R² is hydrogen, halogen, $C_1$–$C_6$ alkyl, $C_1$–$C_6$ alkoxy, or $C_1$–$C_6$ haloalkyl.

6. A compound as claimed in claim 1, wherein D is CH, T is CR⁸, M is C and Q is N(R⁷)$_p$, wherein p is 0, q is 1, R⁷ is hydrogen, methyl, or S(O)$_2$R⁶.

7. A compound as claimed in claim 1, wherein D is CH, T is CR⁸, wherein R⁸ is hydrogen or —Br, M is C and Q is N(R⁷)$_p$, wherein p is 1, q is 0, R⁷ is hydrogen, methyl, —S(O)$_2$R⁶, —RNR⁴R⁵, —RR⁶ or aralkyl.

8. A compound as claimed in claim 1, wherein D is CH, T is CR⁸, wherein R⁸ is hydrogen, M is C and Q is N(R⁷)$_p$, wherein either p or q is 0, the other is 1 and R⁷ is hydrogen.

9. A compound as claimed in claim 1, wherein R³ is —C(O) R⁶, —C(O)NR⁴R⁵, —C(O)OR⁶, —C(O)RO R⁶, —C(O)RC(O)OR⁶, —C(O)ROR'OR''OR⁶, —C(O)ROR'OR⁶, —C(O)RNR⁴R⁵, —C(O)RNR⁴C(O)R⁶, —C(O)RNR⁴C(O)OR⁶, —SO$_2$R⁶, or —SO$_2$NR⁴R⁵.

10. A compound as claimed in claim 1, wherein A is phenyl; X is O; Z is O; R¹ is $C_1$–$C_6$ alkyl, $C_1$–$C_6$ alkoxy, $C_1$–$C_6$ haloalkyl, or —NO$_2$; R² is hydrogen, halogen, $C_1$–$C_6$ alkyl, or $C_1$–$C_6$ alkoxy; and R³ is —C(O)R⁶, —C(O)NR⁴R⁵, —C(O)OR⁶, —C(O)ROR⁶, —C(O)RC(O)OR⁶, —C(O)ROR'OR''OR⁶, —C(O)ROR'OR⁶, —C(O)RNR⁴R⁵, —C(O)RNR⁴C(O)R⁶, —C(O)RNR⁴C(O)OR⁶, —SO$_2$R⁶, or —SO$_2$NR⁴R⁵.

11. A compound as claimed in claim 1, wherein A is phenyl; X is S; Z is O; R¹ is $C_1$–$C_6$ alkyl, $C_1$–$C_6$ alkoxy, $C_1$–$C_6$ haloalkyl, or —NO$_2$; R² is hydrogen, halogen, $C_1$–$C_6$ alkyl, or $C_1$–$C_6$ alkoxy; and R³ is —C(O)R⁶, —C(O)NR⁴R⁵, —C(O)OR⁶, —C(O)ROR⁶, —C(O)RC(O)OR⁶, —C(O)ROR'OR''OR⁶, —C(O)ROR'OR⁶, —C(O)RNR⁴R⁵, —C(O)RNR⁴C(O)R⁶, —C(O)RNR⁴C(O)OR⁶, —SO$_2$R⁶, or —SO$_2$NR⁴R⁵.

12. A compound as claimed in claim 1, wherein A is pyridyl; X is O; Z is O; R¹ is $C_1$–$C_6$ alkyl, $C_1$–$C_6$ alkoxy, $C_1$–$C_6$ haloalkyl, or —NO$_2$; R² is hydrogen, halogen, $C_1$–$C_6$ alkyl, or $C_1$–$C_6$ alkoxy; and R³ is —C(O)R⁶, —C(O)NR⁴R⁵, —C(O)OR⁶, —C(O)ROR⁶, —C(O)RC(O)OR⁶, —C(O)ROR'OR''OR⁶, —C(O)ROR'OR⁶, —C(O)RNR⁴R⁵, —C(O)RNR⁴C(O)R⁶, —C(O)RNR⁴C(O)OR⁶, —SO$_2$R⁶, or —SO$_2$NR⁴R⁵.

13. A compound as claimed in claim 1, wherein A is pyridyl; X is S; Z is O; R¹ is $C_{1-6}$ alkyl, $C_1$–$C_6$ alkoxy, $C_1$–$C_6$ haloalkyl, or —NO$_2$; R² is hydrogen, halogen, $C_1$–$C_6$ alkyl, or $C_1$–$C_6$ alkoxy; and R³ is —C(O)R⁶, —C(O)NR⁴R⁵, —C(O)OR⁶, —C(O)ROR⁶, —C(O)RC(O)OR⁶, —C(O)ROR'OR"OR⁶, —C(O)ROR'OR⁶, —C(O)RNR⁴R⁵, —C(O)RNR⁴C(O)R⁶, —C(O)RNR⁴C(O)OR⁶, —SO₂R⁶, or —SO₂NR⁴R⁵.

14. A compound as claimed in claim 2, wherein the compound is a compound of formula (IV) where E is heteroaryl substituted with R¹, or heteroaryl substituted with R¹ and R²; A is phenyl; X is O; Z is O; R¹ is C₁–C₆ alkyl, aryl, C₃–C₇ cycloalkyl, heterocyclyl, C₁–C₆ haloalkyl, or C₁–C₆ alkylsulfanyl; R² is hydrogen, halogen, C₁–C₆ alkyl, or C₁–C₆ haloalkyl; and R³ is —C(O)R, —C(O)NR⁴R⁵, —C(O)OR⁶, —C(O)ROR⁶, —C(O)RC(O)OR⁶, —C(O)ROR'OR"OR⁶, —C(O)ROR'OR⁶, —C(O)RNR⁴R⁵, —C(O)RNR⁴C(O)R⁶, —C(O)RNR⁴C(O)OR⁶, —SO₂R⁶, or —SO₂NR⁴R⁵.

15. A compound as claimed in claim 1, selected from the group consisting of:

methyl N-(5-(4-((5-tert-butylisoxazole-3-yl)aminocarbonylamino)phenoxy)-1H-benzimidazol-2-yl)carbamate;

methyl N-(5-(3-((5-tert-butylisoxazole-3-yl)aminocarbonylamino)phenoxy)-1H-benzimidazol-2-yl)carbamate;

methyl N-(5-(4-((5-tert-butylisoxazole-3-yl)aminocarbonylamino)phenylthio)-1H-benzimidazol-2-yl)carbamate;

methyl N-(5-(3-((3-phenyl-1,2,4-thiadiazol-5-yl)aminocarbonylamino)phenoxy)-1H-benzimidazol-2-yl)carbamate;

N-(5-(4-((5-methylisoxazol-3-yl)aminocarbonylamino)phenoxy)-1H-benzimidazol-2-yl)acetamide;

N-(5-(4-((thiazol-2-yl)aminocarbonylamino)phenoxy)-1H-benzimidazol-2-yl)acetamide;

N-(5-(4-((1,3,4-thiadiazol-2-yl)aminocarbonylamino)phenoxy)-1H-benzimidazol-2-yl)acetamide;

N-(5-(4-((4-methylthiazol-2-yl)aminocarbonylamino)phenoxy)-1H-benzimidazol-2-yl)acetamide;

N-(5-(4-((5-methylthiazol-2-yl)aminocarbonylamino)phenoxy)-1H-benzimidazol-2-yl)acetamide;

N-(5-(4-((5-methyl-1,3,4-thiadiazol-2-yl)aminocarbonylamino)phenoxy)-1H-benzimidazol-2-yl)acetamide;

N-(5-(4-((5-ethyl-1,3,4-thiadiazol-2-yl)aminocarbonylamino)phenoxy)-1H-benzimidazol-2-yl)acetamide;

N-(5-(4-((5-cyclopropyl-1,3,4-thiadiazol-2-yl)aminocarbonylamino)phenoxy)-1H-benzimidazol-2-yl)acetamide;

N-(5-(4-((4-tert-butylthiazol-2-yl)aminocarbonylamino)phenoxy)-1H-benzimidazol-2-yl)acetamide;

N-(5-(4-((5-tert-butyl-1,3,4-thiadiazol-2-yl)aminocarbonylamino)phenoxy)-1H-benzimidazol-2-yl)acetamide;

N-(5-(4-((4,5-dimethylthiazol-2-yl)aminocarbonylamino)phenoxy)-1H-benzimidazol-2-yl)acetamide;

N-(5-(4-((5-morpholino-1,3,4-triazol-2-yl)aminocarbonylamino)phenoxy)-1H-benzimidazol-2-yl)acetamide;

N-(5-(4-((5-methylisoxazol-3-yl)aminocarbonylamino)phenoxy)-1H-benzimidazol-2-yl)(2-(methoxy)ethoxy)acetamide;

N-(5-(4-((thiazol-2-yl)aminocarbonylamino)phenoxy)-1H-benzimidazol-2-yl)(2-(methoxy)ethoxy)acetamide;

N-(5-(4-((1,3,4-thiadiazol-2-yl)aminocarbonylamino)phenoxy)-1H-benzimidazol-2-yl)(2-(methoxy)ethoxy)acetamide;

N-(5-(4-((4-methylthiazol-2-yl)aminocarbonylamino)phenoxy)-1H-benzimidazol-2-yl)(2-(methoxy)ethoxy)acetamide;

N-(5-(4-((5-methylthiazol-2-yl)aminocarbonylamino)phenoxy)-1H-benzimidazol-2-yl)(2-(methoxy)ethoxy)acetamide;

N-(5-(4-((5-methyl-1,3,4-thiadiazol-2-yl)aminocarbonylamino)phenoxy)-1H-benzimidazol-2-yl)(2-(methoxy)ethoxy)acetamide;

N-(5-(4-((5-ethyl-1,3,4-thiadiazol-2-yl)aminocarbonylamino)phenoxy)-1H-benzimidazol-2-yl)(2-(methoxy)ethoxy)acetamide;

N-(5-(4-((5-cyclopropyl-1,3,4-thiadiazol-2-yl)aminocarbonylamino)phenoxy)-1H-benzimidazol-2-yl)(2-(methoxy)ethoxy)acetamide;

N-(5-(4-((4tert-butylthiazol-2-yl)aminocarbonylamino)phenoxy)-1H-benzimidazol-2-yl)(2-(methoxy)ethoxy)acetamide;

N-(5-(4-((5-tert-butyl-1,3,4-thiadiazol-2-yl)aminocarbonylamino)phenoxy)-1H-benzimidazol-2-yl)(2-(methoxy)ethoxy)acetamide;

N-(5-(4-((5-ethylthio-1,3,4-thiadiazol-2-yl)aminocarbonylamino)phenoxy)-1H-benzimidazol-2-yl)(2-(methoxy)ethoxy)acetamide;

N-(5-(4-((5-propylthio-1,3,4-thiadiazol-2-yl)aminocarbonylamino)phenoxy)-1H-benzimidazol-2-yl)(2-(methoxy)ethoxy)acetamide;

N-(5-(4-((4,5-dimetylthiazol-2-yl)aminocarbonylamino)phenoxy)-1H-benzimidazol-2-yl)(2-(methoxy)ethoxy)acetamide;

N-(5-(4-((5-morpholino-1,3,4-triazol-2-yl)aminocarbonylamino)phenoxy)-1H-benzimidazol-2-yl)(2-(methoxy)ethoxy)acetamide;

N-(5-(4-((5-methylisoxazol-3-yl)aminocarbonylamino)phenoxy)-1H-benzimidazol-2-yl)(2-furyl)formamide;

N-(5-(4-((thiazol-2-yl)aminocarbonylamino)phenoxy)-1H-benzimidazol-2-yl)(2-furyl)formamide;

N-(5-(4-((1,3,4-thiadiazol-2-yl)aminocarbonylamino)phenoxy)-1H-benzimidazol-2-yl)(2-furyl)formamide;

N-(5-(4-((4-methylthiazol-2-yl)aminocarbonylamino)phenoxy)-1H-benzimidazol-2-yl)(2-furyl)formamide;

N-(5-(4-((5-methylthiazol-2-yl)aminocarbonylamino)phenoxy)-1H-benzimidazol-2-yl)(2-furyl)formamide;

N-(5-(4-((5-methyl-1,3,4-thiadiazol-2-yl)aminocarbonylamino)phenoxy)-1H-benzimidazol-2-yl)(2-fury)formamide;

N-(5-(4-((5-ethyl-1,3,4-thiadiazol-2-yl)aminocarbonylamino)phenoxy)-1H-benzimidazol-2-yl)(2-furyl)formamide;

N-(5-(4-((5-cycloproyl-1,3,4-thiadiazol-2-yl)aminocarbonylamino)phenoxy)-1H-benzimidazol-2-yl)(2-furyl)formamide;

N-(5-(4-((4-tert-butylthiazol-2-yl)aminocarbonylamino)phenoxy)-1H-benzimidazol-2-yl)(2-furyl)formamide;

N-(5-(4-((5-tert-butyl-1,3,4-thiadiazol-2-yl)aminocarbonylamino)phenoxy)-1H-benzimidazol-2-yl)(2-furyl)formamide;

N-(5-(4-((5-ethylthio-1,3,4-thiadiazol-2-yl)aminocarbonylamino)phenoxy)-1H-benzimidazol-2-yl)(2-furyl)formamide;

N-(5-(4-((4,5-dimethylthiazol-2-yl)aminocarbonylamino)phenoxy)-1H-benzimidazol-2-yl)(2-furyl)formamide;

N-(5-(4-((5-morpholino-1,3,4-triazol-2-yl)aminocarbonylamino)phenoxy)-1H-benzimidazol-2-yl)(2-furyl)formamide;

N-(5-(4-((5-methylthio-1,3,4-thiadiazol-2-yl)aminocarbonylamino)phenoxy)-1H-benzimidazol-2-yl)acetamide;

N-(5-(4-((5-methylthio-1,3,4-thiadiazol-2-yl)aminocarbonylamino)phenoxy)-1H-benzimidazol-2-yl)(2-(methoxy)ethoxy)acetamide; and N-(5-(4-((5-methylthio-1,3,4-thiadiazol-2-yl)aminocarbonylamino)phenoxy)-1H-benzimidazol-2-yl)(2-furyl)formamide;
or a salt or solvate thereof.

16. A pharmaceutical composition, comprising: a therapeutically effective amount of a compound as claimed in claim 1, or a salt or solvate, thereof and one or more of pharmaceutically acceptable carriers, diluents and excipients.

17. A pharmaceutical composition, comprising: a therapeutically effective amount of a compound as claimed in claim 2, or a salt or solvate thereof and one or more of pharmaceutically acceptable carriers, diluents and excipients.

18. A pharmaceutical composition, comprising: a therapeutically effective amount of a compound as claimed in claim 15, or a salt or solvate thereof and one or more of pharmaceutically acceptable carriers, diluents and excipients.

* * * * *

UNITED STATES PATENT AND TRADEMARK OFFICE
CERTIFICATE OF CORRECTION

PATENT NO. : 7,238,813 B2
APPLICATION NO. : 10/433128
DATED : July 3, 2007
INVENTOR(S) : Cheung et al.

Page 1 of 1

It is certified that error appears in the above-identified patent and that said Letters Patent is hereby corrected as shown below:

Claim 1, col. 172, lines 53-60, the structure of Formula (I) is missing the – X—moiety and should be:

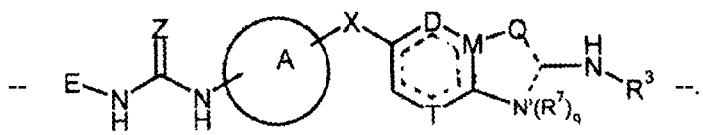

Claim 15, col. 176, line 10, delete "4tert" and insert --4-tert--.

Claim 15, col. 176, line 22, delete "4,5-dimetylthiazol-2-yl" and insert therefor --4,5-dimethylthiazol-2-yl--.

Claim 15, col. 176, line 45, delete "5-cycloproyl" and insert therefor --5-cyclopropyl--.

Signed and Sealed this

First Day of July, 2008

JON W. DUDAS
*Director of the United States Patent and Trademark Office*